United States Patent
Wrobleski et al.

(10) Patent No.: US 8,921,368 B2
(45) Date of Patent: Dec. 30, 2014

(54) PYRROLOPYRIDAZINE JAK3 INHIBITORS AND THEIR USE FOR THE TREATMENT OF INFLAMMATORY AND AUTOIMMUNE DISEASES

(75) Inventors: Stephen T. Wrobleski, Flemington, NJ (US); Gregory D. Brown, Landsdale, PA (US); Lidia M. Doweyko, Vero Beach, FL (US); Jingwu Duan, Yardley, PA (US); Junqing Guo, Princeton, NJ (US); John Hynes, Washington Crossing, PA (US); Bin Jiang, Norristown, PA (US); James Kempson, Princeton, NJ (US); Shuqun Lin, Newtown, PA (US); Zhonghui Lu, King of Prussia, PA (US); Steven H. Spergel, Warrington, PA (US); John S. Tokarski, Princeton, NJ (US); Hong Wu, New Hope, PA (US); Bingwei Vera Yang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/005,570

(22) PCT Filed: Mar. 16, 2012

(86) PCT No.: PCT/US2012/029334
§ 371 (c)(1),
(2), (4) Date: Sep. 17, 2013

(87) PCT Pub. No.: WO2012/125886
PCT Pub. Date: Sep. 20, 2012

(65) Prior Publication Data
US 2014/0011795 A1 Jan. 9, 2014

Related U.S. Application Data

(60) Provisional application No. 61/453,609, filed on Mar. 17, 2011.

(51) Int. Cl.
*C07D 487/04* (2006.01)
*C07D 471/04* (2006.01)
*A01N 43/58* (2006.01)
*A61K 31/50* (2006.01)

(52) U.S. Cl.
USPC .......................................... 514/248; 544/235

(58) Field of Classification Search
USPC .......................................... 514/248; 544/235
See application file for complete search history.

(56) References Cited

FOREIGN PATENT DOCUMENTS

WO   WO 2004/099204    11/2004
WO   WO 2011/014817    2/2011

OTHER PUBLICATIONS

Coombs, J.H. et al., "Improved pain, physical functioning and health status in patients with rheumatoid arthritis treated with CP-690,550, an orally active Janus kinase (JAK) inhibitor: results from a randomised, double-blind, placebo-controlled trial", Ann. Rheum. Dis., vol. 69, pp. 413-416 (2010).
Ghoreschi, K. et al., "Modulation of Innate and Adaptive Immune Responses by Tofacitinib (CP-690,550)", The Journal of Immunology, vol. 186, pp. 4234-4243 (2011).
Milici, A.J. et al., "Cartilage preservation by inhibition of Janus kinase 3 in two rodent models of rheumatoid arthritis", Arthritis Research & Therapy, vol. 10, R14 (2008).
O'Shea, J.J. et al., A New Modality for Immunosuppression: Targeting the JAK/STAT Pathway, Nature Reviews: Drug Discovery, vol. 3, pp. 555-564 (2004).
Pesu, M. et al., "Jak3, severe combined immunodeficiency, and a new class of immunosuppressive drugs", Immunological Reviews, vol. 203, pp. 127-142 (2005).
Shi, M. et al., "Janus-Kinase-3-Dependent Signals Induce Chromatin Remodeling at the *Ifng* Locus during T Helper 1 Cell Differentiation", Immunity, vol. 28, pp. 763-773 (2008).

*Primary Examiner* — Paul V. Ward
(74) *Attorney, Agent, or Firm* — Mary VanAtten

(57) ABSTRACT

Disclosed are compounds of Formula (I), and pharmaceutically acceptable salts thereof. The compounds of formula (I) inhibit tyrosine kinase activity of JAK3, thereby making them useful for the treatment of inflammatory and autoimmune diseases.

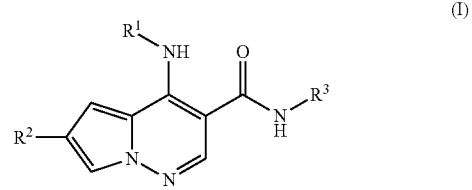

9 Claims, No Drawings

PYRROLOPYRIDAZINE JAK3 INHIBITORS AND THEIR USE FOR THE TREATMENT OF INFLAMMATORY AND AUTOIMMUNE DISEASES

This application is a 371 application of PCT/US2012/029334 filed Mar. 16, 2012 which claims priority from U.S. Provisional Application Ser. No. 61/453,609 filed Mar. 17, 2011 which are incorporated by reference herein in their entirety.

FIELD OF THE INVENTION

This invention relates to novel pyrrolopyridazine compounds that are useful as inhibitors of Janus kinases (JAKs), more particularly JAK3. This invention also relates to a method of using the compounds in the treatment of inflammatory and autoimmune diseases, and to pharmaceutical compositions containing the compounds.

BACKGROUND OF THE INVENTION

The present invention relates to pyrrolopyridazine compounds, the methods of preparation of these compounds, and their use in the treatment of conditions in which selective modulation of the JAK signaling pathway via inhibition of the Janus kinases (JAKs) kinases, particularly JAK3 kinase, may be therapeutically beneficial.

The Janus kinases (JAKs) belong to the non-receptor protein tyrosine kinase family and are known to be critical intracellular regulators of cytokine signaling via modulation of the JAK-STAT pathway (see, Murray, P. J. *Immunity*, 2008, 28, 763). There are four known mammalian JAK isoforms which include JAK1, JAK2, JAK3 and TYK2.

JAK3 has been shown to play a specific role in the signaling of a subset of cytokines known as the gamma common chain cytokine family which includes the interleukins IL-2, IL-4, IL-7, IL-9, IL-15, and IL-21. Deficiency of JAK3 in rodents and humans results in a severe combined immunodeficient (SCID) phenotype (see, Pesu, M. et al *Immunol. Rev.* 2005, 203, 127). Furthermore, JAK3 is known to have limited expression in hematopoeitic cells whereas JAK1, JAK2 and TYK2 have been shown to be more ubiquitously expressed. As a result of its specific role in regulating the immune response and its localized expression in lymphoid cells, inhibition of JAK3 has been recognized as a promising strategy for development of novel and selective immunosuppressive agents useful for transplant rejection prevention and in the treatment of autoimmune and inflammatory diseases such as psoriasis, rheumatoid arthritis, psoriatic arthritis, multiple sclerosis, inflammatory bowel diosease, and lupus (see, O'Shea J. J. et al, *Nat. Rev. Drug Discov.* 2004, 3(7), 555). Moreover, the reported JAK inhibitor CP-690,550 which potently inhibits JAK3 has been shown to be effective in the treatment arthritis in rodent models as well as in patients with rheumatoid arthritis (see, Milici, A. J. et. al. *Arthritis Res. & Therapy,* 2008, R14 and Coombs, J. H. et al *Ann. Rheum. Dis.* 2010, 69, 413). It has been suggested that the clinical efficacy of CP-690,550 (Tofacitinib) may be related to its ability to inhibit other JAK family members (see Ghoreschi, K et al, *J. Immunol.* 2011, 186, 4234). While JAK3 and JAK1 are both capable of modulating gamma common chain induce phosphorylation of STAT signalling, JAK1 inhibition can also decrease non-gamma common chain cytokine signalling (e.g. IL-6 signalling). As such, orally available compounds that inhibit JAK3 and/or JAK1 may be useful for the treatment of inflammatory and autoimmune diseases.

Accordingly, novel compounds which inhibit the JAK/STAT pathway, more particularly via selective inhibition of JAK3 and/or JAK1, may be therapeutically useful. The closely related isoform JAK2 is classically associated with interferon-γ production through the IL-12 pathway, but it also mediates the signaling of important hematopoietic growth factors such as erythropoietin (EPO), thromobopoetin (TPO) and granulocyte macrophage-stimulating factor (GM-CSF). As a result, inhibition of JAK2 may result in adverse hematopoietic effects such as anemia, thrombocytopenia and generalized leukopenia. As such, novel compounds which selectively inhibit JAK3 and/or JAK1 over JAK2 may be especially desirable in the safe treatment of chronic inflammatory and automimmune diseases.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I:

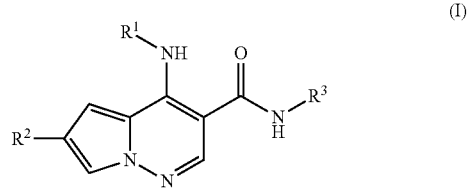

or salts, stereoisomers, or prodrugs thereof, wherein:

$R^1$ is $C_{3-10}$ saturated or partially saturated carbocycle substituted with 0-5 $R^{1a}$, $R^{1a}$ is =O, F, Cl, Br, —OCF$_3$, —CF$_3$, —CN, —NO$_2$, —(CH$_2$)$_r$OR$^b$, —(CH$_2$)$_r$SR$^b$, —(CH$_2$)$_r$C(O)R$^{1d}$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^1$e, —(CH$_2$)$_r$NR$^b$C(O)OR$^c$, —(CH$_2$)$_r$NR$^b$C(O)NR$^{11}$R$^{11}$, —(CH$_2$)$_r$S(O)$_2$NR$^{11}$R$^{11}$, —(CH$_2$)$_r$NR$^b$S(O)$_2$R$^c$, —(CH$_2$)$_r$S(O)R$^c$, —(CH$_2$)$_r$S(O)$_2$R$^c$, $C_{1-6}$ alkyl substituted with 0-2 $R^a$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$, substituted with 0-1 $R^a$;

$R^{1c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5-10 membered heterocycle containing 1-4 heteroatoms selected from N, O, and S, substituted with 0-3 $R^a$, a 5-10 membered heteroaryl containing 1-4 heteroatoms selected from N, O, and S, substituted with 0-3 $R^a$;

$R^{1d}$ is hydrogen, $C_{1-6}$ alkyl substituted with 0-2 $R^d$, $C_{1-6}$ haloalkyl, $C_{3-6}$ cycloalkyl substituted with 0-2 $R^d$, or —(CH$_2$)$_r$-phenyl substituted with 0-2 $R^a$, a 5-10 membered heterocycle containing 1-4 heteroatoms selected from N, O, and S, substituted with 0-3 $R^a$;

$R^2$ is —NR$^b$C(O)NR$^{11}$R$^{11}$, —NR$^b$C(O)R$^{2b}$, —NR$^b$C(O)OR$^{2d}$, —NR$^b$S(O)$_2$R$^{2b}$, —(CH$_2$)$_r$—C$_{6-10}$ aryl substituted with 0-3 $R^{2a}$, or —(CH$_2$)$_r$-4-10 membered heterocycle containing 1-4 heteroatoms selected from N, O, and S, substituted with 0-3 $R^{2a}$;

$R^{2a}$ is =O, F, Cl, Br, —OCF$_3$, —CF$_3$, —CN, —NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C (O)NR¹¹R¹¹, —(CH₂)ᵣNRᵇC(O)R²ᵇ, —(CH₂)ᵣNRᵇC(O)ORᶜ, —NRᵇC(O)NR¹¹R¹¹, —S(O)₂NR¹¹R¹¹ —NRᵇS(O)₂Rᶜ, —S(O)Rᶜ, —S(O)₂Rᶜ, —(CH₂)ᵣNH(C=NCN)NHR¹¹, $C_{1-6}$ alkyl substituted with 0-2 $R^a$, $C_{2-6}$ alkenyl, $C_{1-6}$ haloalkyl, —(CH₂)ᵣ-3-14 membered carbocycle substituted with 0-1 $R^a$, or —(CH₂)ᵣ-5-10 membered heterocycle comprising carbon atoms and 1-4 heteroatoms selected from N, O, and $S(O)_p$, substituted with 0-1 $R^a$;

$R^{2b}$ is hydrogen, $C_{1-6}$ alkyl substituted with 0-2 $R^a$, $C_{1-6}$ haloalkyl, $C_{3-6}$ cycloalkyl substituted with 0-2 $R^a$, or —(CH₂)ᵣ-phenyl substituted with 0-2 $R^a$, or —(CH₂)ᵣ-5-10 membered heterocycle comprising carbon atoms and 1-4 heteroatoms selected from N, O, and $S(O)_p$, substituted with 0-1 $R^a$;

$R^{2d}$ is $C_{1-6}$ alkyl substituted with 0-2 $R^a$, $C_{1-6}$ haloalkyl, $C_{3-6}$ cycloalkyl substituted with 0-2 $R^a$, or —(CH₂)ᵣ-phenyl substituted with 0-2 $R^a$, or —(CH₂)ᵣ-5-10 membered heterocycle comprising carbon atoms and 1-4 heteroatoms selected from N, O, and $S(O)_p$, substituted with 0-1 $R^a$;

$R^3$ is hydrogen, $C_{1-6}$ alkyl substituted with 0-1 $R^a$, phenyl substituted with 0-1 $R^a$, or $C_{3-6}$ cycloalkyl substituted with 0-1 $R^a$;

$R^{11}$ is independently hydrogen or $C_{1-4}$ alkyl substituted with 0-1 $R^a$, —(CH₂)ᵣ-3-6 membered carbocycle substituted with 0-1 $R^a$, or —(CH₂)ᵣ-5-7 membered heterocycle comprising carbon atoms and 1-4 heteroatoms selected from N, O, and $S(O)_p$;

$R^a$ is hydrogen, =O, F, Cl, Br, —OCF₃, —CF₃, —CHF₂, —CN, —NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNRᶜRᶜ, —(CH₂)ᵣC(O)NRᶜRᶜ, —(CH₂)ᵣNRᵇC(O)Rᶜ, —(CH₂)ᵣNRᵇC(O)ORᶜ, —NRᵇC(O)NRᶜRᶜ, —S(O)₂NRᶜRᶜ, —NRᵇS(O)₂Rᶜ, —S(O)Rᶜ, —S(O)₂Rᶜ, —(CH₂)ᵣNH(C=NCN)NHRᶜ, $C_{1-6}$ alkyl substituted with 0-2 $R^d$, $C_{1-6}$ haloalkyl, —(CH₂)ᵣ-3-14 membered carbocycle substituted with 0-1 $R^d$, or —(CH₂)ᵣ-5-7 membered heterocycle comprising carbon atoms and 1-4 heteroatoms selected from N, O, and $S(O)_p$, substituted with 0-1 $R^d$, alternatively two $R^a$ on adjacent or the same carbon atom form a cyclic acetal of the formula —O—, (CH₂)ₙ—O—, or —O—CF₂—O—, wherein n is selected from 1 and 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —(CH₂)ᵣ-phenyl substituted with 0-2 $R^d$, or —(CH₂)ᵣ-5-7 membered heterocycle comprising carbon atoms and 1-4 heteroatoms selected from N, O, and $S(O)_p$, substituted with 0-1 $R^d$;

$R^c$ is $C_{1-6}$ alkyl substituted with 0-1 $R^f$, $C_{3-6}$ cycloalkyl, or —(CH₂)ᵣ-phenyl substituted with 0-1 $R^f$;

$R^d$ is hydrogen, F, Cl, Br, —OCF₃, —CF₃, —CN, —NO₂, —ORᵉ, —(CH₂)ᵣC(O)Rᵉ, —NRᵉRᵉ, —NRᵉC(O)ORᵉ, —C(O)ORᵉ, —S(O)₂NRᵉRᵉ, $C_{1-6}$ alkyl, or —(CH₂)ᵣ-phenyl;

$R^e$ is hydrogen, $C_{1-6}$ alkyl, $C_{3-6}$ cycloalkyl, or (CH₂)ᵣ-phenyl;

$R^f$ is hydrogen, halo, —CN, —SO₂(CH₃), phenyl, —NH₂, —NHC(O)(CH₃), —OH, or —OCH₃;

r is 0, 1, 2, 3, or 4; and p is 0, 1, or 2.

In one embodiment, there are provided compounds of Formula (I) or salts, stereoisomers, or prodrugs thereof, wherein $R^3$ is hydrogen. The compounds of this embodiment have the structure of Formula (II):

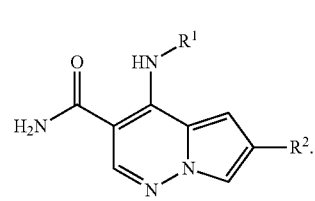

In one embodiment, there are provided compounds of Formula (II) or salts, stereoisomers, or prodrugs thereof, wherein:

$R^1$ is $C_{3-6}$ cycloalkyl or adamantanyl, each substituted with 1, 2, 3, or 4 substituents independently selected from F, Cl, —OH, —CN, $C_{1-4}$ alkyl, =O, —O($C_{1-6}$ alkyl), —NH₂, —NH($C_{1-4}$ alkyl), —NH(benzyl), —N($C_{1-4}$ alkyl)₂, —NHC(O)($C_{1-4}$ alkyl), —NHC(O)O($C_{1-4}$ alkyl), —NHS(O)₂($C_{1-4}$ alkyl), —NHC(O)NH($C_{1-4}$ alkyl), —NHC(O)NH($C_{1-4}$ alkyl), —NHC(O)NH(phenyl), —C(O)NH₂, and/or —CH₂NHC(O)CH(OH)($C_{1-4}$ alkyl);

$R^2$ is -L-$R^x$ or $R^y$;

L is —NHC(O)—, —NHS(O)₂—, —NHC(O)NH—, —NHC(O)O—, or —C(O)NH—;

$R^x$ is $C_{1-6}$ alkyl, benzyl, or phenyl substituted with zero or 1 substituent selected from F, Cl, and —O($C_{1-4}$ alkyl); and $R^y$ is:
  a) phenyl substituted with zero, 1, or 2 substituents independently selected from F, Cl, $C_{1-6}$ alkyl, —NH₂, —N($C_{1-4}$ alkyl)₂, —O($C_{1-4}$ alkyl), $C_{1-6}$ hydroxyalkyl, $C_{1-4}$ aminoalkyl, —CN, —C(O)($C_{1-4}$ alkyl), —CH₂NHC(O)($C_{1-4}$ alkyl), —C(O)OH, —C(O)O($C_{1-4}$ alkyl), —C(O)NH₂, —C(O)NH($C_{1-4}$ alkyl), —C(O)N($C_{1-4}$ alkyl)₂, —C(O)NH($C_{3-6}$ cycloalkyl), —C(O)NH($C_{3-6}$ cycloalkyl), —S(O)₂($C_{1-4}$ alkyl), —NHC(O)($C_{1-4}$ alkyl), —NHC(O)O($C_{1-4}$ alkyl), —NHC(O)CH₂CH₂O($C_{1-4}$ alkyl), —NHS(O)₂($C_{1-4}$ alkyl), —O($C_{1-4}$ alkyl), —O($C_{1-4}$ fluoroalkyl), —S(O)₂NH₂, —C(O)(morpholinyl), —CH₂(morpholinyl), phenyl, pyrazolyl, tetrazolyl, and/or morpholinyl;
  b) azetidinonyl, pyrrolidinyl, pyrrolidinonyl, 1H-pyrrol-2(5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1 or 2 substituents independently selected from —OH, $C_{1-4}$ alkyl, —O($C_{1-4}$ alkyl), —C(O)($C_{1-4}$ alkyl), phenyl, and/or benzyl; or
  c) pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, $C_{1-4}$ alkyl, $C_{1-3}$ fluoroalkyl, —NH₂, —CN, $C_{1-4}$ hydroxyalkyl, —O($C_{1-4}$ alkyl), —O(phenyl), —O(benzyl), —C(O)OH, —C(O)O($C_{1-4}$ alkyl), —C(O)NH₂, —C(O)NH($C_{1-4}$ alkyl), —NHC(O)($C_{1-4}$ alkyl), phenyl, benzyl, fluorophenyl, chlorophenyl, —NH($C_{3-6}$ cycloalkyl), —NH(tetrahydropyranyl), —NH($C_{1-6}$alkyl), —NH(CH₂—$C_{3-6}$cycloalkyl), —NH(CH(CH₃)—$C_{3-6}$ cycloalkyl), and/or —NH(tetrahydropyranyl).

In one embodiment, there are provided compounds of Formula (II) or salts, stereoisomers, or prodrugs thereof, wherein:

$R^1$ is $C_{5-6}$ cycloalkyl or adamantanyl, each substituted with 1, 2, 3, or 4 substituents independently selected from F, —OH, —CN, —CH$_3$, =O, —OCH$_3$, —OCH(CH$_3$)$_2$, —NH$_2$, —NH(C$_{1-2}$ alkyl), —NH(benzyl), —N(CH$_3$)$_2$, —NHC(O)(C$_{1-2}$ alkyl), —NHC(O)O(t-butyl), —NHS(O)$_2$CH$_3$, —NHC(O)NH(CH$_3$), —NHC(O)NH(t-butyl), —NHC(O)NH(phenyl), —C(O)NH$_2$, and/or —CH$_2$NHC(O)CH(OH)CH$_3$;

$R^2$ is -L-R$^x$ or R$^y$;

L is —NHC(O)—, —NHS(O)$_2$—, —NHC(O)NH—, —NHC(O)O—, or —C(O)NH—;

$R^x$ is $C_{1-4}$ alkyl, benzyl, or phenyl substituted with zero or 1 substituent selected from F, Cl, and —O(C$_{1-2}$ alkyl); and $R^y$ is:
  a) phenyl substituted with zero, 1, or 2 substituents independently selected from F, Cl, $C_{1-4}$ alkyl, —NH$_2$, —N(C$_{1-3}$ alkyl)$_2$, —O(C$_{1-3}$ alkyl), $C_{1-4}$ hydroxyalkyl, $C_{1-3}$ aminoalkyl, —CN, —C(O)(C$_{1-3}$ alkyl), —CH$_2$NHC(O)(C$_{1-3}$ alkyl), —C(O)OH, —C(O)O(C$_{1-3}$ alkyl), —C(O)NH$_2$, —C(O)NH(C$_{1-4}$ alkyl), —C(O)N(C$_{1-3}$ alkyl)$_2$, —C(O)NH(C$_{3-5}$ cycloalkyl), —C(O)NH(C$_{3-6}$ cycloalkyl), —S(O)$_2$(C$_{1-3}$ alkyl), —NHC(O)(C$_{1-4}$ alkyl), —NHC(O)O(C$_{1-4}$ alkyl), —NHC(O)CH$_2$CH$_2$O(C$_{1-3}$ alkyl), —NHS(O)$_2$(C$_{1-3}$ alkyl), —O(C$_{1-4}$ alkyl), —O(C$_{1-3}$ fluoroalkyl), —S(O)$_2$NH$_2$, —C(O)(morpholinyl), —CH$_2$(morpholinyl), phenyl, pyrazolyl, tetrazolyl, and/or morpholinyl;
  b) azetidinonyl, pyrrolidinyl, pyrrolidinonyl, 1H-pyrrol-2(5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1, or 2 substituents independently selected from —OH, —CH$_3$, —OCH$_3$, —C(O)CH$_3$, and/or benzyl; or
  c) pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, $C_{1-3}$ alkyl, —CF$_3$, —NH$_2$, —CN, $C_{1-4}$ hydroxyalkyl, —O(C$_{1-3}$ alkyl), —O(benzyl), —C(O)OH, —C(O)O(C$_{1-4}$ alkyl), —C(O)NH$_2$, —C(O)NH(C$_{1-4}$ alkyl), —NHC(O)(C$_{1-4}$ alkyl), phenyl, benzyl, chlorophenyl, —NH(cyclobutyl), —NH(tetrahydropyranyl), —NH(C$_{4-5}$ alkyl), —NH(CH(CH$_3$)-cyclopropyl), and/or —NH(tetrahydropyranyl).

In one embodiment, there are provided compounds of Formula (II) or salts, stereoisomers, or prodrugs thereof, wherein:

$R^1$ is:
  a) cyclopentyl substituted with 1, 2, 3, or 4 substituents independently selected from F, —OH, —CN, —CH$_3$, =O, —OCH$_3$, —OCH(CH$_3$)$_2$, —NH$_2$, —NH(C$_{1-2}$ alkyl), —NH(benzyl), —N(CH$_3$)$_2$, —NHC(O)(C$_{1-2}$ alkyl), —NHC(O)O(t-butyl), —NHS(O)$_2$CH$_3$, —NHC(O)NH(CH$_3$), —NHC(O)NH(t-butyl), —NHC(O)NH(phenyl), —C(O)NH$_2$, and/or —CH$_2$NHC(O)CH(OH)CH$_3$,
  b) cyclohexyl substituted with 2 substituents independently selected from methyl and/or —OH; or
  c) adamantanyl substituted with 1 or 2-OH;

$R^2$ is -L-Rx or R$^y$;

L is —NHC(O)—, —NHS(O)$_2$—, —NHC(O)NH—, —NHC(O)O—, or —C(O)NH—;

$R^x$ is $C_{1-4}$ alkyl, benzyl, or phenyl substituted with zero or 1 substituent selected from Cl and —OCH$_3$; and $R^y$ is:
  a) phenyl substituted with zero, 1, or 2 substituents independently selected from F, Cl, $C_{1-3}$ alkyl, —NH$_2$, —N(CH$_3$)$_2$, —OCH$_3$, —CH$_2$OH, —CH(CH$_3$)$_2$OH, —CH$_2$NH$_2$, —CN, —C(O)CH$_3$, —CH$_2$NHC(O)CH$_3$, —C(O)OH, —C(O)OCH$_3$, —C(O)NH$_2$, —C(O)N(CH$_3$)$_2$, —C(O)NH(C$_{1-4}$ alkyl), —C(O)NH(cyclopropyl), —C(O)NH(cyclopentyl), —S(O)$_2$CH$_3$, —NHC(O)CH$_3$, —NHC(O)OCH$_3$, —NHC(O)CH$_2$CH$_2$OCH$_3$, —NHS(O)$_2$CH$_3$, —O(ethyl), —OCHF$_2$, —S(O)$_2$NH$_2$, —C(O)(morpholinyl), —CH$_2$(morpholinyl), phenyl, pyrazolyl, tetrazolyl, and/or morpholinyl;
  b) azetidinonyl, pyrrolidinyl, pyrrolidinonyl, pyrrolidinonyl substituted with —OH, 3,4-dimethyl-1H-pyrrol-2(5H)-onyl, 4-methoxy-1H-pyrrol-2(5H)-onyl, oxazolidinonyl, piperazinyl, piperazinonyl substituted with benzyl, morpholinyl, morpholinonyl, 3-methyl-1H-pyrrol-2(5H)-onyl, or imidazolidinonyl substituted with zero or 1 substituent selected from —CH$_3$ and —C(O)CH$_3$;
  c) pyrrolyl substituted with —C(O)OH or —C(O)OCH$_3$; pyrazolyl substituted with zero or 1 substituent selected from methyl, —CF$_3$, phenyl, benzyl, and chlorophenyl; thiazolyl substituted with 1 or 2 methyl groups; isoxazolyl substituted with two methyl groups; oxadiazolyl substituted with methyl, —NH(cyclobutyl), —NH(tetrahydropyranyl), —NH(C$_{4-5}$ alkyl), or —NH(CH(CH$_3$)-cyclopropyl): thiadiazolyl substituted with zero or 1 substituent selected from —NH(tetrahydropyranyl); or tetrazolyl substituted with methyl;
  d) pyridinyl substituted with zero, 1, or 2 substituents independently selected from F, Cl, —CH$_3$, —NH$_2$, —CF$_3$, —CN, —OCH$_3$, —OCH(CH$_3$)$_2$, —C(O)NH$_2$, —C(O)NH(CH$_3$), —NHC(O)CH$_3$, and/or —O(benzyl); or pyridinonyl substituted with hydroxybutyl; or
  e) pyrimidinyl substituted with zero or 1 substituent selected from —NH$_2$, pyrazinyl, dihydropyridinyl substituted with —C(O)O(t-butyl), dihydroisoquinolinonyl substituted with —OCH$_3$, 4-methyl-3,4-dihydro-2H-benzo[b][1,4]oxazinyl, 1-methyl-1H-indolyl, imidazo[1,2-a]pyridinyl, indolyl, indazolyl, benzothiazolyl, isoquinolinyl, quinolinyl, and quinoxalinyl.

In one embodiment, there are provided compounds of Formula (II) or salts, stereoisomers, or prodrugs thereof, wherein:

$R^1$ is:
  a) cyclopentyl substituted with 1, 2, 3, or 4 substituents independently selected from F, —OH, —CN, —CH$_3$, =O, —OCH$_3$, —OCH(CH$_3$)$_2$, —NH$_2$, —NH(C$_{1-2}$ alkyl), —NH(benzyl), —N(CH$_3$)$_2$, —NHC(O)(C$_{1-2}$ alkyl), —NHC(O)O(t-butyl), —NHS(O)$_2$CH$_3$, —NHC(O)NH(CH$_3$), —NHC(O)NH(t-butyl), —NHC(O)NH(phenyl), —C(O)NH$_2$, and/or —CH$_2$NHC(O)CH(OH)CH$_3$,
  b) cyclohexyl substituted with 2 substituents independently selected from methyl and/or —OH; or
  c) adamantanyl substituted with 1 or 2 —OH;

$R^2$ is -L-R$^x$ or R$^y$;

L is —NHC(O)—, —NHS(O)$_2$—, —NHC(O)NH—, or —NHC(O)O—;

$R^x$ is $C_{1-4}$ alkyl, benzyl, or phenyl substituted with zero or 1 substituent selected from Cl and —OCH$_3$; and $R^y$ is:
  a) phenyl substituted with zero, 1, or 2 substituents independently selected from F, Cl, $C_{1-3}$ alkyl, —NH$_2$, —N(CH$_3$)$_2$, —OCH$_3$, —CH$_2$OH, —CH(CH$_3$)$_2$OH, —CH$_2$NH$_2$, —CN, —C(O)CH$_3$, —CH$_2$NHC(O)CH$_3$, —C(O)OH, —C(O)OCH$_3$, —C(O)NH$_2$, —C(O)N (CH$_3$)$_2$, —C(O)NH(C$_{1-4}$ alkyl), —C(O)NH(cyclopropyl), —C(O)NH(cyclopentyl), —S(O)$_2$CH$_3$, —NHC(O)CH$_3$, —NHC(O)OCH$_3$, —NHC(O)CH$_2$CH$_2$OCH$_3$, —NHS(O)$_2$CH$_3$, —O(ethyl), —OCHF$_2$, —S(O)$_2$NH$_2$, —C(O)(morpholinyl), —CH$_2$(morpholinyl), phenyl, pyrazolyl, tetrazolyl, and/or morpholinyl;

b) 3,4-dimethyl-1H-pyrrol-2(5H)-onyl, 4-methoxy-1H-pyrrol-2(5H)-onyl, oxazolidinonyl, 3-methyl-1H-pyrrol-2(5H)-onyl, or imidazolidinonyl substituted with zero or 1 substituent selected from —CH$_3$ and —C(O)CH$_3$;

c) pyrrolyl substituted with —C(O)OH or —C(O)OCH$_3$; pyrazolyl substituted with zero or 1 substituent selected from methyl, —CF$_3$, phenyl, benzyl, and chlorophenyl; thiazolyl substituted with 1 or 2 methyl groups; isoxazolyl substituted with two methyl groups; oxadiazolyl substituted with methyl, —NH(cyclobutyl), —NH(tetrahydropyranyl), —NH(C$_{4-5}$ alkyl), or —NH(CH(CH$_3$)-cyclopropyl); thiadiazolyl substituted with zero or 1 substituent selected from —NH(tetrahydropyranyl); or tetrazolyl substituted with methyl);

d) pyridinyl substituted with zero, 1, or 2 substituents independently selected from F, Cl, —CH$_3$, —NH$_2$, —CF$_3$, —CN, —OCH$_3$, —OCH(CH$_3$)$_2$, —C(O)NH$_2$, —C(O)NH(CH$_3$), —NHC(O)CH$_3$, and/or —O(benzyl); or pyridinonyl substituted with hydroxybutyl; or e) pyrimidinyl substituted with zero or 1 substituent selected from —NH$_2$, pyrazinyl, dihydropyridinyl substituted with —C(O)O(t-butyl), dihydroisoquinolinonyl substituted with —OCH$_3$, 4-methyl-3,4-dihydro-2H-benzo[b][1,4]oxazinyl, 1-methyl-1H-indolyl, imidazo[1,2-a]pyridinyl, indolyl, indazolyl, benzothiazolyl, isoquinolinyl, quinolinyl, and quinoxalinyl.

In one embodiment, there are provided compounds of Formula (II) or salts, stereoisomers, or prodrugs thereof, wherein R$^2$ is R$^y$; and R$^y$ is phenyl substituted with zero, 1, or 2 substituents independently selected from F, Cl, C$_{1-6}$ alkyl, —NH$_2$, —N(C$_{1-4}$ alkyl)$_2$, —O(C$_{1-4}$ alkyl), C$_{1-6}$ hydroxyalkyl, C$_{1-4}$ aminoalkyl, —CN, —C(O)(C$_{1-4}$ alkyl), —CH$_2$NHC(O)(C$_{1-4}$ alkyl), —C(O)OH, —C(O)O(C$_{1-4}$ alkyl), —C(O)NH$_2$, —C(O)NH(C$_{1-4}$ alkyl), —C(O)N(C$_{1-4}$ alkyl)$_2$, —C(O)NH(C$_{3-6}$ cycloalkyl), —C(O)NH(C$_{3-6}$ cycloalkyl), —S(O)$_2$(C$_{1-4}$ alkyl), —NHC(O)(C$_{1-4}$ alkyl), —NHC(O)O(C$_{1-4}$ alkyl), —NHC(O)CH$_2$CH$_2$O(C$_{1-4}$ alkyl), —NHS(O)$_2$(C$_{1-4}$ alkyl), —O(C$_{1-4}$ alkyl), —O(C$_{1-4}$ fluoroalkyl), —S(O)$_2$NH$_2$, —C(O)(morpholinyl), —CH$_2$(morpholinyl), phenyl, pyrazolyl, tetrazolyl, and/or morpholinyl. Included in this embodiment are compounds in which R$^y$ is phenyl substituted with zero, 1, or 2 substituents independently selected from F, Cl, C$_{1-4}$ alkyl, —NH$_2$, —N(C$_{1-3}$ alkyl)$_2$, —O(C$_{1-3}$ alkyl), C$_{1-4}$ hydroxyalkyl, C$_{1-3}$ aminoalkyl, —CN, —C(O)(C$_{1-3}$ alkyl), —CH$_2$NHC(O)(C$_{1-3}$ alkyl), —C(O)OH, —C(O)O(C$_{1-3}$ alkyl), —C(O)NH$_2$, —C(O)NH(C$_{1-4}$ alkyl), —C(O)N(C$_{1-3}$ alkyl)$_2$, —C(O)NH(C$_{3-5}$ cycloalkyl), —C(O)NH(C$_{3-6}$ cycloalkyl), —S(O)$_2$(C$_{1-3}$ alkyl), —NHC(O)(C$_{1-4}$ alkyl), —NHC(O)O(C$_{1-4}$ alkyl), —NHC(O)CH$_2$CH$_2$O(C$_{1-3}$ alkyl), —NHS(O)$_2$(C$_{1-3}$ alkyl), —O(C$_{1-4}$ alkyl), —O(C$_{1-3}$ fluoroalkyl), —S(O)$_2$NH$_2$, —C(O)(morpholinyl), —CH$_2$(morpholinyl), phenyl, pyrazolyl, tetrazolyl, and/or morpholinyl. Also included in this embodiment are compounds in which R$^y$ is phenyl substituted with zero, 1, or 2 substituents independently selected from F, Cl, C$_{1-3}$ alkyl, —NH$_2$, —N(CH$_3$)$_2$, —OCH$_3$, —CH$_2$OH, —CH(CH$_3$)$_2$OH, —CH$_2$NH$_2$, —CN, —C(O)CH$_3$, —CH$_2$NHC(O)CH$_3$, —C(O)OH, —C(O)OCH$_3$, —C(O)NH$_2$, —C(O)N(CH$_3$)$_2$, —C(O)NH(C$_{1-4}$ alkyl), —C(O)NH(cyclopropyl), —C(O)NH(cyclopentyl), —S(O)$_2$CH$_3$, —NHC(O)CH$_3$, —NHC(O)OCH$_3$, —NHC(O)CH$_2$CH$_2$OCH$_3$, —NHS(O)$_2$CH$_3$, —O(ethyl), —OCHF$_2$, —S(O)$_2$NH$_2$, —C(O)(morpholinyl), —CH$_2$(morpholinyl), phenyl, pyrazolyl, tetrazolyl, and/or morpholinyl.

In one embodiment, there are provided compounds of Formula (II) or salts, stereoisomers, or prodrugs thereof, wherein R$^2$ is R$^y$; and R$^y$ is azetidinonyl, pyrrolidinyl, pyrrolidinonyl, 1H-pyrrol-2(5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1, or 2 substituents independently selected from —OH, C$_{1-4}$ alkyl, —O(C$_{1-4}$ alkyl), —C(O)(C$_{1-4}$ alkyl), phenyl, and/or benzyl. Included in this embodiment are compounds in which R$^y$ is azetidinonyl, pyrrolidinyl, pyrrolidinonyl, 1H-pyrrol-2(5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1, or 2 substituents independently selected from —OH, —CH$_3$, —OCH$_3$, —C(O)CH$_3$, and/or benzyl. Also included in this embodiment are compounds in which R$^y$ is azetidinonyl, pyrrolidinyl, pyrrolidinonyl, pyrrolidinonyl substituted with —OH, 3,4-dimethyl-1H-pyrrol-2(5H)-onyl, 4-methoxy-1H-pyrrol-2(5H)-onyl, oxazolidinonyl, piperazinyl, piperazinonyl substituted with benzyl, morpholinyl, morpholinonyl, 3-methyl-1H-pyrrol-2(5H)-onyl, or imidazolidinonyl substituted with zero or 1 substituent selected from —CH$_3$ and —C(O)CH$_3$.

In one embodiment, there are provided compounds of Formula (II) or salts, stereoisomers, or prodrugs thereof, wherein R$^2$ is R$^y$; and R$^y$ is pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, C$_{1-4}$ alkyl, C$_{1-3}$ fluoroalkyl, —NH$_2$, —CN, C$_{1-4}$ hydroxyalkyl, —O(C$_{1-4}$ alkyl), O(phenyl), —O(benzyl), —C(O)OH, —C(O)O(C$_{1-4}$ alkyl), —C(O)NH$_2$, —C(O)NH(C$_{1-4}$ alkyl), —NHC(O)(C$_{1-4}$ alkyl), phenyl, benzyl, fluorophenyl, chlorophenyl, —NH(C$_{3-6}$ cycloalkyl), —NH(tetrahydropyranyl), —NH(C$_{1-6}$ alkyl), —NH(CH$_2$—C$_{3-6}$ cycloalkyl), —NH(CH(CH$_3$)—C$_{3-6}$ cycloalkyl), and/or —NH(tetrahydropyranyl). Included in this embodiment are compounds in which R$^y$ is pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, C$_{1-3}$ alkyl, —CF$_3$, —NH$_2$, —CN, C$_{1-4}$ hydroxyalkyl, —O(C$_{1-3}$ alkyl), —O(benzyl), —C(O)OH, —C(O)O(C$_{1-4}$ alkyl), —C(O)NH$_2$, —C(O)NH(C$_{1-4}$ alkyl), —NHC(O)(C$_{1-4}$ alkyl), phenyl, benzyl, chlorophenyl, —NH(cyclobutyl), —NH(tetrahydropyranyl), —NH(C$_{4-5}$ alkyl), —NH(CH(CH$_3$)-cyclopropyl), and/or —NH(tetrahydropyranyl).

In one embodiment, there are provided compounds of Formula (II) or salts, stereoisomers, or prodrugs thereof, wherein R$^2$ is R$^y$; and R$^y$ is pyrrolyl substituted with —C(O)OH or —C(O)OCH$_3$; pyrazolyl substituted with zero or 1 substituent selected from methyl, —CF$_3$, phenyl, benzyl, and chlorophenyl; thiazolyl substituted with 1 or 2 methyl groups; isoxazolyl substituted with two methyl groups; oxadiazolyl substituted with methyl, —NH(cyclobutyl), —NH(tetrahydropyranyl), —NH($C_{4-5}$ alkyl), or —NH(CH($CH_3$)-cyclopropyl); thiadiazolyl substituted with zero or 1 substituent selected from —NH(tetrahydropyranyl); or tetrazolyl substituted with methyl.

In one embodiment, there are provided compounds of Formula (II) or salts, stereoisomers, or prodrugs thereof, wherein $R^2$ is $R^y$; and $R^y$ is pyridinyl substituted with zero, 1, or 2 substituents independently selected from F, Cl, —$CH_3$, —$NH_2$, —$CF_3$, —CN, —$OCH_3$, —OCH($CH_3$)$_2$, —C(O)$NH_2$, —C(O)NH($CH_3$), —NHC(O)$CH_3$, and/or —O(benzyl); or pyridinonyl substituted with hydroxybutyl.

In one embodiment, there are provided compounds of Formula (II) or salts, stereoisomers, or prodrugs thereof, wherein $R^2$ is $R^y$; and $R^y$ is pyrimidinyl substituted with zero or 1 substituent selected from —$NH_2$, pyrazinyl, dihydropyridinyl substituted with —C(O)O(t-butyl), dihydroisoquinolinonyl substituted with —$OCH_3$, 4-methyl-3,4-dihydro-2H-benzo[b][1,4]oxazinyl, 1-methyl-1H-indolyl, imidazo[1,2-a]pyridinyl, indolyl, indazolyl, benzothiazolyl, isoquinolinyl, quinolinyl, and quinoxalinyl.

In one embodiment, there are provided compounds of Formula (II) or salts, stereoisomers, or prodrugs thereof, wherein:

$R^1$ is:

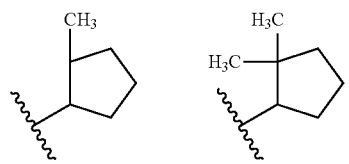
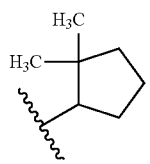
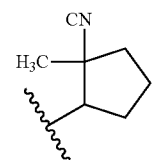
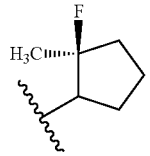
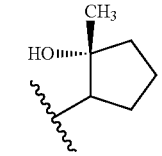
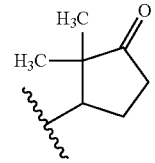
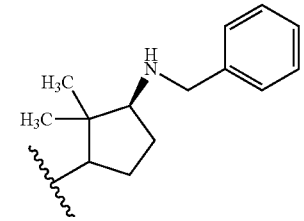
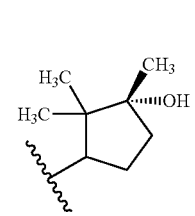
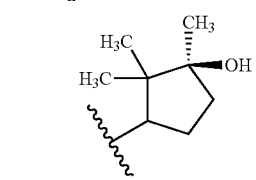
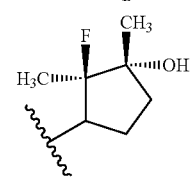
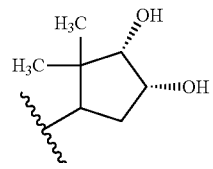
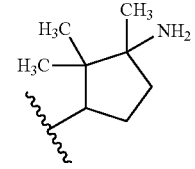

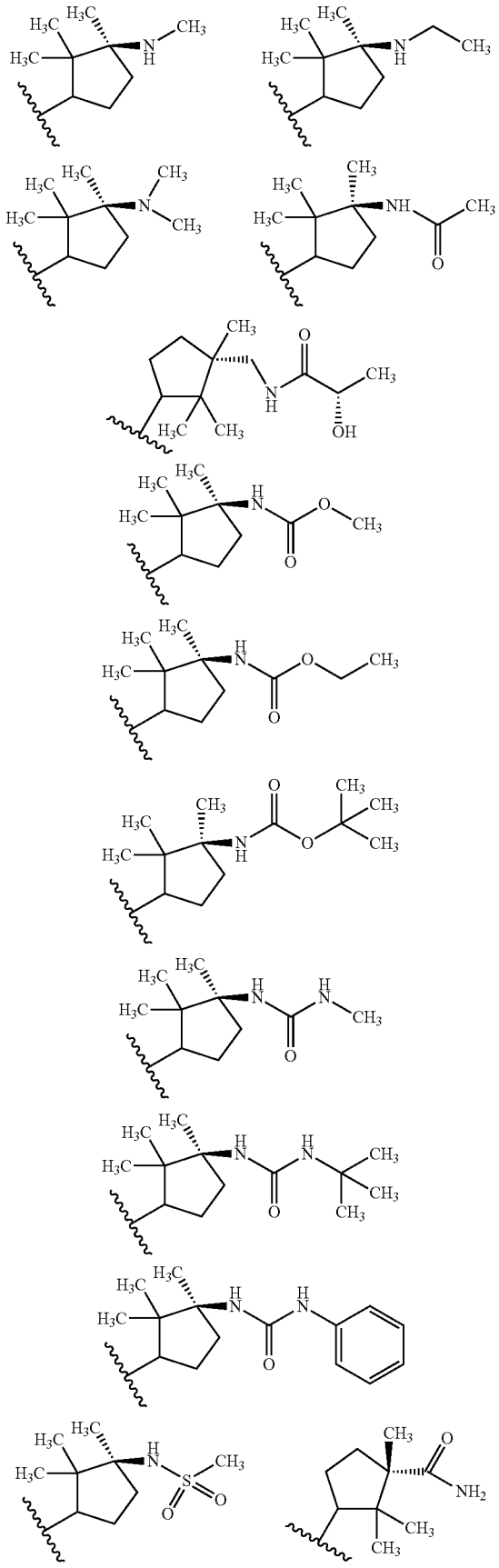

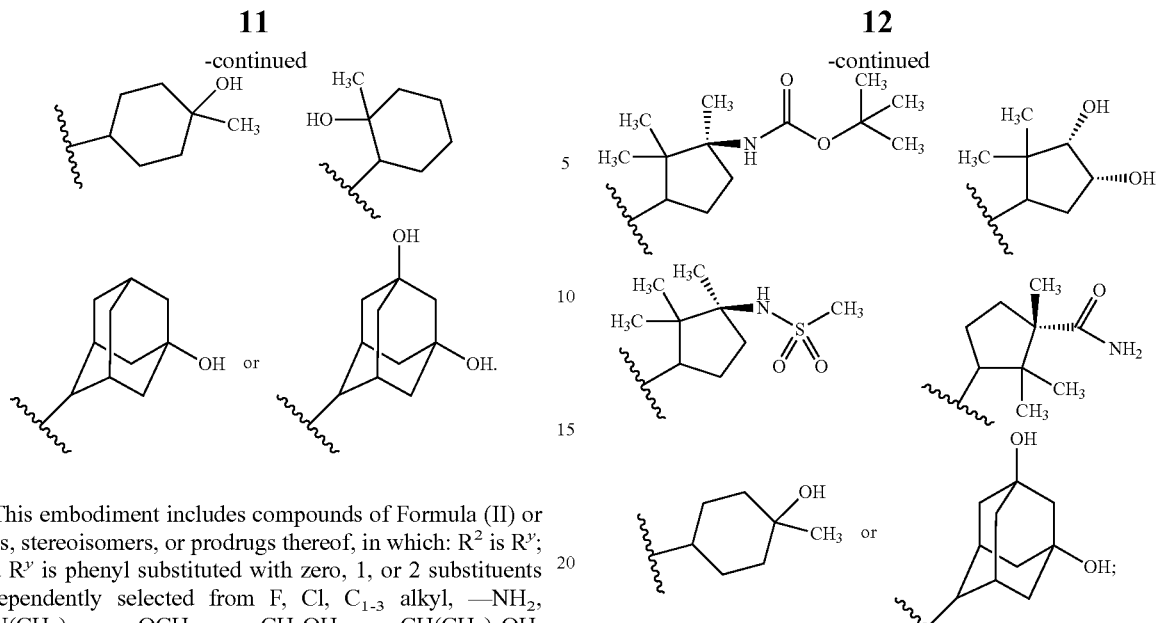

This embodiment includes compounds of Formula (II) or salts, stereoisomers, or prodrugs thereof, in which: $R^2$ is $R^y$; and $R^y$ is phenyl substituted with zero, 1, or 2 substituents independently selected from F, Cl, $C_{1-3}$ alkyl, —$NH_2$, —$N(CH_3)_2$, —$OCH_3$, —$CH_2OH$, —$CH(CH_3)_2OH$, —$CH_2NH_2$, —CN, —$C(O)CH_3$, —$CH_2NHC(O)CH_3$, —$C(O)OH$, —$C(O)OCH_3$, —$C(O)NH_2$, —$C(O)N(CH_3)_2$, —$C(O)NH(C_{1-4}$ alkyl$)$, —$C(O)NH$(cyclopropyl), —$C(O)NH$(cyclopentyl), —$S(O)_2CH_3$, —$NHC(O)CH_3$, —$NHC(O)OCH_3$, —$NHC(O)CH_2CH_2OCH_3$, —$NHS(O)_2CH_3$, —O(ethyl), —$OCHF_2$, —$S(O)_2NH_2$, —$C(O)$(morpholinyl), —$CH_2$(morpholinyl), phenyl, pyrazolyl, tetrazolyl, and/or morpholinyl.

In one embodiment, there are provided compounds of Formula (II) or salts, stereoisomers, or prodrugs thereof, wherein:
$R^1$ is:

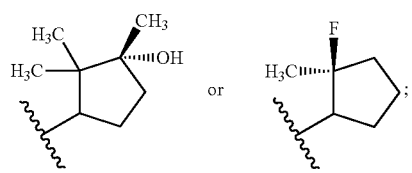

$R^2$ is -L-$R^x$; L is —NHC(O)—, —NHS(O)$_2$—, —NHC(O)NH—, —NHC(O)O—, or —C(O)NH—; and
$R^x$ is $C_{1-4}$ alkyl, benzyl, or phenyl substituted with zero or 1 substituent selected from Cl and —$OCH_3$.

In one embodiment, there are provided compounds of Formula (II) or salts, stereoisomers, or prodrugs thereof, wherein $R^1$ is:

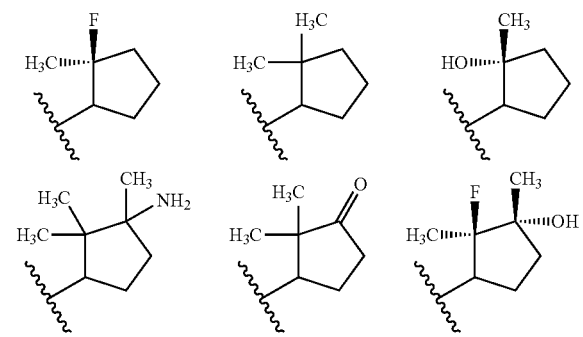

$R^2$ is $R^y$; and $R^y$ is pyridinyl substituted with zero, 1, or 2 substituents independently selected from F, Cl, —$CH_3$, —$NH_2$, —$CF_3$, —CN, —$OCH_3$, —$OCH(CH_3)_2$, —$C(O)NH_2$, —$C(O)NH(CH_3)$, —$NHC(O)CH_3$, and/or —O(benzyl); or pyridinonyl substituted with hydroxybutyl.

In one embodiment, there are provided compounds of Formula (II) or salts, stereoisomers, or prodrugs thereof, wherein $R^1$ is:

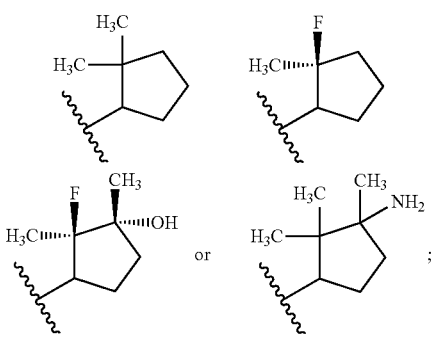

$R^2$ is $R^y$; and $R^y$ is azetidinonyl, pyrrolidinyl, pyrrolidinonyl, pyrrolidinonyl substituted with —OH, 3,4-dimethyl-1H-pyrrol-2(5H)-onyl, 4-methoxy-1H-pyrrol-2(5H)-onyl, oxazolidinonyl, piperazinyl, piperazinonyl substituted with benzyl, morpholinyl, morpholinonyl, 3-methyl-1H-pyrrol-2(5H)-onyl, or imidazolidinonyl substituted with zero or 1 substituent selected from —$CH_3$ and —$C(O)CH_3$.

In one embodiment, there are provided compounds of Formula (II) or salts, stereoisomers, or prodrugs thereof, wherein:

13

R¹ is:

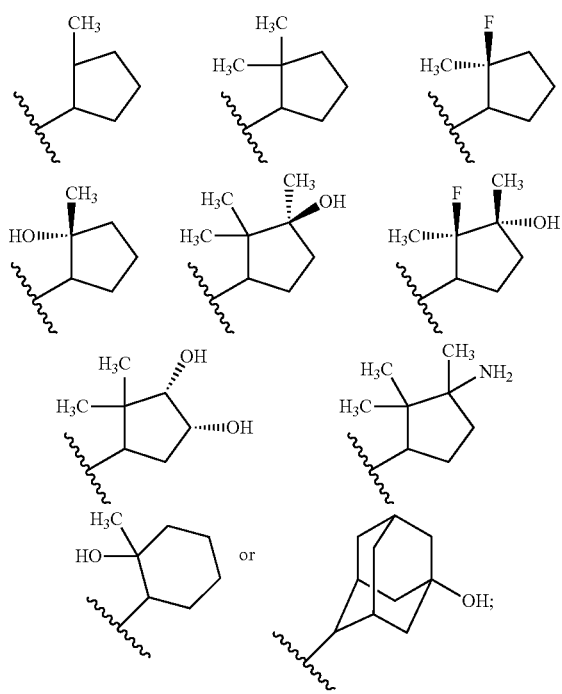

R² is R^y; and R^y is pyrrolyl substituted with —C(O)OH or —C(O)OCH₃; pyrazolyl substituted with zero or 1 substituent selected from methyl, —CF₃, phenyl, benzyl, and chlorophenyl; thiazolyl substituted with 1 or 2 methyl groups; isoxazolyl substituted with two methyl groups; oxadiazolyl substituted with methyl, —NH(cyclobutyl), —NH(tetrahydropyranyl), —NH($C_{4-5}$ alkyl), or —NH (CH(CH₃)-cyclopropyl); thiadiazolyl substituted with zero or 1 substituent selected from —NH(tetrahydropyranyl); and tetrazolyl substituted with methyl. Included in this embodiment are compounds of Formula (II) in which R^y is pyrazolyl is substituted with zero or 1 substituent selected from methyl, —CF₃, phenyl, benzyl, and chlorophenyl.

In one embodiment, there are provided compounds of Formula (II) or salts, stereoisomers, or prodrugs thereof, wherein: R¹ is:

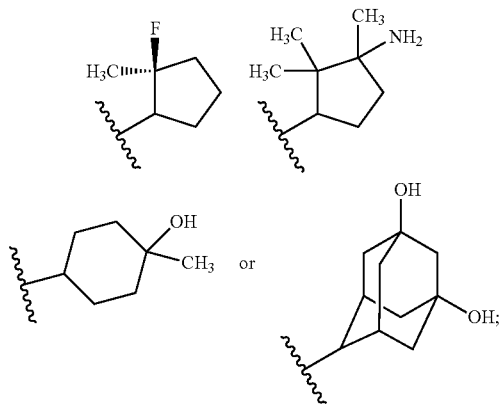

14

R² is R^y; and R^y is pyrimidinyl substituted with zero or 1 substituent selected from —NH₂; pyrazinyl, dihydropyridinyl substituted with —C(O)O(t-butyl), dihydroisoquinolinonyl substituted with —OCH₃, 4-methyl-3,4-dihydro-2H-benzo[b][1,4]oxazinyl, 1-methyl-1H-indolyl, imidazo[1,2-a]pyridinyl, indolyl, indazolyl, benzothiazolyl, isoquinolinyl, quinolinyl, and quinoxalinyl.

In one embodiment, there are provided compounds of Formula (II) or salts, stereoisomers, or prodrugs thereof, wherein: R¹ is:

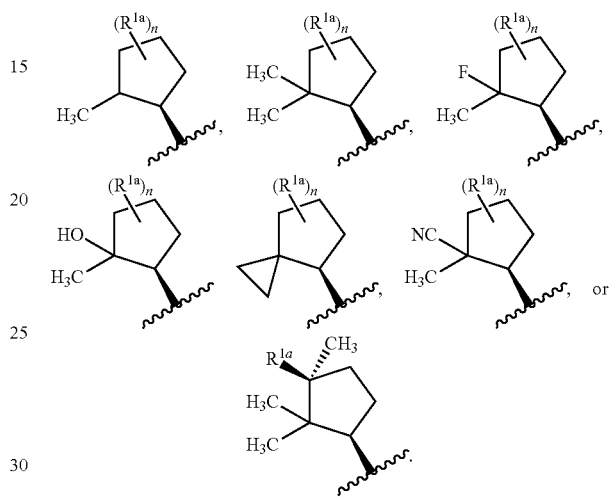

In another embodiment are compounds of Formula (I), wherein: the compound of formula (I) is selected from an Example herein.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition comprising a compound of formula I or pharmaceutically acceptable salt thereof and a pharmaceutically acceptable carrier.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a method for treating inflammatory or autoimmune disease: administering to a patient in need of such treatment a therapeutically effective amount of at least one of the compounds of the present invention or a stereoisomer, tautomer, pharmaceutically acceptable salt, solvate or prodrug thereof, in combination with at least one other therapeutic agent, or a stereoisomer, tautomer, pharmaceutically acceptable salt, solvate or prodrug thereof.

In another embodiment, the present invention provides a method for treating inflammatory and/or autoimmune diseases comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method of treating a patient in need of inflammatory and/or autoimmune diseases treatment, comprising: administering a compound of the present invention or a stereoisomer, tautomer, pharmaceutically acceptable salt, solvate, or prodrug form thereof in an amount effective to treat the inflammatory and/or autoimmune diseases.

In another embodiment, the present invention provides a method of treating inflammatory or autoimmune diseases, wherein the inflammatory or autoimmune diseases is selected from Crohn's, ulcerative colitis, asthma, Graves' disease, rheumatoid arthritis, systemic lupus erythematosis, psoriasis, dry eye, multiple sclerosis, psoriatic arthritis and ankylosing spondylitis, solid organ transplant rejection, islet cell transplant rejection and graft vs. host disease.

In another embodiment, the present invention provides a novel method, comprising: administering a compound of the present invention or a stereoisomer, tautomer, pharmaceutically acceptable salt, solvate, or prodrug form thereof in an amount effective to treat an inflammatory and/or autoimmune diseases.

In another embodiment, the present invention provides a method for treating inflammatory and/or autoimmune diseases comprising: administering to a patient in need of such treatment a therapeutically effective amount of a compound of formula (I) or a stereoisomer, tautomer, pharmaceutically acceptable salt, solvate or prodrug thereof, in combination with at least one other anti-cancer agent or antiproliferative agent and/or another agent, or a stereoisomer, tautomer, pharmaceutically acceptable salt, solvate or prodrug thereof.

In another embodiment, the present invention provides a method for treating inflammatory and/or autoimmune diseases comprising: administering to a patient in need of such treatment a therapeutically effective amount of at least one of the compounds of the present invention or a stereoisomer, tautomer, pharmaceutically acceptable salt, solvate or prodrug thereof, in combination with at least one other therapeutic agent, or a stereoisomer, tautomer, pharmaceutically acceptable salt, solvate or prodrug thereof.

In another embodiment, the present invention provides a compound of the present invention for use in therapy.

In another embodiment, the present invention provides a compound of the present invention for use in therapy for treating an inflammatory and/or autoimmune disease.

In another embodiment, the present invention also provides the use of a compound of formula I of the present invention for the manufacture of a medicament for the treatment of an inflammatory and/or autoimmune disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Definitions

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then two hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl ($—CH_2Cl$), trifluoromethyl ($—CF_3—$, and 2,2,2-trifluoroethyl ($—CH_2CF_3$). When numbers appear in a subscript after the symbol "C", the subscript defines with more specificity the number of carbon atoms that a particular haloalkyl group may contain. For example, "$C_1$-$C_4$ haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$-fluoroalkyl" is intended to include $C_1$, $C_2$, $C_3$, and $C_4$ alkyl groups substituted with one or more fluorine atoms. Representative examples of fluoroalkyl groups include, but are not limited to, $—CF_3$ and $—CH_2CF_3$.

The term "hydroxyalkyl" includes both branched and straight-chain saturated alkyl groups substituted with one or more hydroxyl groups. For example, "hydroxyalkyl" includes $—CH_2OH$, $—CH_2CH_2OH$, and $C_{1-4}$hydroxyalkyl.

The term "aminoalkyl" includes both branched and straight-chain saturated alkyl groups substituted with one or more $—NH_2$ groups. For example, "aminoalkyl" includes $—CH_2NH_2$, $—CH_2CH_2NH_2$, and $C_{1-4}$-aminoalkyl.

The term "cycloalkyl" refers to cyclized alkyl groups, including mono-, bi- or poly-cyclic ring systems. $C_{3-10}$ cycloalkyl is intended to include $C_2$, $C_3$, $C_4$, $C_5$, $C_6$, and $C_7$, $C_8$, $C_9$, and $C_{10}$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, or 10-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cyclooctenyl, adamantyl, cyclooctyl, cyclooctenyl, cyclooctadienyl, [3.3.0]bicyclooctane, [4.3.0] bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As defined in $R^1$ of the invention, $R^1$ is $C_{3-10}$ saturated or partially saturated carbocycle substituted with 0-5 $R^{1a}$. The definition of carbocycle as used within the definition is limited to saturated and partially saturated structures and does not included substitution which would join to form a heterocyclic ring.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "benzyl," as used herein, refers to a methyl group in which one of the hydrogen atoms is replaced by a phenyl group.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., $N→O$ and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl Also included are smaller heterocyclyls, such as, epoxides and aziridines.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form (with no ionization) or may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include 13C and 14C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) *Design of Prodrugs*, edited by H. Bundgaard, (Elsevier, 1985) and *Methods in Enzymology*, Vol. 112, pp. 309-396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group. The present invention is directed to stable compounds. Compounds of the invention are intended to cover compounds which are stable compounds.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

The compounds of the invention modulate kinase activity, including the modulation of JAK3. Other types of kinase activity that may be modulated by the compounds of the instant invention include, but are not limited to, other members of the JAK family of enzymes, such as JAK1.

Accordingly, compounds of formula (I) have utility in treating conditions associated with the modulation of kinase activity, and particularly the selective inhibition of JAK3 activity or the inhibition of other JAK family kinases such as JAK1. Such conditions include T-cell mediated diseases in which cytokine levels are modulated as a consequence of intracellular signaling. In another embodiment, compounds of formula (I) have advantageous functional selectivity for JAK3 activity versus other JAK family kinases such as JAK2, preferably from at least 10 fold to over 100 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of JAK3 and other JAK family kinases such as JAK1, compounds of Formula (I) are useful in treating cytokine-associated conditions including, but not limited to, autoimmune diseases such as Crohn's and ulcerative colitis, asthma, autoimmune diseases such as Graves' disease, rheumatoid arthritis, systemic lupus erythematosis, psoriasis, dry eye, multiple sclerosis, psoriatic arthritis and ankylosing spondylitis, plus conditions such as solid organ transplant rejection, islet cell transplant rejection and graft vs. host disease.

In view of their activity as inhibitors of JAK3, compounds of Formula (I) are useful in treating malignancies where JAK3 has undergone mutation or overexpression, or where JAK3 plays an important role in growth or survival of the malignant cells. Such malignancies include acute megakaryoblastic leukemia (AMKL), cutaneous T cell lymphoma (CTCL), anaplastic lymphoma kinase (ALK)-expressing anaplastic large cell lymphoma (ALK(+)ALCL), acute lymphoblastic leukemia (ALL) with JAK3 mutations, and cutaneous T-cell lymphoma (CTCL).

More particularly, the specific conditions or diseases that may be treated with the inventive compounds include, without limitation, asthma, allergies, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, myasthenia gravis, multiple sclerosis, inflammatory bowel disease, ulcerative colitis, Crohn's disease, psoriasis, graft vs. host disease, pancreatic β-cell disease; rheumatoid spondylitis, allograft rejections, ulcerative colitis, dry eye and pemphigus vulgaris. Preferred methods of treatment are those wherein the condition is selected from allograft rejection, rheumatoid arthritis, psoriasis, ankylosing spondylitis, psoriatic arthritis, multiple sclerosis, lupus and dry eye.

When the terms "JAK3-associated condition" or "JAK3-associated disease or disorder" are used herein, each is intended to encompass all of the conditions identified above as if repeated at length, as well as any other condition that is affected by JAK3 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit JAK3 and other JAK family kinases and/or treat diseases.

The methods of treating JAK3 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit JAK3 and/or treat diseases associated with JAK3.

Exemplary of such other therapeutic agents include abatacept, belatacept, corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; p38 inhibitors such as BMS-582949, steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating JAK3 kinase-associated conditions, including IL-2, IL-4, IL-6, IL-7, IL-9, IL-15, IL-21, and IFNγ mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Biological Assays

JAK3 Kinase Assay Protocol (Caliper)

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate 0.015% Brij35 and 4 mM DTT). The reaction was initiated by the combination of GST-JAK3 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assay was: ATP, 8 µM; fluoresceinated peptide, 1.5 µM; GST-JAK3, 4.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK3 Kinase Assay Protocol (Filter)

Kinase reactions consisted of 5 ng of JAK3 enzyme, 30 uM CSKtide substrate, 0.2 µCi $^{33}P$ γ-ATP, 8 µM ATP in 30 µl kinase buffer (50 mM Hepes, pH 8.0, 10 mM $MgCl_2$, 1 mM EGTA, 2 mM DTT). Reactions were incubated for 30 minutes at room temperature and stopped by the addition of cold trichloroacetic acid (TCA) to a final concentration of 15%. TCA precipitates were collected onto 384 well phosphocellulose filters (Millipore) using a Platemate to transfer the reaction mixture, washed on an EMBLA plate washer and the filters were quantitated using a TopCount 384-well liquid scintillation counter. Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis.

JAK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate, 0.015% Brij35 and 4 mM DTT). The reaction was initiated by the combination of GST-JAK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assay was: ATP, 30 µM; fluoresceinated peptide, 1.5 µM; GST-JAK2, 1.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK1 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of GST-JAK1 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assays was: ATP, 100 µM; fluoresceinated peptide, 1.5 µM; GST-JAK1, 12.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

TYK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of HIS-TYK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 70 µM; fluoresceinated peptide, 1.5 µM; HIS-TYK2, 2.25 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

IL-2 Dependent T Cell Proliferation Assay Protocol

IL-2 Expanded PHA Blasts (Activated T cells) were prepared from peripheral blood mononuclear cells (PBMC). PBMCs were prepared from human whole blood. 15 ml blood was mixed with 15 ml RPMI (Gibco#61870) in a 50 ml centrifuge tube and under laid with 12 ml lymphocyte separation media (LSM) (MC Biomedicals #1492254). Tubes were centrifuged at 1800 rpm for 25 minutes and allowed to stop without braking. Red blood cells pelleted under the separation media and the PBMCs were trapped at the interface between the LSM and the serum/RPMI layers. The serum/RPMI mix was pipetted from above the PBMC layer and discarded. The PBMCs from 2 tubes were collected in a pipette along with some of the LSM layer and combined into a single tube. Each tube was brought to 50 ml and centrifuged at 1400 rpm for 10 minutes. Cell pellets were resuspended in RPMI, combined into 1 tube and centrifuged for 5 minutes at 1200 rpm. Cells were resuspended in cell culture media (RPMI w/10% fetal bovine serum (Summit Biotechnology # RS-50-05), 100 U/ml penicillin and 100 µg/ml streptomycin (Gibco #14140-122)) with 5 µg/ml PHA (Sigma #L1668) at $2 \times 10^6$ cells/ml and incubated for 3 days at 37° C. in 5% $CO_2$. Cells were washed 3× and resuspended at $5 \times 10^5$ cells/ml and 25 units/ml IL-2 (BD Bioscience #356043) was added. After 4 days incubation at 37° C. in 5% $CO_2$ the cells were washed 3× and resuspended at $2 \times 10^6$ cells/ml and rested 2 hours at 37° C. in 5% $CO_2$ before use.

Compounds were diluted in DMSO (in triplicate) to 800× final high concentration in the assay and 3-fold serial dilutions were performed to give six concentrations. Each concentration was diluted 1:20 in media to give the intermediate concentration. DMSO was diluted 1:20 in media for use in wells without compound.

45 µl media plus 5 µl of the intermediate dilution of compound or DMSO was added to each test well in the assay plate. 100 µl of cells at $3 \times 10^5$ cells/ml were added to each well. Plates were incubated 60 minutes at 37° C. in 5% $CO_2$ and 50 µl of IL-2 at 200 units/ml to each well. Negative control wells received 100 µl media. The plates were incubated 3 days at 37° C. in 5% $CO_2$. 0.5 µC $^3$H-Thymidine in 20 µl media was added to each well and the plates incubated 6 hours at 37° C. in 5% $CO_2$. The plates were harvested onto a Unifilter-96 GF/C Filter Plate (Perkin Elmer 6005174) using a Packard Filtermate Harvester. The bottom of each dried filter plate was sealed, 50 µl Microscint 20 (Perkin Elmer #6013621) added to each well and the top of the plate sealed. Proliferation as measured by $^3$H-Thymidine incorporation was determined by counting on a Packard TopCount-NXT.

IL-2 Induced STAT3 Phosphorylation in PHA Blasts Assay

IL-2 Expanded PHA Blasts were prepared (see IL-2 Dependent T Cell Proliferation Assay Protocol for preparation of IL-2 expanded PHA blasts). Compounds were diluted in DMSO (in duplicate) to 333.3× final high concentration in the assay and 3-fold serial dilutions were performed to give six concentrations. Each concentration was diluted 1:20 in media to give the intermediate concentration. DMSO was diluted 1:20 in RPMI media (Gibco#61870) for use in wells without compound.

173 µl/well of a PHA blast cell suspension at $5.78\times10^6$ cells/ml was added to a round bottom tissue culture plate (Falcon #353077) followed by 12 µl of the Intermediate compound dilution or DMSO for wells without compound. The plate was incubated at 37° C. in 5% $CO_2$ for 30 minutes. 15 µl of 266.7 ng/ml IL-2 (R&D #202-IL-050) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 µl of culture supernatant was removed from each well leaving the pellet intact. Plates were mixed on an orbital shaker for 1 minute and 50 µl of 2× lysis buffer was added (20 mM Tris, pH7.5, 0.2 M NaCl, 2 mM EDTA, 2 mM EGTA, 2 mM NaF, 2 mM β-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2× Protease Inhibitor Cocktail (Sigma P2714, dissolved in 10 ml PBS to give 10× concentration, add at time of use)). The plates were incubated on ice for 1 hour and the lysate in each well was mixed by pipetting up and down 5-6 times. STAT3 phosphorylation levels were determined by ELISA (PathScan Phospho-STAT3 ELISA Antibody Pair, Cell Signaling #7146).

ELISA plates were coated with 100 µl/well of a 1:100 dilution of Capture antibody in PBS and incubated at least overnight at 4° C. On day of use plates were washed 3× with wash buffer (PBS (Gibco #14190)+0.05% Tween 20). Plates were blocked with 200 µl/well of Assay Buffer 1 (AB1) (PBS+1% BSA+0.1% Tween 20(Bio-Rad #161-0416)) for 2 hours at room temperature. Plates were washed 3× and 90 µl/well AB1 buffer added. 10 µl/well of assay sample or standards were added followed by 100 µl/well of a 1:100 dilution of Detection Antibody in AB1 Buffer. Plates were incubated overnight at 4° C. and then washed 6×. 100 µl/well of a 1:1000 dilution of anti-mouse IgG HRP-Linked Antibody in AB 1 Buffer was added to each well and plates were incubated 1 hour at room temperature. Plates were washed 6×. 100 µl of a 1:1 mix of TMB Peroxidase Substrate (KPL #50-76-01) and Peroxidase Substrate Solution (KPL #50-65-00) was added and the plates were incubated in the dark at room temperature for 10-30 min. The reaction was stopped with 100 µl/well of 1N $H_2SO_4$ and the plates were read at 450 nm with correction at 650 nm within 30 min.

pSTAT3 Standards were prepared from IL-6 stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. IL-6 was added to 20 ng/ml and cells incubated at 37° C. in 5% $CO_2$ for 15 minutes, spun 4 minutes at 1500 rpm and the supernatant removed. 150 µl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT3 and used as a standard in the pSTAT3 ELISA assay. Standards were diluted in a 1:2 dilution series using a 1:1 mix of 2× lysis buffer and Media.

EPO Induced STAT5A Phosphorylation in TF-1 Cells

TF-1 Cells were carried in cell culture media (RPMI w/10% fetal bovine serum (Summit Biotechnology # RS-50-05), 100 U/ml penicillin and 100 µg/ml streptomycin (Gibco #14140-122))+2 ng/ml GM-CSF (R&D #215GM). On the day before use the cells were washed 3×, resuspended at $1\times10^6$ cells/ml in media without GM-CSF and rested overnight at 37° C. in 5% $CO_2$. The cells were washed 1× and resuspended in media at $2.78\times10^6$ cells/ml. Compounds were prepared as in the IL-2 Induced STAT3 phosphorylation in PHA blasts assay.

173 µl/well of a TF-1 cell suspension at $2.78\times10^6$ cells/ml was added to each well of a round bottom tissue culture plate (Falcon #353077) followed by 12 µl of the Intermediate compound dilution or DMSO for wells without compound. The plate was incubated at 37° C. in 5% $CO_2$ for 30 minutes. 15 µl of 13.33 units/ml recombinant human EPO(R&D #287-TC) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 µl of culture supernatant was removed from each well leaving the pellet intact. Plates were mixed on an orbital shaker for 1 minute and 50 µl of 2× lysis buffer was added (20 mM Tris, pH7.5, 0.2 M NaCl, 2 mM EDTA, 2 mM EGTA, 2 mM NaF, 2 mM β-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2× Protease Inhibitor Cocktail (Sigma P2714, dissolved in 10 ml PBS to give 10× concentration, add at time of use)). The plates were incubated on ice for 1 hour and the lysate in each well was mixed by pipetting up and down 5-6 times. STAT5A phosphorylation levels were determined by ELISA.

ELISA plates (NUNC #439454) were coated with 100 µl/well of a 1:500 dilution of Capture antibody (Invitrogen #β-3600) in carbonate/bicarbonate buffer (Sigma # C3041) and incubated at least overnight at 4° C. On day of use plates were washed 3× with wash buffer (PBS (Gibco #14190)+0.05% Tween 20 (Bio-Rad #170-6531)). Plates were blocked with 200 µl/well of Assay Buffer 2 (AB2) (PBS+2% BSA (Sigma # A-9576)+0.1% Tween 20 (Bio-Rad #161-0416)) for 2 hours at room temperature. Plates were washed 3× and 90 µl/well AB2 buffer added. 10 µl/well of assay sample or standards were added followed by 100 µl/well of a 1:4000 dilution of Detection Antibody (Genway #18-785-210434) in AB2 Buffer. Plates were incubated overnight at 4° C. and then washed 6×. 100 µl/well of a 1:3000 dilution of HRP-Goat anti-rabbit IgG (Invitrogen #65-6120 in AB2 Buffer was added to each well and plates were incubated 1 hour at room temperature. Plates were washed 6×. 100 µl of a 1:1 mix of TMB Peroxidase Substrate (KPL #50-76-01) and Peroxidase Substrate Solution (KPL #50-65-00) was added and the plates were incubated in the dark at room temperature for 10-30 minutes. The reaction was stopped with 100 µl/well of 1N $H_2SO_4$ and the plates were read at 450 nm with correction at 650 nm within 30 min.

pSTAT5A Standards were prepared from GM-CSF stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at 5×10⁶ cells/ml. GM-CSF was added to 50 ng/ml and cells incubated at 37° C. in 5% $CO_2$ for 15 minutes, spun 4 minutes at 1500 rpm and the supernatant removed. 150 µl lysis buffer was added for every 5×10⁶ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT5A and used as a standard in the pSTAT5A ELISA assay. Standards were diluted in a 1:2 dilution series using a 1:1 mix of 2× lysis buffer and Media.

IFNα Induced STAT3 Phosphorylation in PHA Blasts

IFNα induced STAT3 phosphorylation in PHA blasts was performed exactly as the IL-2 Induced STAT3 phosphorylation in PHA blasts assay except the cells were stimulated with 15 µl/well of 13,333 units/ml IFNα2a (R&D #11105-1) in media.

Examples herein been tested and found to have activity of less than or equal to 1 uM in at least one of the JAK3 assays described above. The compounds listed in Table 1 have been tested in the above assays with the results indicated.

TABLE 1

| Example # | LLE_JAK3_FB (IC50, uM) | LLE_JAK1 (IC50, uM) |
|---|---|---|
| 3 | 0.0060 | 0.0458 |
| 7 | 0.0009 | 0.0082 |
| 22 | 0.0221 | 0.2390 |
| 23 | 0.0234 | 0.2585 |
| 24 | 0.0342 | 0.2269 |
| 25 | 0.0081 | 0.0839 |
| 60 | 0.1356 | 0.2530 |
| 68 | 0.0464 | 0.0981 |
| 72 | 0.0003 | 0.0013 |
| 94 | 0.0005 | 0.0014 |
| 112 | 0.0094 | 0.0127 |
| 123 | 0.0002 | 0.0010 |
| 129 | 0.0010 | 0.0026 |
| 142 | 0.0056 | 0.0109 |
| 148 | 0.0252 | 0.0464 |
| 159 | 0.0005 | 0.0038 |
| 162 | 0.0627 | 0.1079 |
| 166 | 0.0336 | 0.0724 |
| 167 | 0.0016 | 0.0061 |
| 168 | 0.0171 | 0.1051 |
| 176 | 0.0089 | 0.0771 |
| 177 | 0.5242 | NA |
| 178 | 0.0010 | NA |
| 185 | 0.0062 | NA |
| 187 | 0.0061 | 0.0634 |
| 192 | 0.0005 | 0.0007 |
| 195 | 0.0061 | 0.0013 |
| 213 | 0.0095 | 0.0173 |
| 221 | 0.0016 | 0.0007 |
| 255 | 0.0060 | 0.0027 |
| 257 | 0.0369 | 0.0300 |
| 266 | 0.0008 | 0.0006 |
| 271 | 0.0003 | 0.0007 |
| 272 | 0.0138 | 0.0054 |
| 276 | 0.0150 | 0.0352 |
| 278 | 0.0084 | 0.0251 |
| 286 | 0.0055 | 0.0041 |
| 293 | 0.0002 | 0.0001 |
| 298 | 0.0047 | 0.0021 |
| 299 | 0.0073 | 0.0043 |
| 304 | 0.0005 | 0.0029 |
| 312 | 0.0442 | 0.0694 |
| 314 | 0.0051 | 0.0174 |
| 316 | 0.0110 | 0.0373 |
| 317 | 0.0068 | 0.0136 |
| 318 | 0.0071 | 0.0134 |
| 328 | 0.0017 | 0.0202 |

TABLE 1-continued

| Example # | LLE_JAK3_FB (IC50, uM) | LLE_JAK1 (IC50, uM) |
|---|---|---|
| 332 | 0.0088 | 0.0757 |
| 336 | 0.0017 | 0.0043 |
| 337 | 0.0004 | 0.0014 |
| 338 | 0.0003 | 0.0012 |
| 339 | 0.0019 | 0.0022 |
| 340 | 0.0010 | 0.0058 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Abbreviations

Ac acetyl
AcOH or HOAc acetic acid
aq. aqueous
anhyd. anhydrous
ATP adenosine triphosphate
Bn benzyl
Bu butyl
Boc tert-butoxycarbonyl
BOP benzotriazole-1-yl-oxy-tris-(dimethylamino)-phosphonium hexafluorophosphate
CDI carbonyldiimidazole
° C. degrees Centigrade
Cbz carbobenzyloxy
Conc. concentration
d days
DAST (diethylamino)sulfur trifluoride
DBU 1,8-Diazabicyclo[5.4.0]undec-7-ene
DCE 1,2-dichloroethane
DCM dichloromethane
DEA diethylamine
DIEA or DIPEA diisopropylethylamine
DMAP dimethylaminopyridine
DMA N,N-dimethylacetamide
DME 1,2-dimethoxyethane DMF dimethylformamide
DMSO dimethylsulfoxide
DPPA diphenylphosphorylazide
dppf 1,1'-Bis(diphenylphosphino)ferrocene
DTT dithiothreitol
EDCI 1-(3-dimethylaminopropyl)-3-ethylcarbodiimide hydrochloride
EDTA ethylenediaminetetraacetic acid
EGTA ethylene glycol tetraacetic acid
% ee percent enantiomeric excess
(+/−) or (±) racemic
eq. or Eq. or equiv. equivalents
EtOAc ethyl acetate
Et ethyl
Et₃N triethyl amine
EtOH ethanol
Ex example
GST glutathione S-transferase
H hydrogen
HATU N,N,N,N-tetramethyl-O-(7-azabenzotriazol-1-yl) uronium hexafluorophosphate.
HIS histidine
h or hr hours
i iso
IPA isopropanol
Hz hertz
MHz megahertz
HPLC high pressure liquid chromatography
HOBT 1-hydroxybenzotriazole hydrate
Lawesson's Reagent [2,4-bis(4-methoxyphenyl)-1,3-dithia-2,4-diphosphetane-2-4-disufide
LC liquid chromatography
LCMS or LC/MS liquid chromatograph mass spectrometry
LDA lithium diisopropylamide
m-CPBA or MCPBA meta-chloroperbenzoic acid
Me methyl
MeCN acetonitrile
MeOH methanol
min. minutes
M⁺ (M+H)⁺
M⁺¹ (M+H)⁺
MS mass spectrometry
MSA methanesulfonic acid
MTBE methyl tert-butyl ether
m/z mass to charge ratio
N Normal
NH₄OAc ammonium acetate
NMP N-methylpyrrolidinone
NMR nuclear magnetic resonance
PBMC peripheral blood mononuclear cells
PhCONCS benzyolyisothiocyanate
Pd/C palladium on carbon
Ph phenyl
Pr propyl
PHA phytohemagglutinin
ppm parts per million
PSI or psi pounds per square inch
quant. quantitative
Ret Time or Rt retention time
rt or RT room temperature
sat. or sat'd. saturated
SFC super critical fluid
S-Tol-BINAP (S)-(−)-2,2'-Bis(di-p-tolylphosphino)-1,1'-binapthyl
SM starting material
t tert
TEA triethylamine
TFA trifluoroacetic acid
THF tetrahydrofuran
TLC thin layer chromatography
pTSA para-toluenesulfonic acid
Xantphos® (9,9-dimethyl-9H-xanthene-4,5diyl)bis[diphenylphosphine]
t triplet
m multiplet
s singlet
d doublet
br. s. broad singlet
dd doublet of doublets
tt triplet of triplets
ddd doublet of doublet of doublets
q quartet
quin. quintet
W/V or w/v weight to volume
X-Phos dicyclohexyl(2',4',6'-triisopropylbiphenyl-2-yl)phosphine The compounds of formula I may be prepared by the processes described herein in the following reaction schemes. Examples of suitable reagents and procedures for conducting these reactions appear hereinafter and in the working examples included therein. Protection and deprotection in the schemes herein may be carried out by procedures generally known in the art (See, for example, T. W. Greene & P. G. M. Wuts, *Protecting Groups in Organic Synthesis*, 3$^{rd}$ Edition, Wiley, (1999)).

Compounds of the formula I can be prepared from pyrroles of the formula II as depicted in Scheme A. Pyrroles of formula II may be obtained by processes known in the art. Reacting a pyrrole of formula II wherein $R^2$ is as previously defined with an aminating reagent, such as chloramine, in the presence of a base, such as sodium hydride, in a solvent, such as DMF, affords the aminated pyrrole of formula III. When $R^2$ is hydrogen in formula III, this compound can also be obtained from commercial sources or prepared by standard methods known in the art. Compounds of formula III can be reacted with a malonate, such as diethyl-2-(ethoxymethylene)malonate, to afford a compound of formula IV. Compounds of formula III, wherein $R^2$ is most commonly hydrogen, can be thermolyzed in a high boiling solvent, such as Dowtherm, to afford cyclized products of the formula V. Reaction of compounds of formula V with a chlorinating agent, such as phosphorus oxychloride, followed by quenching the obtained intermediate with a nucleophilic alcohol, such as ethanol, affords chloride products of the formula VIa as the major product. Alternatively, quenching the obtained intermediate with a nucleophilic amine of the formula $R^3NH_2$, such as ammonia ($R^3$=H), at ambient temperatures affords products of the formula VII as the major product. Alternatively, compounds of the formula VIa can be reacted with hydrolysing agents, such as lithium hydroxide, to afford products of the formula VIb where $R^{3'}$=H, followed by reaction with a chlorinating agent, such as oxalyl chloride, and quenching the obtained intermediate with a nucleophilic amine of the formula $R^3NH_2$ to afford compounds of the formula VII. Compounds of the formula VII can then be coupled to amines of the formula $R^1NH_2$ in the presence of a suitable base in a suitable solvent to afford compounds of the formula I. Examples of suitable bases for the coupling include NaH, Et₃N, DIPEA, K₂CO₃ or Na₂CO₃ and suitable solvents include THF, CH₃CN, DMF, NMP, DMA, CH₂Cl₂. Most preferable base is DIPEA and more preferable solvents include DMF, NMP, and DMA.

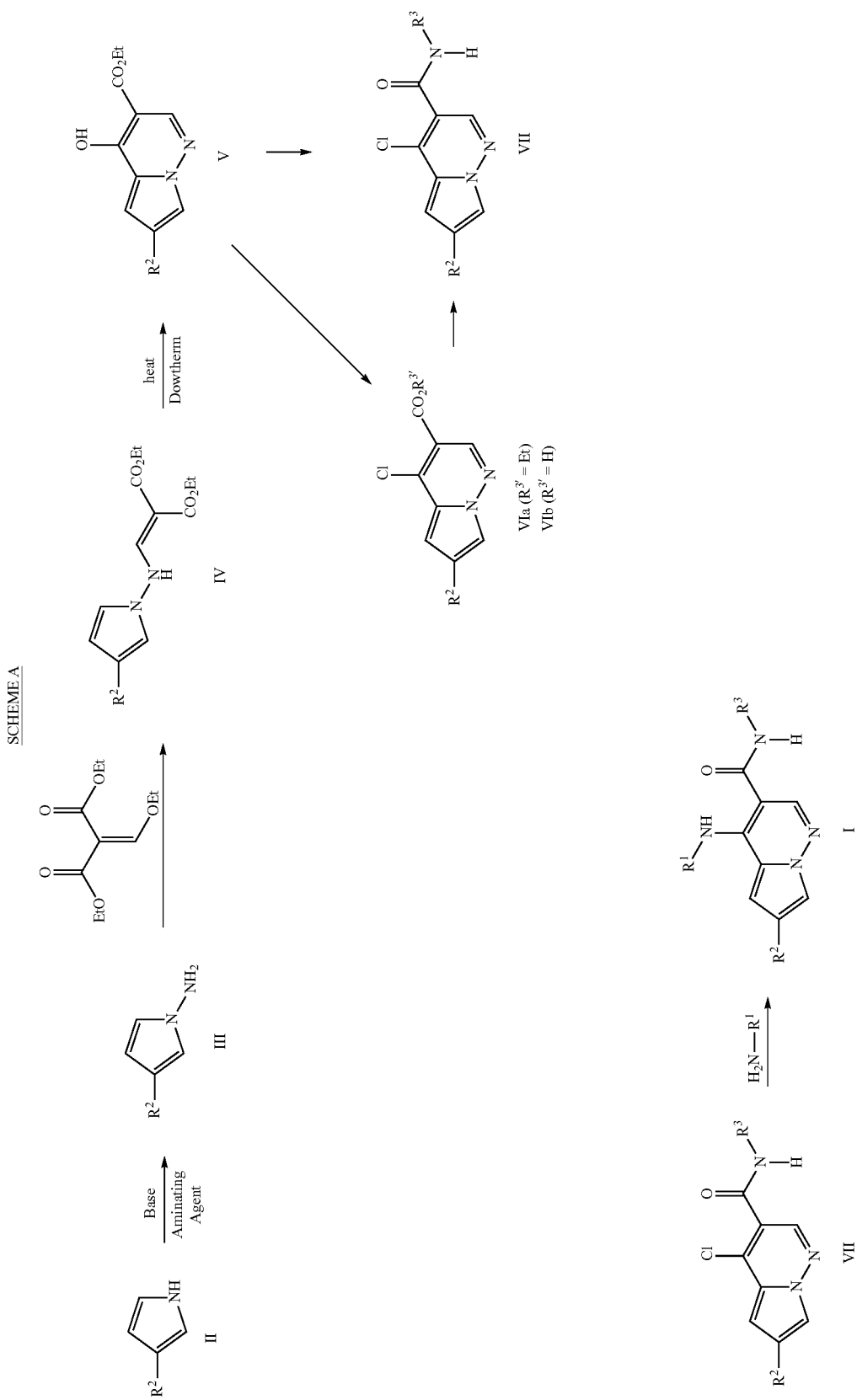

Scheme B depicts an alternative route to the synthesis of compounds of the formula I, wherein $R^3$ is hydrogen, starting from pyrroles of the formula VIII. Pyrroles of formula VIII wherein $R^2$ is as previously defined, but most commonly is fluoro, chloro, bromo, ethyl carboxylate, substituted or unsubstituted aryl or heteroaryl, may be obtained by processes known in the art. Reaction of pyrroles of the formula VIII with an aminating reagent, such as chloramine, in the presence of a suitable base, such as NaH, in a solvent, such as DMF, affords compounds of the formula IX. Compounds of the formula IX can be condensed with an acetal of the formula $(R'O)_2CHCH_2CN$ in the presence of an acid catalyst, such as pTSA, in a solvent, such as toluene, to afford compounds of the formula X followed by base induced cyclization employing a base such as DBU, in a solvent such as toluene to afford compounds of the formula XI. Reaction of compounds of the formula XI with a chlorinating agent, such as $POCl_3$, affords compounds of the formula XII. Hydrolysis of the compounds of the formula XII using an aqueous acid, such as sulfuric acid, affords compounds of the formula XIII which can be coupled with amines of the formula $R^1NH_2$ as previously described in Scheme A to afford compounds of the formula I, wherein $R^3$ is hydrogen.

Scheme C depicts an alternative method for cyclization to afford compounds of the formula I. N-aminated pyrroles of the formula IX wherein $R^2$ is as previously defined, but most commonly is fluoro, chloro, bromo, substituted or unsubstituted aryl or heteroaryl, may be obtained by the methods previously described. Reaction of the compounds of the formula IX with ethyl-3-ethoxy acrylate in the presence of an acid catalyst, such as pTSA, in a suitable solvent, such as ethanol, affords compounds of the formula XIV. Compounds of the formula XIV can be cyclized in the presence of a suitable base, such as DBU, in a suitable solvent, such as EtOH, to afford compounds of the formula VIa. Compounds of the formula VIa can then be converted into compounds of the formula I as previously described in Scheme A.

SCHEME B

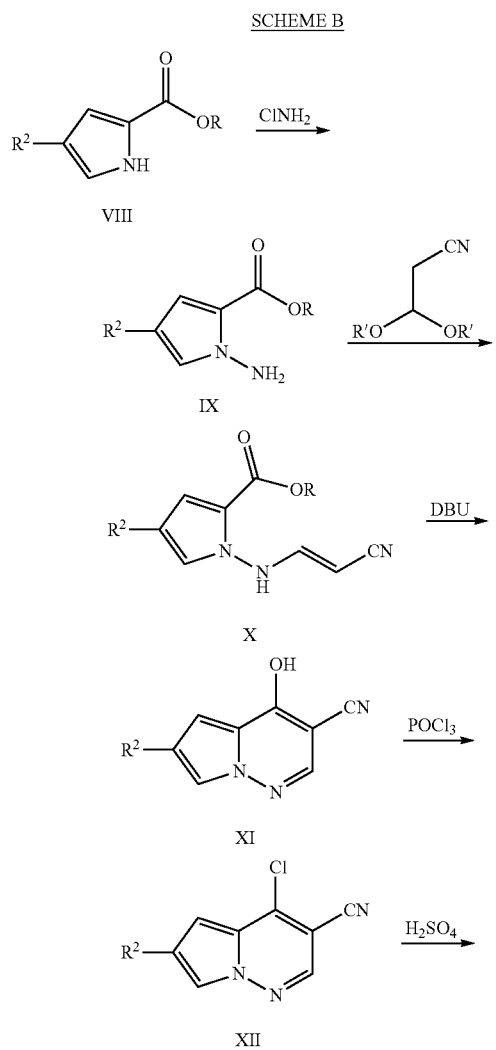

SCHEME C

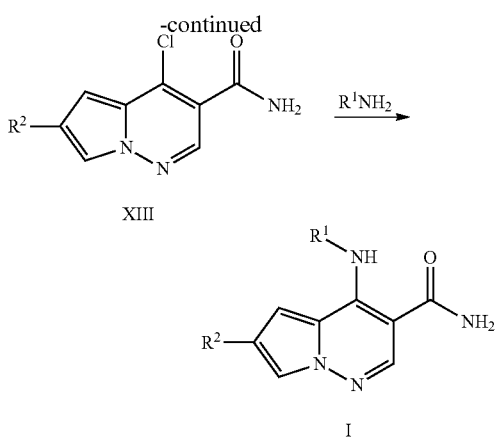

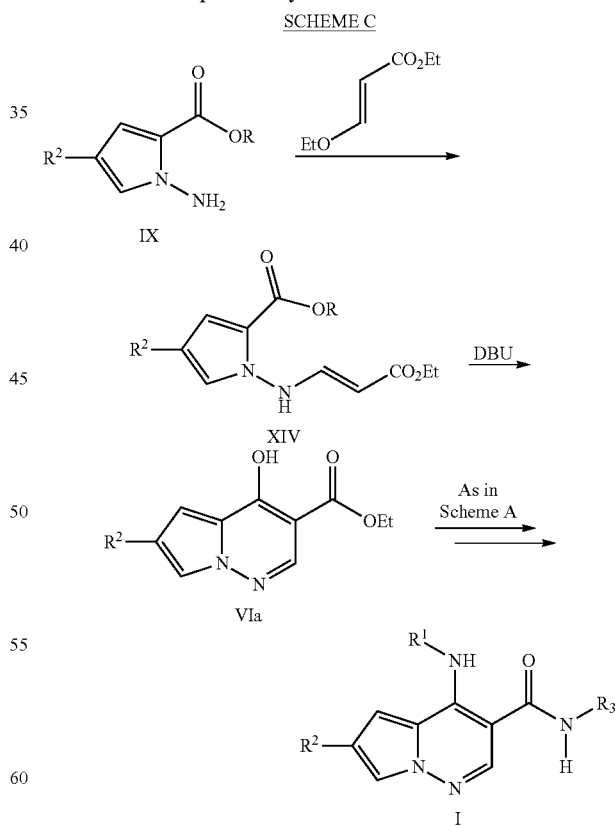

Scheme D depicts the synthetic route to compounds of the formula XVII, which are compounds of the formula I wherein $R^2$ is $—C(O)N(R^4)_2$. Compounds of the formula XV, which belong to compounds of the formula I wherein $R^2$ is —$CO_2R^{2b}$, can be hydrolyzed in the presence of hydroxide, such as sodium hydroxide, in a suitable solvent, such as methanol, to afford compounds of the formula XVI. Compounds of the formula XVI can then be coupled with amines of the formula $(R^4)_2NH$ in the presence of suitable coupling reagents, such as EDCI and HOBt, in the presence of a base, such as DIPEA, in a suitable solvent, such as DMF, to afford products of the formula XVII, which are compounds of the formula I wherein $R^2$ is —$C(O)N(R^4)_2$.

SCHEME D

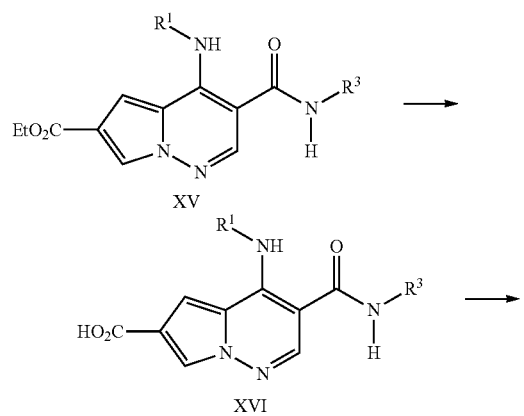

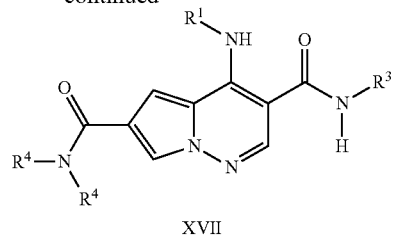

As depicted in Scheme E, compounds of the formula XVIII, which are compounds of the formula I wherein $R^2$ is bromo and prepared as previously described in Scheme B, can be reacted with boronic acids of the formula $R_2B(OH)_2$ or boronate esters of the formula $R_2B(OR)_2$ under Suzuki-Miyaura coupling conditions which are readily known to those skilled in the art, to afford compounds of the formula XIX, which are compounds of the formula I wherein $R^2$ is substituted or unsubstituted aryl, heteroaryl, alkyl, or alkenyl. Alternatively, compounds of the formula XIX can be prepared by reacting compounds of the formula XVIII with diboranes of the general formula $(RO)_2B$—$B(OR)_2$ under palladium catalyzed conditions readily known to those skilled in the art to afford compounds of the formula XX. Compounds of the formula XX can then be coupled to reagents of the type $R^2$—X, where X is most commonly chloro, bromo, or trifluoromethanesulfonate to afford compounds of the formula XIX, which are compounds of the formula I wherein $R^2$ is substituted or unsubstituted aryl, heteroaryl, alkyl or alkenyl.

SCHEME E

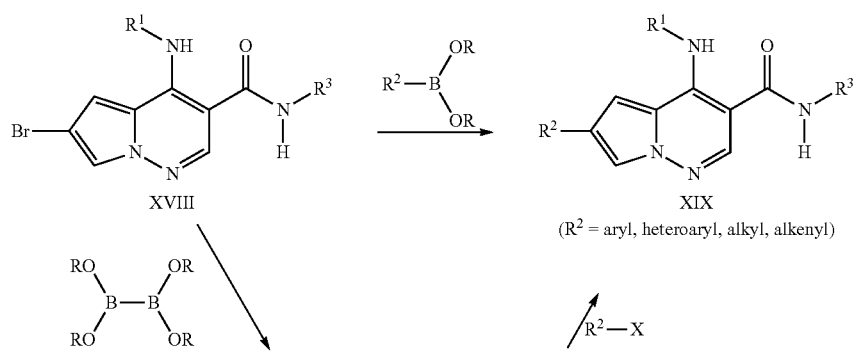

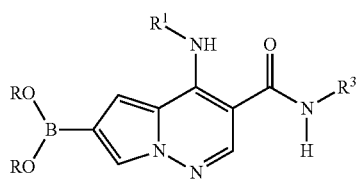

As depicted in Scheme F, compounds of the formula XVIII, which are compounds of the formula I wherein $R^2$ is bromo and prepared as previously described in Scheme B, can be reacted with amides or lactams of the formula $(R^{2b})C(O)NHR^b$ in the presence of a copper catalyst, such as copper iodide, in the presence of a suitable ligand, such as N1,N2-dimethylethane-1,2-diamine, in the presence of a suitable base, such as $K_2CO_3$, in a suitable solvent, such as dioxane, to afford products of the formula XXI, which are compounds of the formula I wherein $R^2$ is —$N(R^b)C(O)R^{2b}$. Under similar reaction conditions, compounds of the formula XVIII can be coupled with carbamates of the formula $(R^{2b}O)C(O)NHR^b$ to afford compounds of the formula XXII, which are compounds of the formula I wherein $R^2$ is —$N(R^b)C(O)OR^{2b}$. Similarly, compounds of the formula XVIII can be coupled with ureas of the formula $(R^{11})_2NC(O)NHR^b$ to afford compounds of the formula XXIII, which are compounds of the formula I wherein $R^2$ is —$N(R^b)C(O)N(R^{11})_2$.

As depicted in Scheme G, compounds of the formula XVIII, which are compounds of the formula I wherein $R^2$ is bromo and prepared as previously described in Scheme B, can be reacted with sulfonamides or sultams of the formula $(R^{2b})S(O)_2NHR^b$ in the presence of a copper catalyst, such as copper iodide, in the presence of a suitable ligand, such as N1,N2-dimethylethane-1,2-diamine, in the presence of a suitable base, such as $K_2CO_3$, in a suitable solvent, such as dioxane, to afford products of the formula XXIV, which are compounds of the formula I wherein R2 is —$N(R^b)S(O)_2R^{2b}$. Under similar reaction conditions, compounds of the formula XVIII can be coupled with sulfonoureas of the formula $(R^{11})_2NS(O)_2NHR^b$ to afford compounds of the formula XXV, which are compounds of the formula I wherein $R^2$ is —$N(R^b)S(O)_2N(R^{11})_2$.

SCHEME F

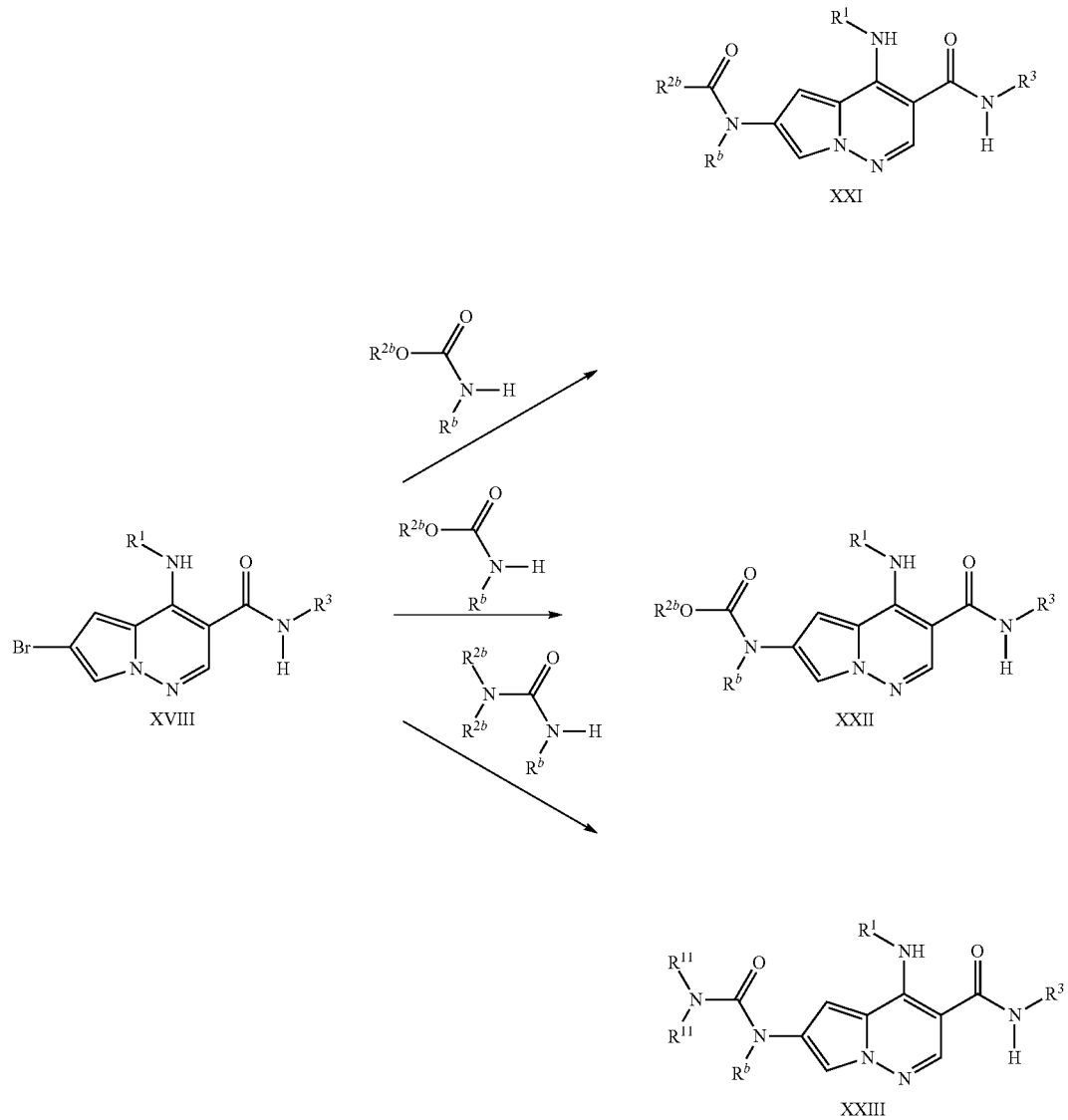

SCHEME G

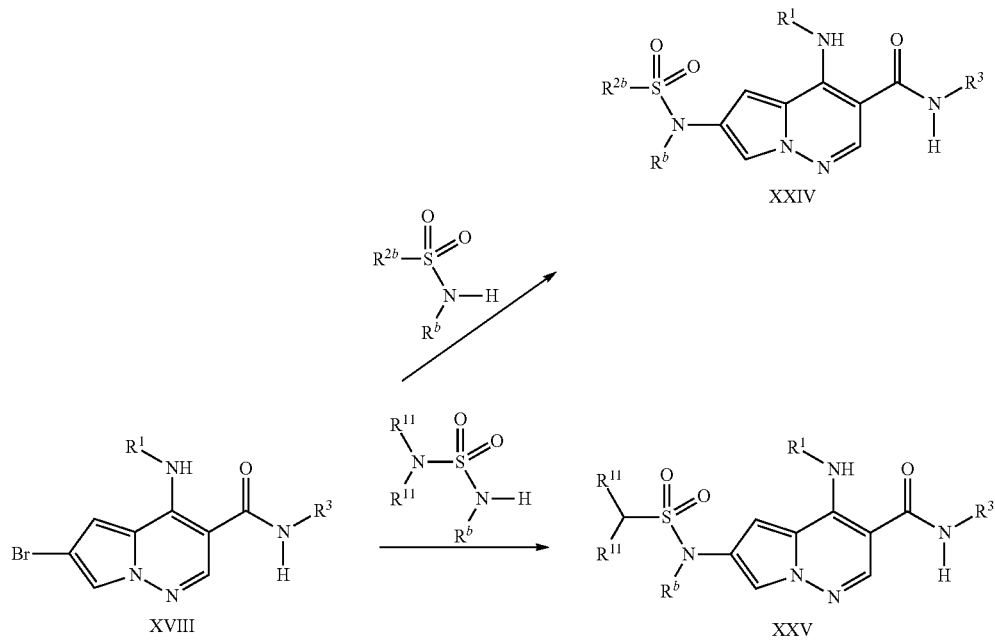

As depicted in Scheme H, compounds of the formula XVIII, which are compounds of the formula I wherein R² is bromo and prepared as previously described in Scheme B, can be coupled with heterocyclo compounds of the formula (Het)NH wherein (Het)NH represents any substituted or unsubstituted 4-10 membered heterocyclo group. Coupling of said heteroaryl groups can be performed in the presence of a copper catalyst, such as copper iodide, in the presence of a suitable ligand, such as N1,N2-dimethylethane-1,2-diamine, in the presence of a suitable base, such as K₂CO₃, in a suitable solvent, such as dioxane, to afford products of the formula XXVI, which are compounds of the formula I wherein R² is —N(Het) as defined previously.

SCHEME H

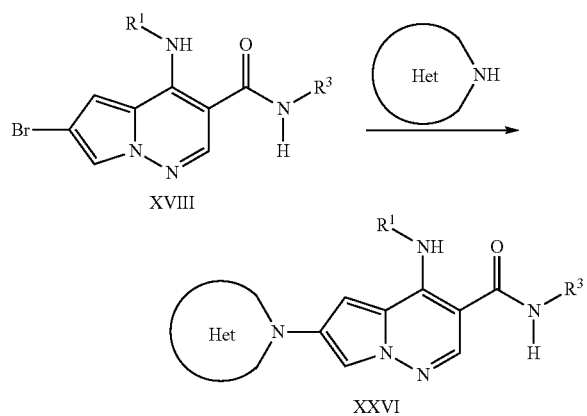

As depicted in Scheme I, compounds of the formula XVI, which are compounds of the formula I wherein R² is —CO₂H and prepared as previously described in Scheme D, can be converted to compounds of the formula XXVII, which are compounds of the formula I wherein R² is —NHCO₂Bn, using standard Curtis rearrangement conditions readily known to those skilled in the art. Preferred conditions include, but are not limited to, heating in the presence of diphenylphosphorylazide (DPPA), in the presence of benzyl alcohol (BnOH) in the presence of a suitable base, such as triethylamine, in a suitable solvent such as toluene. Compounds of the formula XXVII can be deprotected using conditions readily known to those skilled in the art, to afford compounds of the formula XXVIII, which are compounds of formula I wherein R₂ is —NH₂. Preferred conditions for deprotection include, but are not limited to, reacting compounds of the formula XXVII with palladium catalysts, such as palladium on carbon, in the presence of hydrogen, in a suitable solvent, such as ethanol.

SCHEME I

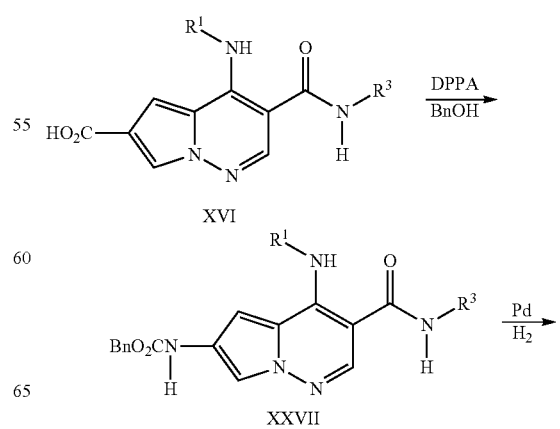

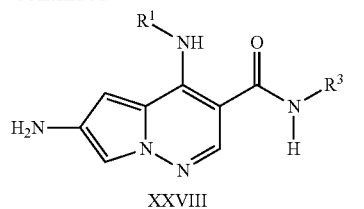

As depicted in Scheme J, alternative routes of preparation for compounds of the formula XXI, XXII, and XXIII as previously described in Scheme F wherein $R^b$ is hydrogen include reacting compounds of the formula XXVIII with acylating agents such as acid chlorides of the formula $(R^{2b})C(O)Cl$, chloroformates of the formula $(R^{2b}O)C(O)Cl$ and carbamoyl chlorides of the formula $—(R^{11})_2NC(O)Cl$ or isocyanates of the formula $—(R^{11})_2NC(O)$, respectively. Couplings can be carried out in the presence of a suitable base, such as triethylamine, in the presence of a suitable solvent, such as dichloromethane.

SCHEME J

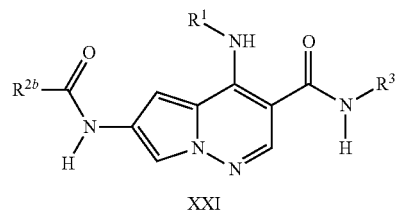

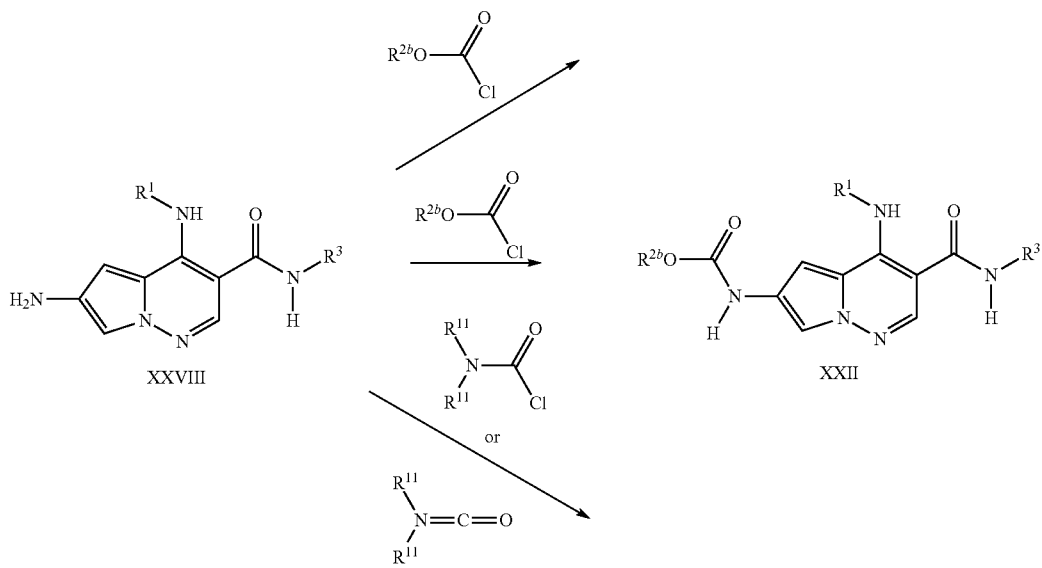

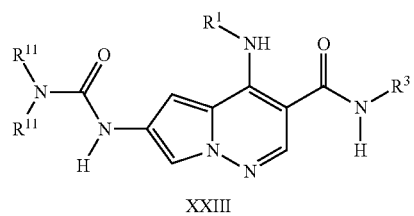

As depicted in Scheme K, compounds of the formula XVIII, which can be prepared as previously described in Scheme B wherein $R^2$ is bromo, can be reacted with cyanide to afford compounds of the formula XXIX, which are compounds of formula I wherein $R^2$ is cyano. Preferred conditions for coupling include, but are not limited to, reacting in the presence of a suitable cyanide reagent, such as zinc(II) cyanide, in the presence of a palladium catalyst, such as $Pd(COCF_3)_2$, in the presence of a phosphine ligand, such as 1,1'-binaphthyl-2-yldi-tert-butylphosphine, in a suitable solvent such as DMA.

SCHEME K

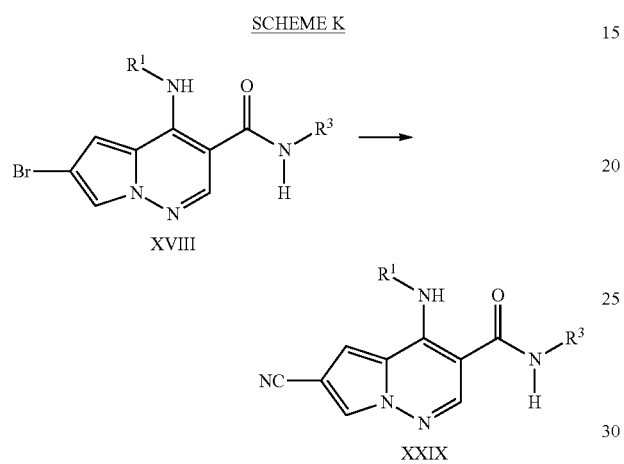

As depicted in Scheme L, compounds of the formula I can also be prepared by reacting compounds of the formula XXX, which are prepared as depicted in Scheme B where $R^2$ is bromo, with a thiolate, such as sodium ethylthiolate, to afford a compound of the formula XXXI. Installation of additional $R^2$ groups can then be accomplished by reacting compounds of the formula XXXI with coupling reagents, such as boronic acids or boronate esters, under standard coupling conditions readily known in the art, to afford compounds of the formula XXXII. Compounds of the formula XXXII can then be oxidized using oxidizing agents, such as oxone, to afford compounds of the formula XXXIII which can be coupled with amines of the formula $R^1$—$NH_2$ to afford compounds of the formula I. Preferred conditions for coupling of $R^1$—$NH_2$ include, but are not limited to, reaction of compounds of the formula XXXIII in the presence of an amine, such as DIPEA, in a suitable solvent, such as THF.

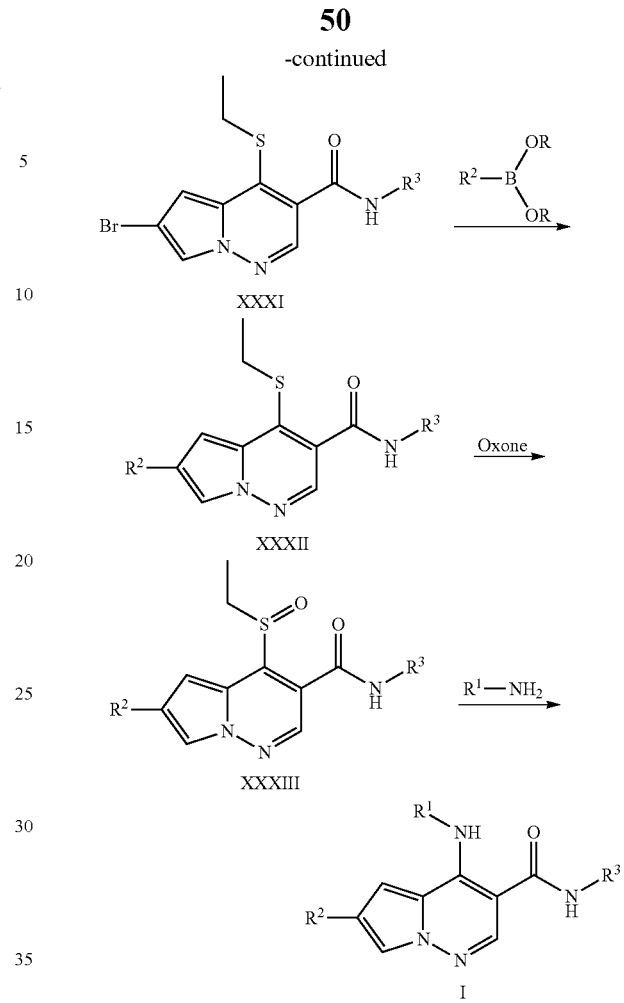

As depicted in Scheme M, compounds of the formula XVI, which are compounds of the formula I wherein $R^2$ is —$CO_2H$ and prepared as previously described in Scheme D, can be converted to compounds of the formula XXXIV using standard amide coupling conditions readily known to those skilled in the art. Compounds of the formula XXXIV can be reacted with di(1H-imidazol-1-yl)methanethione followed by alkylation with iodomethane to afford compounds of the formula XXXV. Compounds of the formula XXXV can be coupled with amines of the formula $(R^{2b})_2NH$ by thermolysis at higher temperatures (>100° C.) or compounds of the formula XXXV can be oxidized to afford a sulfoxide and/or sulfone intermediate using an oxidizing agent, such as oxone, followed by coupling with amines of the formula $(R^{2b})_2NH$ under lower temperatures (<100° C.) to afford compounds of the formula XXXVI.

SCHEME L

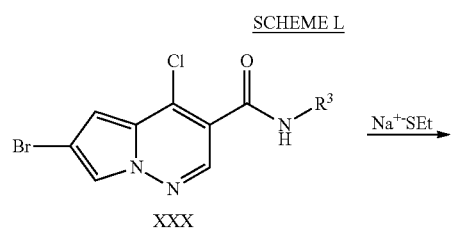

SCHEME M

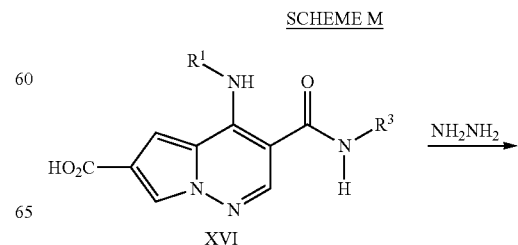

-continued

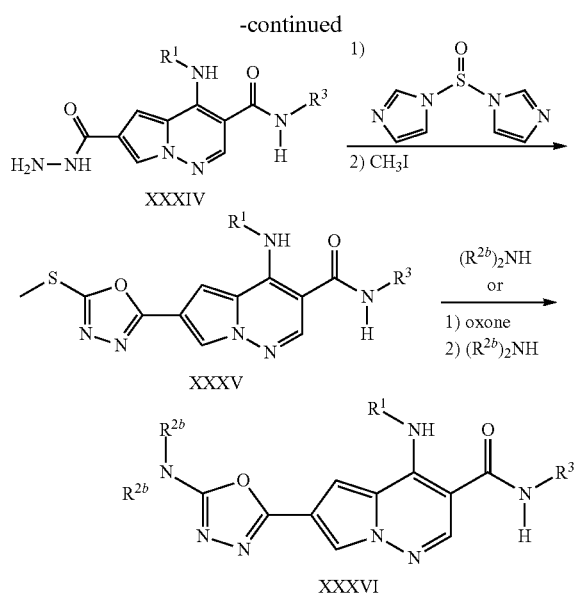

Scheme N illustrates general strategies for the synthesis of functionalized cyclopentylamines that have been used as amines having the formula R¹NH₂ in the preparation of the compounds of formula I as previously defined. In this strategy, 2,2-disubstituted-1,3-cyclopentadiones of the formula XXXVIII were utilized as a key intermediates which could be prepared from compounds of the formula XXXVII by deprotonation with a base such as potassium hydroxide, sodium hydroxide or sodium hydride followed by reaction of the resulting enolates with suitable alkylating agents of the formula R$^{a'}$—X, where X is a suitable leaving group such as iodide, bromide, chloride, triflate or mesylate. Alternatively, compounds of the formula XXXVIII can be prepared via Lewis acid-catalyzed geminal acylation reaction of ketones of the formula XL with 1,2-bis((trimethylsilyl)oxy)cyclobutene (XXXIX) following a literature reported procedure (T. J. Jenkins, D. J. Burnell *J. Org. Chem.* 1994, 59, 1485). Typically, boron trifluoride etherate is used to promote this reaction. Furthermore, compounds of the formula XXXVIII wherein R$^{a'}$ is a fluoro group, can be prepared by heating a mixture of compounds of the formula XXXVII and Selectfluor in a solvent such as acetonitrile. In addition, compounds of the formula XXXVIII wherein R$^{a'}$ is a trifluoromethyl group, can be prepared by reaction of compounds of the formula XXXVII with a suitable base, such as sodium hydride, to form the corresponding enolate intermediate followed by reaction with 5-(trifluoromethyl)dibenzothiolphenium trifluoromethanesulfonate (XLI). Compounds of the formula XXXVIII can then be reduced to the monoalcohol ketone of the formula XLII using various reducing agents such as sodium borohydride or lithium aluminum hydride. Conversion of compounds of the formula XLII to amines of the formula XLIII can be accomplished via reductive amination with an appropriate ammonia source, such as ammonium acetate, in the presence of reducing agents such as sodium cyanoborohydride or sodium triacetoxyborohydride. Alternatively, compounds of the formula XLII can be reductively aminated via treatment with a protected amine, such as benzyl amine, in the presence of reducing agents such as sodium cyanoborohydride or sodium triacetoxyborohydride. Subsequent removal of the benzyl protecting group using standard deprotection methods readily known to those skilled in the art, for example hydrogenolysis in the presence of a suitable palladium catalyst, provides compounds of the formula XLIII. Another route for preparation of compounds of the formula XLIII from compounds of the formula XLII includes oxime formation using hydroxylamine and reduction of the resulting oxime with sodium metal in alcoholic solvent such as n-propanol at elevated temperature.

SCHEME N

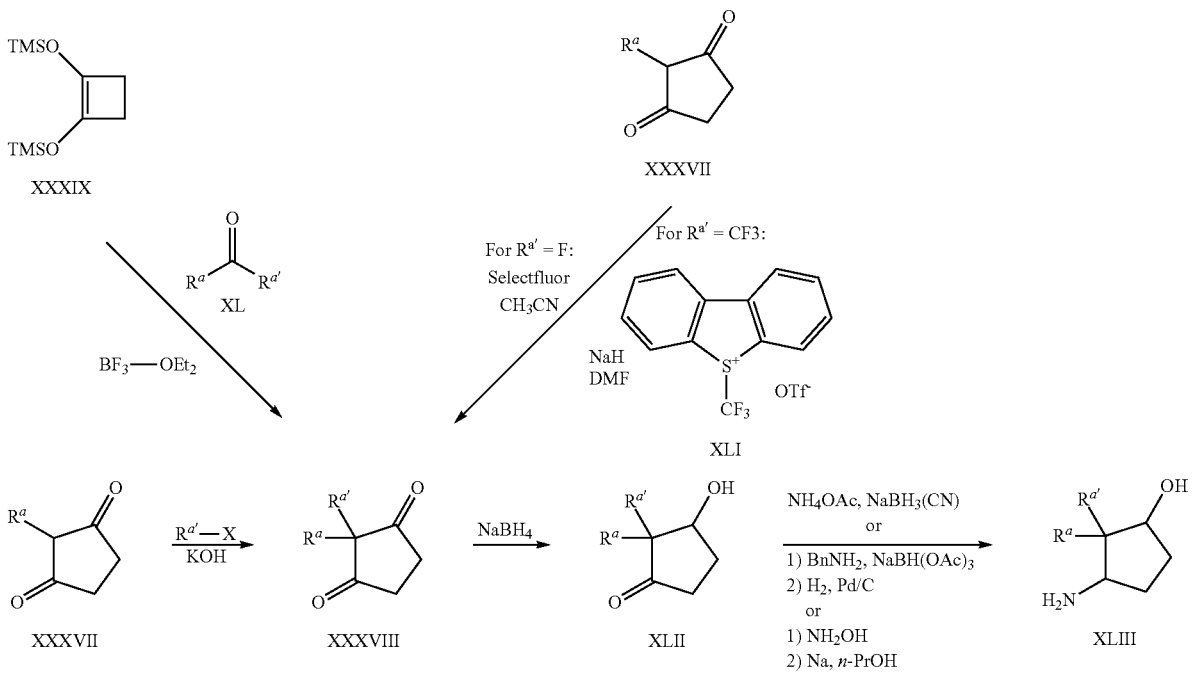

As depicted in Scheme O, compounds of the formula XLV, which represent compounds of the formula R¹—NH₂ as previously defined, can be prepared from compounds of the formula XXXVIII by reacting with 1 equivalent of organometallic reagents of the formula R^{a''}—Li in the presence of cerium(III) chloride, or an appropriate Grignard reagent of the formula R^{a''}MgBr or R^{a''}MgCl to afford compounds of the formula XLIV. Compounds of the formula XLIV can then be converted to compounds of the formula XLV using the methods previously described in Scheme N for the conversion of compounds of the formula XLII to XLIII. In addition, compounds of the formula XLVI, which represent amines of the formula R¹—NH₂ as previously defined, can be prepared from compounds of the formula XXXVIII by reacting with at least 2 equivalents of an ammonia source in the presence of a suitable reducing reagent as previously described in Scheme N for the conversion of compounds of the formula XLII to XLIII.

Scheme P depicts the general methods used for the synthesis of (cis)- or (trans)-cyclopentane-1,3-diamines of the formulas XLVIII and LII, which represent compounds of the formula R¹—NH₂ as previously defined. Commercially available camphoric acid (XLVII) can be converted to the cis di-amine of the formula XLVIII using NaN₃ in H₂SO₄ as reported in Z. H. Yang et al. *Tetrahedron Asymmetry* 2001, 12, 1579; D. Jaramillo et al. *Eur. J. Inorg. Chem.* 2006, 839-849. Preparation of the corresponding trans di-amine of the formula LII can be prepared from camphoric acid (XLVII) by conversion to the corresponding cis di-ester IL using iodomethane under basic conditions, such as with potassium carbonate in DMSO. Treatment of the cis di-ester IL with a base such as sodium hydride at elevated temperature followed by quenching of the resulting enolate intermediate affords a mixture of the trans isomer L along with the cis isomer IL. The sterically hindered trans isomer L can be converted to the corresponding di-acid LI using conditions such as potassium tert-butoxide in DMSO at elevated temperature. Subsequent conversion of LI to the trans diamine LII can be accomplished using the previously described Schmidt rearrangement conditions. Racemic forms or enantioenriched forms of either antipode of the diamines XLVIII or LII can be prepared using these methods starting with racemic camphoric acid, (+)-camphoric acid, or (−)-camphoric acid, all of which are readily available from commercial sources.

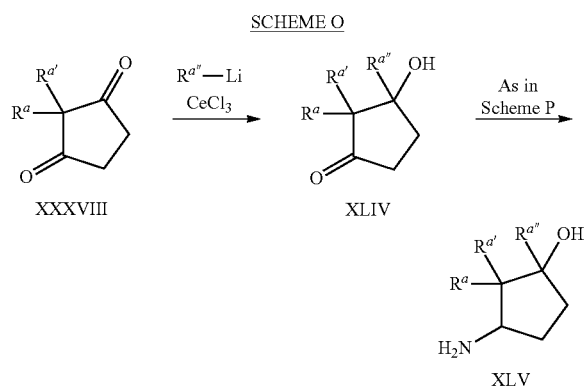

SCHEME O

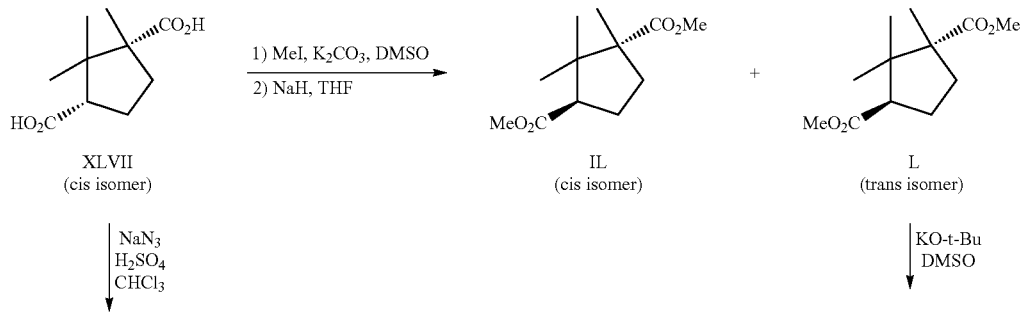

SCHEME P

Scheme Q depicts the general methods used for the synthesis of amines of the formulas LVII and LVIII, which represent compounds of the formula R¹—NH₂ as previously defined. Epoxide compounds of the formula LIII wherein A=CH₂, O, or NCbz can be reacted with ammonia under heating conditions, typically in a sealed vessel, to give the corresponding trans-amino alcohols which can be further reacted with CbzCl using either aqueous THF solvent and sodium carbonate or potassium carbonate base, or in organic solvent such as dichloromethane with bases such as triethylamine or N,N-diisopropylethylamine, to afford compounds of the formula LIV. Compounds of the formula LIV can be oxidized to ketones of the formula LV using various oxidation conditions, such as Swern oxidation or Dess-Martin periodinane oxidation. Addition of organometallic reagents, such as R—Li, typically in the presence of cerium (III) chloride affords compounds of the formula LVI. Deprotection of compounds of the formula LVI under standard conditions readily known to those skilled in the art, such as hydrogenolysis in the presence of a suitable palladium catalyst, such as palladium on charcoal, affords compounds of the formula LVII, which represent compounds of the formula R¹—NH₂ as previously defined. Alternatively, compounds of the formula LVI can be treated with (diethylamino)sulphur trifluoride (DAST) to effect deoxyfluorination followed by removal of the Cbz protecting group as previously described to afford compounds of the formula LVIII, which represent compounds of the formula R¹—NH₂ as previously defined.

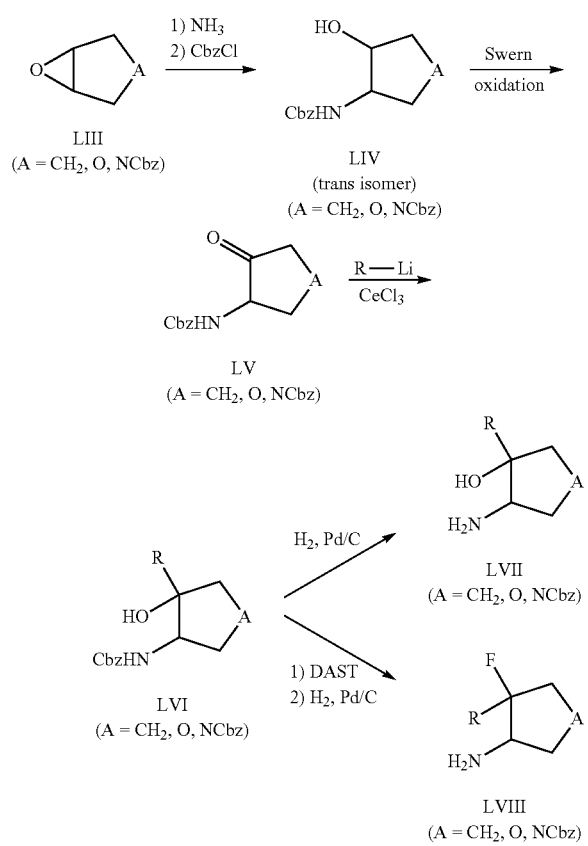

Alternatively, as depicted in Scheme R, compounds of the formulas LVII and LVIII wherein R is a methyl and A is a methylene, can be prepared from the epoxide of the formula LIX using similar methods as described in Scheme Q.

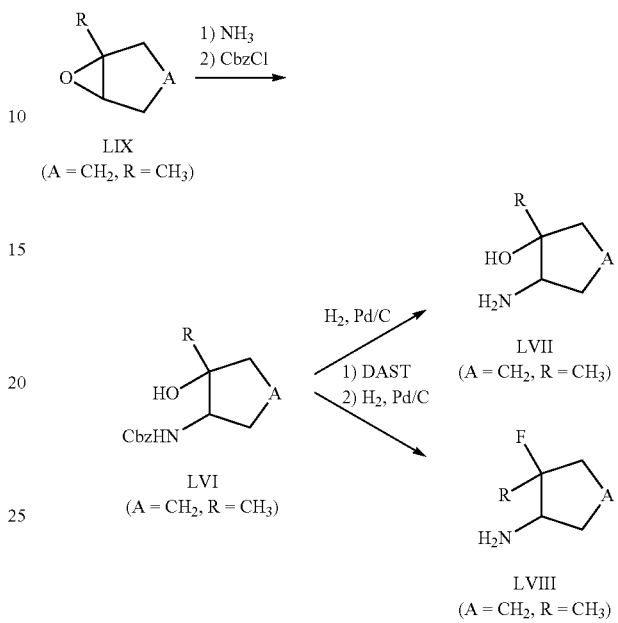

Methods of Preparation

General Procedures:
Analytical HPLC Conditions:
Method A: Column: YMC S5 ODS-A S5 4.6×50 mm. Linear gradient of 0 to 100% solvent B over 4 min, with 1 min hold at 100% B. Flow rate: 4 mL/min. Solvent A: 0.2% phosphoric acid, 90% water, 10% methanol. Solvent B: 0.2% phosphoric acid, 90% methanol, 10% water. Products detected at 220 nm.

Method B: Column: YMC ProC18 S5 ODS (50×4.6 mm) Linear gradient of 0 to 100% solvent B over 4 min, with 1 min hold at 100% B. Solvent A: 10% MeOH-90% H₂O-0.2% H₃PO₄. Solvent B: 90% MeOH-10% H₂O-0.2% H₃PO₄. Flow rate: 4 mL/min. Products detected at 220 nm.

Method C: Column: Supelco Ascentis C18, 4.6×50 mm, 2.7 um. Linear gradient of 0 to 100% solvent B over 4 min, with 1 min hold at 100% B. Flow rate: 4 mL/min. Solvent A: 5:95 acetonitrile:water with 0.05% TFA. Solvent B: 95:5 acetonitrile:water with 0.05% TFA. Products detected at 220 nm.

Method D: Column: Supelco Ascentis C18, 4.6×50 mm, 2.7 um. Linear gradient of 0 to 100% solvent B over 4 min, with 1 min hold at 100% B. Flow rate: 4 mL/min. Solvent A: 5:95 acetonitrile:water with 10 mM NH₄OAc. Solvent B: 95:5 acetonitrile:water with 10 mM NH₄OAc. Products detected at 220 nm.

Method E: Column: Supelco Ascentis C18, 4.6×50 mm, 2.7 um
Linear gradient of 0 to 100% solvent B over 4 min, with 1 min hold at 100% B. Flow rate: 4 mL/min. Solvent A: 5:95 acetonitrile:water with 10 mM NH₄OAc. Solvent B: 95:5 acetonitrile:water with 10 mM NH₄OAc. Products detected at 220 nm.

Method F: Column: YMC CombiScreen ODS-A S5 4.6× 50 mm. Linear gradient of 0 to 100% solvent B over 4 min, with 1 min hold at 100% B. Flow rate: 4 mL/min. Solvent A: 0.2% phosphoric acid, 90% water, 10% methanol. Solvent B: 0.2% phosphoric acid, 90% methanol, 10% water. Products detected at 220 nm.

Method G: Column: Sunfire C18 (3.0×150)mm, 3.5 mm. Linear gradient of 10 to 100% solvent B over 12 min, with 3 min hold at 100% B. Flow rate: 0.5 mL/min. Solvent A: 5:95 acetonitrile:water with 0.05% TFA. Solvent B: 95:5 acetonitrile:water with 0.05% TFA.

Method H: Column: Waters Acquity UPLC BEH C18, 2.1×50 mm, 1.7-μm particles Linear gradient of 0 to 100% solvent B over 3 min, with 0.75 min hold at 100% B. Flow rate: 1.1 mL/min. Solvent A: 5:95 acetonitrile:water with 0.05% TFA. Solvent B: 95:5 acetonitrile:water with 0.05% TFA. Temperature: 50° C. Products detected at 220 nm.

Method I: Column: Mac-mod Halo C18, 4.6×50 mm, 2.7 um. Linear gradient of 0 to 100% solvent B over 4 min, with 1 min hold at 100% B. Flow rate: 4 mL/min. Solvent A: 5:95 acetonitrile:water with 10 mM $NH_4OAc$. Solvent B: 90:10 acetonitrile:water with 10 mM $NH_4OAc$. Products detected at 220 nm.

Method J: Column: Mac-mod Halo C18, 4.6×50 mm, 2.7 um. Linear gradient of 0 to 100% solvent B over 4 min, with 1 min hold at 100% B. Flow rate: 4 mL/min. Solvent A: 5:95 acetonitrile:water with 0.05% TFA. Solvent B: 95:5 acetonitrile:water with 0.05% TFA. Products detected at 220 nm.

Method K: Column: Supelco Ascentis Express C18 (4.6×50)mm, 2.7 μm. Linear gradient of 0 to 100% solvent B over 4 min, with 1 min hold at 100% B. Flow rate: 4 mL/min. Solvent A: 5:95 acetonitrile:water with 0.05% TFA. Solvent B: 95:5 acetonitrile:water with 0.05% TFA. Products detected at 220 nm.

Method L: Column: Sunfire C18 (3.0×150)mm, 3.5 μm. Linear gradient of 10 to 100% solvent B over 12 min, with 3 min hold at 100% B. Flow rate: 0.5 mL/min. Solvent A: 5:95 acetonitrile:water with 0.05% TFA. Solvent B: 95:5 acetonitrile:water with 0.05% TFA. Products detected at 220 nm.

Method M: Column: Waters BEH C18, 1.7 um, 2.1×50 mm. Linear gradient of 0.1 to 99.9% solvent B over 3 min, with 0.75 min hold at 99.9% B. Flow rate: 1.1 mL/min. Solvent A: 5:95 acetonitrile:water with 10 mM $NH_4OAc$. Solvent B: 95:5 acetonitrile:water with 10 mM $NH_4OAc$. Products detected at 220 nm.

Method N: Column: Supelco Ascentis Express C18 (4.6×50)mm, 2.7 μm. Linear gradient of 0 to 100% solvent B over 4 min, with 1 min hold at 100% B. Flow rate: 4 mL/min. Solvent A: 5:95 acetonitrile:water with 10 mM $NH_4OAc$. Solvent B: 95:5 acetonitrile:water with 10 mM $NH_4OAc$. Products detected at 220 nm.

Method O: Column: Chromalith Speedrod C18, (50×4.6 mm) Linear gradient of 0 to 100% solvent B over 12 min, then 3 min hold at 100% B. Flow rate: 4 mL/min. Solvent A: 10% MeOH-90% $H_2O$-0.2% $H_3PO_4$. Solvent B: 90% MeOH-10% $H_2O$-0.2% $H_3PO_4$. Products detected at 220 nm.

Method P: Column: X bridge phenyl (4.6×150 mm). Linear gradient of 0 to 100% solvent B over 12 min, then 3 min hold at 100% B. Flow rate: 1 mL/min Solvent A: 5% MeCN-95% $H_2O$-0.05% TFA. Solvent B: 95% MeOH-5% $H_2O$-0.05% TFA. Products detected at 220 nm.

Method Q: Column: X bridge phenyl (4.6×50 mm). Linear gradient of 0 to 100% solvent B over 4 min, then 1 min hold at 100% B. Flow rate: 4 mL/min Solvent A: 5% MeCN-95% $H_2O$-10 mM $NH_4OAc$. Solvent B: 95% MeOH-5% $H_2O$-10 mM $NH_4OAc$. Products detected at 220 nm.

Method R: Column: Phenominex Synergy, 4.6×50 mm. Linear gradient of 0 to 100% solvent B over 4 min, then 1 min hold at 100% B. Flow rate: 4 mL/min. Solvent A: 10:90 methanol/water with 0.2% $H_3PO_4$. Solvent B: 90:10 methanol/water with 0.2% $H_3PO_4$. Products detected at 220 or 254 nm.

Method S: Column: Sunfire C18, (150×4.6 mm), 3.5 μm, SC/862. Linear gradient of 0 to 100% solvent B over 12 min, then 3 min hold at 100% B. Flow rate: 1 mL/min. Buffer: 0.5% TFA, in water with pH adjusted to 2.5 using dilute ammonia. Solvent A: Buffer: acetonitrile (95:5). Solvent B: acetonitrile. Products detected at 220 nm.

Preparative HPLC Conditions:

Method A: Column: YMC 20×100 mm. Linear gradient of 20-100% solvent B over 12 min, then 1 min hold at 100% B. Flow rate: 4 mL/min. Solvent A: 10% MeOH in $H_2O$ with 0.1% TFA. Solvent B: 90% MeOH in $H_2O$ with 0.1% TFA. Products detected at 220 nm.

Method B: Column: YMC ProC18 S5 ODS 50×4.6 mm. Linear gradient of 20-100% solvent B over 4 min, then 1 min hold at 100% B. Flow rate: 4 mL/min. Solvent A: 10% MeOH-90% $H_2O$-0.2% $H_3PO_4$. Solvent B: 90% MeOH-10% $H_2O$-0.2% $H_3PO_4$. Products detected at 220 nm.

Analytical LCMS Conditions:

Method A: Column: Purosphoer@ star rp-18 (4.6×30) mm, 3 μm.

Linear gradient of 0-100% solvent B over 2 min, then 0.5 min hold at 100% B. Flow rate: 2.5 mL/min. Solvent A: 20 mM of ammonium acetate in 90% water-10% acetonitrile. Solvent B: 20 mM of ammonium acetate in 10% water-90% acetonitrile. Products detected at 220 wavelength w/positive or negative ionization mode.

Method B: Column: Phenomenex Luna 5u C18 30×4.6 mm. Linear gradient of 0-100% solvent B over 2 min, then 0.5 min hold at 100% B. Flow rate: 4 mL/min. Solvent A: 10% MeOH-90% $H_2O$-0.1% TFA. Solvent B: 90% MeOH-10% $H_2O$-0.1% TFA. Products detected at 220 wavelength w/positive or negative ionization mode.

Method C: Column: Supelco Ascentis Express C18, 4.6×50 mm, 2,7-μm particles. Linear gradient of 0-100% solvent B over 4 min, then 1 min hold at 100% B. Flow rate: 4 mL/min. Temperature=35° C. Solvent A: 5:95 acetonitrile:water with 10 mM ammonium acetate. Solvent B: 90:10 acetonitrile:water with 10 mM ammonium acetate. Products detected at 220 wavelength w/positive ionization mode.

Method D: Column: Zorbox SB C18 (4.6×50 mm), 5 μm. Linear gradient of 0-100% solvent B over 4 min, then 1 min hold at 100% B. Flow rate: 5 mL/min. Solvent A: 10% methanol-90% water-0.1% TFA. Solvent B: 90% MeOH-10% water-0.1% TFA. Products detected at 220 wavelength w/positive ionization mode.

Method E: Column: BEH C18 2.1×50 mm 17u. Linear gradient of 0-100% solvent B over 2 min, then 0.5 min hold at 100% B. Flow rate: 1 mL/min. Solvent A: 100% water w/0.05% TFA. Solvent B: 100% acetonitrile w/0.05% TFA. Products detected at 220 wavelength w/positive ionization mode.

Method F: Column: YMC Pack TMS (3.0×50 mm), 3 μm. Linear gradient of 0-100% solvent B over 2 min, then 0.5 min hold at 100% B. Flow rate: 1.2 mL/min. Solvent A: 2% Acetonitrile; 98% $H_2O$; 10 mM $NH_4COOH$. Solvent B: 98% acetonitrile; 2% $H_2O$; 10 mM $NH_4COOH$. Products detected at 220 wavelength w/positive ionization mode.

Method G: Column: Supelco Ascentis Express C18, 4.6×50 mm, 2,7-μm particles. Linear gradient of 0-100% solvent B over 5.3 min, w/1.7 min hold at 100% B. Flow rate: 3 mL/min. Solvent A: 5:95 acetonitrile:water with 10 mM ammonium acetate. Solvent B: 90:10 acetonitrile:water with 10 mM ammonium acetate. Products detected at 220 wavelength w/positive ionization mode.

Method H: Column: ZORBAX_AQ_FA-P.M. Linear gradient of 0-100% solvent B over 2 min, w/0.5 min hold at 100% B. Flow rate: 1 mL/min. Solvent A: 0.1% HCOOH in water. Solvent B: acetonitrile. Products detected at 220 wavelength w/positive ionization mode

PREPARATIONS

Preparations 1 and 2

4-Chloropyrrolo[1,2-b]pyridazine-3-carboxylic acid and 4-Ethyl chloropyrrolo[1,2-b]pyridazine-3-carboxylate

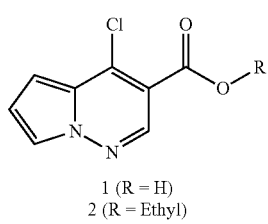

1 (R = H)
2 (R = Ethyl)

Step 1: 2-(1H-pyrrol-1-yl)isoindoline-1,3-dione

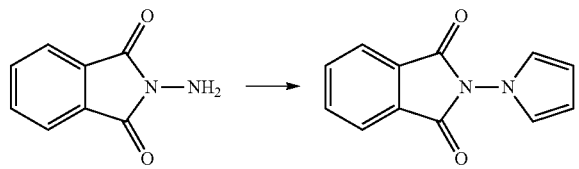 [SMILES: NN1C(=O)c2ccccc2C1=O ; O=C1c2ccccc2C(=O)N1n1cccc1]

To a stirred solution of 1,4-dioxane (50 mL) and N-aminophthalimide (5.0 g, 0.031 mmol) at rt was slowly added 2,5-dimethoxy tetrahydrofuran (15 g, 0.061 mmol). The resulting light yellow solution was heated to 100° C. for ~16 h whereupon 5N HCl was carefully added at 100° C. giving a brown mixture. The mixture was allowed to cool room temperature, the solid thus separated was filtered and was rinsed with 1:3 of 1,4-dioxane in water. Drying afforded 3.5 g (54%) of the title compound as a white solid. LCMS (Condition D) m/z: 213+ve.

Step 2: 1H-pyrrol-1-amine

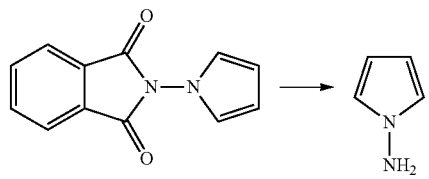 [SMILES: O=C1c2ccccc2C(=O)N1n1cccc1 ; Nn1cccc1]

To a solution of 2-(1H-pyrrol-1-yl)isoindoline-1,3-dione (3.5 g, 0.016 mmol) in methanol (35 mL) was added hydrazine monohydrate (1 mL, 0.021 mmol). The reaction mixture was heated to 65° C. for 1 h then was cooled and filtered. The resulting solid was rinsed with methanol and the resulting filtrate was concentrated to give a light yellow solid which was triturated with diethyl ether. The organic solution was then concentrated to give 1 g (74%) of a brown oil as the title compound. $^1$H NMR (400 MHz, DMSO-d$_6$) δ ppm: 5.84 (t, J=2.0 Hz, 2.4 Hz, 2H), 5.86 (d, exchangeable with D$_2$O, 2H), 6.62 (t, J=2.0, 2.4 Hz, 2H).

Step 3: Diethyl 2-((1H-pyrrol-1-ylamino)methylene)malonate

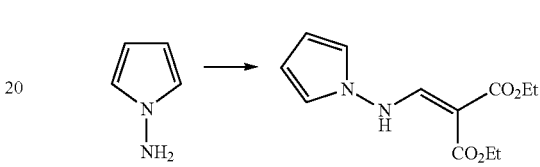

A round bottom flask was charged with 1H-pyrrole-1-amine (1 g, 0.012 mmol) and diethyl-2-(ethoxymethylene) malonate (3.16 g, 0.014 mmol) and the flask was equipped with a short path distillation condenser. The mixture was heated to 125° C. for 4 hr while collecting the ethanol distillate. After the reaction was complete as determined by TLC, the mixture was cooled to rt and hexanes was added to give a slurry. The mixture was filtered and the resulting solid was rinsed with additional hexanes and was dried to afford 2.6 g (85%) of a solid as the title compound. $^1$H NMR (400 MHz, DMSO-d$_6$) δ ppm: 1.18-1.22 (m, 6H), 4.06-4.17 (m, 4H), 6.06 (t, J=2.4 Hz, 2H), 6.98 (t, J=1.6, 2.4 Hz, 2H), 7.84 (d, J=11.2 Hz, 1H), 11.24 (d, J=10.8 Hz, 1H). LCMS (Condition D): m/z 253+ve.

Step 4: Ethyl 4-hydroxypyrrolo[1,2-b]pyridazine-3-carboxylate

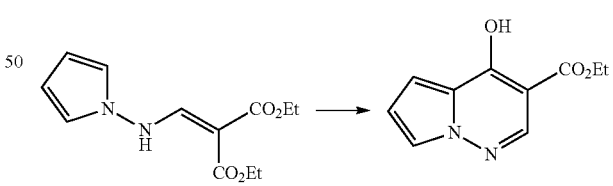

A solution of diethyl-1-(1H pyrrole-1-yl-aminomethylene malonate (2 g, 0.11 mmol) in 135 mL of Dowtherm A was slowly heated to 220° C. using a sand bath and allowed to stir for ~16 h. The reaction mixture was cooled and loaded onto a flash silica gel column and eluted with petroleum ether to remove the Dowtherm followed by a linear gradient of increasing concentration of ethyl acetate in petroleum ether to elute the product. Fractions containing the product were concentrated in vacuo to afford 15 g (68%) of a yellow solid as the title compound. $^1$H NMR (400 MHz, DMSO-d$_6$) δ ppm: 1.36 (t, J=7.2, 7.2 Hz, 3H), 4.38 (q, J=7.2, 6.8 Hz, 2H), 6.86 (q, J=2.8, 6.4 Hz, 1H), 6.99 (q, J=7.2, 6.8 Hz, 1H), 7.96 (q, J=1.6, 3.2 Hz, 1H), 8.32 (s, 1H), 12.1 (s, 1H). LCMS (Condition D): m/z 207+ve.

Step 5A: 4-Chloropyrrolo[1,2-b]pyridazine-3-carboxylic acid (Preparation 1) and 4-Ethyl chloropyrrolo[1,2-b]pyridazine-3-carboxylate (Preparation 2)

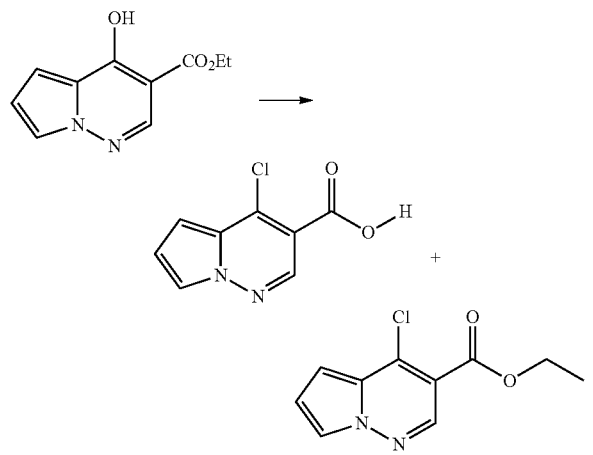

Slurried ethyl 4-hydroxypyrrolo[1,2-b]pyridazine-3-carboxylate (0.296 g, 1.44 mmol) in POCl$_3$ (2.68 mL, 28.7 mmol) and added triethylamine (0.40 mL, 2.87 mmol) dropwise at rt giving a cloudy yellow mixture. This mixture was heated to 110° C. for 10 h, followed by cooling to rt and slowly adding dropwise to crushed ice (~60 mL volume). The resulting mixture was allowed to stir at rt for ~6 h and the resulting solids were collected by vacuum filtration, rinsed with water (5 mL) and air dried in the funnel for ~3 h affording 246 mg (87%) of a brown solid as an ~4:1 mixture of the title compounds, Preparation 1 and Preparation 2, respectively. Material was used as a mixture without any further purification. HPLC (Conditions B): Retention times=2.59 min (Preparation 1) and 3.47 min (Preparation 2). LCMS (Conditions B): Preparation 1 (m/z=197.1, 199.0), Preparation 2 (m/z=225.1, 227.0).

Step 5B: Alternative preparation of Ethyl 4-chloropyrrolo[1,2-b]pyridazine-3-carboxylate (Preparation 2)

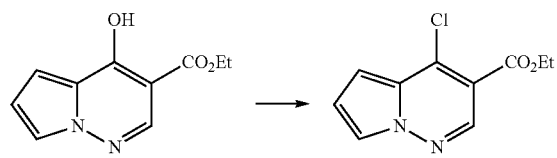 [SMILES: CCOC(=O)c1cnn2cccc2c1O ; CCOC(=O)c1cnn2cccc2c1Cl]

To POCl$_3$ (225 mL, 2.42 mmol) at 0° C. was added ethyl 4-hydroxypyrrolo[1,2-b]pyridazine-3-carboxylate (50 g, 0.242 mmol) and the mixture was stirred until complete dissolution. At this time, triethylamine (36.8 mL, 0.266 mmol) was added dropwise and the resulting mixture was heated to 110° C. and allowed to stir for ~16 h. The resulting mixture was allowed to cool and the POCl$_3$ was removed in vacuo to afford a dark brown residue. This material was dissolved in dichloromethane and was cooled to 0° C. and diluted with 375 mL of ethanol. The resulting mixture was stirred at 0° C. for 30 min and then at rt for 1 h. The ethanol was removed under vacuum and the resulting semi-solid was dissolved in dichloromethane and stirred with 10% aqueous NaHCO$_3$ for 1 h. The mixture was filtered through celite and the phases were separated. The aqueous portion was extracted with additional dichloromethane and the combined organic layers were washed with brine, dried over Na$_2$SO$_4$, decanted and the solvent was removed under vacuum to give the crude product. The crude material was purified by flash silica gel column chromatography to yield 47 g (86%) of a solid as the title compound. $^1$H NMR (400 MHz, CDCl$_3$) δ ppm: 1.43 (t, J=7.2, 6.8 Hz, 3H), 4.43 (q, J=7.2, 6.8 Hz, 2H), 6.940-6.99 (m, 2H), 7.84 (q, J=0.8, 1.6 Hz, 1H), 8.51 (s, 1H).). $^{13}$C-NMR (400 MHz, DMS-d$_6$) ppm: 163.30, 141.89, 138.16, 124.86, 120.69, 114.99, 109.90, 105.22, 61.55, 14.21. LCMS (conditions A): m/z 225. HPLC (condition B): Retention time=3.47 min.

Step 6: Alternative preparation of 4-chloropyrrolo[1,2-b]pyridazine-3-carboxylic acid (Preparation 1)

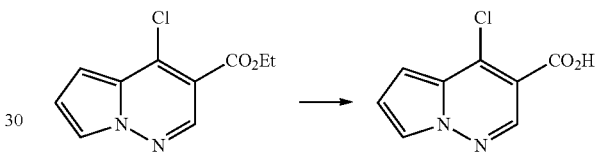

Dissolved ethyl 4-chloropyrrolo[1,2-b]pyridazine-3-carboxylate (Preparation 2 from Step 5B, 2 g, 8.90 mmol) in THF (12 mL) and added water (2 mL) followed by monohydrated lithium hydroxide (0.747 g, 17.81 mmol) and the resulting yellow mixture was sonicated to give a fine dispersion followed by heating to 55° C. and stirring vigorously for one hour. After removing the organics under vacuum, the resulting residue was dissolved in ~50 mL of water and 6 N aqueous HCl added until acidic giving a yellow slurry of the product. The product was extracted with ethyl acetate, washed with brine, dried over Na$_2$SO$_4$, decanted and conc. in vacuo to afford 1.8 g (~quant.) of a yellow solid as the title compound. LCMS (condition B): m/z=197.1, 199.0. HPLC (condition B): Retention time=2.59 min.

Preparation 3

4-chloropyrrolo[1,2-b]pyridazine-3-carboxamide

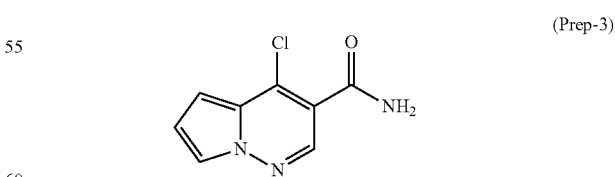

To POCl$_3$ (450 mL, 4.85 mmol) at 0° C. was slowly added ethyl 4-hydroxypyrrolo[1,2-b]pyridazine-3-carboxylate (from step 4 of Preparations 1 and 2, 100 g, 0.484 mmol) and the resulting mixture was stirred until complete dissolution. At this time, triethylamine (73.7 mL, 0.532 mmol) was added dropwise and the resulting mixture was heated at 110° C. for ~16 h. After cooling to rt, the mixture was carefully concentrated in vacuo and the resulting dark brown residue was dissolved in dichloromethane and cooled to 0° C. This solution was carefully purged with ammonia gas for ~45 min. And then it was allowed to stir at rt for 1 h. The solvent was removed under vacuum and the residue was diluted with ethyl acetate and water and the mixture was filtered through Celite. The organic portion was separated, and aqueous was extracted with ethyl acetate. The combined organic portions were dried over anhyd. sodium sulfate and concentrated under vacuum to afford a semi-solid which was dissolved in ethyl acetate and diluted with petroleum ether to precipitate a solid which was collected by filtration and dried to afford 30 g (69%) of a solid as the title compound. $^1$H NMR (400 MHz, DMSO-$d_6$) δ ppm: 6.86 (q, J=1.6, 5.2 Hz, 1H), 7.03 (q, J=2.4, 2.0 Hz, 1 H), 7.83 (s, 1H), 7.99 (s, 1H), 8.06 (q, J=2.4, 1.2 Hz, 1H), 8.27 (s, 1H). $^{13}$C-NMR (400 MHz, DMS-$d_6$) ppm: 165.25, 141.39, 132.01, 123.84, 120.09, 117.68, 115.11, 102.47. LCMS (condition H): m/z 195.

Alternative preparation of 4-chloropyrrolo[1,2-b]pyridazine-3-carboxamide (Preparation 3)

Slurried 4-chloropyrrolo[1,2-b]pyridazine-3-carboxylic acid (Preparation 1 from Step 6, 0.4 g, 2.04 mmol) in dichloromethane (6 mL) and cooled in ice bath and successively added oxalyl chloride (0.534 mL, 6.10 mmol) and DMF (0.01 mL, 0.129 mmol). Allowed slurry to warm to rt and stir for 1.5 h giving a clear, yellow-green solution. The reaction was concentrated under vacuum to yield a yellow solid which was redissolved in dichloromethane (10 mL) and reconcentrated to remove all residual oxalyl chloride. This solid was dissolved in dichloromethane (6 mL) and the solution was added dropwise via pipette into a well-stirred ammonia in dichloromethane solution (prepared by extracting 15 mL of conc aq ammonium hydroxide with 3×10 mL portions of dichloromethane) at 0° C. After stirring for 1.5 h at 0° C., water was added to dissolve most solids (~15 mL) and the layers were separated and the aqueous portion was extracted with additional dichloromethane. The combined extracts were washed with brine, dried over anhyd. $Na_2SO_4$, decanted and concentrated on rotovap to yield 370 mg (93%) of a yellow solid as the title compound. Material was used as is without any further purification. LCMS (condition B): m/z 195, 197. HPLC (condition B): retention time=1.75 min.

Preparation 4

Ethyl 3-carbamoyl-4-chloropyrrolo[1,2-b]pyridazine-6-carboxylate

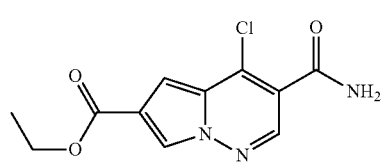
(Prep-4)

Step 1: Ethyl 2-formamidoacetate

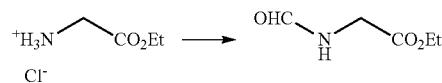

To a 5 L three neck round bottom flask equipped with a mechanic stirrer, a pressure-equalizing funnel and a condenser bearing a calcium chloride drying tube was added glycine ethyl ester hydrochloride (500 g, 3.583 mol) and methyl formate (1.8 L). The suspension was brought to reflux and triethylamine (556 mL) was added to the reaction. The reaction was stirred and refluxed overnight. The reaction was cooled to room temperature and filtered through a Buchner funnel to remove triethylamine hydrochloride salt. The filtrate was concentrated and dried over high vacuum to yield 320 g (93%) of the title compound.

Step 2: Ethyl 2-isocyanoacetate

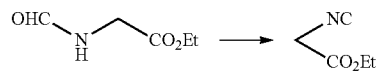

To a round bottom flask was added ethyl 2-formamidoacetate (600 g, 4.5 mol), dry $CH_2Cl_2$ (6 L) and triethylamine (1.512 kg). The reaction mixture was cooled to −10° C. and then $POCl_3$ (700 g) was added dropwise at −10° C. After the addition, the reaction was stirred at 0° C. for additional 1 hour. The reaction was cooled to −20° C. and slowly was saturated sodium carbonate solution (3.6 L) added to the reaction. After the addition, the reaction was brought to room temperature and was stirred at room temperature for 0.5 hr. Then the organic layer was separated and the aqueous layer was extracted with $CH_2Cl_2$ (2×3 L). The combined organic layer was washed with brine and dried over anhydrous $K_2CO_3$ solid. The solution was filtered and concentrated at 45° C. to yield 560 g (96%) title compound. $^1$H NMR (400 MHz, $CDCl_3$) δ ppm: 8.2 (1H, s), 6.9 (1H, br s), 4.14 (2H, q, J=4 Hz), 3.91 (2H, d, J=6.4 Hz), 1.19 (3H, t, J=4 Hz).

Step 3: Diethyl 1H-pyrrole-2,4-dicarboxylate

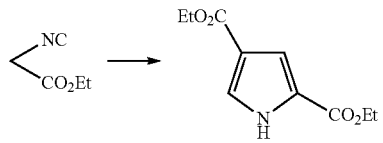

To a round bottom flask under argon was added ethyl 2-isocyanoacetate (100 g, 0.884 mol), dry THF (1.0 L) followed by DBU (132 g, 0.867 mol). The reaction was cooled to 0° C. and formaldehyde (16 g) was added portionwise into the reaction mixture. The reaction was then stirred at room temperature overnight. Then THF was removed under high vacuum and the residue as dissolved with water and extracted with EtOAc (2×1 L). The combined organic layer was washed with water and brine and concentrated. The residue was purified by flash silica gel column chromatography to yield 40 g (26%) of a white solid as the title compound. $^1$H NMR (400 MHz, $CDCl_3$) δ ppm: 9.85 (1H, br s), 7.54 (1H, m), 7.30 (1H, m), 4.36-4.6 (4H, merging quartets), 1.37-1.26 (6H, merging triplets). LCMS (condition A): m/z=210.2−ve.

Step 4: Diethyl 1-amino-1H-pyrrole-2,4-dicarboxylate

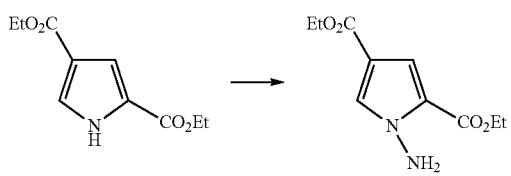 [SMILES: CCOC(=O)c1c[nH]c(C(=O)OCC)c1 ; CCOC(=O)c1cc(C(=O)OCC)n(N)c1]

To a flask was added MTBE (2 L) and ammonium chloride (60 g, 1.13 mol). The reaction was cooled to −20° C. Then concentrated aq ammonium hydroxide (160 mL) was added to the reaction followed by slow addition of commercial-grade sodium hypochlorite solution (149 g, 1.5 L). After addition, the reaction was stirred at −20° C. for additional 30 minutes. The MTBE layer was separated and washed with brine and dried over $Na_2SO_4$. In a separate flask under nitrogen was added diethyl 1H-pyrrole-2,4-dicarboxylate (40 g, 190 mmol) and dry DMF (400 mL). The reaction was cooled to 0° C. whereupon sodium hydroxide (190 mmol) was added portionwise to the reaction. The reaction was stirred at 0° C. for additional 1 hour before it was cooled to −20° C. At this time, the previously prepared MTBE solution of chloramine was added slowly to the reaction and the reaction was stirred at −20° C. for 1 hour. The reaction was quenched with saturated sodium hyposulfite solution. The organic layer of the reaction was separated and washed with water and brine, dried over sodium sulfate, filtered and concentrated to yield 40 g (95%) of the title compound. $^1$H NMR (400 MHz, $CDCl_3$) δ ppm: 7.48 (1H, d, J=1.6 Hz), 7.24 (1H, d, J=1.6 Hz), 5.65 (2H, s), 4.32-4.23 (4H, merging quartets), 1.367-1.32 (6H, merging triplets). LCMS (condition A) m/z=227.2+ve.

Step 5: Ethyl 3-cyano-4-hydroxypyrrolo[1,2-b]pyridazine-6-carboxylate

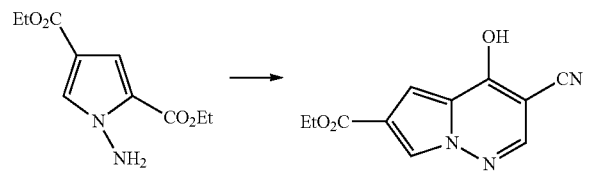 [SMILES: CCOC(=O)c1cc(C(=O)OCC)n(N)c1 ; CCOC(=O)c1cc2c(O)c(C#N)cnn2c1]

To a round bottom flask was added diethyl 1-amino-1H-pyrrole-2,4-dicarboxylate (40 g, 177 mmol), diethoxypropionitrile (53 mL) and pTSA (10 g, 0.052 mmol). The reaction was heated at 125° C. for 3 hours and the EtOH was removed. The reaction was cooled to room temperature before DBU (30 g, 340 mmol) was added. The reaction was then heated at 80° C. for 2 hours. The reaction was cooled to room temperature and diluted with $CH_2Cl_2$. The mixture was washed with 5% citric acid solution (2×), water and brine solution. The organic layer was concentrated and the residue was purified by flash silica gel column chromatography (10% MeOH in $CHCl_3$) to yield 20 g (50%) of the title compound as a brown oil. LCMS (condition A): m/z=230.2−ve. $^1$H NMR (400 MHz, $CDCl_3$) δ ppm: 9.53 (1H, br s), 8.32 (1H, s), 7.75 (1H, s), 6.75 (1H, s), 4.25 (2H, q), 1.28 (3H, t).

Step 6: Ethyl 4-chloro-3-cyanopyrrolo[1,2-b]pyridazine-6-carboxylate

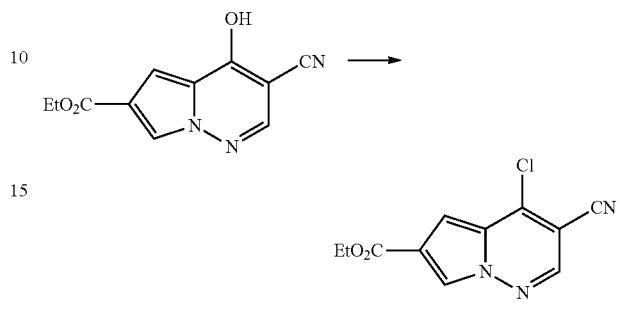

To a round bottom flask was added $POCl_3$ (200 mL) and ethyl 3-cyano-4-hydroxypyrrolo[1,2-b]pyridazine-6-carboxylate (20 g, 80 mmol). The reaction was heated under nitrogen at 75° C. for 2 hours. The reaction was cooled to room temperature and $POCl_3$ was removed under vacuum. The residue was poured onto ice-water. The aqueous solution was extracted with $CH_2Cl_2$. The organic layer was washed with saturated sodium carbonate solution, dried and concentrated. The resulting residue was purified by flash silica gel column chromatography to yield 10 g (48%) of the title compound as a yellow solid. $^1$H NMR (400 MHz, $CDCl_3$) δ ppm: 8.33 (1H, d, J=1.3 Hz), 8.11 (1H, s), 7.41 (1H, d, J=1.6 Hz), 4.41 (2H, q, J=6.8 Hz), 1.41 (3H, t, J=6.8 Hz).

Step 7: Ethyl 3-carbamoyl-4-chloropyrrolo[1,2-b]pyridazine-6-carboxylate

To a round bottom flask was added concentrated $H_2SO_4$ (100 mL) followed by ethyl 4-chloro-3-cyanopyrrolo[1,2-b]pyridazine-6-carboxylate (10 g, 40 mmol). The reaction was stirred at room temperature under nitrogen overnight. The reaction mixture was poured onto ice cold saturated sodium carbonate solution. The aqueous solution was extracted with EtOAc (4×) and the combined organic layer was concentrated to yield 7 g (70%) of the title compound as a yellow solid. HPLC (condition S): retention time=8.04 min. LCMS (condition A): m/z=268.0+ve. $^1$H NMR (400 MHz, $CDCl_3$) δ ppm: 8.49 (1H, d, J=1.6 Hz), 8.40 (1H, s), 8.08 & 7.98 (1H, two br s), 7.12 (1H, d, J=1.6 Hz), 4.34 (2H, q, J=7.2 Hz), 1.34 (3H, t, J=7.2 Hz).

Preparation 5

6-bromo-4-chloropyrrolo[1,2-b]pyridazine-3-carboxamide (Prep-5)

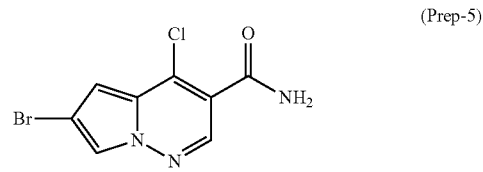

Step 1: 1-(4-Bromo-1H-pyrrol-2-yl)-2,2,2-trichloroethanone

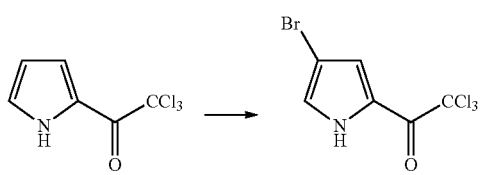

To a 100 mL 3-neck round bottom equipped with a dropping funnel was added trichloroacetyl pyrrole (50 g, 236.4 mmol) and CCl$_4$ (1.0 L). After trichloroacetyl pyrrole was dissolved, the reaction was cooled to 0° C. and iodine (0.176 g) was added to the reaction. At this time, a solution of bromine (12 mL) in CCl$_4$ (100 mL) was added dropwise very slowly to the reaction through a dropping funnel over 20 minutes and the resulting mixture was stirred at 0° C. for additional 20 minutes. The resulting mixture was transferred into a separatory funnel and washed with 10% Na$_2$S$_2$O$_3$ solution, saturated NaHCO$_3$ solution and brine (2×). The organic layer was dried and concentrated to give 50 g (60%) of the title compound as a white solid. LCMS (condition A): m/z=287.8, 289.8, 290.8−ve. $^1$H NMR (400 MHz, CDCl$_3$) δ ppm: 12.8 (1H, br.s), 7.56 (1H, m), 7.33 (1H, m).

Step 2: Methyl 4-bromo-1H-pyrrole-2-carboxylate

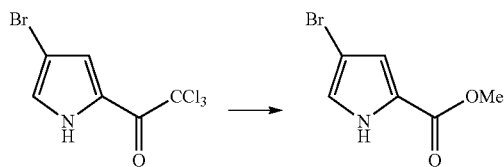

To a dry round bottom flask containing dry MeOH (60 mL) was added sodium (5 g, 257.7 mmol) portionwise. After all the sodium was dissolved, the solution was slowly added to a flask which contained 1-(4-bromo-1H-pyrrol-2-yl)-2,2,2-trichloroethanone (50.0 g, 171.8 mmol) in MeOH (860 mL) through a dropping funnel giving a yellow reaction mixture. After the addition was complete, the reaction was stirred for an additional 10 minutes, then concentrated and cooled in an ice bath. The resulting solid that precipitated was collected by vacuum filtration and washed with water until neutral pH. The solid was dried to yield 25 g (71%) of the title compound as a white solid. LCMS (condition A): m/z=204.0−ve. $^1$H NMR (400 MHz, DMSO-d$_6$) δ ppm: 7.16 (1H, d, 1.2H), 6.89 (1H, d, 1.2H).

Step 3: Methyl 1-amino-4-bromo-1H-pyrrole-2-carboxylate

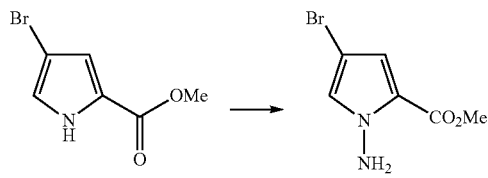 [SMILES: COC(=O)c1cc(Br)c[nH]1 ; COC(=O)c1cc(Br)cn1N]

To a 5 L 3-neck round bottom flask was added conc. NH$_4$OH (2.0 L) and the solution was cooled to −20° C. Ammonia gas was purged into the solution until the volume doubled. In a separate 10 L 3-neck round bottom flask was added solid NH$_4$Cl (87 g) and MTBE (5.0 L) and the mixture was cooled to −5° C. At this time, 555 mL of the previously prepared concentrated NH$_4$OH solution was added to this mixture followed by a slow addition of commercial grade sodium hypochlorite solution (2.0 L) over 60 minutes. After the addition was complete, the reaction was stirred at −5° C. for additional 30 minutes. The MTBE layer was separated and washed with brine (720 mL) and was dried over Na$_2$SO$_4$ and decanted. To a separate 20 L round bottom flask was added methyl 4-bromo-1H-pyrrole-2-carboxylate (100 g, 0.49 mol) and DMF (2.0 L) under nitrogen. Then sodium hydride (60% dispersion in mineral oil, 24 g, 0.58 mol) was added to the reaction portionwise at room temperature. After the addition was complete, the reaction mixture was stirred at room temperature for 45 minutes, cooled to −20° C., and then the previously prepared chloramine solution was added in one portion to the reaction mixture. The resulting mixture was allowed to warm to ambient temperature and stirred for 30 minutes. The reaction mixture was washed with 10% aq. Na$_2$S$_2$O$_3$ solution (720 mL) and the organic layer was separated and washed again with water (720 mL) and brine (720 mL) before drying over Na$_2$SO$_4$, filtering and concentrating under vacuum to afford ~52 g of a semi-solid as the crude product. To this material was added toluene (1.2 L) to give a homogeneous mixture. Methane sulfonic acid (60 g, 0.62 mol) was added dropwise and stirred for 30 minutes. The resulting precipitated solid was collected by vacuum filtration and was rinsed with additional toluene and dried to yield 139 g (90%) of the methane sulfonic acid salt of the title compound. HPLC (condition S): retention time=8.922 min. LCMS (condition A): m/z 218.0−ve. $^1$H NMR (400 MHz, DMSO-d$_6$) δ ppm: 7.21 (1H, d, 2.0 Hz), 6.77 (1H, d, 2.0 Hz), 3.75 (3H, s), 2.50 (3H, s).

Step 4: 6-Bromo-4-hydroxypyrrolo[1,2-b]pyridazine-3-carbonitrile

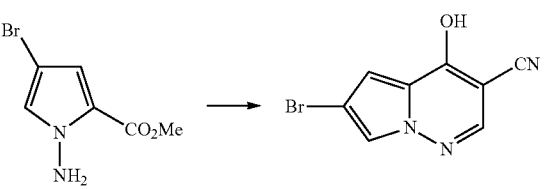 [SMILES: COC(=O)c1cc(Br)cn1N ; N#Cc1cnn2cc(Br)cc2c1O]

To a round bottom flask was added the methane sulfonic acid salt of methyl 1-amino-4-bromo-1H-pyrrole-2-carboxylate (140 g, 0.444 mol), isopropanol (700 mL) and 3,3-diethoxypropionitrile (128 g, 0.888 mol). The reaction mixture was slowly brought to 85° C. over 1 hour and then stirred at 85° C. for 2 hours. At this time, the ethanol that was generated and the isopropanol was removed under vacuum. The resulting residue was dissolved in CH$_2$Cl$_2$ and washed with water and brine solution. The organic layer was separated, dried over Na$_2$SO$_4$, filtered and concentrated. The resulting residue was transferred into a 2 L round bottom flask and dichloroethane (900 mL) and DBU (210 gm, 1.36 mol) were successively added to the reaction mixture. The resulting mixture was then stirred at 85° C. for 5 hours then cooled to rt and diluted with $CH_2Cl_2$ followed by washing with water then brine solution. The organic layer was separated, dried over $Na_2SO_4$, filtered and concentrated. The resulting residue was purified by flash silica gel column chromatography to yield 58 g of title compound as the crude product containing residual DBU. This material was used as is in the next transformation. LCMS (condition A) m/z=236.0–ve. $^1$H NMR (400 MHz, DMSO-$d_6$) δ ppm: 9.76 (1H, br.s), 7.62 (1H, s), 7.39 (1H, d, 2.0 Hz), 6.43 (1H, d, 2.0 Hz). The product is contaminated with DBU and was used directly as such without further purification in the next step.

Step 5: 6-Bromo-4-chloropyrrolo[1,2-b]pyridazine-3-carbonitrile

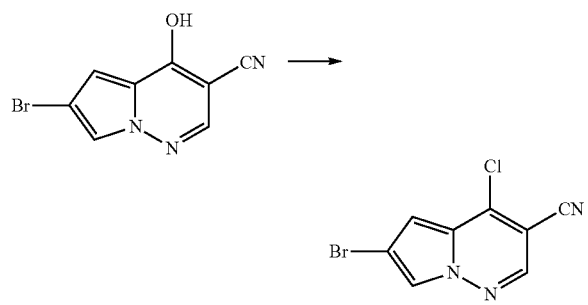

To a 25 mL round bottom flask was added 6-bromo-4-hydroxypyrrolo[1,2-b]pyridazine-3-carbonitrile (16.5 g, 69.47 mmol) and $POCl_3$ (85 mL, 0.88 mol) and the reaction mixture was stirred and heated at 75° C. for 3 hours. The $POCl_3$ was removed under vacuum and the resulting residue was dissolved in $CH_2Cl_2$. The solution was cooled to 0° C. and saturated aq. $NaHCO_3$ solution was added and the biphasic mixture was stirred vigorously while allowing to warm to rt. The organic layer was separated and concentrated and the obtained residue was purified by flash silica gel column chromatography to yield 8.5 g (29%) of the title compound as a yellow solid. HPLC (condition P): retention time=16.74 min. $^1$H NMR (400 MHz, CDCl$_3$) δ ppm: 8.09 (1H, s), 7.94 (1H, d, 2.0 Hz), 7.06 (1H, d, 2.0 Hz).

Step 6: 6-Bromo-4-chloropyrrolo[1,2-b]pyridazine-3-carboxamide (Preparation 5)

To a 50 mL round bottom flask was added 6-bromo-4-chloropyrrolo[1,2-b]pyridazine-3-carbonitrile (12 g, 0.046 mol) and concentrated $H_2SO_4$ (60 mL). The reaction mixture was heated at 55° C. for 2 hours then cooled to room temperature and slowly diluted with ice water to precipitate the product which was collected by vacuum filtration, rinsed with water and dried to yield 11.2 g (89%) of the title compound as a yellow solid. HPLC (condition P): retention time=7.780 min. LCMS (condition C): m/z 274.0, 276.0–ve. $^1$H NMR (400 MHz, DMSO-$d_6$) δ ppm: 8.32 (2H, s), 8.05 (1H, s), 7.90 (1H, s), 7.01 (1H, s).

Preparation 6

4-chloro-6-fluoropyrrolo[1,2-b]pyridazine-3-carboxamide

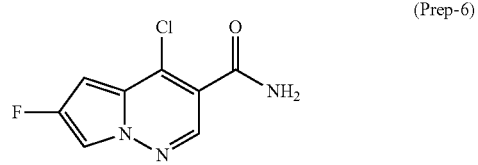 [SMILES: NC(=O)c1cnn2cc(F)cc2c1Cl]

(Prep-6)

Step 1: (R)-1-tert-butyl 2-methyl 4-oxopyrrolidine-1,2-dicarboxylate

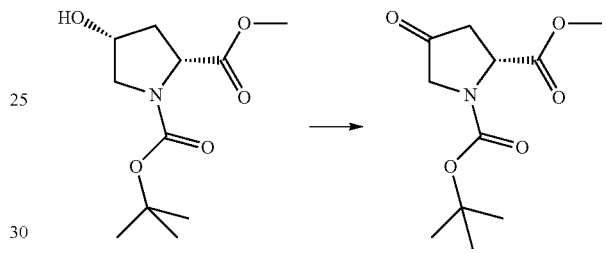

To slurry of pyridinium dichromate (9.97 g, 26.5 mmol) in dichloromethane (60 mL) at rt was added (2R,4R)-1-tert-butyl 2-methyl 4-hydroxypyrrolidine-1,2-dicarboxylate (5.00 g, 20.39 mmol) in several portions. The resulting mixture was stirred overnight at rt. Celite (5 g) was added and the mixture stirred for 40 min, filtered and the filter cake was rinsed with additional dichloromethane (50 mL×3). The resulting filtrate was concentrated and toluene (40 mL) was added followed by concentration again under vacuum to give ~6.5 g of a brown syrup as the crude product. Purification by flash silica gel chromatography (120 g column, EtOAc in Hexane, 0 to 100% gradiant, 85 mL/min) afforded 4.18 g (84%) of the title compound as a white solid. LCMS (condition A): m/z 144 (M-Boc) –ve. $^1$H NMR (400 MHz, CDCl$_3$) δ ppm 4.64-4.89 (1 H, m), 3.84-3.96 (2 H, m), 3.77 (3 H, s), 2.81-3.10 (1 H, m), 2.59 (1 H, dd, J=18.93, 1.76 Hz), 1.52 (9 H, s).

Step 2: (R)-1-tert-butyl 2-methyl 4,4-difluoropyrrolidine-1,2-dicarboxylate

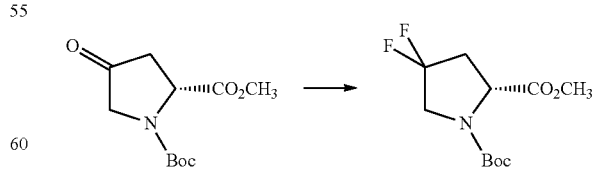

DAST (2.74 mL, 20.72 mmol) was added dropwise to a stirred solution of (R)-1-tert-butyl 2-methyl 4-oxopyrrolidine-1,2-dicarboxylate (1.68 g, 6.91 mmol) in dichloroethane (20 mL) at rt and the resulting mixture was heated at 60° C. for 3 h. After cooling to rt, the mixture was slowly quenched with sat. Aq. sodium bicarbonate (60 mL) and extracted with ethyl acetate (300 mL). The extracts were washed with brine and dried over magnesium sulfate, filtered, and concentrated to give 6.90 g of the crude product as a brown oil. This material was purified by flash silica gel chromatography (120 g column, EtOAc in Hexane 0 to 100%, 85 mL/min) to afford 4.80 g (76%) of the title compound as a tan oil. LCMS (condition A): m/z 288.0 (M+Na) −ve. $^1$H NMR (400 MHz, MeOD) δ ppm 4.50-4.68 (1 H, m), 3.74-3.96 (5 H, m), 2.88 (1 H, d, J=9.79 Hz), 2.46-2.62 (1 H, m), 1.40-1.60 (9 H, m).

Step 3: (R)-methyl 4,4-difluoropyrrolidine-2-carboxylate

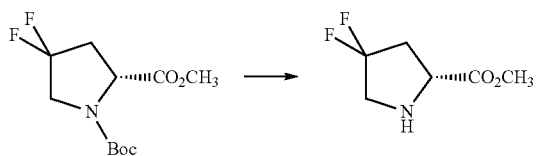 [SMILES: COC(=O)[C@H]1CC(F)(F)CN1C(=O)OC(C)(C)C ; COC(=O)[C@H]1CC(F)(F)CN1]

To solution of (R)-1-tert-butyl 2-methyl 4,4-difluoropyrrolidine-1,2-dicarboxylate (4.33 g, 16.32 mmol) in dichloromethane (30 mL) was added trifluoroacetic acid (12.58 mL, 163 mmol) and the resulting mixture was stirred at rt for 5 h, then concentrated and sat. aqueous sodium bicarbonate (50 mL) was added followed by stirring for 20 min before extracting with diethyl ether (40 mL×3). The combined extracts were washed with brine and dried over sodium sulfate, filtered, and concentrated at rt (note: product is volatile) to afford 2.0 g (74%) of the title compound as a light tan oil that was used directly in the next transformation without any further purification. $^1$H NMR (400 MHz, MeOD) δ ppm 4.03 (1 H, dd, J=8.80, 6.82 Hz), 3.77 (3 H, s), 3.22-3.32 (1 H, m), 3.07-3.23 (1 H, m), 2.51-2.69 (1 H, m), 2.30-2.50 (1 H, m).

Step 4: methyl 4-fluoro-1H-pyrrole-2-carboxylate

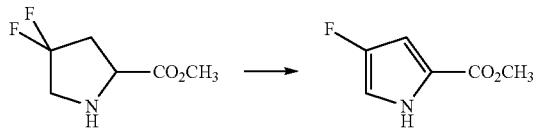 [SMILES: COC(=O)C1CC(F)(F)CN1 ; COC(=O)c1cc(F)c[nH]1]

To solution of (R)-methyl 4,4-difluoropyrrolidine-2-carboxylate (2.00 g, 12.11 mmol) in THF (40 mL) was added manganese dioxide (8.42 g, 97 mmol) and the resulting mixture was heated at reflux (oil bath temp ~70° C.) for 3 h. After cooling to rt, the reaction mixture was filtered through a pad of Celite, rinsed with additional THF (20 mL×4), and DCM (40 mL×4) and the resulting filtrate was concentrated under vacuum to afford a dark brown oil as the crude product which was purified via flash silica gel chromatography (eluent: CH$_2$Cl$_2$/MeOH, 0-10%) to afford 0.98 g (56%) of the title compound as a white solid. HPLC (condition B): retention time=1.71 min. LCMS (condition B): m/z 144+ve. $^1$H NMR (400 MHz, MeOD) δ ppm 6.81 (1 H, dd, J=3.63, 1.87 Hz), 6.59 (1 H, d, J=1.32 Hz), 3.86 (3 H, s).

Step 5: methyl 1-amino-4-fluoro-1H-pyrrole-2-carboxylate

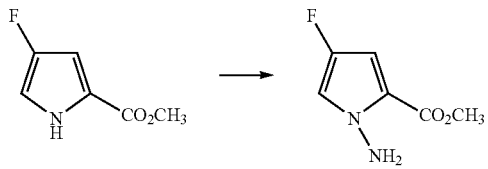 [SMILES: COC(=O)c1cc(F)c[nH]1 ; COC(=O)c1cc(F)cn1N]

A mixture of ammonium chloride (6.0 g, 112 mmol) in diethyl ether (220 mL) was cooled to −5° C., and concentrated aq. ammonium hydroxide (9.4 mL) was added dropwise with vigorous stirring. After the addition was complete, commercial grade aq. sodium hypochlorite solution (145 mL) was added via addition funnel at a rate such that the internal temperature was maintained below 0° C. The mixture was then stirred for 15 min, then the layers were separated, and the organic layer was washed with brine and dried over anhyd. calcium chloride. The resulting solution of chloramine was used directly as follows: In a separate flask, containing a solution of methyl 4-fluoro-1H-pyrrole-2-carboxylate (0.98 g, 6.85 mmol) in DMF (15 mL) at 0° C. was added 60% sodium hydride dispersion (0.329 g, 8.22 mmol) and the resulting mixture was allowed to warm to rt and stir for 45 minutes. At this time, a portion of the previously prepared chloramine solution (55 mL) was added via syringe over ~1 minute. After stirring for an additional 1.5 h at rt, the reaction mixture was quenched by adding sat. aq. Na$_2$S$_2$O$_3$ followed by diluting with water and extracting with diethyl ether (100 mL×2). The combined extracts were dried over anhyd. sodium sulfate, filtered and concentrated under vacuum to afford 0.98 g (91%) of the title compound as a light tan oil. HPLC (condition B): retention time=1.57 min. LCMS (condition B): m/z 159+ve. $^1$H NMR (400 MHz, MeOD) δ ppm 6.86 (1 H, d), 6.51 (1 H, d, J=2.42 Hz), 3.85 (3 H, s).

Step 6: ethyl 6-fluoro-4-hydroxypyrrolo[1,2-b]pyridazine-3-carboxylate

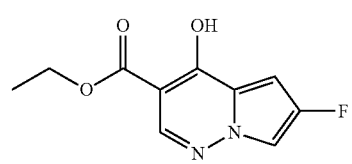

A mixture of methyl 1-amino-4-fluoro-1H-pyrrole-2-carboxylate (0.980 g, 6.20 mmol), (E)-ethyl 3-ethoxyacrylate (1.25 g, 8.68 mmol) and toluenesulfonic acid (0.059 g, 0.310 mmol) in ethanol (15 mL) was heated at 85° C. for 2 h then at reflux (100° C. bath) for an additional 2 h. The mixture was cooled and concentrated to remove the ethanol/water and additional ethanol was added and reconcentrated. The process was repeated until all of the water had been removed then residue was dissolved in ethanol (15 mL) and sodium tert-butoxide (1.190 g, 12.39 mmol) was added to make orange clear solution. This mixture was heated at 85° C. for 1 h, then cooled and concentrated to remove the ethanol and the reaction mixture was neutralized with HCl in dioxane (0.5 mL of 4N solution) then concentrated to afford a tan semi solid. This material was slurried in water and stirred for 1 h and the resulting solid was collected and rinsed with water and filtered and dried to afford the title compound (740 mg, 3.30 mmol, 53.3% yield) as a light yellow solid. HPLC (condition B): retention time=3.57 min. LCMS (condition B): m/z 224.9+ve.

Step 7: 6-fluoro-4-hydroxypyrrolo[1,2-b]pyridazine-3-carboxylic acid

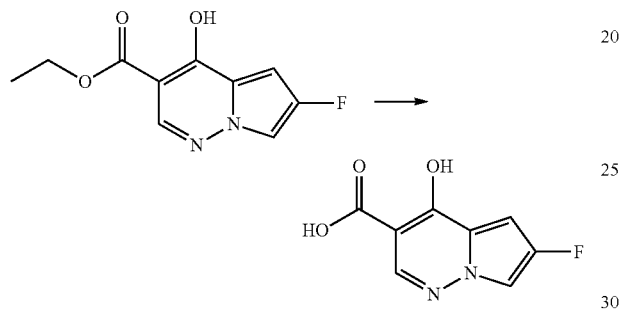

To a solution of ethyl 6-fluoro-4-hydroxypyrrolo[1,2-b]pyridazine-3-carboxylate (700 mg, 3.12 mmol) in methanol (3 mL) and THF (3 mL) was added 3 N aq. sodium hydroxide (5.20 mL, 15.61 mmol) and the resulting mixture was stirred at 65° C. for 3 h. The mixture was cooled and concentrated to remove the methanol and THF and the obtained residue was cooled in an ice bath and 3N aq. HCl was added dropwise with stirring until pH of the mixture was ~2. The resulting slurry was stirred for 30 min, and filtered to collect the solid. The solid was rinsed with water and dried to afford 550 mg (90%) of the title compound as a white solid. HPLC (condition B): retention time=2.37 min. LCMS (condition B): m/z 197+ve.

Step 8: 4-chloro-6-fluoropyrrolo[1,2-b]pyridazine-3-carboxamide

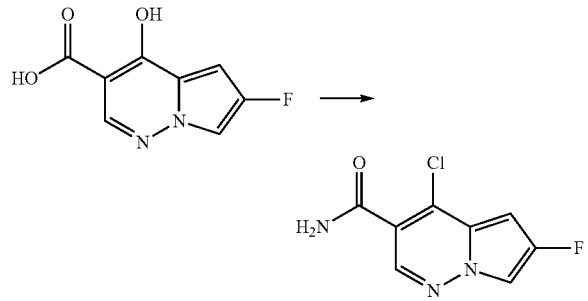

To a slurry of 6-fluoro-4-hydroxypyrrolo[1,2-b]pyridazine-3-carboxylic acid (0.400 g, 2.039 mmol) in POCl$_3$ (15.64 g, 102 mmol) was added diisopropylethylamine (0.39 mL, 2.24 mmol) and the resulting mixture was heated at 120° C. for 3 h with stirring. The reaction was cooled to rt and concentrated to remove the excess POCl$_3$ and the resulting residue was dissolved in dichloromethane (15 mL) and reconcentrated and the process was repeated 2 more times to afford a brown oil. This material was dissolved in dichloromethane (10 mL) and the solution was added dropwise via pipette into a 0° C. well stirred solution of ammonia in dichloromethane (~100 mL, prepared by extracting 100 mL of conc. Aq ammonium hydroxide with 3×30 mL portions of dichloromethane). After the addition was complete, the mixture was concentrated under vacuum and water was added to give a slurry which was filtered to collect the precipitated solid. The solid was rinsed with additional water and dried to afford 355 mg (81%) of the title compound as a yellow solid. HPLC (condition B): retention time=2.05 min. LCMS (condition B): m/z 197+ve.

Preparation 7

4,6-dichloropyrrolo[1,2-b]pyridazine-3-carboxamide

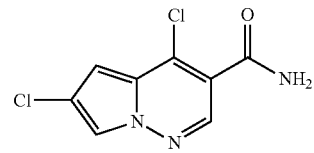

(Prep-7)

Step 1: Ethyl 4-chloro-1H-pyrrole-2-carboxylate

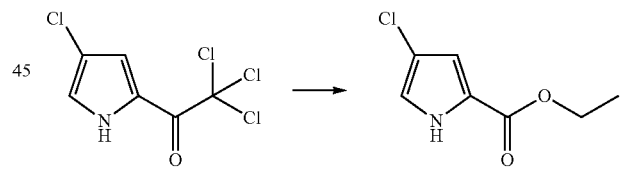

Sodium (0.168 g, 7.29 mmol) was dissolved in anhydrous ethanol (10 mL) then 2,2,2-trichloro-1-(4-chloro-1H-pyrrol-2-yl)ethanone (1.50 g, 6.08 mmol) was added in small portions and the resulting dark brown solution was stirred at room temperature for 30 minutes. The reaction mixture was concentrated under vacuum to dryness and the obtained residue was cooled in an ice bath and 3 N aq. HCl (~2 mL) was added slowly and the mixture was extracted with diethyl ether (100 mL×2). The combined extracts were successively washed with water, sat. aqueous sodium bicarbonate and brine, then dried over magnesium sulfate, filtered and concentrated to afford 1.0 g (95%) of the title compound as a tan oil which solidified upon standing. HPLC (condition B): retention time=2.71 min. LCMS (condition B): m/z 174+ve. $^1$H NMR (400 MHz, MeOD) δ ppm 6.97 (1 H, d, J=1.54 Hz), 6.78 (1 H, d, J=1.54 Hz), 4.34 (2 H, q, J=7.19 Hz), 1.39 (3 H, t, J=7.15 Hz).

Step 2: Ethyl 1-amino-4-chloro-1H-pyrrole-2-carboxylate

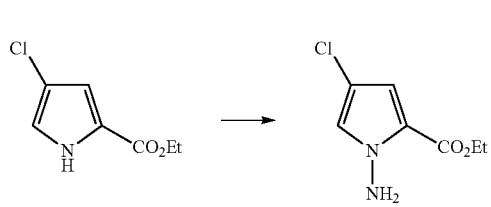 [SMILES: CCOC(=O)c1cc(Cl)c[nH]1 ; CCOC(=O)c1cc(Cl)cn1N]

Prepared using the procedure described in Step 5 of Preparation 5 to afford the title compound as a yellow solid (86% yield). HPLC (condition B): retention time=2.66 min. LCMS (condition B): m/z 189+ve. $^1$H NMR (400 MHz, MeOD) δ ppm 6.99 (1 H, d, J=2.20 Hz), 6.72 (1 H, d, J=2.20 Hz), 4.34 (2 H, q, J=7.04 Hz), 1.38 (3 H, t, J=7.15 Hz).

Step 3: Ethyl 6-chloro-4-hydroxypyrrolo[1,2-b]pyridazine-3-carboxylate

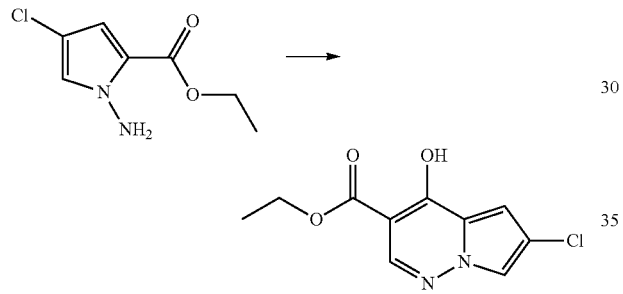

Prepared using the procedure described in Step 6 of Preparation 6 to afford the title compound as a yellow solid (20% yield). HPLC (condition B): retention time=3.88 min. LCMS (condition B): m/z 241+ve.

Step 4: 6-Chloro-4-hydroxypyrrolo[1,2-b]pyridazine-3-carboxylic acid

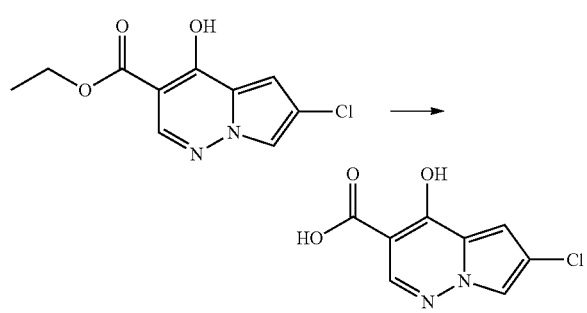

Prepared using the procedure described in Step 7 of Preparation 6 to afford the title compound as a yellow solid (91% yield). HPLC (condition B): retention time=2.25 min. LCMS (condition B): m/z 197+ve.

Step 5: 4,6-Dichloropyrrolo[1,2-b]pyridazine-3-carboxamide

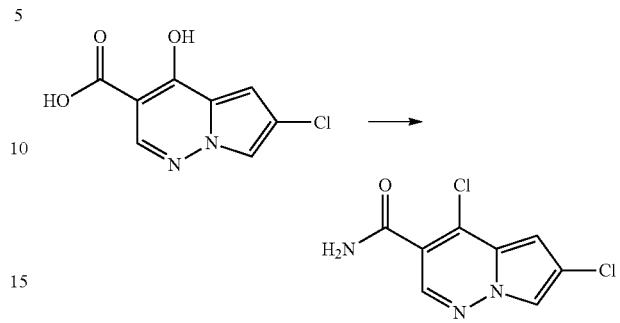

Prepared using the procedure described in Step 8 of Preparation 6 to afford the title compound as a yellow solid (58% yield). HPLC (condition B): retention time=2.61 min. LCMS (condition B): m/z 230.9, 232.9+ve.

Intermediate Procedures and Compounds

Intermediate 1

4-((4-hydroxycyclohexyl)amino)pyrrolo[1,2-b]pyridazine-3-carboxamide

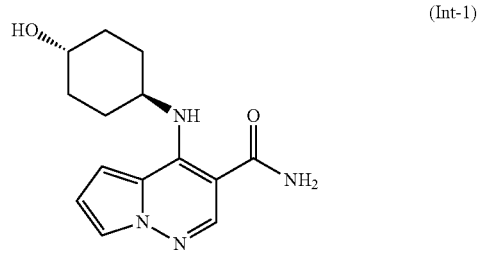 [SMILES: NC(=O)c1cnn2cccc2c1N[C@H]1CC[C@H](O)CC1]

(Int-1)

A solution of 4-chloropyrrolo[1,2-b]pyridazine-3-carboxamide, Preparation 3 (15 mg, 0.077 mmol) and (trans)-4-aminocyclohexanol (22.08 mg, 0.192 mmol) in NMP (0.3 ml) was heated at 80° C. for 1.5 h. The product mixture was diluted with methanol and purified by preparative HPLC (condition A) to afford the title compound as a white solid (17.8 mg, 85% yield). $^1$H NMR (400 MHz, MeOD) δ ppm 1.44-1.56 (m, 4 H) 1.97-2.08 (m, 2 H) 2.17-2.28 (m, 2 H) 3.62-3.76 (m, 1 H) 4.03-4.19 (m, 1 H) 6.69 (dd, J=4.52, 2.76 Hz, 1 H) 6.91 (dd, J=4.77, 1.51 Hz, 1 H) 7.56 (dd, J=2.64, 1.63 Hz, 1 H) 8.10 (s, 1 H). HPLC (method F): ret. Time 2.105 min.; LC/MS [m/z, (M+H)] 275.0.

Intermediates 2 and 3

(E)- and (Z)-4-((5-hydroxyadamantan-2-yl)amino)pyrrolo[1,2-b]pyridazine-3-carboxamide

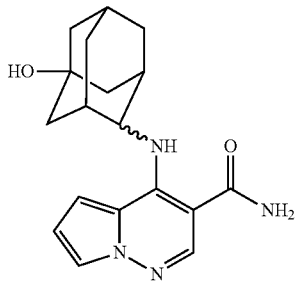 [SMILES: NC(=O)c1cnn2cccc2c1NC1C2CC3CC1CC(O)(C3)C2]

A solution of 4-chloropyrrolo[1,2-b]pyridazine-3-carboxamide (Preparation 3, 50 mg, 0.256 mmol) and a 3:1 mixture of (E)- and (Z)-5-hydroxy-2-adamantamine, respectively (prepared as described in Rhode, J. J. et. Al. *J. Med. Chem.* 2007, 50, 149-164) in NMP (0.50 mL) was heated at 110° C. for 1 hour. HPLC analysis (condition B) of the reaction mixture at this time showed conversion to 2 major products consistent with the expected (E) and (Z) products. After cooling to rt, the resulting mixture was diluted with methanol and was purified by reverse phase preparative HPLC (condition B). Fractions containing the first eluted major product were collected, combined, and concentrated to afford an aqueous slurry of the product. Saturated aq. sodium bicarbonate (~0.1 mL) was added to neutralize the TFA and the resulting aqueous slurry was sonicated. The solid was collected by vacuum filtration and rinsed with water. After drying, 15 mg (18%) of the (E)-isomer of the title compound was obtained as a cream-colored solid. HPLC fractions containing the second eluted major product were worked up similarly to afford 15 mg (18%) of the (Z)-isomer of the title compound as cream-colored solid. (E)-isomer: HPLC (condition B): retention time=2.60 min. LCMS (condition B): m/z 327.2+ve. $^1$H NMR (400 MHz, DMSO-$d_6$) δ ppm 11.19 (1 H, d, J=8.28 Hz), 8.21 (1 H, s), 7.66 (1 H, dd, J=2.64, 1.63 Hz), 6.38-6.86 (2 H, m), 4.53 (1 H, s), 4.22-4.30 (1 H, m), 2.12-2.22 (2 H, m), 2.00-2.12 (1 H, m), 1.76-1.91 (4 H, m), 1.61-1.74 (4 H, m), 1.37-1.50 (1 H, m). (Z)-isomer: HPLC (condition B): retention time=3.17 min. LCMS (condition B): m/z 327.2+ve. $^1$H NMR (400 MHz, DMSO-$d_6$) δ ppm 11.23 (1 H, s), 8.22 (1 H, s), 7.66 (1 H, d, J=1.25 Hz), 6.59-6.87 (2 H, m), 4.55 (1 H, s), 4.07-4.25 (1 H, m), 2.19-2.30 (2 H, m), 2.00-2.14 (1 H, m), 1.74-1.93 (4 H, m), 1.56-1.74 (4 H, m), 1.42-1.55 (2 H, m).

Intermediate 4

(Cis)-4-(5-aminoadamantan-2-yl)amino)pyrrolo[1,2-b]pyridazine-3-carboxamide (Int-4)

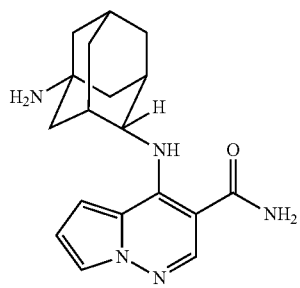

Step 1: 2-adamantanone-5-carboxylic acid

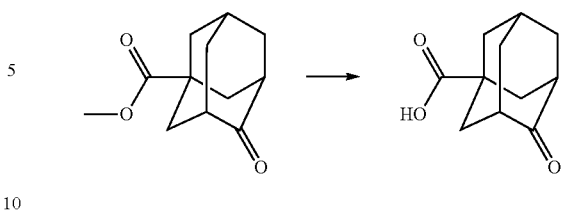

To solution of 1.92 g (9.22 mmol) of methyl-2-adamantanone-5-carboxylate (prepared as in US20050245534) in THF (9 mL) and methanol (3 mL) was added 3 N aq. sodium hydroxide (6.15 mL, 18.4 mmol) and the resulting mixture was stirred at rt for 16 h. The mixture was concentrated to remove the methanol and THF and the resulting residue was cooled in an ice bath and 6N aq HCl was added slowly until pH of mixture was ~1. After stirring for ~30 min, solid was collected by filtration and rinsed with water and partially dried on filter. The resulting solid was then dissolved in dichloromethane (400 mL), dried over anhyd. magnesium sulfate, then filtered, concentrated and dried under vacuum to afford 1.50 g (84%) of the title compound as a white solid. HPLC (condition B): retention time=1.61 min. LCMS (condition B): m/z 193.3+ve.

Step 2: tert-butyl-2-adamantanone-5-carbamate

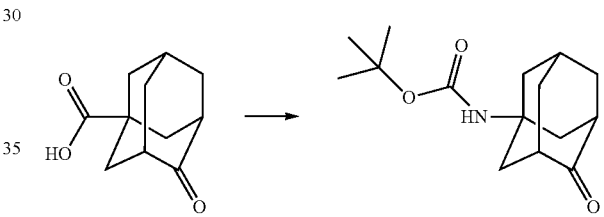

A solution of 2-adamantanone-5-carboxylic acid from the previous step (1.50 g, 7.77 mmol) in thionyl chloride (9 mL, 123 mmol) was heated at 85° C. for 2 h. The reaction mixture was cooled and concentrated to remove excess of thionyl chloride and the resulting residue was dissolved in acetone (8 mL) and cooled in an ice bath. With stirring, a cold solution of sodium azide (2.02 g, 31.1 mmol) in water (8 mL) was added dropwise over 15 minutes. The cold bath was removed and the resulting mixture was allowed to warm to rt and stir for 2 h. At this time, the mixture was diluted with water (30 mL), extracted with ether (3×50 mL) and the combined ether portions were washed with brine, dried over anhyd. sodium sulfate, filtered and concentrated to give 1.57 g of a white solid. This material was dissolved in anhyd. toluene (15 mL) and was slowly added dropwise to refluxing toluene (60 mL) over 30 minutes. After stirring at reflux for an additional 30 min., the solution was cooled to rt and was concentrated to afford a white solid which was redissolved in toluene (10 mL) and potassium tert-butoxide (1.74 g, 15.6 mmol) was added and the resulting slurry was stirred for 16 h at rt. At this time, water (30 mL) was added and the mixture was extracted with ethyl acetate (3×150 mL) and the combined extracts were washed with brine, dried over anhyd. magnesium sulfate, filtered and concentrated to give 1.67 g (81%) of the title compound as a tan oil. $^1$H NMR (400 MHz, MeOD) δ ppm 2.50 (1 H, br. s.), 2.21 (4 H, d, J=2.26 Hz), 2.17 (1 H, br. s.), 2.06 (3 H, d, J=11.54 Hz), 1.92 (4 H, d, J=12.30 Hz), 1.41 (9 H, s).

Step 3: (cis) and (trans)-tert-butyl-(2-benzylamino)-adamantane-5-carbamate

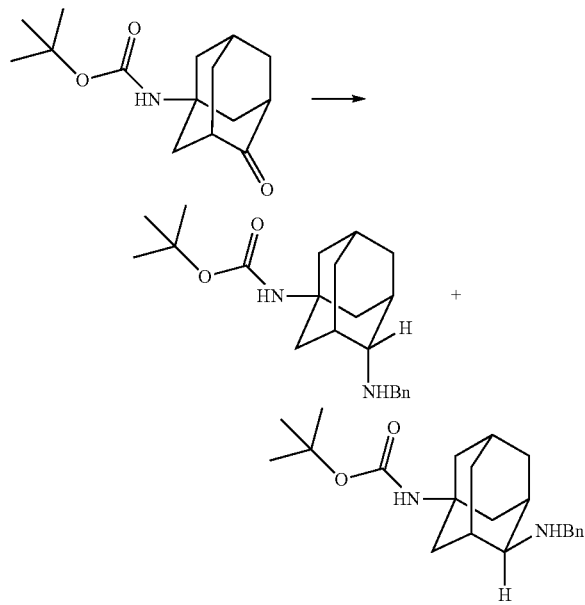

To a solution of tert-butyl-2-adamantanone-5-carbamate from the previous step (1.57 g, 5.92 mmol) in dichloromethane (20 mL) at rt was added benzylamine (0.840 mL, 7.69 mmol) and the resulting mixture was stirred for 10 min. followed by successive addition of sodium triacetoxyborohydride (2.51 g, 11.8 mmol) and acetic acid (3.39 µL, 0.059 mmol). The resulting mixture was allowed to stir at rt for 3 days then 3N aq. sodium hydroxide (15 mL) was added dropwise and the mixture was extracted with ethyl acetate (3×100 mL) and the combined organic portions were washed with brine, dried over anhyd. magnesium sulfate, filtered and concentrated to give 2.66 g of the crude product mixture as a clear oil. This material was purified by chiral SFC preparative chromatography [column=Chiralpak AD-H 25×3 cm, 5 µm; column temperature=30° C.; flow rate=150 mL/min; mobile phase=CO$_2$/MeOH w/0.1% DEA=88:12; injection volume=1.0 mL (conc. 50 mg/mL); detector wavelength=220 nm] to afford 0.56 g (21%) of the cis isomer of the title compound and 0.93 g (35%) of the trans isomer of the title compound as white solids.

Cis isomer: HPLC (condition B): retention time=2.60 min. LCMS (condition E): m/z 357.3+ve. $^1$H NMR (400 MHz, MeOD) δ ppm 7.17-7.43 (5 H, m), 3.76 (2 H, s), 2.65 (1 H, br. s.), 2.05-2.20 (4 H, m), 1.98 (1 H, d, J=2.76 Hz), 1.87 (2 H, br. s.), 1.76 (2 H, d, J=12.05 Hz), 1.69 (2 H, d, J=12.30 Hz), 1.60 (2 H, d, J=12.30 Hz), 1.40 (9 H, s).

Trans isomer: HPLC (condition B): retention time=2.43 min. LCMS (condition E): m/z 357.3+ve. $^1$H NMR (400 MHz, MeOD) δ ppm 7.17-7.39 (5 H, m), 3.75 (2 H, s), 2.74 (1 H, br. s.), 1.83-2.07 (11 H, m), 1.44 (2 H, d, J=12.30 Hz), 1.39 (9 H, s).

Step 4: (cis)-tert-butyl-(2-amino-adamantane)-5-carbamate

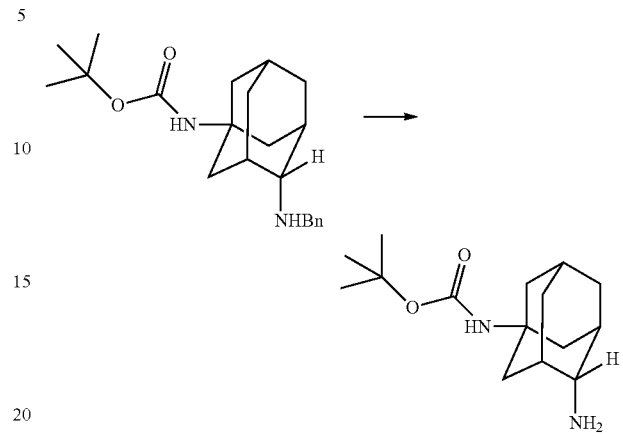

A solution of (cis)-tert-butyl-(2-benzylamino)-adamantane-5-carbamate from the previous step (0.56 g, 1.67 mmol) in ethanol (40 mL) was hydrogenated under 30 psi of hydrogen in the presence of 10% palladium on carbon (0.090 g, 0.084 mmol) for 6 h. At this time, the mixture was purged with argon and filtered through a pad of Celite washing the filter cake with additional ethanol (~50 mL). The clear filtrate was concentrated to afford a colorless oil which solidified upon further concentration under vacuum to afford 0.44 g (98%) of the title compound as a white solid.

Step 5: (Cis)-Ethyl-4-(tert-butyl-5-carbamoyl-adamantan-2-yl)amino)pyrrolo[1,2-b]-pyridazine-3-carboxylate

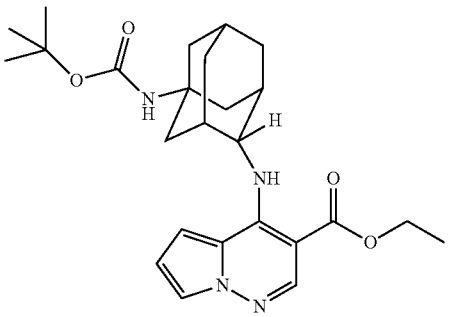 [SMILES: CCOC(=O)c1cnn2cccc2c1NC1C2CC3CC1CC(NC(=O)OC(C)(C)C)(C3)C2]

Dissolved ethyl 4-chloropyrrolo[1,2-b]pyridazine-3-carboxylate (Preparation 2, 0.050 g, 0.223 mmol), (cis)-tert-butyl-(2-amino-adamantane)-5-carbamate from previous step (0.065 g, 0.245 mmol) and diisopropylethylamine (0.078 mL, 0.445 mmol) in NMP (0.3 mL) and heated resulting solution to 100° C. for 4 h. After cooling to rt, water (4 mL) was added and the resulting slurry was stirred for 1 h then the solid was collected by filtration. Drying on the filter afforded 65 mg (64%) of the title compound as a tan solid. HPLC (condition B): retention time=4.30 min. LCMS (condition B): m/z 455.1+ve. $^1$H NMR (400 MHz, MeOD) δ ppm 10.17 (1 H, d, J=7.78 Hz), 8.25 (1 H, s), 7.58 (1 H, dd, J=2.51, 1.51 Hz), 6.87 (1 H, dd, J=4.77, 1.51 Hz), 6.68 (1 H, dd, J=4.64, 2.64 Hz), 4.31 (3 H, q, J=7.03 Hz), 2.39 (2 H, br. s.), 2.18 (1

H, d, J=2.76 Hz), 2.02 (2 H, d, J=12.05 Hz), 1.84 (4 H, t, J=12.17 Hz), 1.77 (2 H, br. s.), 1.65 (2 H, d, J=12.55 Hz), 1.37 (3 H, t, J=7.15 Hz).

Step 6: (C is)-4-(tert-butyl-5-carbamoyl-adamantan-2-yl)amino)pyrrolo[1,2-b]-pyridazine-3-carboxylic acid

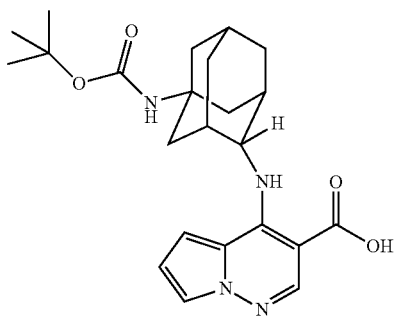 [SMILES: CC(C)(C)OC(=O)NC12CC3CC(C1)C(Nc1c(C(=O)O)cnn4cccc14)C(C3)C2]

To solution of (C is)-Ethyl-4-(tert-butyl-5-carbamoyl-adamantan-2-yl)amino)pyrrolo-[1,2-b]-pyridazine-3-carboxylate from previous step (65 mg, 0.143 mmol) in THF (0.3 mL) and MeOH (0.300 mL) was added 3 N aq sodium hydroxide (0.191 mL, 0.572 mmol) and the mixture was heated at 50° C. for ~20 h. The reaction mixture was concentrated to remove the organic solvents and the resulting aqueous portion was carefully acidified to pH ~2-3 with 1 N aq HCl. After stirring resulting slurry for ~30 min, the precipitated solid was collected by vacuum filtration, rinsed with water and dried on the filter to give 56 mg (92%) of the title compound as a light tan solid. HPLC (condition B): retention time=3.93 min. LCMS (condition B): m/z 427.1+ve. $^1$H NMR (400 MHz, MeOD) δ ppm 10.17 (1 H, d, J=7.78 Hz), 8.25 (1 H, s), 7.58 (1 H, dd, J=2.51, 1.51 Hz), 6.87 (1 H, dd, J=4.77, 1.51 Hz), 6.68 (1 H, dd, J=4.64, 2.64 Hz), 4.31 (3 H, q, J=7.03 Hz), 2.39 (2 H, br. s.), 2.18 (1 H, d, J=2.76 Hz), 2.02 (2 H, d, J=12.05 Hz), 1.84 (4 H, t, J=12.17 Hz), 1.77 (2 H, br. s.), 1.65 (2 H, d, J=12.55 Hz), 1.37 (3 H, t, J=7.15 Hz).

Step 7: (C is)-4-(tert-butyl-5-carbamoyl-adamantan-2-yl)amino)pyrrolo[1,2-b]-pyridazine-3-carboxamide

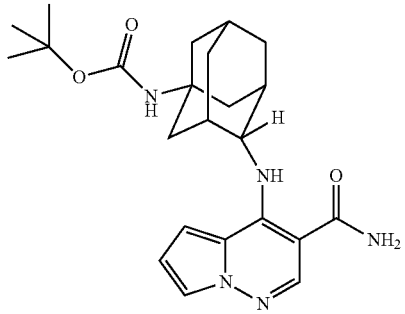 [SMILES: CC(C)(C)OC(=O)NC12CC3CC(C1)C(Nc1c(C(N)=O)cnn4cccc14)C(C3)C2]

(C is)-4-(tert-butyl-5-carbamoyl-adamantan-2-yl)amino)pyrrolo[1,2-b]-pyridazine-3-carboxylic acid from previous step (15 mg, 0.035 mmol), EDCI (8.76 mg, 0.046 mmol) and HOBT (6.46 mg, 0.042 mmol) were dissolved in DMF (0.3 mL) and the resulting solution was stirred at rt for 20 min. followed by addition of 30% aqueous ammonia (10.2 μL, 0.14 mmol) and stirring at rt for an additional 2 h. The reaction mixture was diluted with water (4 mL) and the solid was collected by vacuum filtration, rinsed with water, and dried on the filter to give 10 mg (67%) of the title compound as a light tan solid. HPLC (condition B): retention time=3.82 min. LCMS (condition E): m/z 426.1+ve.

Step 8: (C is)-4-(5-aminoadamantan-2-yl)amino) pyrrolo[1,2-b]pyridazine-3-carboxamide (Intermediate 4)

(C is)-4-(tert-butyl-5-carbamoyl-adamantan-2-yl)amino) pyrrolo[1,2-b]-pyridazine-3-carboxamide from previous step (10 mg, 0.024 mmol) was mixed with a 2.5 M solution of anhyd. HCl in ethanol (0.30 mL, 0.75 mmol) and the resulting mixture was heated at 70° C. for 6 h then cooled to rt. The resulting slurry was diluted with acetonitrile (3 mL), sonicated and the solid was collected by vacuum filtration and rinsed with additional acetonitrile (3×1 mL) to afford 7 mg (78%) of the hydrochloride salt of the title compound as a tan solid. HPLC (condition B): retention time=2.28 min. LCMS (condition E): m/z 326.1+ve. $^1$H NMR (400 MHz, MeOD) δ ppm 8.14 (1 H, s), 7.58 (1 H, dd, J=2.51, 1.51 Hz), 6.86 (1 H, dd, J=4.77, 1.51 Hz), 6.70 (1 H, dd), 4.35-4.45 (1 H, m), 2.40-2.47 (2 H, m), 2.19-2.27 (1 H, m), 2.09-2.19 (2 H, m), 1.97-2.04 (2 H, m), 1.84-1.93 (4 H, m), 1.75-1.83 (2 H, m).

Intermediate 5

(R)-Ethyl 3-carbamoyl-4-((2,2-dimethylcyclopentyl) amino)pyrrolo[1,2-b]pyridazine-6-carboxylate

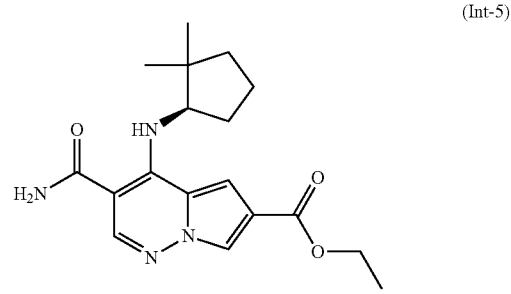 [SMILES: CCOC(=O)c1cc2c(N[C@@H]3CCCC3(C)C)c(C(N)=O)cnn2c1]

(Int-5)

Step 1: (R,E)-N-(2,2-dimethylcyclopentylidene)-1-phenylethanamine

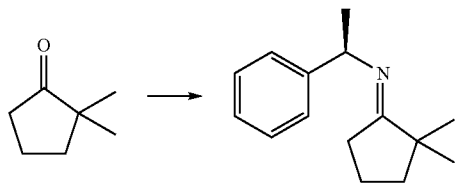

To an ice cold solution of (R)-1-phenylethanamine (3.11 g, 25.7 mmol) and triethylamine (17.9 mL, 128 mmol) in dichloromethane (60 mL) was added dropwise neat titanium tetrachloride (10.7 mL, 10.7 mmol) to afford a light brown mixture. The cold bath was removed and 2,2-dimethylcyclopentanone (2.68 mL, 21.4 mmol) was added and the resulting mixture was allowed to stir at rt for ~16 h. To this mixture was added 75 mL of diethyl ether and the resulting mixture was stirred at rt for 15 min then filtered thru a pad of Celite to remove the solids. The solids were rinsed with additional ether (30 mL×2) and the resulting clear yellow filtrate was concentrated on a rotovap to afford 4.86 g (quantitative) of the title compound as a yellow liquid. HPLC (condition B): retention time=1.58 min. LCMS (condition E): m/z 216+ve.

Step 2: (R)-2,2-dimethyl-N—((R)-1-phenylethyl) cyclopentanamine

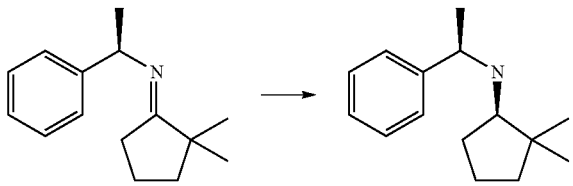 [SMILES: C[C@@H](/N=C1\CCCC1(C)C)c1ccccc1 ; C[C@@H](N[C@@H]1CCCC1(C)C)c1ccccc1]

(R,E)-N-(2,2-dimethylcyclopentylidene)-1-phenylethanamine (4.61 g, 21.4 mmol) in ethanol (50 mL) was cooled to −78° C. and sodium borohydride (0.41 g, 10.7 mmol) was added and the resulting mixture was allowed to stir at −78° C. for 2 h. At this time, the mixture was slowly treated with 6 N aq HCl (15 mL) followed by warming to rt with vigorous stirring. The organics were removed under vacuum and the remaining aqueous portion was cooled and made basic by addition of 10% aq sodium carbonate and the mixture was then extracted with ethyl acetate (3×100 mL). The combined extracts were washed with brine, dried over anhyd. sodium sulfate and the organic was decanted and concentrated on rotovap to yield a yellow liquid as the crude product. This material was purified by flash chromatography on silica gel using ethyl acetate/hexanes mixture as the eluent to afford 3.50 g (75%) of the title compound as a clear oil. HPLC (condition B): retention time=1.90 min. LCMS (condition E): m/z 218+ve. $^1$H NMR (400 MHz, MeOD) δ 7.29-7.41 (4 H, m), 7.20-7.29 (1 H, m), 3.90 (1 H, q, J=6.60 Hz), 2.59 (1 H, dd, J=9.46, 7.92 Hz), 1.66-1.81 (1 H, m), 1.51-1.67 (1 H, m), 1.38-1.50 (3 H, m), 1.37 (3 H, d, J=6.60 Hz), 1.24-1.36 (1 H, m), 1.05 (3 H, s), 0.92 (3 H, s).

Step 3: (R)-2,2-dimethylcyclopentylamine

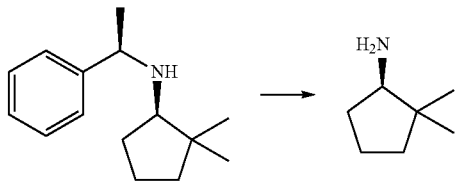

Dissolved (R)-2,2-dimethyl-N—((R)-1-phenylethyl)cyclopentanamine (3.40 g, 15.6 mmol) in 10 mL of methanol and added conc. aq. HCl (1.63 mL, 18.8 mmol) followed by dilution with additional methanol (50 mL) to afford a solution. To this solution was added 20% palladium on carbon (1.1 g, 1.56 mmol) and the reaction flask was purged with hydrogen and allowed to stir under an atmosphere of hydrogen at rt for ~16 h. At this time, an additional 700 mg of catalyst was added and the reaction was allowed to continue for an additional 2 days at rt. The reaction mixture was purged with nitrogen and the mixture was filtered thru Celite to remove the catalyst. The clear filtrate was concentrated to yield a white semi-solid which was dissolved in methanol and reconcentrated to yield a semi-solid. Addition of diethyl ether (25 mL) and sonication provided a slurry which was filtered to collect the solid, rinsed with additional diethyl ether and dried to afford 1.86 g (79%) of the hydrochloride salt of the title compound as a white solid. $^1$H NMR (400 MHz, MeOD) δ ppm 3.13-3.21 (1 H, m), 2.16-2.31 (1 H, m), 1.57-1.92 (5 H, m), 1.14 (3 H, s), 1.05 (3 H, s).

Step 4: (R)-Ethyl 3-carbamoyl-4-((2,2-dimethylcyclopentyl)amino)pyrrolo[1,2-b]pyridazine-6-carboxylate (Intermediate 5)

Prepared by reacting (R)-2,2-dimethylcyclopentylamine with ethyl 3-carbamoyl-4-chloropyrrolo[1,2-b]pyridazine-6-carboxylate (Preparation 4) according to the procedure described in Step 5 of Intermediate 4. HPLC (condition B): retention time=3.67 min. LCMS (condition E): m/z 345+ve. $^1$H NMR (400 MHz, MeOD) δ ppm 10.86 (1 H, br. s.), 8.20 (1 H, s), 8.01 (1 H, d, J=1.76 Hz), 7.38 (1 H, d, J=1.54 Hz), 4.27-4.43 (2 H, m), 4.13-4.29 (1 H, m), 2.29-2.46 (1 H, m), 1.58-1.92 (5 H, m), 1.38 (3 H, t, J=7.15 Hz), 1.13 (3 H, s), 1.10 (3 H, s).

Intermediate 6

(+/−)-4-((cis-3-amino-2,2,3-trimethylcyclopentyl)amino)pyrrolo[1,2-b]pyridazine-3-carboxamide

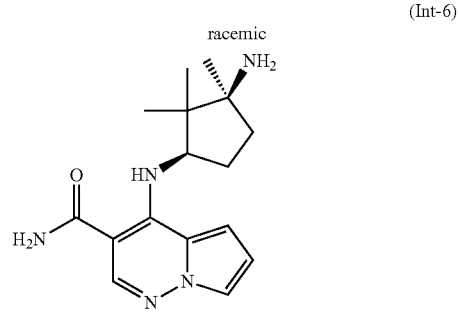 [SMILES: CC1(C)[C@H](Nc2c(C(N)=O)cnn3cccc23)CC[C@]1(C)N]

(Int-6)

A mixture of 4-chloropyrrolo[1,2-b]pyridazine-3-carboxamide (120 mg, 0.613 mmol, from Preparation 3), cis-1,2,2-trimethylcyclopentane-1,3-diamine (175 mg, 1.227 mmol, prepared according to conditions described in *Tetrahedron Asymmetry* 2001, 12, 1579 and *Eur. J. Inorg. Chem.* 2006, 839) and N,N-diisopropylethylamine (0.321 mL, 1.840 mmol) in 1-methyl-2-pyrrolidinone (3 mL) was heated to 100° C. for 2 h. The mixture was cooled to room temperature, diluted with ethyl acetate (100 mL), washed with water, brine, dried (MgSO$_4$), filtered and concentrated. Silica gel chromatography, eluting with dichloromethane/methanol/ammonium hydroxide (90:9:1), gave the title compound (90 mg, 49% yield). $^1$H NMR (400 MHz, methanol-d$_4$) δ ppm 8.12 (1 H, s), 7.56 (1 H, dd, J=2.64, 1.54 Hz), 6.94 (1 H, dd, J=4.73, 1.43 Hz), 6.68 (1 H, dd, J=4.51, 2.75 Hz), 4.23-4.68 (1 H, m), 2.13-2.50 (1 H, m), 1.75-1.94 (2 H, m), 1.58-1.71 (1 H, m), 1.18 (3 H, s), 1.07 (3 H, s), 0.93 (3 H, s); MS (ES+) m/z: 302.3 (M+H); HPLC retention time: 1.775 min (analytical HPLC Method A).

Intermediate 7

(+/−)-4-((cis-3-acetamido-2,2,3-trimethylcyclopentyl)amino)pyrrolo[1,2-b]pyridazine-3-carboxamide

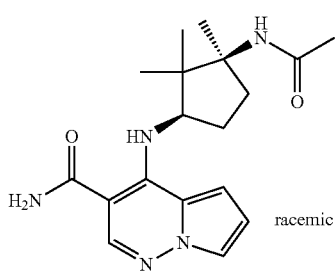
(Int-7)
racemic

Acetyl chloride (7 μL, 0.100 mmol) was added to a mixture of 4-((cis-3-amino-2,2,3-trimethylcyclopentyl)amino)pyrrolo[1,2-b]pyridazine-3-carboxamide (20 mg, 0.066 mmol, from Intermediate 6) and triethylamine (0.028 mL, 0.199 mmol) in dichloromethane (2 mL). After 1 h at room temperature, the mixture was diluted ethyl acetate (60 mL), washed with water, brine, dried (MgSO₄), filtered and concentrated. Silica gel chromatography, eluting with dichloromethane/methanol/ammonium hydroxide (90:9:1), gave the title compound (18 mg, 79% yield). ¹H NMR (400 MHz, chloroform-d) δ ppm 10.58 (1 H, d, J=9.24 Hz), 7.95 (1 H, d, J=2.42 Hz), 7.48-7.78 (1 H, m), 6.85 (1 H, d, J=4.62 Hz), 6.43-6.73 (1 H, m), 5.86 (2 H, br. s.), 5.65 (1 H, s), 4.38-4.67 (1 H, m), 2.56-3.07 (1 H, m), 2.23-2.56 (2 H, m), 2.05 (3 H, s), 1.65-1.92 (1 H, m), 1.45 (3 H, s), 0.91-1.19 (6 H, m); MS (ES+) m/z: 344.3 (M+H); HPLC retention time: 2.726 min (analytical HPLC Method A).

Intermediate 8

(+/−)-4-((cis-3-(benzylamino)-2,2,3-trimethylcyclopentyl)amino)pyrrolo[1,2-b]-pyridazine-3-carboxamide

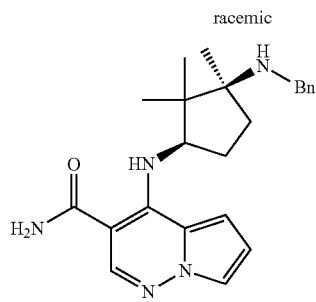
racemic
(Int-8)

Sodium triacetoxyborohydride (35.2 mg, 0.166 mmol) was added to a mixture of 4-((cis-3-amino-2,2,3-trimethylcyclopentyl)amino)pyrrolo[1,2-b]pyridazine-3-carboxamide (20 mg, 0.066 mmol, from Intermediate 6) and benzaldehyde (10 μL, 0.100 mmol) in 1,2-dichloroethane (3 mL). After 15 h at room temperature, additional benzaldehyde (10 μL, 0.100 mmol) and sodium triacetoxyborohydride (35.2 mg, 0.166 mmol) were added. After another 72 h, the mixture was diluted with ethyl acetate (80 mL), washed with water (10 mL), brine (10 mL), dried (MgSO₄), filtered and concentrated. Silica gel chromatography, eluting with dichloromethane/methanol/ammonium hydroxide (90:9:1), gave the title compound (2 mg, 8% yield). ¹H NMR (400 MHz, methanol-d₄) δ ppm 8.11 (1 H, s), 7.56 (1 H, dd, J=2.64, 1.54 Hz), 7.39-7.50 (2 H, m), 7.16-7.37 (3 H, m), 6.94 (1 H, d, J=3.30 Hz), 6.67 (1 H, dd, J=4.51, 2.75 Hz), 4.51 (1 H, t, J=8.25 Hz), 3.69-4.04 (2 H, m), 2.23-2.44 (1 H, m), 1.89-2.11 (1 H, m), 1.73-1.92 (1 H, m), 1.51-1.74 (1 H, m), 1.30 (3 H, s), 1.16 (3 H, s), 1.06 (3 H, s); MS (ES+) m/z: 392.3 (M+H); HPLC retention time: 2.247 min (analytical HPLC Method A).

Intermediate 9

4-(((1R,3S)-3-amino-2,2,3-trimethylcyclopentyl)amino)pyrrolo[1,2-b]pyridazine-3-carboxamide

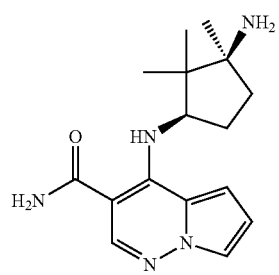
(Int-9)

Following conditions described in Intermediate 1,4-chloropyrrolo[1,2-b]pyridazine-3-carboxamide (80 mg, 0.409 mmol, from Preparation 3) was reacted with (1S,3R)-1,2,2-trimethylcyclopentane-1,3-diamine (116 mg, 0.818 mmol, prepared according to conditions described in *Tetrahedron Asymmetry* 2001, 12, 1579 and *Eur. J. Inorg. Chem.* 2006, 839). Purification with reverse phase HPLC (Sunfire S10 30×250 mm column), eluting with 30-80% solvent B (10% methanol-90% water-0.1% TFA) in solvent A (90% methanol-10% water-0.1% TFA), gave only partially pure product. Further purification with silica gel chromatography, eluting with dichloromethane/methanol/ammonium hydroxide (90:9:1), gave the title compound (34 mg, 27% yield). ¹H NMR (400 MHz, methanol-d₄) δ ppm 8.11 (1 H, s), 7.55 (1 H, dd, J=2.64, 1.54 Hz), 6.92 (1 H, dd, J=4.62, 1.54 Hz), 6.67 (1 H, dd, J=4.62, 2.64 Hz), 4.51 (1 H, t, J=8.36 Hz), 2.20-2.43 (1 H, m), 1.71-1.90 (2 H, m), 1.54-1.70 (1 H, m), 1.17 (3 H, s), 1.06 (3 H, s), 0.91 (3 H, s); MS (ES+) m/z: 302.2 (M+H); HPLC retention time: 1.810 min (analytical HPLC Method A).

Intermediate 10

Ethyl 4-(((1R,3S)-3-amino-2,2,3-trimethylcyclopentyl)amino)-3-carbamoylpyrrolo[1,2-b]pyridazine-6-carboxylate

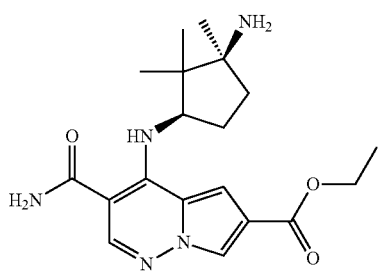
(Int-10)

N,N-Diisopropylethylamine (7.18 mL, 41.1 mmol) was added to a mixture of ethyl 3-carbamoyl-4-chloropyrrolo[1,2-b]pyridazine-6-carboxylate (3.67 g, 13.71 mmol, from Preparation 4), (1S,3R)-1,2,2-trimethylcyclopentane-1,3-diamine (2.93 g, 20.57 mmol, prepared according to conditions described in *Tetrahedron Asymmetry* 2001, 12, 1579 and *Eur. J. Inorg. Chem.* 2006, 839) and N,N-dimethylformamide (50 mL). The mixture was stirred in a 90° C. oil bath for 1 h, quenched with saturated sodium bicarbonate (250 mL) and extracted with ethyl acetate (4×200 mL). The combined extracts were dried (MgSO$_4$), filtered, concentrated and pumped under vacuum. The solid residue was treated with ethyl acetate (60 mL) and sonicated for 10 min. Vacuum filtration gave the first batch of the title compound (2.292 g). The filtrate was concentrated to dryness. The solid residue was treated with dichloromethane (5 mL), ethyl acetate (4 mL) and hexanes (16 mL). The mixture was sonicated for 15 min and filtered. The solid was washed with 20% ethyl acetate in hexanes to give second batch of the title compound (2.146 g). The combined amount of the title compound was 4.438 g (87% yield). $^1$H NMR (500 MHz, methanol-d$_4$) δ ppm 8.19 (1 H, s), 8.00 (1 H, d, J=1.66 Hz), 7.33 (1 H, d, J=1.66 Hz), 4.47 (1 H, t, J=8.18 Hz), 4.35 (2 H, q, J=7.03 Hz), 2.21-2.49 (1 H, m), 1.77-1.93 (2 H, m), 1.63-1.75 (1 H, m), 1.38 (3 H, t, J=7.21 Hz), 1.21 (3 H, s), 1.07 (3 H, s), 0.96 (3 H, s); MS (ES+) m/z: 374.2 (M+H); HPLC retention time: 2.975 min (analytical HPLC Method F).

Intermediates 11 and 12

4-(((1R,3R)-3-amino-2,2,3-trimethylcyclopentyl)amino)pyrrolo[1,2-b]pyridazine-3-carboxamide and 4-(((1S,3R)-3-amino-2,2,3-trimethylcyclopentyl)amino)pyrrolo[1,2-b]pyridazine-3-carboxamide, respectively

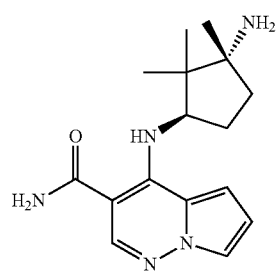
(Int-11)

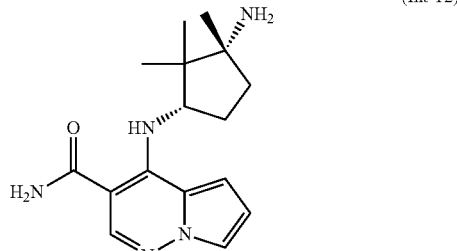
(Int-12)

Step 1: (1R,3S)-dimethyl 1,2,2-trimethylcyclopentane-1,3-dicarboxylate

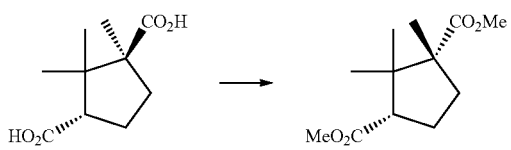

Iodomethane (10.93 mL, 175 mmol) was added to a mixture of (1R,3S)-1,2,2-trimethylcyclopentane-1,3-dicarboxylic acid (10.0 g, 49.9 mmol), potassium carbonate (41.4 g, 300 mmol) and dimethyl sulfoxide (50 mL) in a room temperature water bath. The resultant mixture was stirred at room temperature for 3.5 h, diluted with ethyl acetate (400 mL) and hexanes (400 mL), washed with water (3×200 mL), brine (100 mL), dried (MgSO$_4$) and filtered through a silica gel pad. The pad was rinsed with ethyl acetate (100 mL). The filtrate was concentrated to give the title compound (11.40 g, 100% yield). $^1$H NMR (400 MHz, chloroform-d) δ ppm 3.69 (3 H, s), 3.68 (3 H, s), 2.80 (1 H, t, J=9.46 Hz), 2.58 (1 H, td, J=12.65, 7.48 Hz), 2.09-2.32 (1 H, m), 1.73-1.92 (1 H, m, J=13.86, 9.79, 9.79, 7.48 Hz), 1.51 (1H, ddd, J=13.64, 9.57, 3.85 Hz), 1.25 (3 H, s), 1.20 (3 H, s), 0.76 (3 H, s); MS (ES+) m/z: 229.1 (M+H); HPLC retention time: 3.623 min (analytical HPLC Method F).

Step 2: (1R,3R)-dimethyl 1,2,2-trimethylcyclopentane-1,3-dicarboxylate

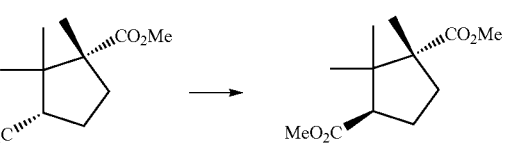

Sodium hydride (0.788 g, 19.71 mmol, 60% suspension in mineral oil) was added to a solution of (1R,3S)-dimethyl 1,2,2-trimethylcyclopentane-1,3-dicarboxylate (1.50 g, 6.57 mmol, from Step 1) in tetrahydrofuran (20 mL) at room temperature. The resulting mixture was heated to reflux for 1 h, cooled to room temperature, and carefully quenched with saturated ammonium chloride (10 mL). After dilution with ethyl acetate (100 mL), the mixture was washed with water, brine, dried (MgSO$_4$), filtered and concentrated to give crude product (1.45 g), which was found to be roughly a 1:1 mixture of the desired (1R,3R)-product and the (1R,3S)-starting material based on ¹H NMR analysis. The mixture was taken to the next reaction without purification.

Step 3: (R)-1,2,2-trimethylcyclopentane-1,3-dicarboxylic acid

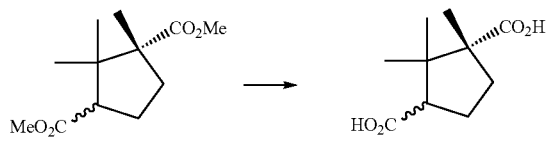 [SMILES: COC(=O)C1CC[C@@](C)(C(=O)OC)C1(C)C ; CC1(C)C(C(=O)O)CC[C@@]1(C)C(=O)O]

A 1 N aqueous solution of sodium hydroxide (36.8 mL, 36.8 mmol) was added to a solution of the crude di-ester mixture from Step 2 (1.4 g) in methanol (40 mL) at room temperature. The resulting mixture was heated to reflux for a total of 30 h then cooled to room temperature. After removal of methanol in vacuo, the aqueous residue was washed with dichloromethane (2×20 mL), acidified with 6 N hydrochloric acid and extracted with dichloromethane (3×80 mL). The combined organic extracts were dried (MgSO₄), filtered and concentrated to give the crude product (730 mg), which was taken to the next step without purification.

Step 4: (R)-1,2,2-trimethylcyclopentane-1,3-diamine

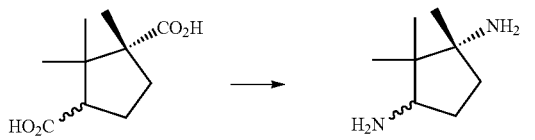

Sodium azide (312 mg, 4.79 mmol) was added in small portions to a solution of the crude (R)-1,2,2-trimethylcyclopentane-1,3-dicarboxylic acid from Step 3 (320 mg) in sulfuric acid (1 mL, 18.76 mmol) and chloroform (5 mL) at 55° C. until gas evolution ceased after each addition. The mixture was kept at 55° C. for 3 h, cooled to room temperature, carefully adjusted to pH>14 with saturated sodium hydroxide and extracted with chloroform (3×40 mL). The combined organic extracts were washed with brine (10 mL), dried (MgSO₄), filtered and concentrated to give crude (R)-1,2,2-trimethylcyclopentane-1,3-diamine mixture (160 mg), which was taken to the next step without purification.

Step 5: 4-(((1R,3R)-3-amino-2,2,3-trimethylcyclopentyl)amino)pyrrolo[1,2-b]pyridazine-3-carboxamide (Intermediate 11) and 4-(((1S,3R)-3-amino-2,2,3-trimethylcyclopentyl)amino)pyrrolo[1,2-b]pyridazine-3-carboxamide (Intermediate 12)

According to the procedure described in Example 1, 4-chloropyrrolo[1,2-b]-pyridazine-3-carboxamide (50 mg, 0.256 mmol, from Preparation 3) and crude (R)-1,2,2-trimethylcyclopentane-1,3-diamine mixture (72.7 mg, from Step 4) were coupled to give a mixture of two products. Silica gel chromatography, eluting with dichloromethane/methanol/ammonium hydroxide (90:9:1), separated the two product peaks. The first peak was found to be 4-(((1R,3R)-3-amino-2,2,3-trimethylcyclopentyl)amino)pyrrolo[1,2-b]pyridazine-3-carboxamide (Intermediate 11). ¹H NMR (500 MHz, methanol-d₄) δ ppm 8.12 (1H, s), 7.45-7.76 (1 H, m), 7.10-7.34 (1 H, m), 6.38-6.84 (1 H, m), 4.69-4.82 (1 H, m), 2.39-2.48 (1 H, m), 1.95-2.02 (1 H, m), 1.70-1.85 (1 H, m), 1.52-1.70 (1 H, m), 1.26 (3 H, s), 1.07 (3 H, s), 0.97 (3 H, s); MS (ES+) m/z: 302.2 (M+H); HPLC retention time: 1.822 min (analytical HPLC Method A). The second peak was found to be 4-(((1S,3R)-3-amino-2,2,3-trimethylcyclopentyl)amino)pyrrolo[1,2-b]pyridazine-3-carboxamide (Intermediate 12). ¹H NMR (500 MHz, methanol-d₄) δ ppm 8.12 (1 H, s), 7.56 (1 H, dd, J=2.77, 1.39 Hz), 6.90-6.98 (1 H, m), 6.68 (1 H, dd, J=4.58, 2.64 Hz), 4.52 (1 H, t, J=8.46 Hz), 2.25-2.42 (1 H, m), 1.73-1.94 (2 H, m), 1.57-1.73 (1 H, m), 1.21 (3 H, s), 1.08 (3 H, s), 0.93 (3 H, s); MS (ES+) m/z: 302.2 (M+H); HPLC retention time: 1.897 min (analytical HPLC Method A).

Intermediates 13 and 14

(+/−)-4-((cis-3-amino-2,2-dimethylcyclopentyl)amino)pyrrolo[1,2-b]pyridazine-3-carboxamide and (+/−)-4-((trans-3-amino-2,2-dimethylcyclopentyl)amino)pyrrolo[1,2-b]pyridazine-3-carboxamide

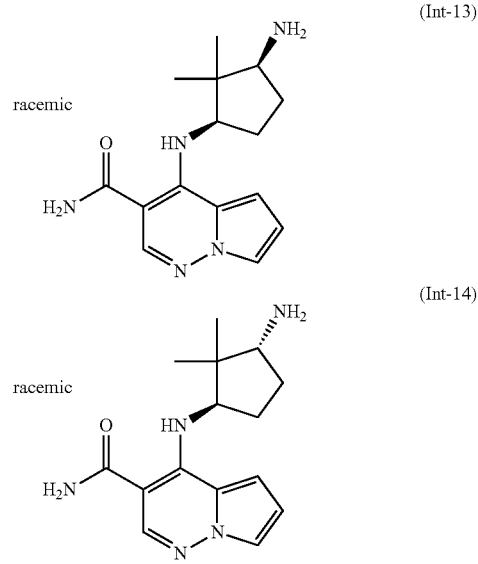

Step 1: 2,2-dimethylcyclopentane-1,3-dione

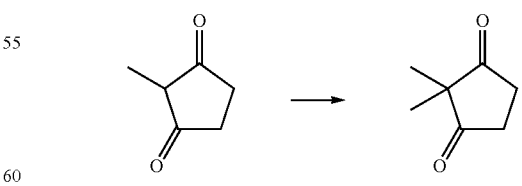

A mixture of 2-methylcyclopentane-1,3-dione (49.98 g, 446 mmol), potassium hydroxide (25.5 g, 455 mmol) and iodomethane (30.1 mL, 481 mmol) in dioxane (390 mL) and water (130 mL) was heated to reflux for 5 h. A biphasic mixture of potassium hydroxide (10.4 g), iodomethane (12.5 mL), water (26 mL) and dioxane (78 mL) was added. The mixture was heated at reflux for 3 additional hours and then stirred at ambient temperature overnight. Another portion of a biphasic mixture of potassium hydroxide (10.4 g), iodomethane (12.5 mL), water (26 mL) and dioxane (78 mL) was added. The mixture was heated at reflux for 3 h, cooled to room temperature and extracted with ether (600 mL, then 2×400 mL). The combined extracts were concentrated using a rotavap while keeping the bath temperature at or below room temperature to prevent loss of volatile product. The residue was treated with 10% hydrochloric acid (250 mL) and placed in a 120° C. oil bath until it started to boil (~15 min). The mixture was cooled with an ice-water bath, diluted with water (250 mL) and treated with careful addition of sodium carbonate until carbon dioxide release stopped. The pH of the solution was 8-9. The mixture was extracted with dichloromethane (4×200 mL). The combined extracts were dried (MgSO$_4$), filtered and concentrated while keeping water bath at or below room temperature. The residue was further dried under vacuum briefly to remove residual solvent to give 2,2-dimethylcyclopentane-1,3-dione as tan solid (38.1 g, 68% yield). $^1$H NMR (400 MHz, chloroform-d) δ ppm 2.81 (4H, s), 1.16 (6H, s); LC retention time: 0.990 min (analytical HPLC Method F).

Step 2: 2,2-dimethylcyclopentane-1,3-dione dioxime

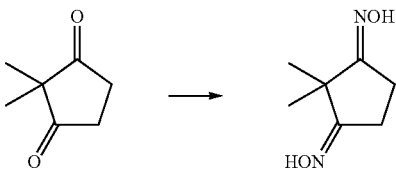

Sodium acetate (208 mg, 2.54 mmol) and hydroxylamine hydrochloride (165 mg, 2.378 mmol) were added to a solution of 2,2-dimethylcyclopentane-1,3-dione (100 mg, 0.793 mmol) in ethanol (2 mL) and water (0.5 mL). The resultant mixture was heated to reflux for 15 h, cooled to room temperature and adjusted pH 2-3 with 1 N hydrochloric acid. After addition of ethyl acetate (100 mL), the mixture was washed with brine (10 mL), dried (MgSO$_4$), filtered and concentrated, to give 2,2-dimethylcyclopentane-1,3-dione dioxime (125 mg). NMR analysis showed spectra consistent with the expected product as well as the presence of ~1 equivalent of acetic acid. This crude material was taken to the next step without purification.

Step 3: 2,2-dimethylcyclopentane-1,3-diamine

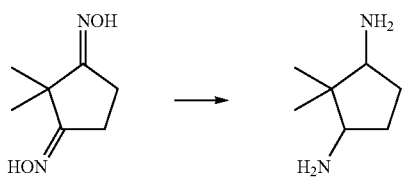

Sodium (177 mg, 7.68 mmol) was added to a solution of crude 2,2-dimethylcyclopentane-1,3-dione dioxime (120 mg) in n-propanol (10 mL) at 80° C. The mixture was heated to reflux for 2 h, cooled to room temperature and poured into brine (30 mL). The mixture was extracted with dichloromethane (3×50 mL). The combined organic extracts were dried (MgSO$_4$), filtered and concentrated to give crude 2,2-dimethylcyclopentane-1,3-diamine (85 mg), which was used in the next step without purification.

Step 4: (+/−)-4-((cis-3-amino-2,2-dimethylcyclopentyl)amino)pyrrolo[1,2-b]pyridazine-3-carboxamide (Intermediate 13) and (+/−)-4-((trans-3-amino-2,2-dimethylcyclopentyl)amino)pyrrolo[1,2-b]pyridazine-3-carboxamide (Intermediate 14)

According to the procedure described in Intermediate 1, 4-chloropyrrolo[1,2-b]pyridazine-3-carboxamide (50 mg, 0.256 mmol, from Preparation 3) was reacted with crude 2,2-dimethylcyclopentane-1,3-diamine (82 mg, from Step 3). Purification with reverse phase HPLC (Sunfire S10 30×250 mm column), eluting with 20 to 80% solvent B (10% methanol-90% water-0.1% TFA) in solvent A (90% methanol-10% water-0.1% TFA), gave separation of the two major components. The first eluting component was found to be 4-((cis-3-amino-2,2-dimethylcyclopentyl)amino)-pyrrolo[1,2-b]pyridazine-3-carboxamide (Intermediate 13, 13 mg, 18% yield). $^1$H NMR (400 MHz, methanol-d$_4$) δ ppm 8.12 (1 H, s), 7.57 (1 H, dd, J=2.64, 1.54 Hz), 7.03 (1 H, dd, J=4.73, 1.43 Hz), 6.68 (1 H, dd, J=4.62, 2.64 Hz), 4.33 (1 H, t, J=8.91 Hz), 2.92-3.13 (1 H, m), 2.22-2.47 (1 H, m), 2.04-2.22 (1 H, m), 1.44-1.78 (2 H, m), 1.08 (3 H, s), 1.00 (3 H, s); MS (ES+) m/z: 288.3 (M+H); HPLC retention time: 1.630 min (analytical HPLC Method A). The second eluting component was found to be 4-((trans-3-amino-2,2-dimethylcyclopentyl)amino)pyrrolo[1,2-b]pyridazine-3-carboxamide (Intermediate 14, 10 mg, 14% yield). $^1$H NMR (400 MHz, methanol-d$_4$) δ ppm 8.11 (1 H, s), 7.56 (1 H, dd, J=2.64, 1.54 Hz), 7.01-7.16 (1 H, m), 6.67 (1 H, dd, J=4.62, 2.64 Hz), 4.44 (1 H, t, J=6.71 Hz), 3.16-3.23 (1 H, m), 2.36-2.54 (1 H, m), 2.13-2.32 (1 H, m), 1.46-1.79 (2 H, m), 1.14 (3 H, s), 1.05 (3 H, s); MS (ES+) m/z: 288.2 (M+H); HPLC retention time: 1.715 min (analytical HPLC Method A).

Intermediates 15 and 16 (+/−)-4-((trans-3-hydroxy-2,2-dimethylcyclopentyl)amino)pyrrolo[1,2-b]pyridazine-3-carboxamide and (+/−)-4-((cis-3-hydroxy-2,2-dimethylcyclopentyl)amino)pyrrolo[1,2-b]pyridazine-3-carboxamide

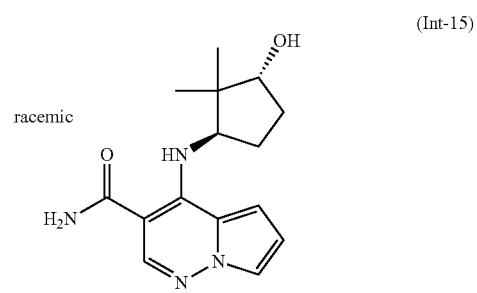

(Int-15)

racemic

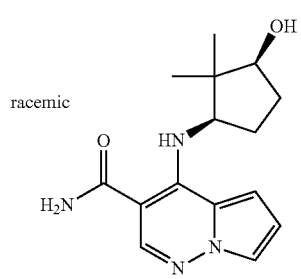

(Int-16)

Step 1: 3-hydroxy-2,2-dimethylcyclopentanone

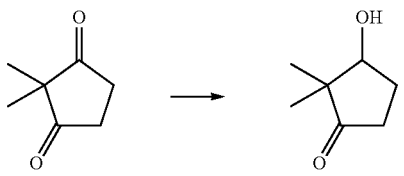

Sodium borohydride (0.379 g, 10.01 mmol) was added to a solution of 2,2-dimethylcyclopentane-1,3-dione (5.05 g, 40.0 mmol, from Step 1 of Intermediates 13 and 14) in methanol (40 mL) in small portions over 15 min. The resultant mixture was stirred at room temperature for 30 min and quenched with saturated ammonium chloride (40 mL). After removal of methanol in vacuo, the residue was diluted with ethyl acetate (300 mL), washed with brine (30 mL), dried (MgSO$_4$), filtered and concentrated. Silica gel chromatography, eluting with 20 to 50% ethyl acetate in hexanes, gave 3-hydroxy-2,2-dimethylcyclopentanone (3.60 g, 70% yield). $^1$H NMR (400 MHz, chloroform-d) δ ppm 4.05 (1 H, s), 2.35-2.66 (1 H, m), 2.12-2.37 (2 H, m), 1.67-2.00 (1 H, m), 0.84-1.09 (6 H, m).

Step 2: 3-hydroxy-2,2-dimethylcyclopentanone oxime

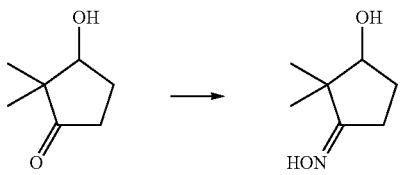

Sodium acetate (3.58 g, 43.7 mmol) and hydroxylamine hydrochloride (2.85 g, 41.0 mmol) were added to a solution of 3-hydroxy-2,2-dimethylcyclopentanone (3.50 g, 27.3 mmol, from Step 1) in ethanol (50 mL) and water (10 mL). The resultant mixture was heated to 80° C. for 15 h, cooled to room temperature and acidified to pH 2-3 with 1 N hydrochloric acid. After removal of ethanol in vacuo, the aqueous residue was extracted with ethyl acetate (3×200 mL). The combined organic extracts were washed with brine (30 mL), dried (MgSO$_4$), filtered and concentrated, to give 3-hydroxy-2,2-dimethylcyclopentanone oxime (3.60 g, 92% yield). $^1$H NMR (400 MHz, methanol-d$_4$) δ ppm 3.76 (1 H, t, J=6.16 Hz), 2.51-2.80 (1 H, m), 2.32-2.53 (1 H, m), 1.91-2.16 (1 H, m), 1.58-1.81 (1 H, m), 0.92-1.13 (6 H, m).

Step 3: 3-amino-2,2-dimethylcyclopentanol

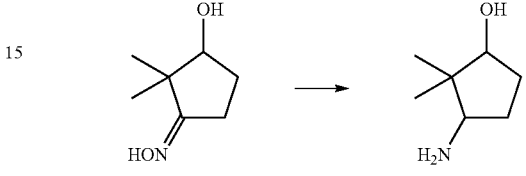

Sodium (2.312 g, 101 mmol) was added in small portions over 30 min to a solution of 3-hydroxy-2,2-dimethylcyclopentanone oxime (3.60 g, 25.1 mmol, from Step 2) in n-propanol (50 mL) at 80° C. The resultant mixture was heated to 100° C. for 2 h, cooled to room temperature, poured into brine (100 mL) and extracted with ethyl acetate (3×200 mL). The combined organic extracts were dried (MgSO$_4$), filtered and concentrated to give crude 3-amino-2,2-dimethylcyclopentanol (3.10 g), which was used in the next reaction without purification.

Step 4: (+/−)-4-((trans-3-hydroxy-2,2-dimethylcyclopentyl)amino)pyrrolo[1,2-b]pyridazine-3-carboxamide (Intermediate 15) and (+/−)-4-((cis-3-hydroxy-2,2-dimethylcyclopentyl)amino)pyrrolo[1,2-b]pyridazine-3-carboxamide (Intermediate 16)

According to the procedure described in Intermediate 1, 4-chloropyrrolo[1,2-b]pyridazine-3-carboxamide (42.4 mg, 0.217 mmol, from Preparation 3) was reacted with crude 3-amino-2,2-dimethylcyclopentanol (28 mg, from Step 3). Purification with reverse phase HPLC (Sunfire S10 30×250 mm column), eluting with 30 to 100% solvent B (10% methanol-90% water-0.1% TFA) in solvent A (90% methanol-10% water-0.1% TFA), gave separation of the two major components. The first eluted component was found to be 4-((trans-3-hydroxy-2,2-dimethylcyclopentyl)-amino)pyrrolo[1,2-b]pyridazine-3-carboxamide (Intermediate 15, 12 mg, 19% yield). $^1$H NMR (400 MHz, methanol-d$_4$) δ ppm 8.01 (1 H, s), 7.45 (1 H, s), 6.94 (1 H, d, J=4.18 Hz), 6.57 (1 H, dd, J=4.40, 2.64 Hz), 4.40 (1 H, t, J=8.03 Hz), 3.73 (1 H, dd, J=6.38, 2.20 Hz), 2.22-2.53 (1 H, m), 1.96-2.21 (1 H, m), 1.45-1.61 (2 H, m), 0.89-1.03 (6 H, m); MS (ES+) m/z: 289.3 (M+H); HPLC retention time: 2.473 min (analytical HPLC Method A). The second eluted component was found to be 4-((cis-3-hydroxy-2,2-dimethylcyclopentyl)amino)pyrrolo[1,2-b]pyridazine-3-carboxamide (Intermediate 16, 5 mg, 7% yield). $^1$H NMR (400 MHz, methanol-d$_4$) δ ppm 8.10 (1 H, s), 7.55 (1 H, d, J=1.10 Hz), 6.99 (1 H, d, J=4.62 Hz), 6.54-6.82 (1 H, m), 4.25 (1 H, t, J=7.59 Hz), 3.82 (1 H, t, J=7.26 Hz), 2.19-2.43 (1 H, m), 2.04-2.20 (1 H, m), 1.61-1.87 (2 H, m), 0.98-1.11 (6 H, m); MS (ES+) m/z: 289.2 (M+H); HPLC retention time: 2.563 min (analytical HPLC Method A).

Intermediate 17

(+/−)-4-((trans-3-hydroxy-2,2,3-trimethylcyclopentyl)amino)pyrrolo[1,2-b]pyridazine-3-carboxamide

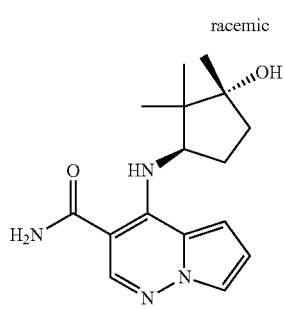
(Int-17)

Step 1: 3-hydroxy-2,2,3-trimethylcyclopentanone

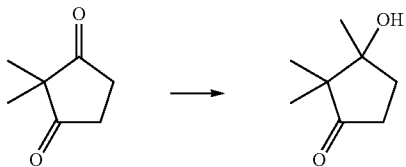

A 1.6 M ether solution of methyllithium (73.9 mL, 118 mmol) was added dropwise over 20 min to a suspension of 2,2-dimethylcyclopentane-1,3-dione (14.2 g, 113 mmol, from Step 1 of Intermediates 13 and 14) and cerium(III) chloride (30.5 g, 124 mmol) in tetrahydrofuran (250 mL) at −78° C. The resultant mixture was stirred at −78° C. for 30 min, quenched with saturated ammonium chloride (200 mL), warmed to room temperature and filtered through a celite cake. The filter cake was rinsed with tetrahydrofuran until free of product. The filtrate was concentrated in vacuo to remove the volatile tetrahydrofuran. The aqueous residue was extracted with ethyl acetate (3×200 mL). The combined organic extracts were washed with brine (80 mL), dried (MgSO₄), filtered and concentrated. Silica gel chromatography, eluting with 20 to 50% ethyl acetate in hexanes, gave 3-hydroxy-2,2,3-trimethylcyclopentanone (8.20 g, 51% yield). ¹H NMR (400 MHz, chloroform-d) δ ppm 2.18-2.58 (2 H, m), 1.88-2.21 (2 H, m), 1.30 (3 H, s), 1.03 (3 H, s), 0.93 (3 H, s).

Step 2: 3-hydroxy-2,2,3-trimethylcyclopentanone oxime

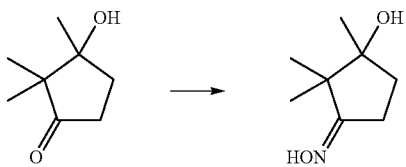

Sodium acetate (7.57 g, 92 mmol) and hydroxylamine hydrochloride (6.01 g, 87 mmol) were added to a solution of 3-hydroxy-2,2,3-trimethylcyclopentanone (8.20 g, 57.7 mmol, from Step 1) in ethanol (80 mL) and water (16 mL). The resultant mixture was heated to 80° C. for 15 h, then cooled to room temperature. After removal of ethanol in vacuo, the aqueous residue was diluted with water (20 mL) and extracted with ethyl acetate (3×100 mL). The combined organic extracts were washed with brine (30 mL), dried (MgSO₄), filtered and concentrated to give crude 3-hydroxy-2,2,3-trimethylcyclopentanone oxime (9.05 g). ¹H NMR (400 MHz, methanol-d₄) δ ppm 2.29-2.80 (2 H, m), 1.63-1.94 (2 H, m), 1.22 (3 H, s), 1.08 (3 H, s), 0.99 (3 H, s).

Step 3: 3-amino-1,2,2-trimethylcyclopentanol

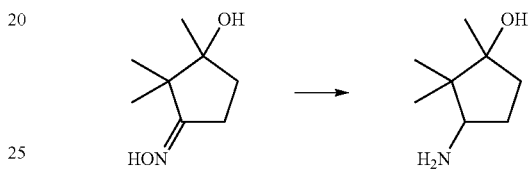

Sodium (4.63 g, 201 mmol) was added in small portions over 1 h to a solution of the crude 3-hydroxy-2,2,3-trimethylcyclopentanone oxime (9.05 g, from Step 2) in n-propanol (80 mL) at 80° C. The resultant mixture stirred at 80° C. for 2 h, cooled to room temperature, poured into brine (100 mL) and extracted with dichloromethane (3×200 mL). The combined organic extracts were dried (MgSO₄), filtered and concentrated to give crude 3-amino-1,2,2-trimethylcyclopentanol (9.1 g), which was taken to the next reaction without purification.

Step 4: (+/−)-benzyl trans-3-hydroxy-2,2,3-trimethylcyclopentylcarbamate and (+/−)-benzyl cis-3-hydroxy-2,2,3-trimethylcyclopentylcarbamate

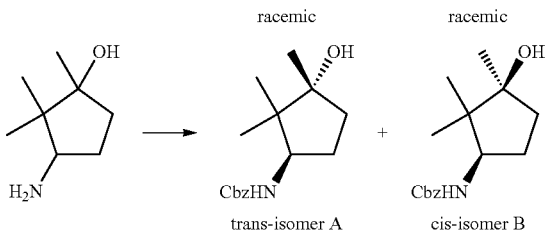

Triethylamine (15.33 mL, 110 mmol) and benzyl chloroformate (9.66 g, 56.7 mmol) were added to a solution of the crude 3-amino-1,2,2-trimethylcyclopentanol (7.88 g, from Step 3) in dichloromethane (200 mL) at 0° C. The resultant mixture was stirred at room temperature for 15 h, quenched with saturated sodium bicarbonate (200 mL) and extracted with dichloromethane (3×200 mL). The combined organic extracts were washed with water (50 mL), brine (50 mL), dried (MgSO₄), filtered and concentrated. Silica gel chromatography, eluting with 10 to 50% ethyl acetate in hexanes, gave benzyl trans-3-hydroxy-2,2,3-trimethylcyclopentylcarbamate (isomer A, 4.20 g, 28% for 3 steps). ¹H NMR (400 MHz, chloroform-d) δ ppm 7.30-7.45 (5 H, m), 4.98-5.29 (2 H, m), 4.56 (1 H, br. s.), 4.31 (1 H, t, J=9.46 Hz), 2.08-2.44 (1 H, m), 1.78-1.96 (1 H, m), 1.65-1.76 (1 H, m), 1.57 (3 H, s), 1.29-1.38 (1 H, m), 1.21 (3 H, s), 0.72 (3 H, s). A small amount of benzyl cis-3-hydroxy-2,2,3-trimethylcyclopentylcarbamate (isomer B) was also isolated. ¹H NMR (400 MHz, chloroform-d) δ ppm 7.31-7.48 (5 H, m), 5.68 (1 H, br. s.), 4.95-5.32 (2 H, m), 4.70 (1 H, d, J=3.52 Hz), 3.62-4.13 (1 H, m), 2.09-2.50 (1 H, m), 1.74-1.94 (2 H, m), 1.53-1.70 (1 H, m), 1.22 (3 H, s), 0.96 (3 H, s), 0.88 (3 H, s).

Step 5: (+/−)-trans-3-amino-1,2,2-trimethylcyclopentanol

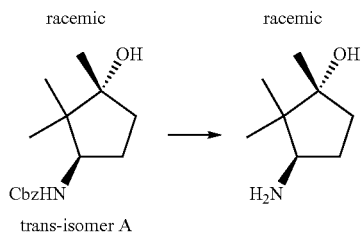

A mixture of trans-benzyl-3-hydroxy-2,2,3-trimethylcyclopentylcarbamate (3.30 g, 11.90 mmol, trans-isomer A from Step 4) and 10% palladium on carbon (0.633 g) in methanol (30 mL) was stirred under hydrogen at 20 psi for 3 h. The mixture was filtered to remove the catalyst. The filtrate was concentrated to give trans-3-amino-1,2,2-trimethylcyclopentanol (1.60 g, 94% yield). ¹H NMR (400 MHz, methanol-d₄) δ ppm 3.20-3.33 (1 H, m), 2.00-2.22 (1 H, m), 1.76-1.95 (1 H, m), 1.65 (1 H, ddd, J=14.20, 9.79, 4.62 Hz), 1.35 (1 H, dddd, J=13.40, 12.30, 8.97, 4.73 Hz), 1.16 (3 H, s), 0.94 (3 H, s), 0.73 (3 H, s).

Step 6: (+/−)-4-((trans-3-hydroxy-2,2,3-trimethylcyclopentyl)amino)pyrrolo[1,2-b]-pyridazine-3-carboxamide (Intermediate 17)

According to the procedure described in Intermediate 1, 4-chloropyrrolo[1,2-b]pyridazine-3-carboxamide (30 mg, 0.153 mmol, from Preparation 3) was reacted with trans-3-amino-1,2,2-trimethylcyclopentanol (25 mg, from Step 5). Purification with reverse phase HPLC (Sunfire S10 30×250 mm column), eluting with 30 to 100% solvent B (10% methanol-90% water-0.1% TFA) in solvent A (90% methanol-10% water-0.1% TFA), gave the title compound (15 mg, 32% yield). ¹H NMR (400 MHz, methanol-d₄) δ ppm 10.53 (1 H, d, J=9.46 Hz), 8.01 (1 H, s), 7.44 (1 H, dd, J=2.86, 1.54 Hz), 6.97 (1 H, dd, J=4.73, 1.43 Hz), 6.55 (1 H, dd, J=4.51, 2.75 Hz), 4.71 (1 H, t, J=9.35 Hz), 2.12-2.41 (1 H, m), 1.80-1.91 (1 H, m), 1.58-1.74 (1 H, m), 1.30-1.54 (1 H, m), 1.13 (3 H, s), 0.88 (3 H, s), 0.82 (3 H, s); MS (ES+) m/z: 303.3 (M+H); HPLC retention time: 2.542 min (analytical HPLC Method A).

Intermediate 18

(+/−)-ethyl 3-carbamoyl-4-((trans-3-hydroxy-2,2,3-trimethylcyclopentyl)amino)pyrrolo[1,2-b]pyridazine-6-carboxylate

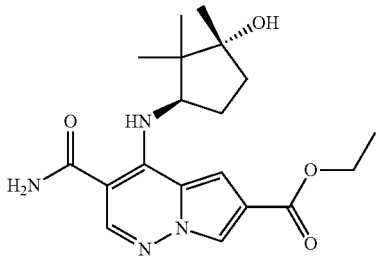

A mixture of ethyl 3-carbamoyl-4-chloropyrrolo[1,2-b]pyridazine-6-carboxylate (2.10 g, 7.85 mmol, from Preparation 4), trans-3-amino-1,2,2-trimethylcyclopentanol (1.348 g, 9.41 mmol, from Step 5 of Intermediate 17) and N,N-diisopropylethylamine (2.74 mL, 15.69 mmol) in 1-methyl-2-pyrrolidinone (20 mL) was heated to 100° C. for 1 h. LCMS analysis indicated that the chloride starting material was consumed. The mixture was cooled to room temperature, treated with water (40 mL) and stirred for 10 min. The pale solid was collected by filtration, washed with water, dried under vacuum to give the title compound (2.51 g, 85% yield). ¹H NMR (400 MHz, methanol-d₄) δ ppm 8.20 (1 H, s), 8.00 (1 H, d, J=1.54 Hz), 7.45 (1 H, d, J=1.76 Hz), 4.62-4.82 (1 H, m), 4.34 (2 H, q, J=7.26 Hz), 2.26-2.60 (1 H, m), 1.94-2.19 (1 H, m), 1.72-1.91 (1 H, m), 1.51-1.67 (1 H, m), 1.37 (3 H, t, J=7.04 Hz), 1.24 (3 H, s), 1.00 (3 H, s), 0.96 (3 H, s); MS (ES+) m/z: 375.3 (M+H); HPLC retention time: 2.995 min (analytical HPLC Method A).

Intermediate 19

(+/−)-3-carbamoyl-4-((trans-3-hydroxy-2,2,3-trimethylcyclopentyl)amino)pyrrolo[1,2-b]pyridazine-6-carboxylic acid

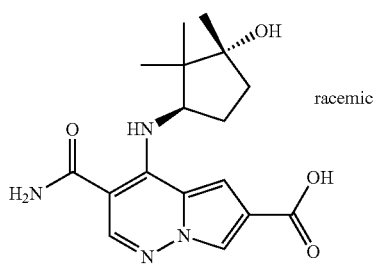

A mixture of ethyl 3-carbamoyl-4-((trans-3-hydroxy-2,2,3-trimethylcyclopentyl)amino)pyrrolo[1,2-b]pyridazine-6-carboxylate (2.51 g, 6.70 mmol, from Intermediate 18) and 1 N aqueous sodium hydroxide (20.11 mL, 20.11 mmol) in methanol (20 mL) and tetrahydrofuran (20.00 mL) was heated to 50° C. for 3 h. After cooling to room temperature, the organic solvents were removed in vacuo. The aqueous residue was adjusted pH 1-2 with 1 N hydrochloric acid. The white precipitate was collected by filtration, washed with water, dried under vacuum to give the title compound (2.30 g, 99% yield). $^1$H NMR (400 MHz, methanol-$d_4$) δ ppm 10.84 (1 H, d, J=9.24 Hz), 8.19 (1 H, s), 8.00 (1 H, d, J=1.76 Hz), 7.46 (1 H, d, J=1.54 Hz), 4.63-4.86 (1 H, m), 2.28-2.58 (1 H, m), 2.01 (1 H, ddd, J=14.03, 12.27, 5.39 Hz), 1.74-1.88 (1 H, m), 1.51-1.68 (1 H, m), 1.24 (3 H, s), 1.00 (3 H, s), 0.97 (3 H, s); MS (ES+) m/z: 347.2 (M+H); HPLC retention time: 2.547 min (analytical HPLC Method A).

Intermediate 20

Ethyl 3-carbamoyl-4-(((1R,3R)-3-hydroxy-2,2,3-trimethylcyclopentyl)amino)pyrrolo[1,2-b]pyridazine-6-carboxylate (Int-20)

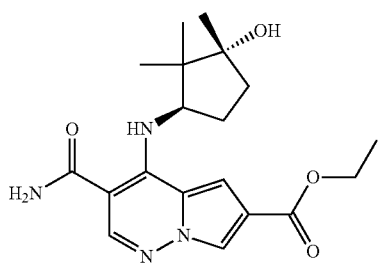

Step 1: Benzyl (1R,3R)-3-hydroxy-2,2,3-trimethylcyclopentylcarbamate and benzyl (1S,3 S)-3-hydroxy-2,2,3-trimethylcyclopentylcarbamate racemic

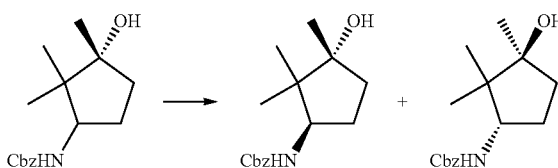

Racemic benzyl trans-3-hydroxy-2,2,3-trimethylcyclopentylcarbamate (1.97 g, from Step 4 of Intermediate 17) was separated using preparative SFC using the following conditions: Column: ChiralPak AD-H 25×3 cm, 5 μm; Column Temp: 40° C.; Flow rate: 150 mL/min; Mobile Phase: $CO_2$/methanol=65/35; Injection Volume: 1.5 mL (66.6 mg/mL, 2 g solid in 30 mL methanol); Detector Wavelength: 220 nm. The first eluted enantiomer was found to be benzyl (1R,3R)-3-hydroxy-2,2,3-trimethylcyclopentylcarbamate (900 mg). The second eluted enantiomer was found to be benzyl (1S, 3S)-3-hydroxy-2,2,3-trimethylcyclopentylcarbamate (900 mg).

Step 2: (1R,3R)-3-amino-1,2,2-trimethylcyclopentanol

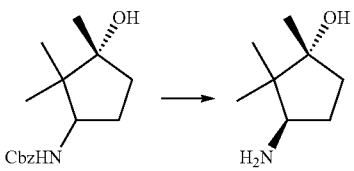

A mixture of benzyl (1R,3R)-3-hydroxy-2,2,3-trimethylcyclopentylcarbamate (900 mg, 3.24 mmol, from Step 1) and 10% palladium on carbon (173 mg) in methanol (15 mL) was stirred under hydrogen at 20 psi for 2 h. The mixture was filtered to remove the catalyst. The filtrate was concentrated to give (1R,3R)-3-amino-1,2,2-trimethylcyclopentanol (450 mg, 97% yield). $^1$H NMR (400 MHz, methanol-$d_4$) δ ppm 3.11-3.52 (1 H, m), 1.98-2.43 (1 H, m), 1.75-1.93 (1 H, m), 1.56-1.71 (1 H, m), 1.27-1.48 (1 H, m), 1.16 (3 H, s), 0.93 (3 H, s), 0.72 (3 H, s).

Step 3: Ethyl 3-carbamoyl-4-(((1R,3R)-3-hydroxy-2, 2,3-trimethylcyclopentyl)amino) pyrrolo[1,2-b]pyridazine-6-carboxylate (Intermediate 20)

According to the procedure described in Intermediate 1, ethyl 3-carbamoyl-4-chloropyrrolo[1,2-b]pyridazine-6-carboxylate (20 mg, 0.075 mmol, from Preparation 4) was reacted with (1R,3R)-3-amino-1,2,2-trimethylcyclopentanol (13.91 mg, 0.097 mmol, from Step 2). The reaction mixture was cooled to room temperature, diluted with water (2 mL) and stirred for 10 min. The pale solid was collected by filtration and washed with water, dried under vacuum to give the title compound (20 mg, 72% yield). $^1$H NMR (400 MHz, methanol-$d_4$) δ ppm 8.19 (1 H, s), 8.00 (1 H, s), 7.45 (1 H, s), 4.67-4.84 (1 H, m), 4.34 (2H, q, J=6.97 Hz), 2.22-2.50 (1 H, m), 1.94-2.11 (1 H, m), 1.73-1.89 (1 H, m), 1.61 (1 H, d, J=4.18 Hz), 1.37 (3 H, t, J=7.15 Hz), 1.24 (3 H, s), 1.00 (3 H, s), 0.96 (3 H, s); MS (ES+) m/z: 375.3 (M+H); HPLC retention time: 2.78 min (analytical HPLC Method A).

Intermediate 21

(+/−)-ethyl 3-carbamoyl-4-((trans-3-hydroxy-2,2-dimethylcyclopentyl)amino)pyrrolo[1,2-b]pyridazine-6-carboxylate (Int-21)

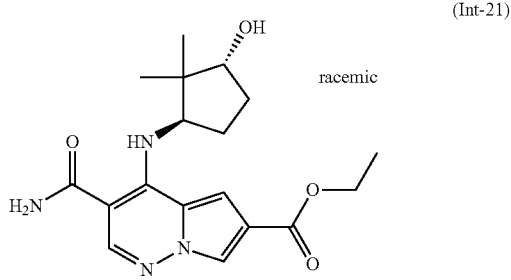 [SMILES: CCOC(=O)c1cc2c(N[C@@H]3CC[C@@H](O)C3(C)C)c(C(N)=O)cnn2c1]

Step 1: Benzyl trans-3-hydroxy-2,2-dimethylcyclopentylcarbamate and benzyl cis-3-hydroxy-2,2-dimethylcyclopentylcarbamate

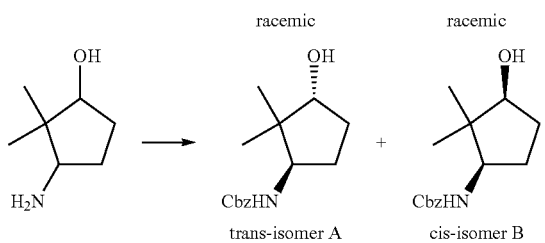

Triethylamine (6.69 mL, 48.0 mmol) and benzyl chloroformate (4.22 g, 24.71 mmol) were added to a solution of 3-amino-2,2-dimethylcyclopentanol (3.10 g, 23.99 mmol, from Step 3 of Intermediates 15 and 16) in dichloromethane (100 mL) at 0° C. The resulting mixture was stirred at room temperature for 15 h, treated with saturated sodium bicarbonate (50 mL) and extracted with dichloromethane (3×150 mL). The combined organic extracts were washed with water (50 mL), brine (50 mL), dried (MgSO$_4$), filtered and concentrated. Silica gel chromatography, eluting with 0 to 40% ethyl acetate in hexanes, gave separation of the two major components. The first eluted product was found to be benzyl cis-3-hydroxy-2,2-dimethylcyclopentylcarbamate (cis-isomer B, 640 mg, 10% yield). $^1$H NMR (400 MHz, methanol-d$_4$) δ ppm 7.13-7.53 (5 H, m), 5.06 (2 H, s), 3.53-3.86 (2 H, m), 1.81-2.05 (2 H, m), 1.36-1.71 (2 H, m), 0.86-1.07 (3 H, m), 0.78 (3 H, s); MS (ES+) m/z: 264.2 (M+H); HPLC retention time: 2.32 min (analytical HPLC Method A). The second eluted product was benzyl trans-3-hydroxy-2,2-dimethylcyclopentylcarbamate (trans-isomer A, 1.77 g, 28% yield). $^1$H NMR (400 MHz, methanol-d$_4$) δ ppm 7.21-7.51 (5 H, m), 5.06 (2 H, s), 3.91 (1 H, t, J=8.25 Hz), 3.64-3.79 (1 H, m), 1.99-2.20 (2 H, m), 1.33-1.62 (2 H, m), 0.94 (3 H, s), 0.79 (3 H, s); MS (ES+) m/z: 264.3 (M+H); HPLC retention time: 2.29 min (analytical HPLC Method A).

Step 2: trans-3-amino-2,2-dimethylcyclopentanol

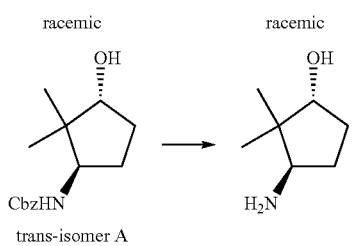

A mixture of benzyl trans-3-hydroxy-2,2-dimethylcyclopentylcarbamate (1.60 g, 6.08 mmol, isomer A from Step 1) and 10% palladium on carbon (0.323 g) in methanol (30 mL) was stirred under hydrogen at 20 psi for 2 h. The mixture was filtered to remove the catalyst. The filtrate was concentrated to give trans-3-amino-2,2-dimethylcyclopentanol (800 mg, 100% yield). $^1$H NMR (400 MHz, methanol-d$_4$) δ ppm 3.65-3.91 (1H, m), 2.95-3.17 (1H, m), 1.98-2.37 (2H, m), 1.28-1.63 (2H, m), 0.98 (3H, s), 0.84 (3H, s).

Step 3: (+/−)-ethyl 3-carbamoyl-4-((trans-3-hydroxy-2,2-dimethylcyclopentyl)amino) pyrrolo[1,2-b]pyridazine-6-carboxylate (Intermediate 21)

According to the procedure described in Example 1, trans-3-amino-2,2-dimethylcyclopentanol (499 mg, 3.86 mmol, from Step 2) was reacted with ethyl 3-carbamoyl-4-chloropyrrolo[1,2-b]pyridazine-6-carboxylate (795 mg, 2.97 mmol, from Preparation 4). The reaction mixture was cooled to room temperature, diluted with water (20 mL) and stirred for 10 min. The pale solid was collected by filtration, washed with water, dried under vacuum to give the title compound (940 mg, 88% yield). $^1$H NMR (400 MHz, methanol-d$_4$) δ ppm 8.19 (1 H, s), 8.00 (1 H, s), 7.41 (1 H, s), 4.40-4.55 (1 H, m), 4.35 (2 H, q, J=7.19 Hz), 3.62-3.94 (1 H, m), 2.33-2.61 (1 H, m), 2.06-2.35 (1 H, m), 1.54-1.89 (2 H, m), 1.38 (3 H, t, J=7.04 Hz), 1.06 (6 H, s); MS (ES+) m/z: 361.2 (M+H); HPLC retention time: 3.373 min (analytical HPLC Method A).

Intermediate 22

(+/−)-4-((2,2-dimethyl-3-oxocyclopentyl)amino) pyrrolo[1,2-b]pyridazine-3-carboxamide

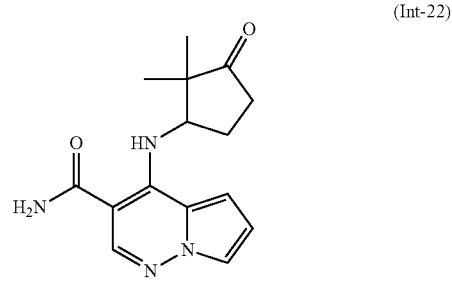 [SMILES: CC1(C)C(=O)CCC1Nc1c(C(N)=O)cnn2cccc12]

(Int-22)

Step 1: benzyl 2,2-dimethyl-3-oxocyclopentylcarbamate

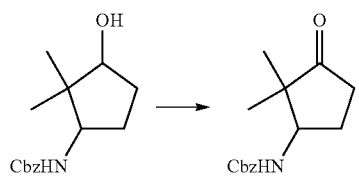 [SMILES: CC1(C)C(O)CCC1NC(=O)OCc1ccccc1 ; CC1(C)C(=O)CCC1NC(=O)OCc1ccccc1]

Dess-Martin periodinane (9.49 g, 22.39 mmol) was added to a solution of cis/trans mixture of benzyl 3-hydroxy-2,2-dimethylcyclopentylcarbamate (3.93 g, 14.92 mmol, from Step 1 of Intermediate 21) in dichloromethane (150 mL) at room temperature. After 2 h at room temperature, the mixture was filtered to remove the precipitate. The filtrate was washed with 10% aqueous sodium thiosulfate (10 mL), saturated sodium bicarbonate (20 mL), brine (20 mL), dried (MgSO$_4$), filtered and concentrated. Silica gel chromatography, eluting with 10 to 50% ethyl acetate in hexanes, gave benzyl 2,2-dimethyl-3-oxocyclopentylcarbamate (3.20 g, 82% yield). $^1$H NMR (400 MHz, chloroform-d) δ ppm 7.30-7.74 (5 H, m), 4.97-5.33 (2 H, m), 4.60-4.93 (1 H, m), 2.17-2.42 (2 H, m), 1.47-1.82 (2 H, m), 1.12 (3 H, s), 0.91 (3 H, s); MS (ES+) m/z: 262.3 (M+H); HPLC retention time: 2.643 min (analytical HPLC Method A).

Step 2: 3-amino-2,2-dimethylcyclopentanone

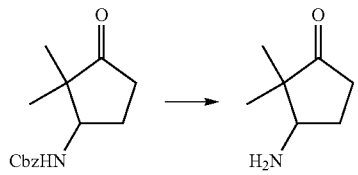

A mixture of benzyl 2,2-dimethyl-3-oxocyclopentylcarbamate (950 mg, 3.64 mmol, from Step 1) and 10% palladium on carbon (193 mg) in methanol (20 mL) was stirred under hydrogen (20 psi) for 2 h. After filtration to remove the catalyst, the filtrate was concentrated to give crude 3-amino-2,2-dimethylcyclopentanone (430 mg), which was used in the next reaction without purification.

Step 3: (+/−)-4-((2,2-dimethyl-3-oxocyclopentyl)amino)pyrrolo[1,2-b]pyridazine-3-carboxamide (Intermediate 22)

According to the procedure described in Example 1, 4-chloropyrrolo[1,2-b]-pyridazine-3-carboxamide (100 mg, 0.511 mmol, from Preparation 3) was reacted crude 3-amino-2,2-dimethylcyclopentanone (195 mg, from Step 2). Purification with reverse phase HPLC (Sunfire S10 30×250 mm column), eluting with 30 to 100% solvent B (10% methanol-90% water-0.1% TFA) in solvent A (90% methanol-10% water-0.1% TFA), gave the title compound (27 mg, 18% yield). $^1$H NMR (400 MHz, methanol-d$_4$) δ ppm 8.15 (1 H, s), 7.50-7.70 (1 H, m), 6.86-7.37 (1 H, m), 6.47-6.90 (1 H, m), 4.49-4.78 (1 H, m), 2.18-2.70 (3 H, m), 1.75-2.26 (1 H, m), 1.03-1.17 (6 H, m); MS (ES+) m/z: 287.2 (M+H); HPLC retention time: 2.487 min (analytical HPLC Method A).

Example 1

(+/−)-benzyl (3-carbamoyl-4-((trans-3-hydroxy-2,2,3-trimethylcyclopentyl)amino)pyrrolo[1,2-b]pyridazin-6-yl)carbamate

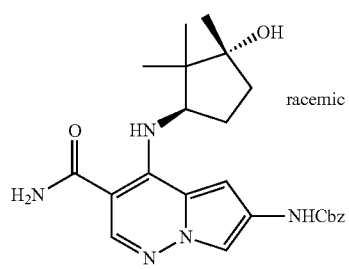

A mixture of 3-carbamoyl-4-((trans-3-hydroxy-2,2,3-trimethylcyclopentyl)amino)-pyrrolo[1,2-b]pyridazine-6-carboxylic acid (340 mg, 0.982 mmol, from Intermediate 19), triethylamine (0.274 mL, 1.963 mmol) and diphenylphosphoryl azide (0.296 mL, 1.374 mmol) in benzene (10 mL) and tetrahydrofuran (10 mL) was stirred at room temperature for 15 h. Benzyl alcohol (1.021 mL, 9.82 mmol) was added. The mixture was heated to reflux for 3 h, then cooled to room temperature. After addition of ethyl acetate (80 mL), the mixture was washed with water, brine, dried (MgSO$_4$), filtered and concentrated. Silica gel chromatography, eluting with ammonium hydroxide/methanol/dichloromethane (1/9/90), gave the title compound (350 mg, 70% yield). $^1$H NMR (500 MHz, methanol-d$_4$) δ ppm 10.44 (1 H, d, J=9.71 Hz), 8.08 (1 H, s), 7.78 (1 H, s), 7.14-7.49 (5 H, m), 6.86 (1 H, s), 5.18 (2 H, s), 4.57-4.75 (1 H, m), 2.21-2.44 (1 H, m), 1.91-2.06 (1 H, m), 1.69-1.87 (1 H, m), 1.42-1.64 (1 H, m), 1.22 (3 H, s), 0.93-1.06 (6 H, m); MS (ES+) m/z: 452.2 (M+H); HPLC retention time: 3.265 min (analytical HPLC Method A).

Intermediate 23

(+/−)-6-amino-4-((trans-3-hydroxy-2,2,3-trimethylcyclopentyl)amino)pyrrolo[1,2-b]-pyridazine-3-carboxamide

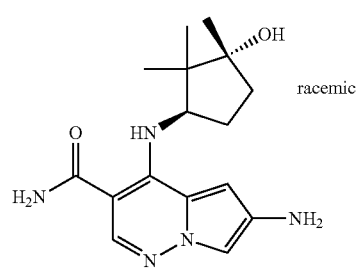

A mixture of benzyl (3-carbamoyl-4-((trans-3-hydroxy-2,2,3-trimethylcyclopentyl)-amino)pyrrolo[1,2-b]pyridazin-6-yl)carbamate (6.0 mg, 0.013 mmol, from Example 1) and 10% palladium on carbon (4.2 mg) in methanol (2 mL) was stirred under hydrogen (20 psi) for 2 h. After filtration to remove the catalyst, the filtrate was concentrated and purified by silica gel chromatography, eluting with ammonium hydroxide/methanol/dichloromethane (1/9/90), to give the title compound (3.0 mg, 71% yield). $^1$H NMR (400 MHz, methanol-d$_4$) δ ppm 8.00 (1 H, s), 7.19 (1 H, d, J=1.54 Hz), 6.60 (1 H, s), 4.64-4.78 (1 H, m), 2.24-2.43 (1 H, m), 1.94-2.10 (1 H, m), 1.64-1.80 (1 H, m), 1.44-1.62 (1 H, m), 1.24 (3 H, s), 0.80-1.02 (6 H, m); MS (ES+) m/z: 318.2 (M+H); HPLC retention time: 1.867 min (analytical HPLC Method A).

Intermediates 24 and 25

(+/−)-6-(benzylamino)-4-((trans-3-hydroxy-2,2,3-trimethylcyclopentyl)amino) pyrrolo[1,2-b]pyridazine-3-carboxamide, and (+/−)-6-(dibenzylamino)-4-((trans-3-hydroxy-2,2,3-trimethylcyclopentyl)amino)pyrrolo[1,2-b]pyridazine-3-carboxamide

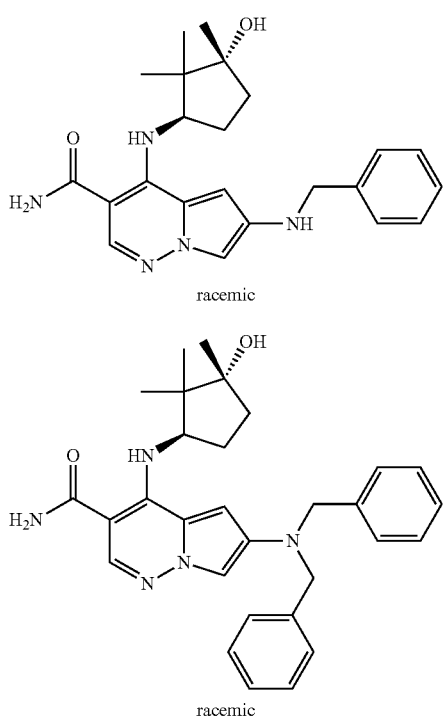

(Int-24)

(Int-25)

racemic

Potassium carbonate (32.7 mg, 0.236 mmol) was added to a mixture of 6-amino-4-((trans-3-hydroxy-2,2,3-trimethylcyclopentyl)amino)pyrrolo[1,2-b]pyridazine-3-carboxamide (25 mg, 0.079 mmol, from Intermediate 23), benzyl bromide (0.011 mL, 0.095 mmol) and N,N-dimethylformamide (1 mL). After 1 h at room temperature, the mixture was treated with water (0.5 mL) and purified by reverse phase HPLC (Sunfire S10 30×250 mm column), eluting with 0 to 100% solvent B (10% methanol-90% water-0.1% TFA) in solvent A (90% methanol-10% water-0.1% TFA). The major product was found to be (+/−)-6-(dibenzylamino)-4-((trans-3-hydroxy-2,2,3-trimethylcyclopentyl)amino)pyrrolo[1,2-b]pyridazine-3-carboxamide (Intermediate 28, 8 mg, 20% yield). $^1$H NMR (400 MHz, methanol-$d_4$) δ ppm 7.75-8.36 (1 H, m), 6.94-7.60 (12 H, m), 4.61 (1 H, t, J=8.91 Hz), 4.39-4.57 (4 H, m), 2.02-2.26 (1 H, m), 1.69-1.93 (2 H, m), 1.30-1.52 (1 H, m), 1.24 (3 H, s), 0.88-1.03 (6 H, m); MS (ES+) m/z: 498.3 (M+H); HPLC retention time: 3.685 min (analytical HPLC Method A). The minor product was found to be (+/−)-6-(benzylamino)-4-((trans-3-hydroxy-2,2,3-trimethylcyclopentyl)amino)pyrrolo[1,2-b]pyridazine-3-carboxamide (Intermediate 27, 1.5 mg, 5% yield). $^1$H NMR (400 MHz, methanol-$d_4$) δ ppm 8.09 (1 H, s), 6.95-7.67 (7 H, m), 4.56-4.80 (1 H, m), 4.16-4.56 (2 H, m), 2.12-2.48 (1 H, m), 1.86-2.12 (1 H, m), 1.62-1.82 (1 H, m), 1.42-1.60 (1 H, m), 1.23 (3 H, s), 0.99 (3 H, s), 0.94 (3 H, s); MS (ES+) m/z: 408.2 (M+H); HPLC retention time: 2.455 min (analytical HPLC Method A).

Examples 2 to 4

According to the procedure described in Intermediate 7, Examples 2 to 4 were prepared by reacting 6-amino-4-((trans-3-hydroxy-2,2,3-trimethylcyclopentyl)amino)pyrrolo[1,2-b]pyridazine-3-carboxamide (from Intermediate 23) with pivaloyl chloride, methanesulfonyl chloride and isopropyl isocyanate, respectively. According to the procedure described in Intermediate 7, Examples 2 to 4 were prepared by reacting 4-(((1R,3S)-3-amino-2,2,3-trimethylcyclopentyl)amino)pyrrolo[1,2-b]pyridazine-3-carboxamide (from Intermediate 9) with benzoyl chloride, ethyl chloroformate and methanesulfonyl chloride, respectively. Examples 2 and 3 were analyzed using HPLC Method C. Example 4 was analyzed using HPLC Method D.

| Ex # | Structure | HPLC Rt (minutes) | LCMS [m/z (M + H)] |
|---|---|---|---|
| 2 | racemic 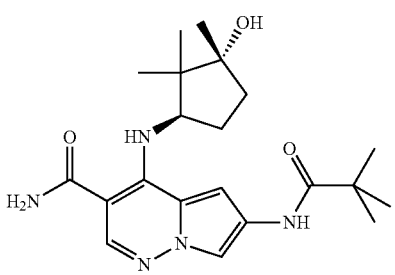 | 1.708 | 402.10 |

-continued

| Ex # | Structure | HPLC Rt (minutes) | LCMS [m/z (M + H)] |
|---|---|---|---|
| 3 | racemic 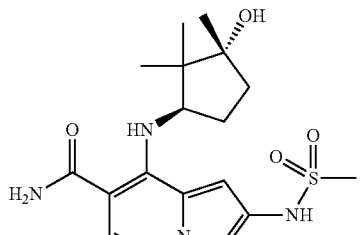 | 1.307 | 396.01 |
| 4 | racemic 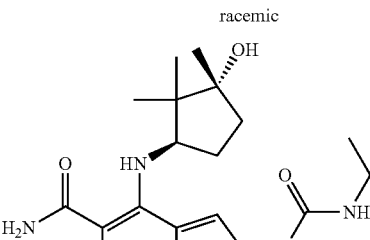 | 1.497 | 403.11 |

Intermediates 26 and 27

(+/−)-4-((cis-2-methylcyclopentyl)amino)pyrrolo[1,2-b]pyridazine-3-carboxamide and (+/−)-4-((trans-2-methylcyclopentyl)amino)pyrrolo[1,2-b]pyridazine-3-carboxamide

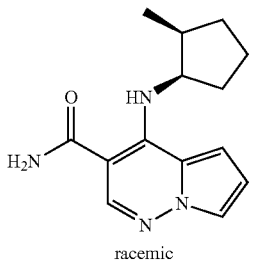
(Int-26)
racemic

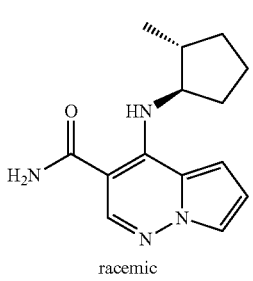
(Int-27)
racemic

Step 1: 2-methylcyclopentanone oxime

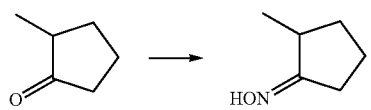

Sodium acetate (1.605 g, 19.56 mmol) and hydroxylamine hydrochloride (1.275 g, 18.34 mmol) were added to a solution of 2-methylcyclopentanone (1.20 g, 12.23 mmol) in ethanol (20 mL) and water (4 mL). The resultant mixture was heated to reflux for 3 h, cooled to room temperature and adjusted pH 2-3 with 1 N hydrochloric acid. After removal of the ethanol in vacuo, the residue was diluted with ethyl acetate (100 mL), washed with brine (10 mL), dried ($MgSO_4$), filtered and concentrated to give 2-methylcyclopentanone oxime (1.05 g, 76% yield). $^1$H NMR (400 MHz, chloroform-d) δ ppm 2.49-2.67 (2 H, m), 2.39-2.48 (1 H, m), 1.92-2.08 (1 H, m), 1.80-1.92 (1 H, m), 1.55-1.74 (1 H, m), 1.27-1.40 (1 H, m), 1.12-1.21 (3 H, m).

Step 2: 2-methylcyclopentanamine

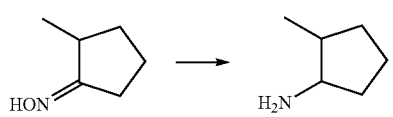

Sodium (0.853 g, 37.1 mmol) was added to a solution of 2-methylcyclopentanone oxime (1.05 g, 9.28 mmol, from Step 1) in n-propanol (20 mL) at 80° C. in small portions over 30 min. The resultant mixture was heated to reflux for 2 h, cooled to room temperature and poured into brine (20 mL). The mixture was extracted with dichloromethane (3×80 mL). The combined organic extracts were dried (MgSO₄), filtered and concentrated to give crude 2-methylcyclopentanamine (700 mg), which was directly taken to the next reaction without purification.

Step 3: (+/−)-4-((cis-2-methylcyclopentyl)amino) pyrrolo[1,2-b]pyridazine-3-carboxamide and (+/−)-4-((trans-2-methylcyclopentyl)amino)pyrrolo[1,2-b]pyridazine-3-carboxamide (Intermediates 26 and 27)

According to the procedure described in Intermediate 1, 4-chloropyrrolo[1,2-b]pyridazine-3-carboxamide (40 mg, 0.204 mmol, from Preparation 3) was reacted with crude 2-methylcyclopentanamine from Step 2 to give a mixture of cis and trans 4-((2-cyanocyclopentyl)amino)pyrrolo[1,2-b]pyridazine-3-carboxamide. Silica gel chromatography, eluting with 10 to 100% ethyl acetate in hexanes, gave a 6:1 mixture of two isomers (40 mg). The two isomers were separated using preparative reverse phase HPLC. The cis/trans stereochemistry of the products were not assigned. The major isomer was designated as Intermediate 26 (24 mg, 41% yield). ¹H NMR (400 MHz, methanol-d₄) δ ppm 8.02-8.25 (1 H, m), 7.46-7.59 (1 H, m), 6.82-7.10 (1 H, m), 6.50-6.74 (1 H, m), 4.08 (1 H, q, J=6.02 Hz), 2.16-2.41 (1 H, m), 1.90-2.08 (2 H, m), 1.72-1.92 (2 H, m), 1.59-1.71 (1 H, m), 1.26-1.42 (1 H, m), 1.10 (3 H, d, J=6.60 Hz); MS (ES+) m/z: 259.1 (M+H); HPLC retention time: 3.250 min (analytical HPLC Method A). The minor isomer was designated as Intermediate 27 (4 mg, 7% yield). ¹H NMR (400 MHz, methanol-d₄) δ ppm 8.10 (1 H, s), 7.56 (1 H, dd, J=2.64, 1.54 Hz), 7.00 (1 H, dd, J=4.62, 1.54 Hz), 6.66 (1 H, dd, J=4.51, 2.75 Hz), 4.50-4.65 (1 H, m), 2.23-2.43 (1 H, m), 2.08-2.25 (1 H, m), 1.90-2.06 (1 H, m), 1.76-1.88 (2 H, m), 1.64-1.76 (1 H, m), 1.42-1.60 (1 H, m), 1.06 (3 H, d); MS (ES+) m/z: 259.2 (M+H); HPLC retention time: 3.250 min (analytical HPLC Method A).

Intermediates 28 and 29

(+/−)-4-((cis-2-cyano-2-methylcyclopentyl)amino)pyrrolo[1,2-b]pyridazine-3-carboxamide, and (+/−)-4-((trans-2-cyano-2-methylcyclopentyl)amino)pyrrolo[1,2-b]pyridazine-3-carboxamide

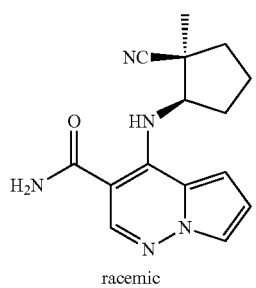

(Int-28)

racemic

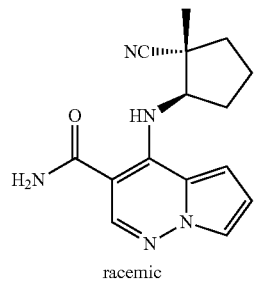

(Int-29)

racemic

Step 1: 1-methyl-2-oxocyclopentanecarbonitrile

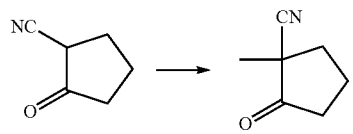

A solution of lithium hydroxide (0.2226 g, 9.30 mmol) in water (5 mL) and iodomethane (0.591 mL, 9.46 mmol) were added to a stirred solution of 2-oxocyclopentanecarbonitrile (0.86 g, 7.88 mmol) in methanol (5 mL) at room temperature. The resulting mixture was heated to 50° C. for 1.5 h. The methanol solvent was removed in vacuo. The aqueous residue was extracted with ether (2×25 mL). The combined ether extracts were dried (Na₂SO₄), decanted and concentrated to give 1-methyl-2-oxocyclopentanecarbonitrile (0.76 g, 78% yield). ¹H NMR (500 MHz, chloroform-d) δ ppm 2.63-2.74 (1 H, m), 2.43 (2 H, t, J=7.21 Hz), 1.59-1.93 (4 H, m), 1.34 (3 H, d, J=6.94 Hz).

Step 2: 2-amino-1-methylcyclopentanecarbonitrile

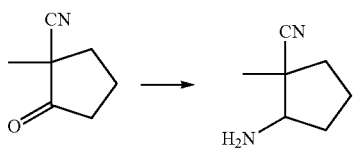

A mixture of 1-methyl-2-oxocyclopentanecarbonitrile (272 mg, 2.209 mmol, from Step 1) and ammonium acetate (917 mg, 11.90 mmol) in methanol (2 mL) was stirred at room temperature for 2 h. Sodium cyanoborohydride (69.4 mg, 1.104 mmol) was added. After 17 h at room temperature, the mixture was concentrated. The residue was dissolved in water and ethyl acetate and stirred vigorously. The ethyl acetate phase was separated, dried (MgSO₄), filtered and concentrated to give crude 2-amino-1-methylcyclopentanecarbonitrile (0.2436 g), which was taken to the next reaction without purification.

Step 3: (+/−)-4-((cis-2-cyano-2-methylcyclopentyl)amino)pyrrolo[1,2-b]pyridazine-3-carboxamide (Intermediate 28), and (+/−)-4-((trans-2-cyano-2-methylcyclopentyl)amino)pyrrolo[1,2-b]pyridazine-3-carboxamide (Intermediate 32)

According to the procedure described in Intermediate 1, 4-chloropyrrolo[1,2-b]-pyridazine-3-carboxamide (37.6 mg, 0.192 mmol, from Preparation 3) was reacted with crude 2-amino-1-methylcyclopentanecarbonitrile from Step 2 to give a mixture of cis and trans products. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM NH$_4$OAc; Mobile Phase B: 95:5 acetonitrile:water with 10-mM ammonium acetate;

Gradient: 10-45% B over 25 minutes, then a 5-minute hold at 100% B; Flow: 20 mL/min. The major product was found to be 4-((cis-2-cyano-2-methylcyclopentyl)amino)pyrrolo[1,2-b]pyridazine-3-carboxamide (Intermediate 28, 9.7 mg, 17% yield). $^1$H NMR (400 MHz, 1:1 mixture of methanol-d$_4$/chloroform-d) δ ppm 8.09 (1 H, s), 7.58 (1 H, dd, J=2.86, 1.54 Hz), 6.86 (1 H, dd, J=4.62, 1.32 Hz), 6.65-6.71 (1 H, m), 4.49 (1 H, t, J=7.26 Hz), 2.31-2.45 (2 H, m), 1.99-2.08 (1 H, m), 1.82-1.99 (3 H, m), 1.48 (3 H, s); MS (ES+) m/z: 284.14 (M+H); HPLC retention time: 1.658 min (analytical HPLC Method C). The minor product was found to be 4-((trans-2-cyano-2-methylcyclopentyl)amino)pyrrolo-[1,2-b]pyridazine-3-carboxamide (Intermediate 29, 3.7 mg, 7% yield). $^1$H NMR (400 MHz, 1:1 mixture of methanol-d$_4$/chloroform-d) δ ppm 8.09 (1 H, s), 7.59 (1 H, dd, J=2.86, 1.54 Hz), 7.00 (1 H, dd, J=4.73, 1.43 Hz), 6.70 (1 H, dd, J=4.62, 2.64 Hz), 4.97 (1 H, t, J=6.49 Hz), 2.41-2.52 (1 H, m), 2.25-2.36 (1 H, m), 1.78-2.00 (4 H, m), 1.45 (3 H, s); MS (ES+) m/z: 284.2 (M+H); HPLC retention time: 1.698 min (analytical HPLC Method K).

Intermediates 30 and 31

(+/−)-4-((cis-2-fluoro-2-methylcyclopentyl)amino)pyrrolo[1,2-b]pyridazine-3-carboxamide, and (+/−)-4-((trans-2-fluoro-2-methylcyclopentyl)amino)pyrrolo[1,2-b]-pyridazine-3-carboxamide

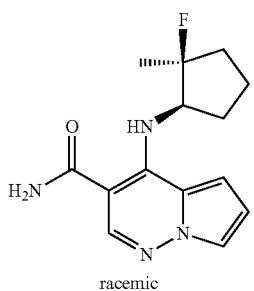

(Int-30)

racemic

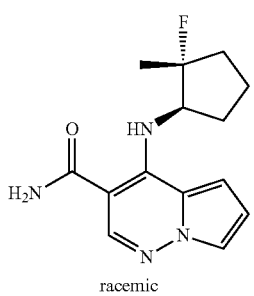

(Int-31)

racemic

Step 1: tert-butyl trans-2-hydroxycyclopentylcarbamate

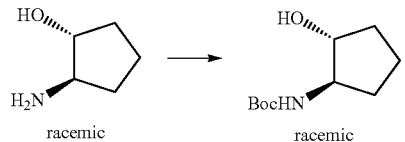 [SMILES: N[C@@H]1CCC[C@H]1O ; CC(C)(C)OC(=O)N[C@@H]1CCC[C@H]1O]

racemic            racemic

N,N-diisopropylethylamine (1.269 mL, 7.27 mmol) was added to a stirred suspension of 2-aminocyclopentanol hydrochloride (1.00 g, 7.27 mmol) and di-t-butyl dicarbonate (1.687 mL, 7.27 mmol) in dichloromethane (45 mL). After 20 h at room temperature, the clear solution was concentrated. Silica gel chromatography, eluting with 0 to 50% ethyl acetate in hexanes, gave tert-butyl trans-2-hydroxycyclopentylcarbamate as white solid (1.23 g, 84% yield). $^1$H NMR (400 MHz, chloroform-d) δ ppm 5.00 (1 H, br. s.), 3.99-4.29 (1 H, m), 3.81-3.93 (1 H, m), 3.53 (1 H, td, J=7.81, 5.72 Hz), 1.93-2.06 (1 H, m), 1.80-1.93 (1 H, m), 1.61-1.74 (1 H, m), 1.45-1.61 (2 H, m), 1.34 (9 H, s), 1.23-1.32 (1 H, m).

Step 2: tert-butyl 2-oxocyclopentylcarbamate

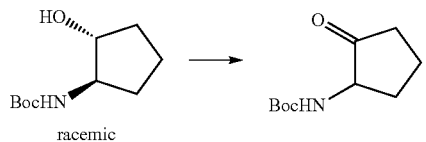 [SMILES: CC(C)(C)OC(=O)N[C@@H]1CCC[C@H]1O ; CC(C)(C)OC(=O)NC1CCCC1=O]

racemic

Dess-Martin periodinane (2.72 g, 6.41 mmol) was added to a stirred solution of tert-butyl 2-hydroxycyclopentylcarbamate (1.23 g, 6.11 mmol, from Step 1) in dichloromethane (30 mL) while the reaction container was placed in a room temperature water bath. After 1.5 h at room temperature, the mixture was quenched with 1 M aqueous sodium thiosulfate. After shaking the mixture vigorously, the dichloromethane phase was separated and concentrated. Silica gel chromatography, eluting with 0 to 50% ethyl acetate in hexanes, gave tert-butyl 2-oxocyclopentylcarbamate as white crystalline solid (824.6 mg, 68% yield). $^1$H NMR (400 MHz, chloroform-d) δ ppm 5.03 (1 H, br. s.), 3.90 (1 H, br. s.), 2.56 (1 H, br. s.), 2.38 (1 H, dd, J=19.15, 8.80 Hz), 2.08-2.22 (1 H, m), 1.96-2.08 (1 H, m), 1.73-1.89 (1 H, m), 1.52-1.69 (1 H, m), 1.42 (9 H, s).

Step 3: tert-butyl 2-hydroxy-2-methylcyclopentylcarbamate

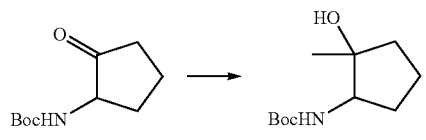

A 1.6 M ether solution of methyllithium (13.59 mL, 21.75 mmol) was added to a stirred suspension of tert-butyl 2-oxocyclopentylcarbamate (1.97 g, 9.89 mmol, from Step 2) and cerium(III) chloride (5.36 g, 21.75 mmol) in tetrahydrofuran (50 mL) at −78° C. under nitrogen. After 2.5 h at −78° C., the mixture was quenched with saturated ammonium chloride, allowed to warm to room temperature, and filtered through a short bed of Celite to remove insoluble cerium salt. The filter cake was rinsed with ethyl acetate. The filtrated was extracted with ethyl acetate three times. The combined ethyl acetate phase was washed with saturated ammonium chloride and brine respectively, dried (MgSO$_4$), filtered and concentrated. Silica gel chromatography, eluting with 0 to 50% ethyl acetate in hexanes, gave tert-butyl 2-hydroxy-2-methylcyclopentylcarbamate as yellow solid (1.47 g, 82% yield). $^1$H NMR analysis indicated the presence of approximately a 3:1 diastereomeric mixture.

Step 4: tert-butyl 2-fluoro-2-methylcyclopentylcarbamate

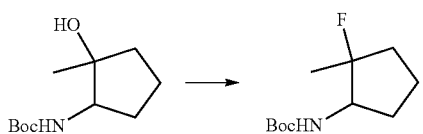

(Diethylamino)sulphur trifluoride (2.75 mL, 20.84 mmol) was added to a solution of tert-butyl 2-hydroxy-2-methylcyclopentylcarbamate (2.243 g, 10.42 mmol, from Step 3) in dichloromethane (40 mL) at −78° C. under nitrogen. After 4 h at −78° C., the mixture was quenched with saturated sodium bicarbonate, allowed to warm to room temperature, and extracted with dichloromethane. The dichloromethane phase was concentrated and purified by silica gel chromatography, eluting with 0 to 50% ethyl acetate in hexanes, to give tert-butyl 2-fluoro-2-methylcyclopentylcarbamate as brown oil (1.095 g, 48% yield). $^1$H NMR analysis indicated approximately 3.5:1 mixture of two diastereomers.

Step 5: 2-fluoro-2-methylcyclopentanamine

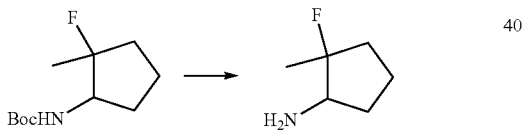

A 4 M dioxane solution of hydrogen chloride (6.30 mL, 25.2 mmol) was added to a stirred solution of tert-butyl 2-fluoro-2-methylcyclopentylcarbamate (1.0954 g, 5.04 mmol, from Step 4) in dichloromethane (4 mL) at room temperature. After 1.5 h at room temperature, the solvent was evaporated to give 2-fluoro-2-methylcyclopentanamine hydrochloride (740 mg, 96% yield).

Step 6: (+/−)-4-((cis-2-fluoro-2-methylcyclopentyl)amino)pyrrolo[1,2-b]pyridazine-3-carboxamide (Intermediate 30) and (+/−)-4-((trans-2-fluoro-2-methylcyclopentyl)amino)-pyrrolo[1,2-b]-pyridazine-3-carboxamide (Intermediate 31)

According to the procedure described in Intermediate 1, 4-chloropyrrolo[1,2-b]-pyridazine-3-carboxamide (160 mg, 0.818 mmol, from Preparation 3) was reacted with 2-fluoro-2-methylcyclopentanamine hydrochloride (188 mg, from Step 5) in the presence of excess disopropylethylamine to give a mixture of cis and trans products. Purification with reverse phase HPLC (Waters Xbridge C18 19×100 mm column), eluting with 25 to 100% solvent B (10% methanol-90% water-0.1% TFA) in solvent A (90% methanol-10% water-0.1% TFA), separated the two isomers. The major isomer was found to be 4-((cis-2-fluoro-2-methylcyclopentyl)amino)pyrrolo-[1,2-b]pyridazine-3-carboxamide (Intermediate 30, 87.6 mg, 38% yield). $^1$H NMR (400 MHz, 1:1 mixture of methanol-d$_4$/chloroform-d) δ ppm 10.68 (1 H, d, J=8.80 Hz), 8.10 (1 H, s), 7.58 (1 H, dd, J=2.75, 1.43 Hz), 6.87 (1 H, dd, J=4.62, 1.54 Hz), 6.69 (1 H, dd, J=4.51, 2.75 Hz), 4.24-4.38 (1 H, m), 2.34-2.44 (1 H, m), 2.08-2.24 (1 H, m), 1.73-2.02 (4 H, m), 1.49 (3 H, d); MS (ES+) m/z: 277.1 (M+H); HPLC retention time: 3.495 min (analytical HPLC Method F). The minor isomer was found to be 4-((trans-2-fluoro-2-methylcyclopentyl)amino)pyrrolo[1,2-b]pyridazine-3-carboxamide (Intermediate 31, 14.4 mg, 5% yield). $^1$H NMR (400 MHz, 1:1 mixture of methanol-d$_4$/chloroform-d) δ ppm 10.51 (1 H, d, J=8.80 Hz), 8.10 (1 H, s), 7.58 (1 H, dd, J=2.64, 1.54 Hz), 7.09 (1 H, d, J=4.40 Hz), 6.68 (1 H, dd, J=4.51, 2.75 Hz), 4.67-4.77 (1 H, m), 2.39-2.50 (1 H, m), 2.07-2.21 (1 H, m), 1.69-1.99 (4 H, m), 1.51 (3 H, d); MS (ES+) m/z: 277.1 (M+H); HPLC retention time: 3.796 min (analytical HPLC Method F).

Intermediates 32 and 33

4-(((1R,2S)-2-fluoro-2-methylcyclopentyl)amino)pyrrolo[1,2-b]pyridazine-3-carboxamide, and
4-(((1S,2R)-2-fluoro-2-methylcyclopentyl)amino)pyrrolo[1,2-b]-pyridazine-3-carboxamide

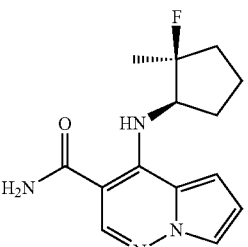

(Int-32)

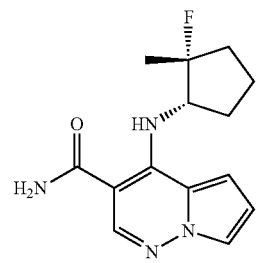

(Int-33)

Step 1: trans-2-amino-1-methylcyclopentanol

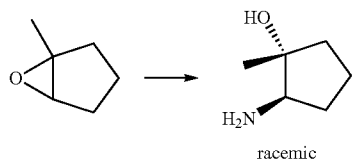

racemic

A mixture of methyl-1,2-cyclopentene-oxide (32.50 g, 331 mmol) and 7 N methanol solution of ammonia (284 mL, 1987 mmol) in a steel bomb was heated to 110-120° C. for 19 h and at 130-140° C. for 2 h. After cooling to room temperature, the mixture was concentrated in vacuo, pumped under house vacuum for 1 h and under high vacuum for 5 min (product volatile) to give crude trans-2-amino-1-methylcyclopentanol as brown liquid (37.5 g). This material was taken to the next reaction without purification.

Step 2: benzyl trans-2-hydroxy-2-methylcyclopentylcarbamate

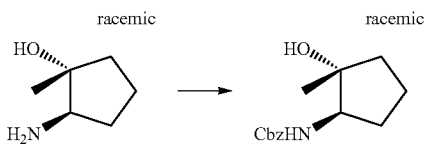

A mixture of the crude trans-2-amino-1-methylcyclopentanol (38.1 g, from Step 1), sodium carbonate (42.1 g, 397 mmol), tetrahydrofuran (400 mL) and water (400 mL) was cooled to 0° C. and stirred vigorously. Benzyl chloroformate (54.7 mL, 364 mmol, 95% pure) was added dropwise over 30 min. The resulting mixture was stirred overnight while the ice-water bath was allowed to slowly warm to room temperature. After evaporation of tetrahydrofuran in vacuo, the aqueous residue was diluted with water (200 mL) and extracted with ethyl acetate (3×200 mL). The combined extracts were washed with brine (50 mL), dried (MgSO$_4$), filtered and concentrated. The solid residue was transferred to a 500 mL flask, dissolved in methanol (25 mL), dichloromethane (50 mL) and ethyl acetate (125 mL). The mixture was slowly concentrated to ~120 mL in total volume while keeping the bath below room temperature. Upon triturating with ethyl acetate-hexanes (1:3, 100 mL), solid crashed out. The mixture was stirred vigorously to break up the solid chunks, then filtered. The solid was washed with 10% ethyl acetate in hexanes (2×50 mL) to give the first batch of benzyl trans-2-hydroxy-2-methylcyclopentylcarbamate as white solid (26.14 g). The filtrate was concentrated. Silica gel chromatography, eluting with 10 to 60% ethyl acetate in hexanes, gave second batch of the product as white solid (20.42 g). The combined amount of benzyl trans-2-hydroxy-2-methylcyclopentylcarbamate was 46.56 g (56% yield over two steps). $^1$H NMR (400 MHz, chloroform-d) δ ppm 7.28-7.50 (5 H, m), 5.12 (2 H, s), 4.76 (1 H, br. s.), 3.87 (1 H, ddd, J=9.79, 8.25, 5.94 Hz), 3.69 (1 H, s), 2.00-2.29 (1 H, m), 1.85 (1 H, br. s.), 1.68-1.82 (2 H, m), 1.56-1.69 (1 H, m), 1.23-1.43 (1 H, m), 1.16 (3 H, s).

Step 3: benzyl cis-2-fluoro-2-methylcyclopentylcarbamate

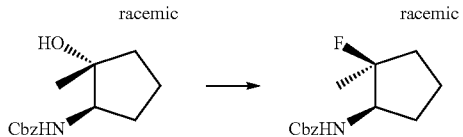 [SMILES: C[C@@]1(O)CCC[C@H]1NC(=O)OCc1ccccc1 ; C[C@]1(F)CCC[C@H]1NC(=O)OCc1ccccc1]

(Diethylamino)sulphur trifluoride (10.60 mL, 80 mmol) was added dropwise to a stirred suspension of benzyl 2-hydroxy-2-methylcyclopentylcarbamate (10.0 g, 40.1 mmol, from Step 2) in dichloromethane (401 mL) at −78° C. After 1 h at −78° C., the mixture was quenched with isopropanol (40 mL), allowed to warm to room temperature with vigorous stirring and concentrated. This material was combined with two additional runs (5.00 g and 8.48 g of alcohol starting material). Silica gel chromatography, eluting with 0 to 30% ethyl acetate in hexanes, gave benzyl cis-2-fluoro-2-methylcyclopentylcarbamate as white solid (17.26 g, 73% yield). $^1$H NMR (400 MHz, chloroform-d) δ ppm 7.29-7.40 (5 H, m), 5.12 (2 H, d, J=0.88 Hz), 4.97 (1 H, d, J=8.80 Hz), 3.75-3.91 (1 H, m), 1.94-2.16 (2 H, m), 1.72-1.88 (2 H, m), 1.56-1.67 (2 H, m), 1.40 (3 H, d, J=21.80 Hz).

Step 4: cis-2-fluoro-2-methylcyclopentanamine

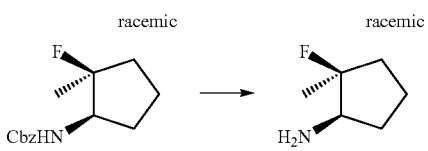

A stirred mixture of benzyl 2-fluoro-2-methylcyclopentylcarbamate (6.38 g, 25.4 mmol, from Step 3), Pearlman's catalyst (3.6 g) and 2 N hydrochloric acid (15.23 mL, 30.5 mmol) in methanol (85 mL) was hydrogenated under 50 psi hydrogen at room temperature for 17 h. Additional Pearlman's catalyst (0.4 g) was added and the hydrogenation continued at 50 psi hydrogen for 4 h. The mixture was filtered to remove the catalyst. The filtrate was concentrated and dried under vacuum overnight to give cis-2-fluoro-2-methylcyclopentanamine hydrochloride as white solid (3.792 g, 97% yield). $^1$H NMR (400 MHz, methanol-d$_4$) δ ppm 3.36-3.50 (1 H, m), 2.02-2.26 (2 H, m), 1.61-2.02 (4 H, m), 1.54 (3 H, d, J=21.70 Hz).

Step 5: 4-((cis-2-fluoro-2-methylcyclopentyl)amino) pyrrolo[1,2-b]pyridazine-3-carboxamide

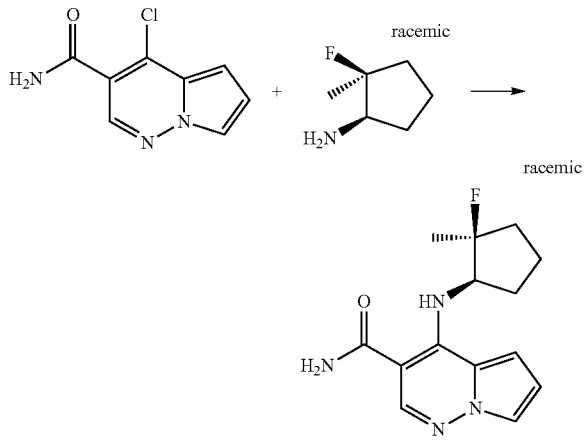

A mixture of 4-chloropyrrolo[1,2-b]pyridazine-3-carboxamide (7.00 g, 35.8 mmol, from Preparation 3), cis-2-fluoro-2-methylcyclopentanamine hydrochloride (6.05 g, 39.4 mmol, from Step 4), N,N-diisopropylethylamine (18.75 mL, 107 mmol) and N,N-dimethylformamide (71.6 mL) was purged with argon and heated in a sealed pressure bottle at 115° C. for 2 h. After cooling to room temperature, the mixture was poured into vigorously stirred water (800 mL) and the resulting suspension was filtered. The solid was triturated with dichloromethane (800 mL), filtered and dried under vacuum to give first batch of crude product (4.43 g). The filtrate was washed with brine (20 mL), dried (MgSO$_4$), filtered and concentrated to give second batch of crude product (4.36 g).

Step 6: 4-(((1R,2S)-2-fluoro-2-methylcyclopentyl)amino)pyrrolo[1,2-b]pyridazine-3-carboxamide (Intermediate 32), and 4-(((1S,2R)-2-fluoro-2-methylcyclopentyl)amino)-pyrrolo[1,2-b]-pyridazine-3-carboxamide (Intermediate 36)

The combined material from Step 5 was purified via preparative SFC with the following conditions: Column: Princeton CN (3×25 cm), 25×3 cm, 5 µm; Column Temp: 35° C.; Flow rate: 180 mL/min; Mobile Phase: CO$_2$/methanol=87/13; Detector Wavelength: 240 nm; Sample Solvent: DMSO/methanol=1:3(v/v); Sample Conc.=40 mg/mL. All fractions containing product were collected and the two enantiomers were resolved via preparative SFC with the following conditions: Column: Lux-AMY-2 (3×25 cm), 25×3 cm, 5 µm; Column Temp: 35° C.; Flow rate: 180 mL/min; Mobile Phase: CO$_2$/methanol=83/17; Detector Wavelength: 240 nm; Sample Solvent: dichloromethane/methanol/ACN=1:1:1(v/v/v); Sample Conc.=17 mg/mL. 4-(((1R,2S)-2-fluoro-2-methylcyclopentyl)amino)pyrrolo[1,2-b]pyridazine-3-carboxamide was obtained as white solid (Intermediate 32, 3.18 g). $^1$H NMR (400 MHz, 1:1 mixture of methanol-d$_4$/chloroform-d) δ ppm 8.05 (1 H, s), 7.53-7.55 (1 H, m), 6.83 (1 H, dd, J=4.62, 1.32 Hz), 6.65 (1 H, dd, J=4.62, 2.64 Hz), 4.20-4.32 (1 H, m), 2.30-2.40 (1 H, m), 2.05-2.20 (1 H, m), 1.68-2.00 (4 H, m), 1.45 (3 H, d, J=21.60 Hz); MS (ES+) m/z:=277.2 (M+H); HPLC retention time: 3.483 min (analytical HPLC Method F). 4-(((1S,2R)-2-fluoro-2-methylcyclopentyl)amino)-pyrrolo[1,2-b]pyridazine-3-carboxamide was obtained as white solid (Intermediate 36, 3.30 g). $^1$H NMR (400 MHz, methanol-d$_4$) δ ppm 8.12 (1 H, s), 7.58 (1 H, dd, J=2.64, 1.54 Hz), 6.96 (1 H, dd, J=4.62, 1.32 Hz), 6.69 (1 H, dd, J=4.62, 2.64 Hz), 4.33-4.47 (1 H, m), 2.33-2.43 (1 H, m), 1.72-2.17 (6 H, m), 1.46 (3 H, d); MS (ES+) m/z:=277.1 (M+H); HPLC retention time: 3.483 min (analytical HPLC Method F).

Intermediate 34

(+/−)-4((2,2-dimethyl-3-cyclopenten-1-yl)amino)pyrrolo[1,2-b]pyridazine-3-carboxamide (Int-34)

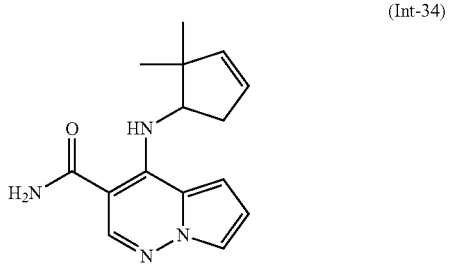 [SMILES: CC1(C)C=CCC1Nc1c(C(N)=O)cnn2cccc12]

Step 1: cis-3-(3-carbamoylpyrrolo[1,2-b]pyridazin-4-ylamino)-2,2-dimethylcyclopentyl methanesulfonate

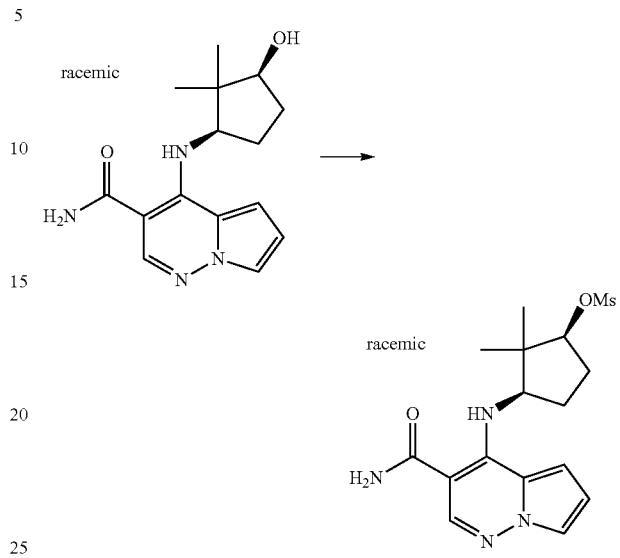

Triethylamine (0.131 mL, 0.936 mmol) and methanesulfonyl chloride (0.029 mL, 0.375 mmol) were added to a solution of 4-((cis-3-hydroxy-2,2-dimethylcyclopentyl)amino)pyrrolo[1,2-b]pyridazine-3-carboxamide (90 mg, 0.312 mmol, from Intermediate 16) in dichloromethane (5 mL). After 15 h at room temperature, the mixture was diluted with dichloromethane (60 mL), washed with saturated sodium bicarbonate (5 mL), brine (5 mL), dried (MgSO$_4$), filtered and concentrated to give crude cis-3-(3-carbamoylpyrrolo[1,2-b]pyridazin-4-ylamino)-2,2-dimethylcyclopentyl methanesulfonate.

Step 2: (+/−)-4-((2,2-dimethyl-3-cyclopenten-1-yl)amino)pyrrolo[1,2-b]pyridazine-3-carboxamide (Intermediate 34)

A mixture of crude cis-3-(3-carbamoylpyrrolo[1,2-b]pyridazin-4-ylamino)-2,2-dimethylcyclopentyl methanesulfonate (from Step 1), 1,8-diazabiclo[5,4,0]undec-7-ene (0.235 mL, 1.561 mmol) and N,N-dimethylformamide (2 mL) was stirred at 130° C. for 2 h, cooled to room temperature and quenched with saturated sodium bicarbonate (3 mL). Following addition of ethyl acetate (80 mL), the mixture was washed with water, brine, dried (MgSO$_4$), filtered and concentrated. Silica gel chromatography, eluting with 20 to 100% ethyl acetate in hexanes, gave the title compound (40 mg, 47% yield for 2 steps). $^1$H NMR (400 MHz, methanol-d$_4$) δ ppm 10.70 (1 H, d, J=8.58 Hz), 7.87-8.20 (1 H, m), 7.57 (1 H, dd, J=2.64, 1.54 Hz), 6.99 (1 H, dd, J=4.73, 1.43 Hz), 6.67 (1 H, dd, J=4.62, 2.86 Hz), 5.60-5.87 (2 H, m), 4.47-4.64 (1 H, m), 2.78-3.15 (1 H, m), 2.23-2.51 (1 H, m), 1.01-1.24 (6 H, m); MS (ES+) m/z:=271.2 (M+H).

Intermediate 35

(+/−)-4-((trans,cis-3,4-dihydroxy-2,2-dimethylcyclopentyl)amino)pyrrolo[1,2-b]-pyridazine-3-carboxamide

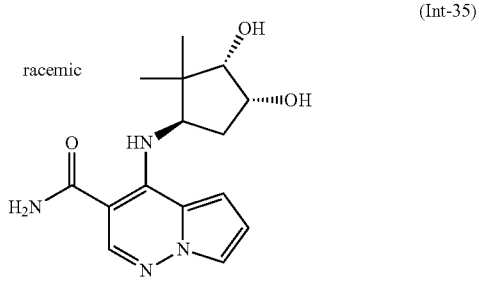 [SMILES: CC1(C)[C@H](O)[C@H](O)C[C@H]1Nc1c(C(N)=O)cnn2cccc12]
(Int-35)

N-methylmorpholine-N-oxide (19.76 mg, 0.084 mmol) and osmium tetraoxide (0.89 mg, 3.51 μmol) were added to a solution of 4-((2,2-dimethyl-3-cyclopenten-1-yl)amino)pyrrolo[1,2-b]pyridazine-3-carboxamide (19 mg, 0.070 mmol, from Intermediate 34) in acetone (0.4 mL), water (0.1 mL), tetrahydrofuran (0.2 mL) and t-butanol (0.2 mL) at 0° C. After 2 h at room temperature, sodium thiosulfate (50 mg) was added. After stirring for 10 min, the mixture was diluted with ethyl acetate (60 mL), washed with saturated sodium bicarbonate (5 mL), brine (5 mL), dried (MgSO$_4$), filtered and concentrated. Silica gel chromatography, eluting with 0 to 100% methanol in dichloromethane, gave the title compound (12 mg, 53% yield). $^1$H NMR (500 MHz, methanol-d$_4$) δ ppm 10.63 (1 H, d, J=9.16 Hz), 8.13 (1 H, s), 7.35-7.76 (1 H, m), 7.06 (1 H, dd, J=4.58, 1.53 Hz), 6.69 (1 H, dd, J=4.58, 2.64 Hz), 4.59-4.73 (1 H, m), 4.22-4.51 (1 H, m), 3.69 (1 H, d, J=4.72 Hz), 2.14-2.43 (1 H, m), 1.85-2.18 (1 H, m), 1.00-1.22 (6 H, m); MS (ES+) m/z:=305.1 (M+H).

Examples 3 to 27

According to the procedure described in Intermediate 7, Examples 3-27 were prepared by reacting 6-amino-4-((trans-3-hydroxy-2,2,3-trimethylcyclopentyl)amino)-pyrrolo[1,2-b]pyridazine-3-carboxamide (from Intermediate 35) with appropriate acid chlorides, isocyanates, sulfonyl chlorides, and chlorocarbonates, which were commercially available. All compounds were analyzed using HPLC Method K.

| Ex # | Structure | HPLC Rt (minutes) | LCMS [m/z (M + H)] |
|---|---|---|---|
| 5 | 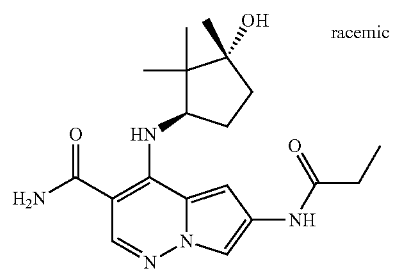 [SMILES: CCC(=O)Nc1cc2c(N[C@@H]3CC[C@@](C)(O)C3(C)C)c(C(N)=O)cnn2c1] | 1.43 | 374.13 |
| 6 | 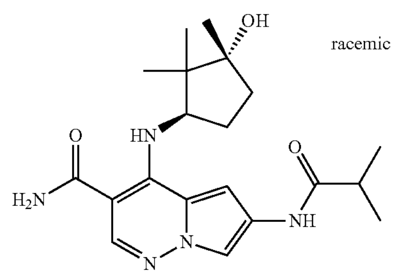 [SMILES: CC(C)C(=O)Nc1cc2c(N[C@@H]3CC[C@@](C)(O)C3(C)C)c(C(N)=O)cnn2c1] | 1.57 | 388.14 |
| 7 | 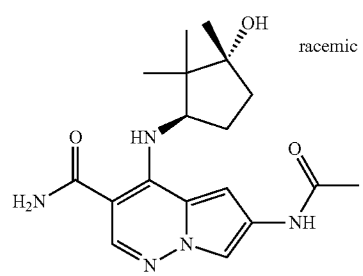 [SMILES: CC(=O)Nc1cc2c(N[C@@H]3CC[C@@](C)(O)C3(C)C)c(C(N)=O)cnn2c1] | 1.3 | 360.15 |

-continued

| Ex # | Structure | HPLC Rt (minutes) | LCMS [m/z (M + H)] |
|---|---|---|---|
| 8 | racemic | 2.11 | 456.04 |
| 9 | racemic | 1.88 | 452.07 |
| 10 | racemic | 1.83 | 422.09 |
| 11 | racemic | 2.00 | 418.12 |
| 12 | racemic | 1.47 | 376.09 |

-continued

| Ex # | Structure | HPLC Rt (minutes) | LCMS [m/z (M + H)] |
|---|---|---|---|
| 13 | racemic | 1.99 | 438.07 |
| 14 | racemic | 2.24 | 472.01 |
| 15 | racemic | 1.73 | 402.11 |
| 16 | racemic | 1.58 | 388.12 |
| 17 | racemic | 1.80 | 437.08 |

-continued
| Ex # | Structure | HPLC Rt (minutes) | LCMS [m/z (M + H)] |
|---|---|---|---|
| 18 | 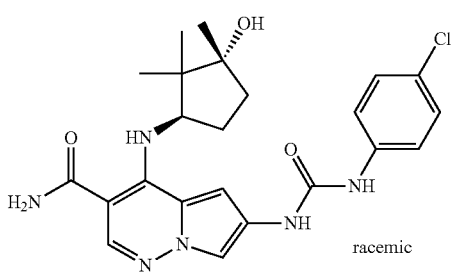 [SMILES: CC1(C)[C@H](Nc2c(C(N)=O)cnn3cc(NC(=O)Nc4ccc(Cl)cc4)cc23)CC[C@@]1(C)O] racemic | 2.07 | 471.05 |
| 19 | 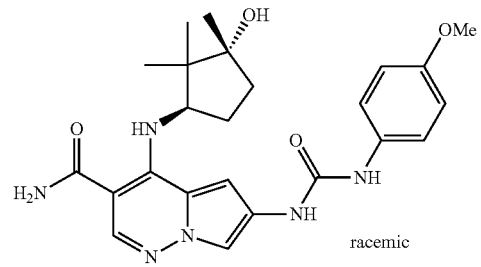 [SMILES: COc1ccc(NC(=O)Nc2cc3c(N[C@@H]4CC[C@@](C)(O)C4(C)C)c(C(N)=O)cnn3c2)cc1] racemic | 1.77 | 467.07 |
| 20 | 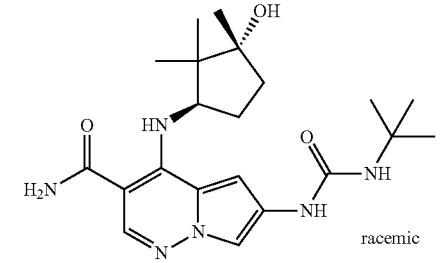 [SMILES: CC(C)(C)NC(=O)Nc1cc2c(N[C@@H]3CC[C@@](C)(O)C3(C)C)c(C(N)=O)cnn2c1] racemic | 1.71 | 417.13 |
| 21 | 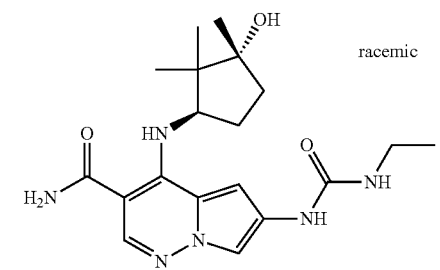 [SMILES: CCNC(=O)Nc1cc2c(N[C@@H]3CC[C@@](C)(O)C3(C)C)c(C(N)=O)cnn2c1] racemic | 1.38 | 389.13 |
| 22 | 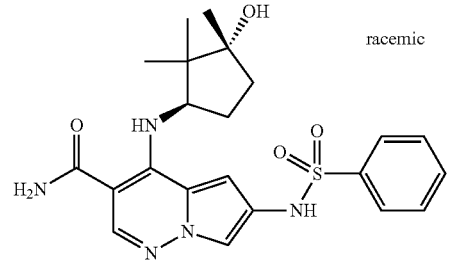 [SMILES: CC1(C)[C@H](Nc2c(C(N)=O)cnn3cc(NS(=O)(=O)c4ccccc4)cc23)CC[C@@]1(C)O] racemic | 1.76 | 458.03 |

-continued
| Ex # | Structure | HPLC Rt (minutes) | LCMS [m/z (M + H)] |
|---|---|---|---|
| 23 | 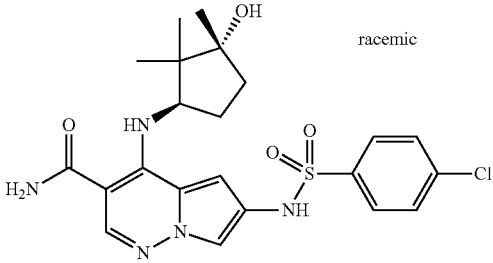 [SMILES: CC1(C)[C@H](Nc2c(C(N)=O)cnn3cc(NS(=O)(=O)c4ccc(Cl)cc4)cc23)CC[C@@]1(C)O] racemic | 2.01 | 491.99 |
| 24 | 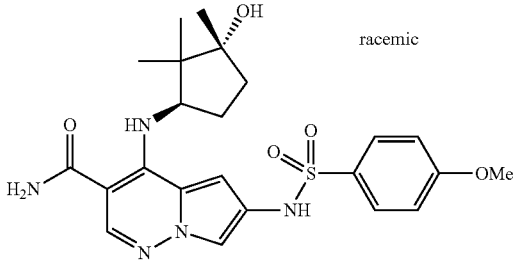 [SMILES: COc1ccc(S(=O)(=O)Nc2cc3c(N[C@@H]4CC[C@@](C)(O)C4(C)C)c(C(N)=O)cnn3c2)cc1] racemic | 1.8 | 488.05 |
| 25 | 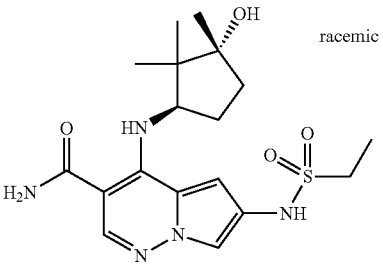 [SMILES: CCS(=O)(=O)Nc1cc2c(N[C@@H]3CC[C@@](C)(O)C3(C)C)c(C(N)=O)cnn2c1] racemic | 1.51 | 410.12 |
| 26 | 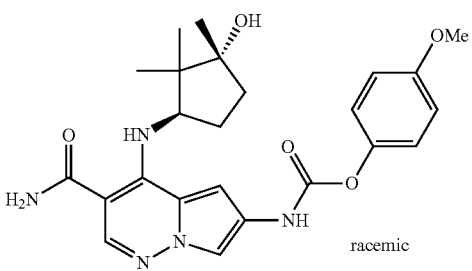 [SMILES: COc1ccc(OC(=O)Nc2cc3c(N[C@@H]4CC[C@@](C)(O)C4(C)C)c(C(N)=O)cnn3c2)cc1] racemic | 2.07 | 468.15 |
| 27 | 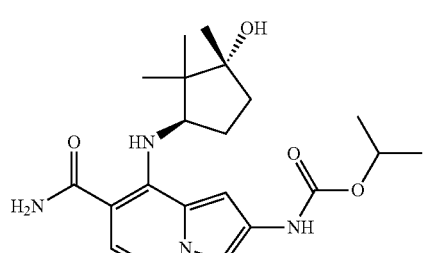 racemic | 1.77 | 404.09 |

Intermediate 36

(+/−)-6-bromo-4-((cis-2-fluoro-2-methylcyclopentyl)amino)pyrrolo[1,2-b]pyridazine-3-carboxamide (Int-36)

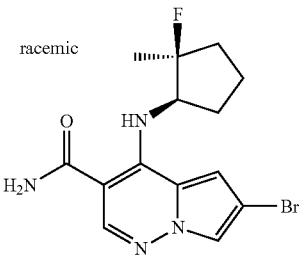

A stirred solution of 6-bromo-4-chloropyrrolo[1,2-b]pyridazine-3-carboxamide (1.58 g, 5.76 mmol, from Preparation 5), cis-2-fluoro-2-methylcyclopentanamine hydrochloride (0.96 g, 6.25 mmol, from Step 4 of Intermediates 29 and 30) and N,N-diisopropylethylamine (3.02 mL, 17.27 mmol) in N,N-dimethylformamide (10 mL) was pumped under vacuum and backfilled with nitrogen twice. The reaction vial was sealed and heated at 95° C. for 2 h. The mixture was cooled to room temperature and poured into vigorously stirred water (50 mL). An off-white solid precipitated out, which was collected by filtration and dried under vacuum to give the title compound (1.939 g, 95% yield). $^1$H NMR (400 MHz, methanol-$d_4$) δ ppm 8.14 (1 H, s), 7.63 (1 H, d, J=1.76 Hz), 7.00 (1 H, d, J=1.76 Hz), 4.26-4.39 (1 H, m), 2.28-2.40 (1 H, m), 1.74-2.15 (5 H, m), 1.45 (3 H, d, J=21.50 Hz); MS (ES+) m/z: 355.0, 357.0 (M+H); HPLC retention time: 4.010 min (analytical HPLC Method F).

Example 28

(+/−)-4-((cis-2-fluoro-2-methylcyclopentyl)amino)-6-(4-(methylcarbamoyl)phenyl)pyrrolo[1,2-b]pyridazine-3-carboxamide (28)

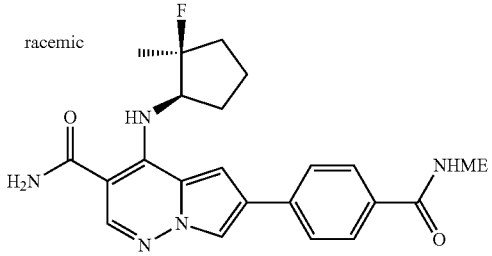

A mixture of 6-bromo-4-((cis-2-fluoro-2-methylcyclopentyl)amino) pyrrolo[1,2-b]pyridazine-3-carboxamide (20 mg, 0.056 mmol, from Intermediate 36), 4-(methylcarbamoyl)phenylboronic acid (20.16 mg, 0.113 mmol), potassium phosphate (35.9 mg, 0.169 mmol), palladium(II) acetate (2.53 mg, 0.011 mmol) and 1,1'-bis(di-tert-butylphosphino)ferrocene (5.41 mg, 0.011 mmol) in N,N-dimethylacetamide (0.5 mL) was pumped and backfilled with nitrogen twice. The reaction tube was sealed and heated to 95° C. for 1.5 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (10.6 mg, 42% yield). $^1$H NMR (400 MHz, 1:1 mixture of methanol-$d_4$/chloroform-d) δ ppm 8.10 (1 H, s), 7.92 (1 H, d, J=1.76 Hz), 7.83 (2 H, d, J=8.36 Hz), 7.70 (2 H, d, J=8.36 Hz), 7.10 (1 H, d, J=1.54 Hz), 4.29-4.41 (1 H, m), 2.63 (3 H, s), 2.38-2.47 (1 H, m), 2.07-2.22 (1 H, m), 1.77-2.05 (4 H, m), 1.49 (3 H, d, J=21.60 Hz); MS (ES+) m/z: 410.3 (M+H); HPLC retention time: 1.801 min (analytical HPLC Method K).

Examples 29-100

According to the procedure described for Example 28, Examples 29-100 were prepared by Suzuki coupling of 6-bromo-4-((cis-2-fluoro-2-methylcyclopentyl)amino)pyrrolo[1,2-b]pyridazine-3-carboxamide (from Intermediate 36) with appropriate boronic acids or boronic acid esters, which were commercially available. In some cases, 1,1'-bis(diphenylphosphino)ferrocene palladium(II) chloride dichloromethane complex was used instead of palladium(II) acetate and 1,1'-bis(di-tert-butylphosphino)ferrocene. Examples 29, 32-34, 39 and 40 were analyzed using HPLC Method F. Examples 30, 36, 38, 41-43, 45, 47-49, 51-53, 55-61 were analyzed using HPLC Method C. Example 50 was analyzed using HPLC Method D. Example 35 was analyzed using HPLC Method I. Examples 31, 37, 44, 47, 55, 62-100 were analyzed using HPLC Method K.

| Ex # | Structure | HPLC Rt (minutes) | LCMS [m/z (M + H)] |
|---|---|---|---|
| 29 | 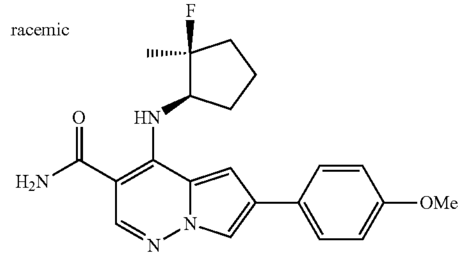 [SMILES: COc1ccc(-c2cc3c(N[C@@H]4CCC[C@]4(C)F)c(C(N)=O)cnn3c2)cc1] | 4.255 | 383.2 |

-continued

| Ex # | Structure | HPLC Rt (minutes) | LCMS [m/z (M + H)] |
|---|---|---|---|
| 30 | racemic | 2.488 | 353.10 |
| 31 | racemic | 2.403 | 378.1 |
| 32 | racemic | 3.388 | 343.2 |
| 33 | racemic | 2.745 | 354.3 |
| 34 | racemic | 4.303 | 371.1 |

-continued

| Ex # | Structure | HPLC Rt (minutes) | LCMS [m/z (M + H)] |
|---|---|---|---|
| 35 | racemic | 1.820 | 357.2 |
| 36 | racemic | 2.223 | 395.1 |
| 37 | racemic | 1.962 | 424.2 |
| 38 | racemic | 2.035 | 484.2 |
| 39 | racemic | 2.753 | 354.2 |

-continued

| Ex # | Structure | HPLC Rt (minutes) | LCMS [m/z (M + H)] |
|---|---|---|---|
| 40 | racemic | 3.738 | 379.2 |
| 41 | racemic | 2.776 | 387.02 |
| 42 | racemic | 2.646 | 458.12 |
| 43 | racemic | 1.728 | 384.12 |
| 44 | racemic | 1.382 | 393.1 |

-continued

| Ex # | Structure | HPLC Rt (minutes) | LCMS [m/z (M + H)] |
|---|---|---|---|
| 45 | racemic | 2.155 | 372.09 |
| 46 | racemic | 2.007 | 372.1 |
| 47 | racemic | 2.478 | 422.05 |
| 48 | racemic | 1.570 | 372.07 |
| 49 | racemic | 1.657 | 396.08 |

| Ex # | Structure | HPLC Rt (minutes) | LCMS [m/z (M + H)] |
|---|---|---|---|
| 50 | racemic 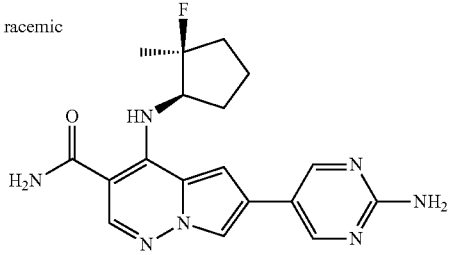 [SMILES: C[C@]1(F)CCC[C@H]1Nc1c(C(N)=O)cnn2cc(-c3cnc(N)nc3)cc12] | 1.588 | 370.04 |
| 51 | racemic 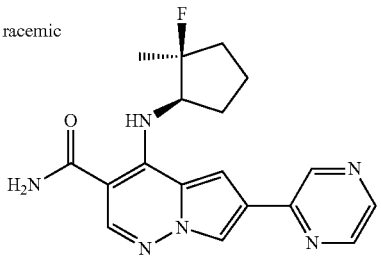 [SMILES: C[C@]1(F)CCC[C@H]1Nc1c(C(N)=O)cnn2cc(-c3cnccn3)cc12] | 1.745 | 355.08 |
| 52 | racemic 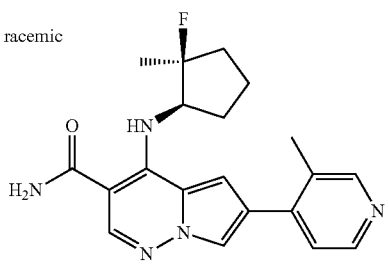 [SMILES: Cc1cnccc1-c1cc2c(N[C@@H]3CCC[C@]3(C)F)c(C(N)=O)cnn2c1] | 1.333 | 368.07 |
| 53 | racemic 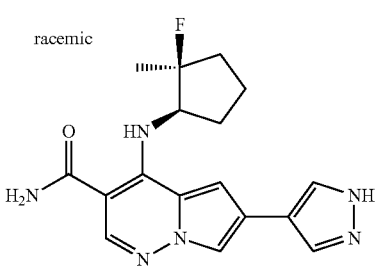 [SMILES: C[C@]1(F)CCC[C@H]1Nc1c(C(N)=O)cnn2cc(-c3cn[nH]c3)cc12] | 1.502 | 343.07 |
| 54 | racemic 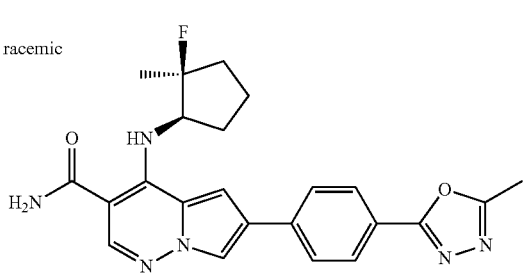 [SMILES: Cc1nnc(-c2ccc(-c3cc4c(N[C@@H]5CCC[C@]5(C)F)c(C(N)=O)cnn4c3)cc2)o1] | 2.088 | 435.3 |

-continued

| Ex # | Structure | HPLC Rt (minutes) | LCMS [m/z (M + H)] |
|---|---|---|---|
| 55 | racemic | 2.373 | 419.07 |
| 56 | racemic | 1.390 | 368.11 |
| 57 | racemic | 1.457 | 382.07 |
| 58 | racemic | 2.850 | 381.06 |
| 59 | racemic | 2.437 | 422.00 |

-continued

| Ex # | Structure | HPLC Rt (minutes) | LCMS [m/z (M + H)] |
|---|---|---|---|
| 60 | racemic | 3.005 | 395.12 |
| 61 | racemic | 1.660 | 355.11 |
| 62 | racemic | 1.89 | 411.04 |
| 63 | racemic | 1.5 | 438.13 |
| 64 | racemic | 2.23 | 387.99 |

-continued

| Ex # | Structure | HPLC Rt (minutes) | LCMS [m/z (M + H)] |
|---|---|---|---|
| 65 | racemic | 2.08 | 439.02 |
| 66 | racemic | 1.95 | 424.04 |
| 67 | racemic | 2.54 | 406.05 |
| 68 | racemic | 2.19 | 404.06 |
| 69 | racemic | 2.15 | 404.06 |

-continued
| Ex # | Structure | HPLC Rt (minutes) | LCMS [m/z (M + H)] |
|---|---|---|---|
| 70 | 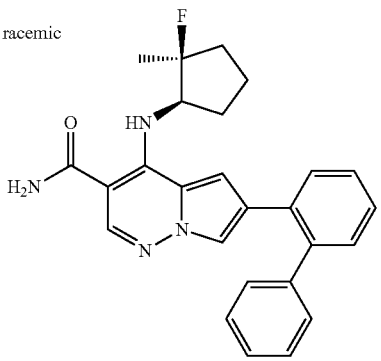 [SMILES: C[C@]1(F)CCC[C@H]1Nc1c(C(N)=O)cnn2cc(-c3ccccc3-c3ccccc3)cc12] | 3.04 | 429.03 |
| 71 | 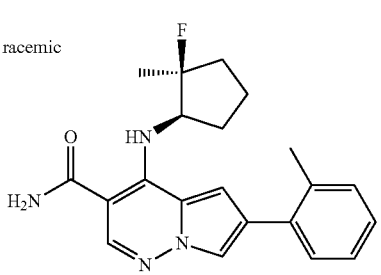 [SMILES: Cc1ccccc1-c1cc2c(N[C@@H]3CCC[C@]3(C)F)c(C(N)=O)cnn2c1] | 2.72 | 367.06 |
| 72 | 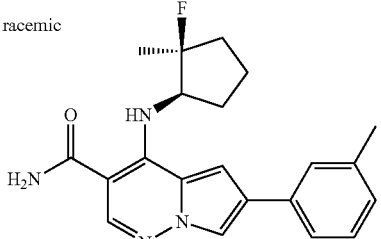 | 2.73 | 367.06 |
| 73 | 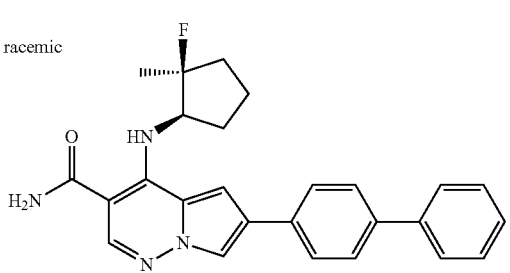 [SMILES: C[C@]1(F)CCC[C@H]1Nc1c(C(N)=O)cnn2cc(-c3ccc(-c4ccccc4)cc3)cc12] | 3.10 | 429.1 |
| 74 | 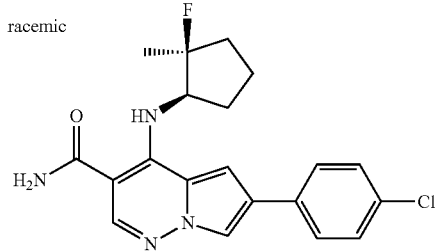 [SMILES: C[C@]1(F)CCC[C@H]1Nc1c(C(N)=O)cnn2cc(-c3ccc(Cl)cc3)cc12] | 2.82 | 387.03 |

| Ex # | Structure | HPLC Rt (minutes) | LCMS [m/z (M + H)] |
|---|---|---|---|
| 75 | racemic | 1.98 | 368.08 |
| 76 | racemic | 2.68 | 389.01 |
| 77 | racemic | 1.85 | 383.06 |
| 78 | racemic | 2.60 | 371.03 |
| 79 | racemic | 2.71 | 387.03 |

| Ex # | Structure | HPLC Rt (minutes) | LCMS [m/z (M + H)] |
|---|---|---|---|
| 80 | racemic | 2.6 | 371.03 |
| 81 | racemic | 2.91 | 381.08 |
| 82 | racemic | 1.83 | 424.04 |
| 83 | racemic | 2.03 | 430.96 |
| 84 | racemic | 2.00 | 446.01 |

| Ex # | Structure | HPLC Rt (minutes) | LCMS [m/z (M + H)] |
|---|---|---|---|
| 85 | racemic | 1.83 | 432.04 |
| 86 | racemic | 1.69 | 396.06 |
| 87 | racemic | 1.83 | 410.02 |
| 88 | racemic | 2.39 | 378.00 |
| 89 | racemic | 2.00 | 430.96 |

-continued

| Ex # | Structure | HPLC Rt (minutes) | LCMS [m/z (M + H)] |
|---|---|---|---|
| 90 | racemic | 3.09 | 429.03 |
| 91 | racemic | 2.74 | 367.06 |
| 92 | racemic | 1.78 | 424.04 |
| 93 | racemic | 2.04 | 405.02 |
| 94 | racemic | 1.73 | 396.06 |

| Ex # | Structure | HPLC Rt (minutes) | LCMS [m/z (M + H)] |
|---|---|---|---|
| 95 | racemic | 2.14 | 404.06 |
| 96 | racemic | 2.13 | 404.00 |
| 97 | racemic | 2.06 | 446.09 |
| 98 | racemic | 2.58 | 378.14 |
| 99 | racemic | 2.32 | 368.11 |

| Ex # | Structure | HPLC Rt (minutes) | LCMS [m/z (M + H)] |
|---|---|---|---|
| 100 | 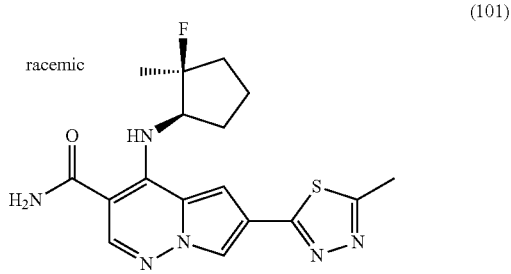 [SMILES: Cc1nnc(-c2cc3c(N[C@@H]4CCC[C@]4(C)F)c(C(N)=O)cnn3c2)s1] | 2.07 | 410.11 |

Example 101

(+/−)-4-((cis-2-fluoro-2-methylcyclopentyl)amino)-6-(5-methyl-1,3,4-thiadiazol-2-yl)pyrrolo[1,2-b]pyridazine-3-carboxamide (101)

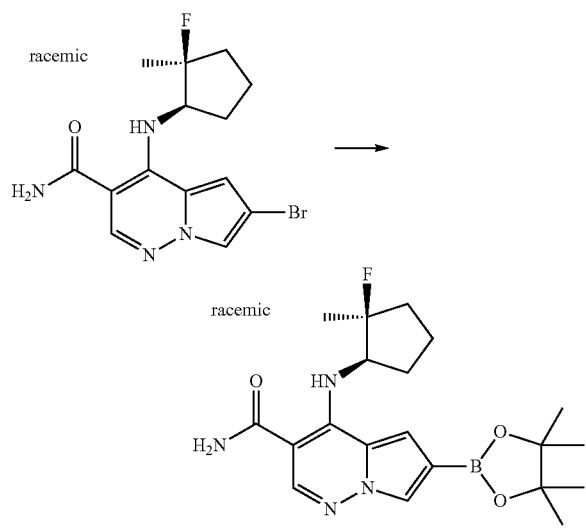

Step 1: 4-(cis-2-fluoro-2-methylcyclopentylamino)-6-(4,4,5,5-tetramethyl-1,3,2-dioxaborolan-2-yl)pyrrolo[1,2-b]pyridazine-3-carboxamide A mixture of 6-bromo-4-((cis-2-fluoro-2-methylcyclopentyl)amino) pyrrolo[1,2-b]pyridazine-3-carboxamide (20 mg, 0.056 mmol, from Intermediate 36), 4,4,4',4',5,5,5',5'-octamethyl-2,2'-bi(1,3,2-dioxaborolane) (28.6 mg, 0.113 mmol), potassium acetate (16.6 mg, 0.169 mmol), 1,1'-bis(diphenylphosphino)ferrocene palladium(II) chloride dichloromethane complex (7.6 mg, 0.009 mmol) and N,N-dimethylformamide (0.5 mL) was pumped and backfilled with nitrogen twice. The reaction tube was sealed and heated to 90° C. for 4 h. The crude mixture was concentrated. The solid residue was diluted with water and ethyl acetate then filtered. The two phases of the filtrate were separated. The ethyl acetate phase was collected and concentrated. Silica gel chromatography, eluting with 0 to 100% ethyl acetate in hexanes, gave 4-(cis-2-fluoro-2-methylcyclopentylamino)-6-(4,4,5,5-tetramethyl-1,3,2-dioxaborolan-2-yl)pyrrolo[1,2-b]pyridazine-3-carboxamide (13 mg) as impure product. This material was taken to the next reaction without purification.

Step 2: (+/−)-4-((cis-2-fluoro-2-methylcyclopentyl)amino)-6-(5-methyl-1,3,4-thiadiazol-2-yl)pyrrolo[1,2-b]pyridazine-3-carboxamide (Example 101)

A stirred mixture of impure 4-(2-fluoro-2-methylcyclopentylamino)-6-(4,4,5,5-tetramethyl-1,3,2-dioxaborolan-2-yl)pyrrolo[1,2-b]pyridazine-3-carboxamide (13 mg, from Step 1), 2-bromo-5-methyl-1,3,4-thiadiazole (6.94 mg, 0.039 mmol), potassium phosphate (35.9 mg, 0.169 mmol), palladium(II) acetate (2.53 mg, 0.011 mmol), 1,1'-bis(di-tert-butylphosphino)ferrocene (5.41 mg, 0.011 mmol) and N,N-dimethylformamide (0.5 mL) was pumped under vacuum and backfilled with nitrogen twice. The reaction vial was sealed and heated to 90° C. for 45 min. Additional 2-bromo-5-methyl-1,3,4-thiadiazole (7 mg) was added. Heating continued for another 40 min. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give the title compound (1.5 mg). $^1$H NMR (500 MHz, 1:1 mixture of methanol-$d_4$/chloroform-d) δ ppm 8.15 (1 H, s), 8.02 (1 H, d, J=1.66 Hz), 7.35 (1 H, d, J=1.66 Hz), 4.27-4.37 (1 H, m), 2.79 (3 H, s), 2.39-2.45 (1 H, m), 2.08-2.19 (1 H, m), 1.79-2.01 (4 H, m), 1.48 (3 H, d, J=21.70 Hz); MS (ES+) m/z: 375.02 (M+H); HPLC retention time: 1.817 min (analytical HPLC Method C).

Example 102

(+/−)-4-((cis-2-fluoro-2-methylcyclopentyl)amino)-6-(4-methyl-2-pyridinyl)pyrrolo[1,2-b]pyridazine-3-carboxamide

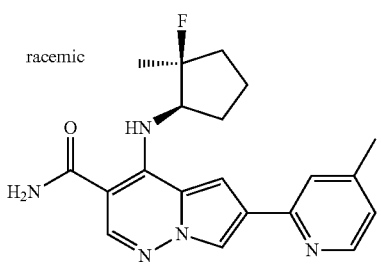
(102)

A stirred mixture of 6-bromo-4-((cis-2-fluoro-2-methylcyclopentyl)amino)pyrrolo[1,2-b]pyridazine-3-carboxamide (20 mg, 0.056 mmol, from Intermediate 36), 4-methyl-2-(tributylstannyl)pyridine (43.0 mg, 0.113 mmol), bis(triphenylphosphine)palladium(II) chloride (7.90 mg, 0.011 mmol) and tetrahydrofuran (0.5 mL) was pumped and backfilled with nitrogen twice. The reaction tube was sealed and heated to 90° C. for 5 h. Additional 4-methyl-2-(tributylstannyl)pyridine (43 mg) and 1,1'-bis(diphenylphosphino)ferrocene palladium(II) chloride dichloromethane complex (12 mg, 0.015 mmol) were added. The mixture was heated to 90° C. for additional 16 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (5.1 mg, 24% yield). $^1$H NMR (400 MHz, 1:1 mixture of methanol-$d_4$/chloroform-d) δ ppm 8.35 (1 H, d, J=5.06 Hz), 8.11 (1 H, s), 8.07 (1 H, d, J=1.76 Hz), 7.55 (1 H, s), 7.43 (1 H, d, J=1.76 Hz), 7.07 (1 H, d, J=5.06 Hz), 4.36-4.47 (1 H, m), 2.43-2.50 (1 H, m), 2.42 (3 H, s), 2.13 (1 H, d, J=18.71 Hz), 1.81-2.05 (4 H, m), 1.48 (3 H, d, J=21.60 Hz); MS (ES+) m/z: 368.3 (M+H); HPLC retention time: 1.363 min (analytical HPLC Method K).

Example 103

(+/−)-4-((cis-2-fluoro-2-methylcyclopentyl)amino)-6-(5-methyl-2-pyridinyl)pyrrolo[1,2-b]pyridazine-3-carboxamide

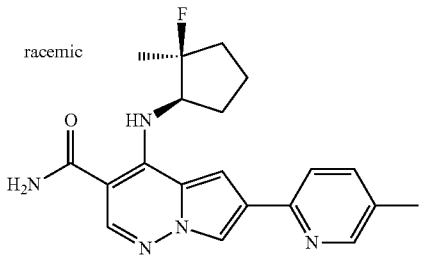
(103)

Following conditions described for preparation of Example 102, Example 103 was prepared from 6-bromo-4-((cis-2-fluoro-2-methylcyclopentyl)amino)pyrrolo[1,2-b]pyridazine-3-carboxamide (from Intermediate 36) and 5-methyl-2-(tributylstannyl)pyridine. $^1$H NMR (500 MHz, 1:1 mixture of methanol-$d_4$/chloroform-d) δ ppm 8.45 (1 H, s), 8.20 (1 H, d, J=1.94 Hz), 8.16 (1 H, s), 7.93-8.01 (2 H, m), 7.54 (1 H, d, J=1.94 Hz), 4.33-4.43 (1 H, m), 2.46 (3 H, s), 2.41-2.45 (1 H, m), 2.08-2.20 (1 H, m), 1.79-2.02 (4 H, m), 1.49 (3 H, d, J=21.60 Hz); MS (ES+) m/z: 368.08 (M+H); HPLC retention time: 1.477 min (analytical HPLC Method C).

Intermediates 37 and 38

4-(((1R,3R)-3-amino-2,2,3-trimethylcyclopentyl)amino)-6-bromopyrrolo[1,2-b]pyridazine-3-carboxamide, and 4-(((1S,3R)-3-amino-2,2,3-trimethylcyclopentyl)amino)-6-bromopyrrolo[1,2-b]pyridazine-3-carboxamide

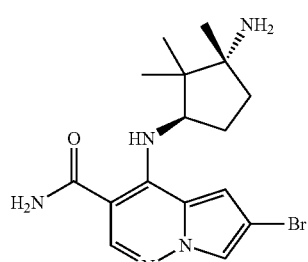
(Int-37)

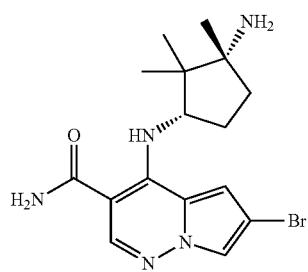
(Int-38)

According to the procedure described in Intermediate 1, 6-bromo-4-chloropyrrolo[1,2-b]pyridazine-3-carboxamide (201 mg, 172 mmol, from Preparation 5), and crude (R)-1,2,2-trimethylcyclopentane-1,3-diamine mixture (208 mg, from Step 4 of Intermediates 11 and 12) were coupled to give a mixture of two products. Silica gel chromatography, eluting with a 90 to 9 to 1 mixture of dichloromethane/methanol/ammonium hydroxide, separated the two products. The first eluted component was found to be 4-(((1R,3R)-3-amino-2,2,3-trimethylcyclopentyl)amino)-6-bromopyrrolo[1,2-b]pyridazine-3-carboxamide (Intermediate 37, 120 mg, 43% yield). $^1$H NMR (400 MHz, methanol-$d_4$) δ ppm 8.11 (1 H, s), 7.59 (1 H, d, J=1.54 Hz), 7.32 (1 H, d, J=1.54 Hz), 4.67 (1 H, t, J=8.80 Hz), 2.25-2.47 (1 H, m), 1.81-1.98 (1 H, m), 1.46-1.71 (2 H, m), 1.18 (3 H, s), 1.01 (3 H, s), 0.94 (3 H, s); MS (ES+) m/z: 380.1 (M+H); HPLC retention time: 4.818 min (analytical HPLC Method L). The second eluted product was found to be 4-(((1S,3R)-3-amino-2,2,3-trimethylcyclopentyl)amino)-6-bromopyrrolo[1,2-b]pyridazine-3-carboxamide (Intermediate 38, 101 mg, 33% yield). $^1$H NMR (400 MHz, methanol-$d_4$) δ ppm 8.11 (1 H, s), 7.58 (1 H, s), 6.87 (1

H, s), 4.35 (1 H, t, J=8.14 Hz), 2.21-2.46 (1 H, m), 1.70-2.05 (2 H, m), 1.55-1.74 (1 H, m), 1.14 (3 H, s), 1.04 (3 H, s), 0.84 (4 H, s); MS (ES+) m/z: 380.1 (M+H); HPLC retention time: 5.156 min (analytical HPLC Method L).

Examples 104-114

According to the procedure described for Example 28, Examples 104-109 were prepared by Suzuki coupling with 4-(((1R,3R)-3-amino-2,2,3-trimethylcyclopentyl)amino)-6-bromopyrrolo[1,2-b]pyridazine-3-carboxamide (from Intermediate 37). Similarly, Examples 110-114 were prepared by Suzuki coupling with 4-(((1S,3R)-3-amino-2,2,3-trimethylcyclopentyl)amino)-6-bromopyrrolo[1,2-b]pyridazine-3-carboxamide (from Intermediate 38). Appropriate boronic acids or boronic acid esters, which were commercially available, were used for the coupling. In some cases, 1,1'-bis(diphenylphosphino)ferrocene palladium(II) chloride dichloromethane complex was used instead of palladium(II) acetate and 1,1'-bis(di-tert-butylphosphino)ferrocene. Examples 109, 111 and 114 were analyzed using HPLC Method C. Example 113 was analyzed using HPLC Method D. Examples 106, 108 and 112 were analyzed using HPLC Method I. Examples 104 and 105 were analyzed using HPLC Method J. Examples 107 and 110 were analyzed using HPLC Method L.

| Ex # | Structure | HPLC Rt (minutes) | LCMS [m/z (M + H)] |
|---|---|---|---|
| 104 | 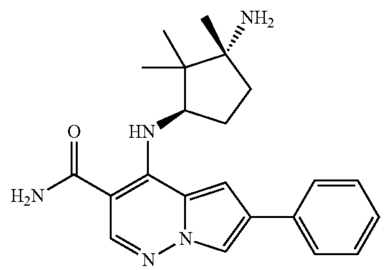 [SMILES: CC1(C)[C@H](Nc2c(C(N)=O)cnn3cc(-c4ccccc4)cc23)CC[C@@]1(C)N] | 1.492 | 378.2 |
| 105 | 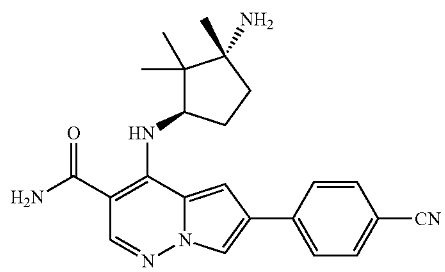 [SMILES: CC1(C)[C@H](Nc2c(C(N)=O)cnn3cc(-c4ccc(C#N)cc4)cc23)CC[C@@]1(C)N] | 1.477 | 403.2 |
| 106 | 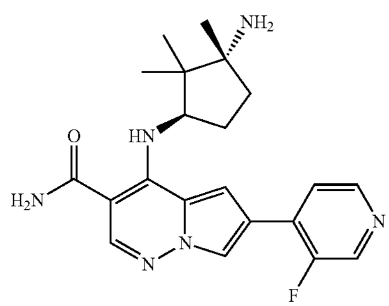 [SMILES: CC1(C)[C@H](Nc2c(C(N)=O)cnn3cc(-c4ccncc4F)cc23)CC[C@@]1(C)N] | 1.342 | 397.7 |
| 107 | 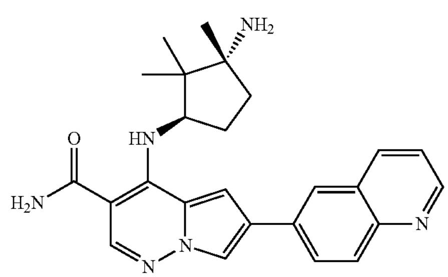 [SMILES: CC1(C)[C@H](Nc2c(C(N)=O)cnn3cc(-c4ccc5ncccc5c4)cc23)CC[C@@]1(C)N] | 0.81 | 429.3 |

-continued

| Ex # | Structure | HPLC Rt (minutes) | LCMS [m/z (M + H)] |
|---|---|---|---|
| 108 | 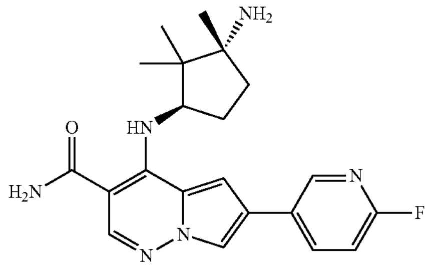 [SMILES: CC1(C)[C@H](Nc2c(C(N)=O)cnn3cc(-c4ccc(F)nc4)cc23)CC[C@@]1(C)N] | 1.252 | 397.3 |
| 109 | 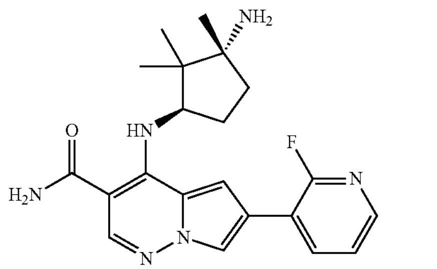 [SMILES: CC1(C)[C@H](Nc2c(C(N)=O)cnn3cc(-c4cccnc4F)cc23)CC[C@@]1(C)N] | 1.345 | 397.06 |
| 110 | 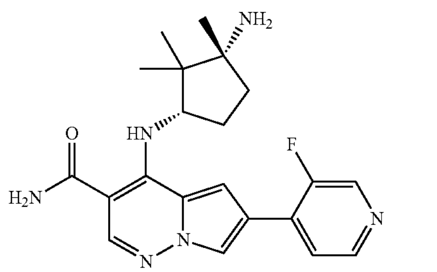 [SMILES: CC1(C)[C@@H](Nc2c(C(N)=O)cnn3cc(-c4ccncc4F)cc23)CC[C@@]1(C)N] | 1.05 | 397.3 |
| 111 | 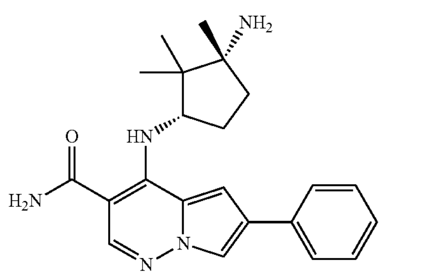 [SMILES: CC1(C)[C@@H](Nc2c(C(N)=O)cnn3cc(-c4ccccc4)cc23)CC[C@@]1(C)N] | 1.568 | 378.14 |
| 112 | 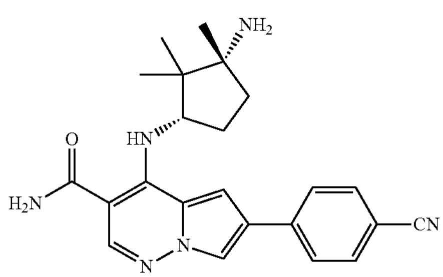 [SMILES: CC1(C)[C@@H](Nc2c(C(N)=O)cnn3cc(-c4ccc(C#N)cc4)cc23)CC[C@@]1(C)N] | 1.523 | 403.2 |

| Ex # | Structure | HPLC Rt (minutes) | LCMS [m/z (M + H)] |
|---|---|---|---|
| 113 | 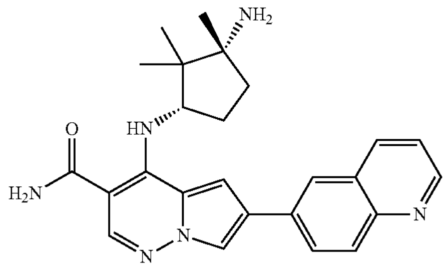 [SMILES: CC1(C)[C@@H](Nc2c(C(N)=O)cnn3cc(-c4ccc5ncccc5c4)cc23)CC[C@@]1(C)N] | 1.525 | 429.08 |
| 114 | 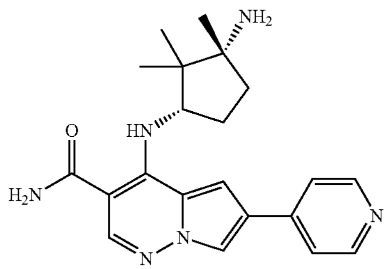 [SMILES: CC1(C)[C@@H](Nc2c(C(N)=O)cnn3cc(-c4ccncc4)cc23)CC[C@@]1(C)N] | 1.147 | 379.08 |

Intermediate 39

(+/−)-6-bromo-4-((trans-2-hydroxy-2-methylcyclopentyl)amino)pyrrolo[1,2-b]pyridazine-3-carboxamide (Int-39)

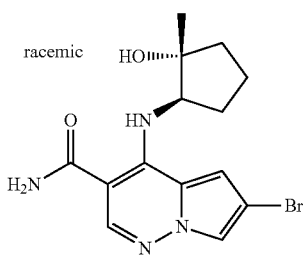

According to the procedure described in Intermediate 1,6-bromo-4-chloropyrrolo[1,2-b]pyridazine-3-carboxamide (201 mg, 172 mmol, from Preparation 5) was coupled with crude cis-2-amino-1-methylcyclopentanol (169 mg, from Step 1 of Intermediates 32 and 33) to give the title compound (210 mg, 77% yield). $^1$H NMR (400 MHz, DMSO-$d_6$) δ ppm 10.62 (1 H, br. s.), 8.09 (1 H, d, J=2.42 Hz), 7.45 (1 H, t, J=1.98 Hz), 7.09 (1 H, t, J=1.98 Hz), 4.26 (1 H, d, J=1.76 Hz), 2.15-2.44 (1 H, m), 1.45-1.88 (5 H, m), 1.26 (3 H, s); MS (ES+) m/z: 353.1, 355.1 (M+H); HPLC retention time: 7.918 min (analytical HPLC Method L).

Examples 115-120

According to the procedure described for Example 28, Examples 115-120 were prepared by Suzuki coupling of 6-bromo-4-((trans-2-hydroxy-2-methylcyclopentyl)amino)pyrrolo[1,2-b]pyridazine-3-carboxamide (from Intermediate 39) with appropriate boronic acids or boronic acid esters, which were commercially available. In some cases, 1,1'-bis(diphenylphosphino)ferrocene palladium(II) chloride dichloromethane complex was used instead of palladium(II) acetate and 1,1'-bis(di-tert-butylphosphino)ferrocene. Examples 115-117 were analyzed using HPLC Method C. Examples 118-120 were analyzed using HPLC Method I.

| Ex # | Structure | HPLC Rt (minutes) | LCMS [m/z (M + H)] |
|---|---|---|---|
| 115 | 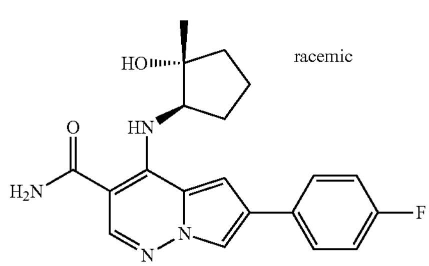 [SMILES: C[C@@]1(O)CCC[C@H]1Nc1c(C(N)=O)cnn2cc(-c3ccc(F)cc3)cc12] | 2.023 | 369.06 |

-continued
| Ex # | Structure | HPLC Rt (minutes) | LCMS [m/z (M + H)] |
|---|---|---|---|
| 116 | 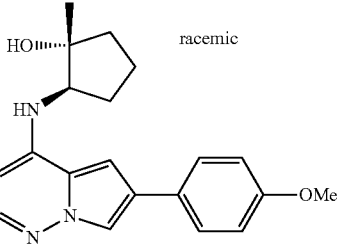 racemic | 1.942 | 381.07 |
| 117 | 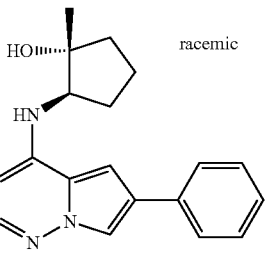 racemic | 1.985 | 351.09 |
| 118 | 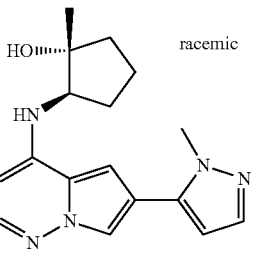 racemic | 1.14 | 355.2 |
| 119 | 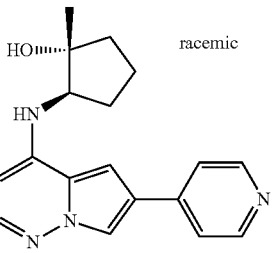 racemic | 1.13 | 352.2 |
| 120 | 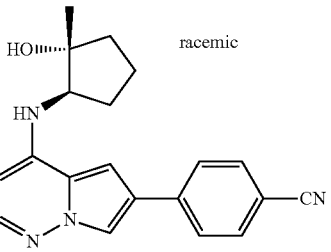 racemic | 1.05 | 376.2 |

Examples 121-126

According to the procedure described for Intermediate 36 and Example 28, Examples 121-126 were prepared from 6-bromo-4-chloropyrrolo[1,2-b]pyridazine-3-carboxamide (from Preparation 5) and appropriate amines. The 2-methylcyclopentanamine for the synthesis of Examples 121 and 122 was from Step 2 of Intermediates 26 and 27. The 2-amino-1-methylcyclopentanecarbonitrile for the synthesis of Examples 123 and 124 was from Step 2 of Intermediates 28 and 29. The trans-3-amino-1,2,2-trimethylcyclopentanol for the synthesis of Example 125 was from Step 5 of Intermediate 17. The (1R,3R)-3-amino-1,2,2-trimethylcyclopentanol for the synthesis of Example 126 was from Step 2 of Intermediate 20. Examples 121, 122, and 124 were analyzed using HPLC Method C. Example 123 was analyzed using HPLC Method D. Example 126 was analyzed using HPLC Method L. Example 125 was analyzed using HPLC Method I.

| Ex # | Structure | HPLC Rt (minutes) | LCMS [m/z (M + H)] |
|---|---|---|---|
| 121 | 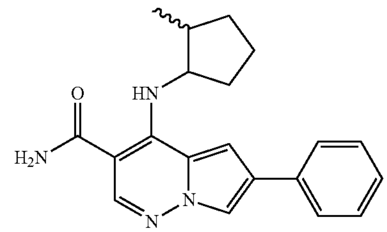 [SMILES: CC1CCCC1Nc1c(C(N)=O)cnn2cc(-c3ccccc3)cc12] | 2.713 | 335.14 |
| 122 | 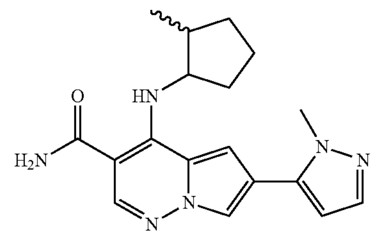 [SMILES: CC1CCCC1Nc1c(C(N)=O)cnn2cc(-c3ccnn3C)cc12] | 1.897 | 339.10 |
| 123 | diastereomer 1 | 2.432 | 360.08 |
| 124 | diastereomer 2 | 2.320 | 360.08 |
| 125 | racemic | 1.08 | 369.2 |

| Ex # | Structure | HPLC Rt (minutes) | LCMS [m/z (M + H)] |
|---|---|---|---|
| 126 | 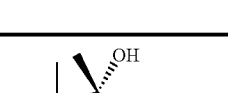 | 6.073 | 369.1 |

Examples 127-137

According to the procedure described for Intermediates 7 and 36 and Example 28, Examples 127-127 were prepared from 6-bromo-4-chloropyrrolo[1,2-b]pyridazine-3-carboxamide (from Preparation 5) and (1S,3R)-1,2,2-trimethylcyclopentane-1,3-diamine (prepared according to conditions described in *Tetrahedron Asymmetry* 2001, 12, 1579 and *Eur. J. Inorg. Chem.* 2006, 839), followed by Suzuki coupling with appropriate boronic acid, and functionalization of the free amine Examples 135-137 were prepared according to conditions described for Intermediate 8. Examples 127, 128, 131, 132 and 135-137 were analyzed using HPLC Method C. Examples 129, 130, 133 and 134 were analyzed using HPLC Method K.

| Ex # | Structure | HPLC Rt (minutes) | LCMS [m/z (M + H)] |
|---|---|---|---|
| 127 | 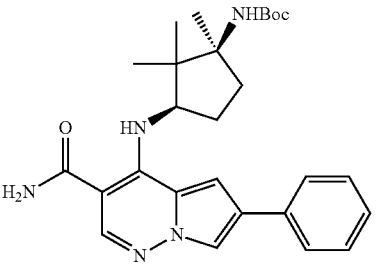 [SMILES: CC(C)(C)OC(=O)N[C@@]1(C)CC[C@@H](Nc2c(C(N)=O)cnn3cc(-c4ccccc4)cc23)C1(C)C] | 3.101 | 478.10 |
| 128 | 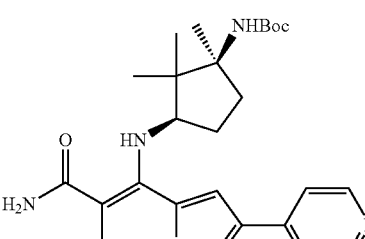 | 1.952 | 479.12 |
| 129 | 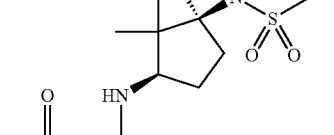 | 2.303 | 456.2 |

-continued

| Ex # | Structure | HPLC Rt (minutes) | LCMS [m/z (M + H)] |
|---|---|---|---|
| 130 | 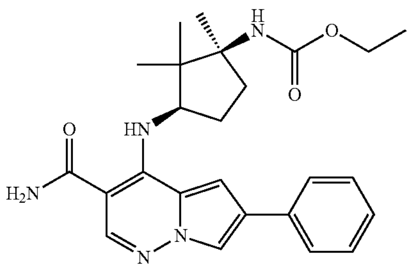 [SMILES: CCOC(=O)N[C@@]1(C)CC[C@@H](Nc2c(C(N)=O)cnn3cc(-c4ccccc4)cc23)C1(C)C] | 2.635 | 450.3 |
| 131 | 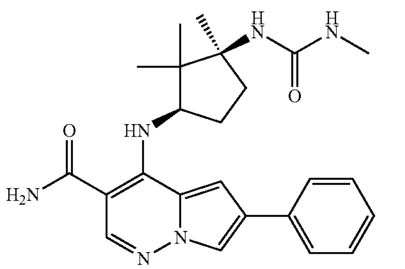 [SMILES: CNC(=O)N[C@@]1(C)CC[C@@H](Nc2c(C(N)=O)cnn3cc(-c4ccccc4)cc23)C1(C)C] | 2.307 | 435.2 |
| 132 | 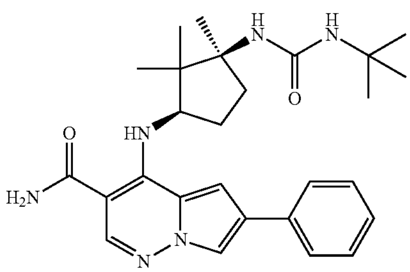 [SMILES: CC(C)(C)NC(=O)N[C@@]1(C)CC[C@@H](Nc2c(C(N)=O)cnn3cc(-c4ccccc4)cc23)C1(C)C] | 2.785 | 477.21 |
| 133 | 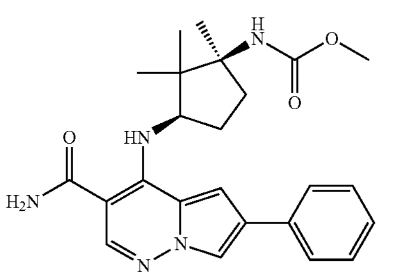 | 2.450 | 436.4 |
| 134 | 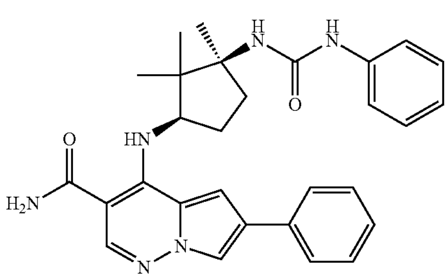 [SMILES: CC1(C)[C@H](Nc2c(C(N)=O)cnn3cc(-c4ccccc4)cc23)CC[C@]1(C)NC(=O)Nc1ccccc1] | 2.851 | 497.2 |

-continued

| Ex # | Structure | HPLC Rt (minutes) | LCMS [m/z (M + H)] |
|---|---|---|---|
| 135 | 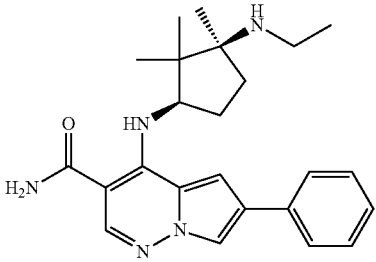 [SMILES: CCN[C@@]1(C)CC[C@@H](Nc2c(C(N)=O)cnn3cc(-c4ccccc4)cc23)C1(C)C] | 1.952 | 406.16 |
| 136 | 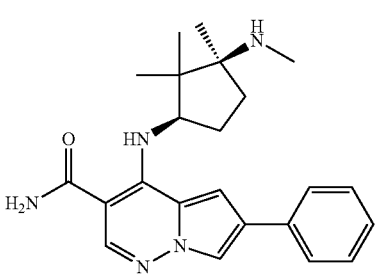 [SMILES: CN[C@@]1(C)CC[C@@H](Nc2c(C(N)=O)cnn3cc(-c4ccccc4)cc23)C1(C)C] | 1.830 | 392.15 |
| 137 | 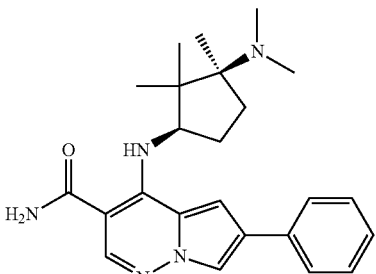 | 1.908 | 406.17 |

Intermediate 40 and Examples 138-143

According to the procedure described for Intermediates 34 and 35, 3-amino-2,2-dimethylcyclopentanol (from Step 3 of Intermediates 15 and 16) was reacted with 6-bromo-4-chloropyrrolo[1,2-b]pyridazine-3-carboxamide (Preparation 5) to give Intermediate 40. According to the procedure described for Example 28, Examples 138-143 were prepared by Suzuki coupling of Intermediate 40 with appropriate boronic acids or boronic acid esters, which were commercially available. In some cases, 1,1'-bis(diphenylphosphino)ferrocene palladium (II) chloride dichloromethane complex was used instead of palladium(II) acetate and 1,1'-bis(di-tert-butylphosphino)ferrocene. Example 141 was analyzed using HPLC Method D. Example 143 was analyzed using HPLC Method K. Intermediate 40 was analyzed using HPLC Method L. Example 140 was analyzed using HPLC Method I. Examples 138, 139 and 142 were analyzed using HPLC Method M.

| Int. or Ex # | Structure | HPLC Rt (minutes) | LCMS [m/z (M + H)] |
|---|---|---|---|
| Int. 40 | 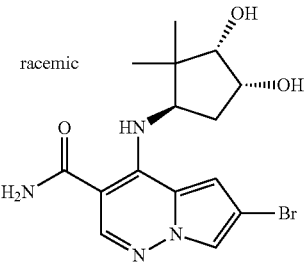 [SMILES: CC1(C)[C@H](O)[C@H](O)C[C@H]1Nc1c(C(N)=O)cnn2cc(Br)cc12] racemic | 6.401 | 384.1 |

-continued

| Int. or Ex # | Structure | HPLC Rt (minutes) | LCMS [m/z (M + H)] |
|---|---|---|---|
| Ex. 138 | racemic, 4-[(1S,3R,4S)-3,4-dihydroxy-2,2-dimethylcyclopentylamino]-6-phenylpyrrolo[1,2-b]pyridazine-3-carboxamide | 1.38 | 381.3 |
| Ex. 139 | racemic, 6-(4-cyanophenyl) analog | 1.28 | 406.3 |
| Ex. 140 | racemic, 6-(4-fluorophenyl) analog | 1.36 | 399.3 |
| Ex. 141 | racemic, 6-(4-methoxyphenyl) analog | 2.095 | 411.10 |
| Ex. 142 | racemic, 6-(1-methyl-1H-pyrazol-5-yl) analog | 0.95 | 385.3 |

| Int. or Ex # | Structure | HPLC Rt (minutes) | LCMS [m/z (M + H)] |
|---|---|---|---|
| Ex. 143 | 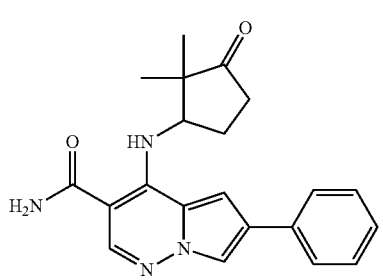 racemic | 1.520 | 400.2 |

Example 144

(+/−)-4-((2,2-dimethyl-3-oxocyclopentyl)amino)-6-phenylpyrrolo[1,2-b]pyridazine-3-carboxamide

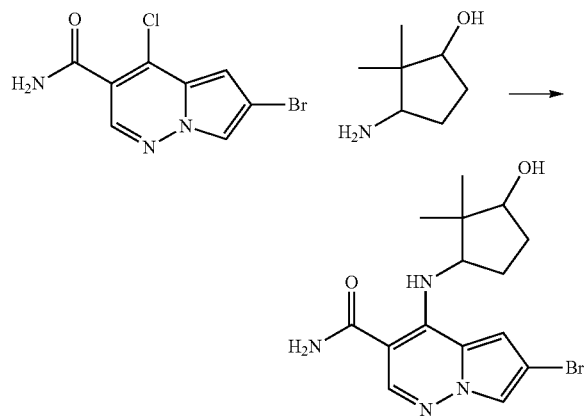

(144)

Step 1: 6-bromo-4-(3-hydroxy-2,2-dimethylcyclopentylamino)pyrrolo[1,2-b]pyridazine-3-carboxamide Following conditions described for Intermediate 1, 6-bromo-4-chloropyrrolo[1,2-b]pyridazine-3-carboxamide (1.40 g, 5.10 mmol, from Preparation 5) was reacted with 3-amino-2,2-dimethylcyclopentanol (0.791 g, from Step 3 of Intermediates 15 and 16) to give 6-bromo-4-(3-hydroxy-2,2-dimethylcyclopentylamino)pyrrolo[1,2-b]pyridazine-3-carboxamide (1.40 g, 75% yield), as a 2:1 mixture of diastereomers. MS (ES+) m/z: 367.1, 369.1 (M+H).

Step 2: 6-bromo-4-(2,2-dimethyl-3-oxocyclopentylamino)pyrrolo[1,2-b]pyridazine-3-carboxamide

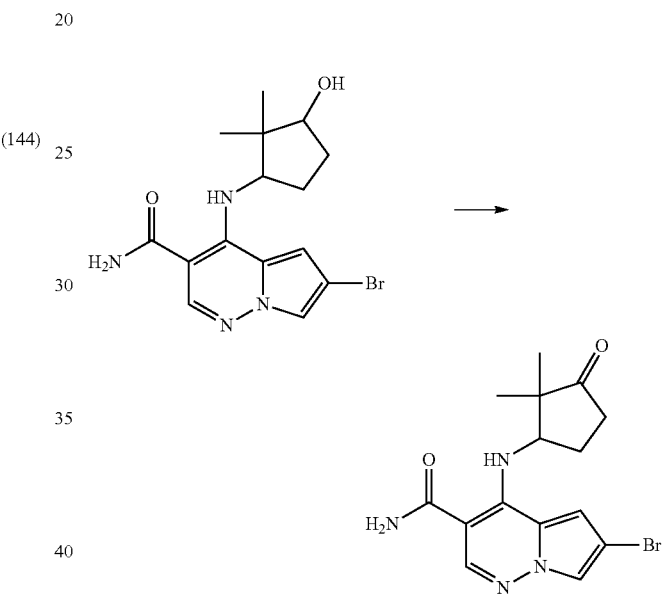

Following conditions described in Step 1 of Intermediate 22, 6-bromo-4-(3-hydroxy-2,2-dimethylcyclopentylamino)pyrrolo[1,2-b]pyridazine-3-carboxamide (395 mg, 1.076 mmol, from Step 1) was converted to 6-bromo-4-(2,2-dimethyl-3-oxocyclopentylamino)pyrrolo[1,2-b]pyridazine-3-carboxamide (320 mg, 80% yield). $^1$H NMR (400 MHz, methanol-$d_4$) δ ppm 8.19 (1 H, s), 7.69 (1 H, d, J=1.76 Hz), 7.16 (1 H, d, J=1.76 Hz), 2.36-2.73 (3 H, m), 1.89-2.06 (1 H, m), 1.15 (6 H, s); MS (ES+) m/z: 365.2, 367.1 (M+H).

Step 3: 4-((2,2-dimethyl-3-oxocyclopentyl)amino)-6-phenylpyrrolo[1,2-b]pyridazine-3-carboxamide (Example 144)

Following conditions described in Example 28, 6-bromo-4-(2,2-dimethyl-3-oxocyclopentylamino)pyrrolo[1,2-b]pyridazine-3-carboxamide (125 mg, 0.342 mmol, from Step 2) was converted to the title compound (87 mg, 63% yield). $^1$H NMR (400 MHz, chloroform-d) δ ppm 10.69 (1 H, d, J=9.02 Hz), 7.81-8.02 (2 H, m), 7.61 (2 H, dd, J=8.25, 1.21 Hz), 7.34-7.48 (2 H, m), 7.31-7.37 (1 H, m), 7.08 (1 H, d, J=1.76 Hz), 4.48-4.81 (1 H, m), 2.51-2.77 (2 H, m), 2.25-2.49 (1 H, m), 2.07-2.17 (1 H, m), 1.17-1.25 (6 H, m); MS (ES+) m/z: 363.3 (M+H); HPLC retention time: 9.406 min (analytical HPLC Method L).

Example 145

(+/−)-4-((cis-3-hydroxy-2,2,3-trimethylcyclopentyl)amino)-6-phenylpyrrolo[1,2-b]-pyridazine-3-carboxamide

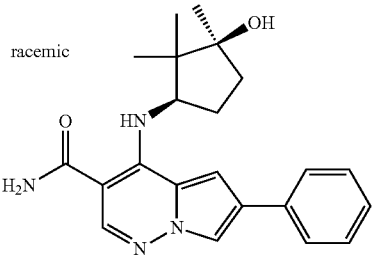
(145)

Following conditions described in Step 3 of Intermediates 27 and 28, 4-((2,2-dimethyl-3-oxocyclopentyl)amino)-6-phenylpyrrolo[1,2-b]pyridazine-3-carboxamide (20 mg, 0.55 mmol, from Example 144) was converted to the title compound (7.2 mg, 33% yield). $^1$H NMR (400 MHz, methanol-$d_4$) δ ppm 8.09 (1 H, s), 7.89 (1 H, d, J=1.54 Hz), 7.65 (2 H, d, J=7.26 Hz), 7.39 (2 H, t, J=7.81 Hz), 7.23-7.30 (1 H, m), 7.19 (1 H, d, J=1.76 Hz), 4.41-4.61 (1 H, m), 2.31-2.72 (1 H, m), 1.69-1.99 (3 H, m), 1.26 (3 H, s), 1.10 (3 H, s), 1.04 (3 H, s); MS (ES+) m/z: 379.3 (M+H); HPLC retention time: 9.824 min (analytical HPLC Method L).

Examples 146-149

Following conditions described in Step 3 of Examples 144 and 145, Examples 146-149 were prepared from 6-bromo-4-(2,2-dimethyl-3-oxocyclopentylamino)pyrrolo[1,2-b]pyridazine-3-carboxamide (from Step 2 of Example 144). Following conditions described in Step 3 of Example 144, Example 149 was prepared. Examples 147 and 148 were analyzed using HPLC Method C. Examples 146 and 149 were analyzed using HPLC Method N.

| Ex # | Structure | HPLC Rt (minutes) | LCMS [m/z (M + H)] |
|---|---|---|---|
| 146 | 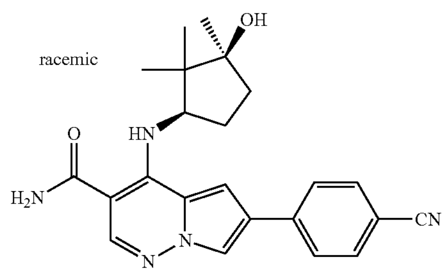 [SMILES: CC1(C)[C@H](Nc2c(C(N)=O)cnn3cc(-c4ccc(C#N)cc4)cc23)CC[C@]1(C)O] | 2.317 | 404.2 |
| 147 | 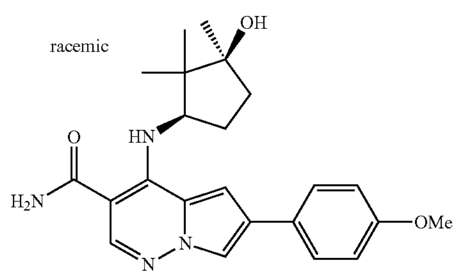 [SMILES: COc1ccc(-c2cc3c(N[C@@H]4CC[C@](C)(O)C4(C)C)c(C(N)=O)cnn3c2)cc1] | 2.495 | 409.14 |
| 148 | 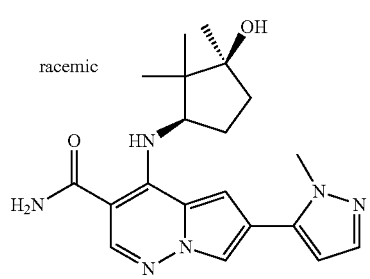 [SMILES: Cn1nccc1-c1cc2c(N[C@@H]3CC[C@](C)(O)C3(C)C)c(C(N)=O)cnn2c1] | 1.908 | 383.12 |

-continued

| Ex # | Structure | HPLC Rt (minutes) | LCMS [m/z (M + H)] |
|---|---|---|---|
| 149 | 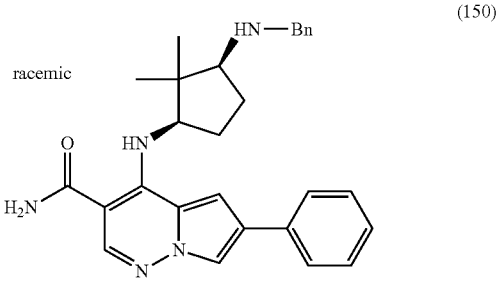 [SMILES: CC1(C)[C@@H](NCc2ccccc2)CC[C@H]1Nc1c(C(N)=O)cnn2cc(-c3ccccc3)cc12] racemic | 1.715 | 364.2 |

Example 150

(+/−)-4-((cis-3-(benzylamino)-2,2-dimethylcyclopentyl)amino)-6-phenylpyrrolo[1,2-b]pyridazine-3-carboxamide (150)

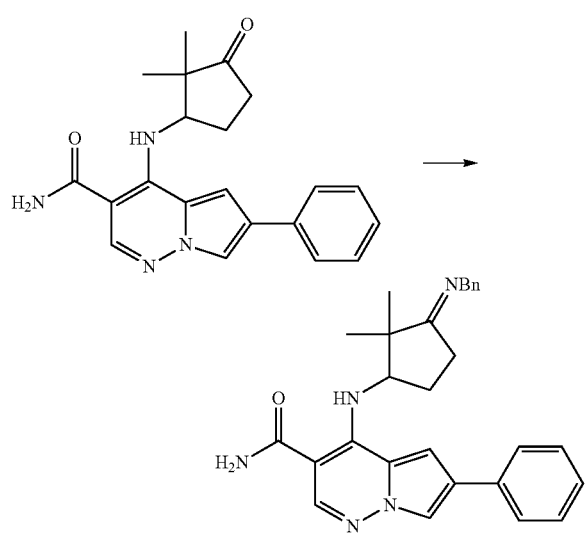

Step 1: 4-(3-(benzylimino)-2,2-dimethylcyclopentylamino)-6-phenylpyrrolo[1,2-b]pyridazine-3-carboxamide A 1.0 M dichloromethane solution of titanium(IV) chloride (0.025 mL, 0.025 mmol) was added to a solution of triethylamine (0.042 mL, 0.298 mmol) and benzylamine (6.39 mg, 0.060 mmol) in benzene (5 mL) at room temperature. The mixture was heated to reflux. A solution of 4-((2,2-dimethyl-3-oxocyclopentyl)amino)-6-phenylpyrrolo[1,2-b]pyridazine-3-carboxamide (18 mg, 0.050 mmol, from Example 144) in benzene (1 mL) was added to the above mixture. The resultant mixture was kept at reflux for 3 h, cooled to room temperature, diluted with ethyl acetate (80 mL), washed with water, brine, dried (MgSO$_4$) and concentrated. The residue was purified by silica gel chromatography, eluting with 30 to 80% ethyl acetate in hexanes, to give 4-(3-(benzylimino)-2,2-dimethylcyclopentylamino)-6-phenylpyrrolo[1,2-b]pyridazine-3-carboxamide (7 mg, 31% yield). $^1$H NMR (400 MHz, chloroform-d) δ ppm 10.66 (1 H, d, J=8.80 Hz), 7.80-8.02 (2 H, m), 7.55-7.76 (2 H, m), 7.20-7.53 (8 H, m), 7.10 (1 H, d, J=1.76 Hz), 5.59 (2 H, br. s.), 4.41-4.51 (1 H, m), 2.56-2.78 (1 H, m), 2.34-2.60 (2 H, m), 1.92-2.01 (1 H, m), 1.19-1.43 (6 H, m); MS (ES+) m/z: 452.3 (M+H).

Step 2: (+/+4-((cis-3-(benzylamino)-2,2-dimethylcyclopentyl)amino)-6-phenylpyrrolo[1,2-b]pyridazine-3-carboxamide (Example 153)

Sodium borohydride (1.5 mg, 0.040 mmol) was added to a solution of 4-(3-(benzylimino)-2,2-dimethylcyclopentylamino)-6-phenylpyrrolo[1,2-b]pyridazine-3-carboxamide (6 mg, 0.013 mmol, from Step 1) in methanol (1 mL) at 0° C. After 30 min at 0° C., the mixture was quenched with saturated ammonium chloride (1 mL), diluted with ethyl acetate (60 mL), washed with water, brine, dried (MgSO$_4$) and concentrated. The residue was purified by silica gel chromatography, eluting with 0 to 10% methanol in dichloromethane, to give the title compound (4.0 mg, 60% yield). $^1$H NMR (400 MHz, methanol-d$_4$) δ ppm 8.13 (1 H, s), 7.91 (1 H, d, J=1.54 Hz), 7.56-7.84 (2 H, m), 7.04-7.53 (9 H, m), 4.32 (1 H, t, J=8.91 Hz), 3.69-4.04 (2 H, m), 2.77-2.95 (1 H, m), 2.08-2.52 (2 H, m), 1.43-1.81 (2 H, m), 0.97-1.15 (6 H, m); MS (ES+) m/z: 454.4 (M+H); HPLC retention time: 6.605 min (analytical HPLC Method L).

Intermediate 41

(+/−)-4-(((1R,2R,3R)-2-fluoro-3-hydroxy-2,3-dimethylcyclopentyl)amino)pyrrolo[1,2-b]pyridazine-3-carboxamide

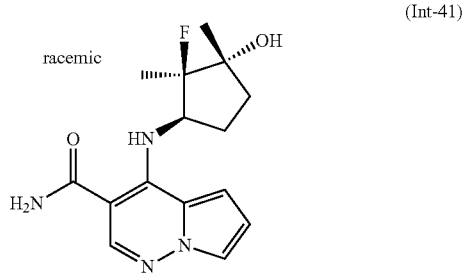 [SMILES: C[C@@]1(O)CC[C@@H](Nc2c(C(N)=O)cnn3cccc23)[C@@]1(C)F]

(Int-41)

Step 1: 2-fluoro-2-methylcyclopentane-1,3-dione

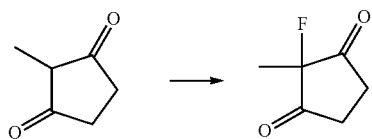

A mixture of 2-methylcyclopentane-1,3-dione (4.50 g, 40.1 mmol) and Selectfluor (17.06 g, 48.2 mmol) in acetonitrile (80 mL) was heated to reflux for 2 h, cooled to room temperature and concentrated in vacuo. The residue was diluted with ethyl acetate (200 mL), washed with saturated sodium bicarbonate, water, brine, dried ($MgSO_4$) and concentrated. Purification by silica gel chromatography, eluting with 20 to 50% ethyl acetate in hexanes, gave 2-fluoro-2-methylcyclopentane-1,3-dione (4.50 g, 82% yield). $^1$H NMR (400 MHz, chloroform-d) δ ppm 2.65-3.19 (4H, m), 1.38-1.77 (3H, m).

Step 2: trans-2-fluoro-3-hydroxy-2,3-dimethylcyclopentanone and cis-2-fluoro-3-hydroxy-2,3-dimethylcyclopentanone

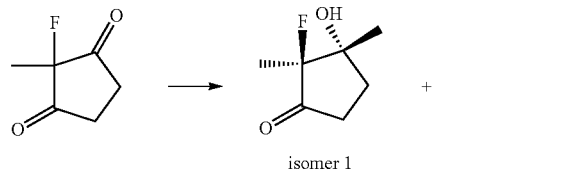

A 1.6 M ether solution of methyllithium (13.62 mL, 21.79 mmol) was added dropwise over 30 min to a solution of 2-fluoro-2-methylcyclopentane-1,3-dione (2.70 g, 20.75 mmol, from Step 1) and cerium(III) chloride (5.63 g, 22.83 mmol) in tetrahydrofuran (100 mL) at −78° C. After 1 h at −78° C., the mixture was quenched with saturated ammonium chloride (50 mL), warmed to room temperature, and filtered through a celite pad. The filter cake was washed with ethyl acetate until free of product. The two phases of the filtrate were separated. The aqueous layer was extracted with ethyl acetate (2×100 mL). The combined organic layers were washed with brine (30 mL), dried ($MgSO_4$) and concentrated. The residue was purified by silica gel chromatography, eluting with 0 to 50% ethyl acetate in hexanes, to give two products. The first eluted product (isomer 1) was found to be trans-2-fluoro-3-hydroxy-2,3-dimethylcyclopentanone (460 mg, 15% yield). The second eluted product was found to be cis-2-fluoro-3-hydroxy-2,3-dimethylcyclopentanone (300 mg, 10% yield).

Step 3: (1R,2R,3R)-3-(benzylamino)-2-fluoro-1,2-dimethylcyclopentanol (racemic mixture)

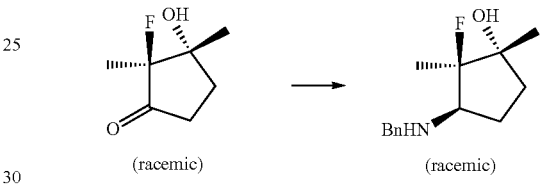

Anhydrous magnesium sulfate (3.064 g, 25.5 mmol) was added to a solution of trans-2-fluoro-3-hydroxy-2,3-dimethylcyclopentanone (620 mg, 4.24 mmol, isomer 1 from Step 2) and benzylamine (0.695 mL, 6.36 mmol) in 1,2-dichloroethane (20 mL). After stirring for 15 h at room temperature, the mixture was filtered. The filtrate was treated with sodium acetoxyborohydride (1.438 g, 6.79 mmol). After 15 h at room temperature, saturated ammonium chloride (10 mL) and ethyl acetate (100 mL) were added. The mixture was washed with water, brine, dried ($MgSO_4$) and concentrated. The residue was purified by silica gel chromatography, eluting with 10 to 80% ethyl acetate in hexanes, to give (1R,2R,3R)-3-(benzylamino)-2-fluoro-1,2-dimethylcyclopentanol as a racemic mixture (580 mg, 58% yield). $^1$H NMR (400 MHz, methanol-$d_4$) δ ppm 7.00-7.72 (5 H, m), 3.64-4.11 (2 H, m), 2.98-3.27 (1 H, m), 2.05-2.29 (1 H, m, J=12.71, 9.27, 9.27, 6.16 Hz), 1.81-1.96 (1 H, m), 1.56-1.71 (1 H, m), 1.45-1.58 (1 H, m), 1.33 (3 H, d), 1.22 (3 H, s); MS (ES+) m/z: 238.1 (M+H).

Step 4: (1R,2R,3R)-3-amino-2-fluoro-1,2-dimethylcyclopentanol (racemic mixture)

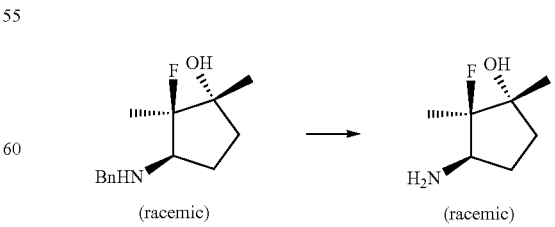

A mixture of 3-(benzylamino)-2-fluoro-1,2-dimethylcyclopentanol (415 mg, 1.749 mmol, from Step 3), 10% palladium on carbon (93 mg) in methanol (10 mL) and 4 N aqueous hydrochloric acid (0.481 mL, 1.924 mmol) was stirred under hydrogen at 34 psi for 15 h. After removal of catalyst by filtration, the filtrate was concentrated to give (1R,2R,3R)-3-amino-2-fluoro-1,2-dimethylcyclopentanol (racemic mixture) as a hydrochloride salt. $^1$H NMR (400 MHz, methanol-d$_4$) δ ppm 3.51-3.85 (1 H, m), 2.21-2.55 (1 H, m), 1.95-2.15 (1 H, m), 1.59-1.83 (2 H, m), 1.13-1.57 (6H, m).

Step 5: (+/−)-4-(((1R,2R,3R)-2-fluoro-3-hydroxy-2,3-dimethylcyclopentyl)amino) pyrrolo[1,2-b]pyridazine-3-carboxamide (Intermediate 41)

Following conditions described for Intermediate 1,4-chloropyrrolo[1,2-b]pyridazine-3-carboxamide (28 mg, 0.143 mmol, from Preparation 3) was reacted with (1R,2R,3R)-3-amino-2-fluoro-1,2-dimethylcyclopentanol hydrochloride (racemic mixture, from Step 4) in the presence of excess N—N-diisopropylethylamine to give the title compound (21 mg, 43% yield). $^1$H NMR (400 MHz, methanol-d$_4$) δ ppm 8.16 (1 H, s), 7.61 (1 H, dd, J=2.64, 1.54 Hz), 7.00 (1 H, dd, J=4.73, 1.43 Hz), 6.71 (1 H, dd, J=4.62, 2.64 Hz), 4.80 (1 H, t, J=8.69 Hz), 2.40-2.56 (1 H, m), 2.08-2.26 (1 H, m), 1.79-1.90 (1 H, m), 1.62-1.79 (1 H, m), 1.37 (3 H, d), 1.31 (3 H, s); MS (ES+) m/z: 307.2 (M+H); HPLC retention time: 6.660 min (analytical HPLC Method L).

Intermediates 42-44 and Examples 151-155

Following conditions described for Steps 3-5 of Intermediate 41, Intermediates 42 and 43 were prepared from isomer 2 from Step 2 of Intermediate 41. Following conditions described for Step 5 of Intermediate 41, Intermediate 44 was prepared from 6-bromo-4-chloropyrrolo[1,2-b]pyridazine-3-carboxamide (Preparation 5). According to the procedure described for Example 28, Examples 151-155 were prepared by Suzuki coupling of Intermediate 44 with appropriate boronic acids or boronic acid esters, which were commercially available. Intermediate 42 and Example 154 were analyzed using HPLC Method A. Example 155 was analyzed using HPLC Method D. Intermediate 43-44 and Example 151 were analyzed using HPLC Method L. Examples 152 and 153 were analyzed using HPLC Method I.

| Int. or Ex # | Structure | HPLC Rt (minutes) | LCMS [m/z (M + H)] |
|---|---|---|---|
| Int. 42 | racemic | 3.111 | 307.2 |
| Int. 43 | racemic | 6.153 | 307.2 |
| Int. 44 | racemic | 8.298 | 385.0 387.0 |

-continued
| Int. or Ex # | Structure | HPLC Rt (minutes) | LCMS [m/z (M + H)] |
|---|---|---|---|
| Ex. 151 | 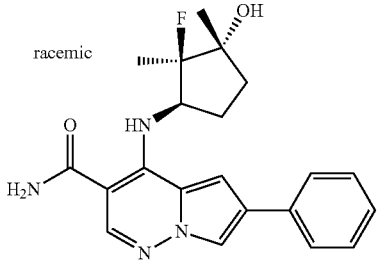 [SMILES: C[C@@]1(O)CC[C@@H](Nc2c(C(N)=O)cnn3cc(-c4ccccc4)cc23)[C@@]1(C)F] racemic | 9.109 | 383.2 |
| Ex. 152 | 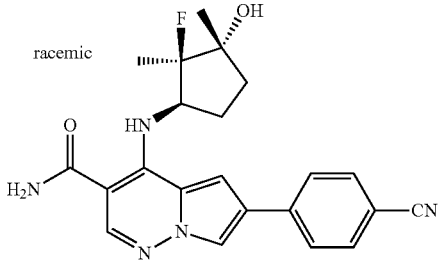 [SMILES: C[C@@]1(O)CC[C@@H](Nc2c(C(N)=O)cnn3cc(-c4ccc(C#N)cc4)cc23)[C@@]1(C)F] racemic | 1.55 | 408.2 |
| Ex. 153 | 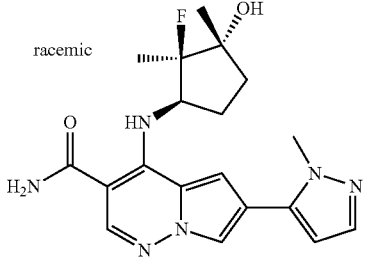 [SMILES: Cn1nccc1-c1cc2c(N[C@@H]3CC[C@@](C)(O)[C@]3(C)F)c(C(N)=O)cnn2c1] racemic | 1.16 | 387.2 |
| Ex. 154 | 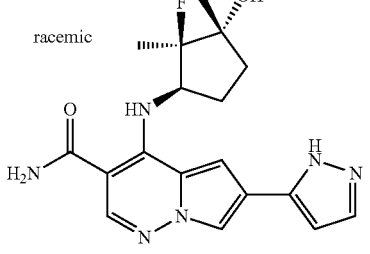 racemic | 2.65 | 373.1 |
| Ex. 155 | 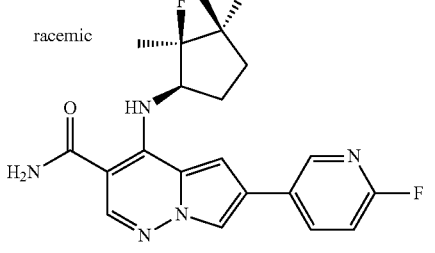 racemic | 1.847 | 402.02 |

Example 156

(+/−)-6-(3-(4-chlorophenyl)-1H-pyrazol-1-yl)-4-(((1R,2R,3R)-2-fluoro-3-hydroxy-2,3-dimethylcyclopentyl)amino)pyrrolo[1,2-b]pyridazine-3-carboxamide

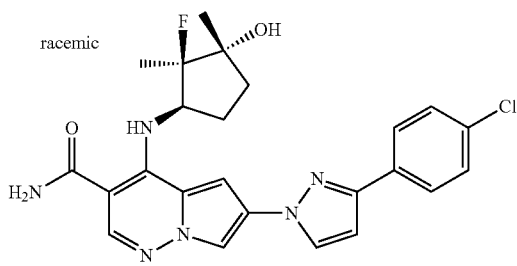

(156)

A mixture of 6-bromo-2-fluoro-3-hydroxy-2,3-dimethyl-cyclopentylamino)pyrrolo[1,2-b]pyridazine-3-carboxamide (17 mg, 0.044 mmol, from Intermediate 44), 3-(4-chlorophenyl)-1H-pyrazole (39.5 mg, 0.221 mmol), potassium phosphate (12.20 mg, 0.088 mmol), copper(I) iodide (2.81 mg, 0.015 mmol) and N,N'-dimethylethylenediamine (3 μL, 0.029 mmol) in dioxane (0.5 mL) was purged with nitrogen for 2 min, heated at 105° C. for 15 h, cooled to room temperature and filtered. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 25-100% B over 25 minutes, then a 5-minute hold at 100% B; Flow: 20 mL/min. Fractions containing the desired product were combined and dried via centrifugal evaporation gave the title compound (6 mg, 28% yield). $^1$H NMR (500 MHz, methanol-$d_4$) δ ppm 8.18 (1H, s), 8.10 (1 H, d, J=2.50 Hz), 7.93-8.05 (2 H, m), 7.72-7.88 (3H, m), 7.41 (1 H, d, J=8.32 Hz), 6.79 (1 H, d, J=2.50 Hz), 4.71-5.13 (1 H, m), 2.43-2.62 (1 H, m), 2.03-2.27 (1 H, m), 1.71-1.98 (2 H, m), 1.16-1.58 (9 H, m); MS (ES+) m/z: 483.2 (M+H); HPLC retention time: 2.602 min (analytical HPLC Method K).

Examples 157-159

Following conditions described for Example 156, Examples 157-159 were prepared. Example 159 was analyzed using HPLC Method F. Examples 157 and 158 were analyzed using HPLC Method I.

| Ex # | Structure | HPLC Rt (minutes) | LCMS [m/z (M + H)] |
|---|---|---|---|
| 157 | 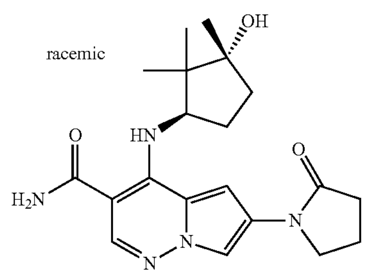 [SMILES: CC1(C)[C@H](Nc2c(C(N)=O)cnn3cc(N4CCCC4=O)cc23)CC[C@@]1(C)O] | 1.12 | 386.3 |
| 158 | 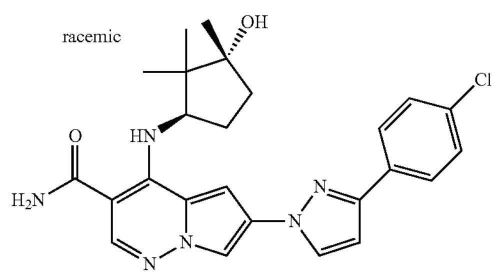 [SMILES: CC1(C)[C@H](Nc2c(C(N)=O)cnn3cc(-n4ccc(-c5ccc(Cl)cc5)n4)cc23)CC[C@@]1(C)O] | 1.95 | 479.3 |
| 159 | 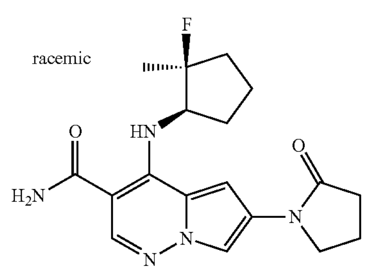 [SMILES: C[C@]1(F)CCC[C@H]1Nc1c(C(N)=O)cnn2cc(N3CCCC3=O)cc12] | 3.411 | 360.2 |

Intermediate 45

(cis) 4-(4-hydroxy-4-methylcyclohexylamino)pyrrolo[1,2-b]pyridazine-3-carboxamide

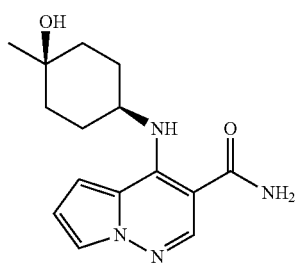

(Int-45)

Step 1: (cis)- and (trans)-4-hydroxy-4-methylcyclohexylamine hydrochloride

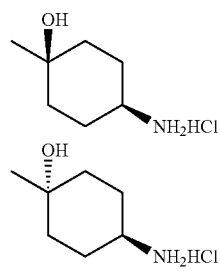

To a suspension of tert-butyl 4-oxocyclohexylcarbamate (213 mg, 1.0 mmol) and dry cerium (III) chloride (308 mg, 1.250 mmol) in THF (16 mL) at −78° C. was added methyllithium, low chloride, 1.6 M solution in diethyl ether (+/−5% W/V) (1.4 mL, 2.240 mmol) dropwise via syringe. The reaction was stirred for 1 h, quenched at −78° C. with sat. aqueous $NH_4Cl$, and allowed to warm to rt. The reaction mixture was diluted with water and ether and the layers were separated. The aq. layer was further extracted with ether (2×), combined and dried over $MgSO_4$. After concentration, the residue was purified on silica gel (hexane to 50% ethyl acetate/hexanes) to afford 2 product fractions which upon concentration afforded the cis isomer (116 mg) and trans isomer (54 mg). Each isomer was then treated with 4N HCl in dioxane (1 mL) for 2 h followed by concentration in vacuo and drying under high vacuum to afford the individual hydrochloride salts which were used without further purification.

Step 2: (cis)-4-(4-hydroxy-4-methylcyclohexylamino)pyrrolo[1,2-b]pyridazine-3-carboxamide (Intermediate 45)

To a solution of 4-chloropyrrolo[1,2-b]pyridazine-3-carboxamide (Preparation 3, 22.7 mg, 0.116 mmol) and cis-4-hydroxy-4-methylcyclohexylamine hydrochloride (22 mg, 0.133 mmol) in DMF (0.3 mL) was added DIPEA (55 µL, 0.315 mmol) and the reaction heated at 80° C. for 48 h. An additional 50 uL of DIPEA was added and the reaction continued at 100° C. overnight. The reaction was cooled, diluted with MeOH and purified via reverse-phase preparative HPLC to afford the title compound (20 mg, 60% yield) as a white solid. HPLC (condition 0): retention time=2.99 min; LCMS: 289.15 (M+H); $^1$H NMR (MeOD-4, 400 MHz) δ 8.00 (s, 1H), 7.45 (dd, J=2.7, 1.6 Hz, 1H), 6.80 (dd, J=4.6, 1.3 Hz, 1H), 6.57 (dd, J=4.6, 2.8 Hz, 1H), 3.98 (m, 1H), 1.88 (m, 2H), 1.67 (m, 4H), 1.52 (m, 2H), 1.15 (s, 3H).

Intermediate 46

6-bromo-cis-4-(-4-hydroxy-4-methylcyclohexylamino)pyrrolo[1,2-b]pyridazine-3-carboxamide

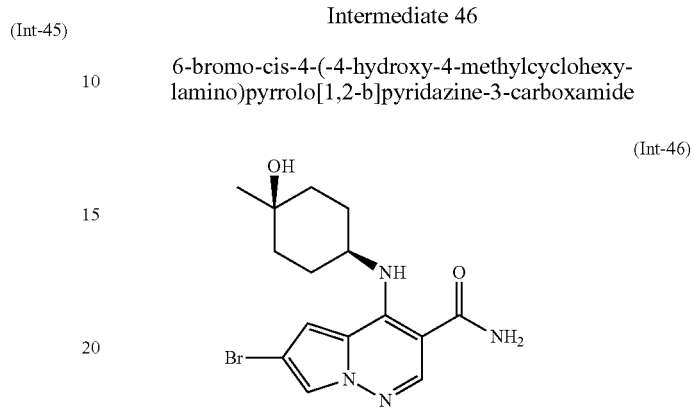

(Int-46)

A solution of 6-bromo-4-chloropyrrolo[1,2-b]pyridazine-3-carboxamide (Preparation 5, 398 mg, 1.449 mmol), cis-4-(4-oxocyclohexylamino) pyrrolo[1,2-b]pyridazine-3-carboxamide hydrochloride (from Step 1 of Intermediate 45, 240 mg, 1.449 mmol) in DMF (2 mL) was added DIPEA (0.566 mL, 3.19 mmol). The mixture was heated at 100° C. for 4 h. After cooling to rt, water was added and the mixture was stirred at rt overnight. The solids were filtered, rinsed with water, and dried to afford the title compound (0.48 g, 1.307 mmol, 90% yield) as a yellow solid. LCMS 369.01 (M+2); $^1$H NMR (CDCl$_3$, 400 MHz) δ 7.83 (s, 1H), 7.57 (s, 1H), 6.76 (s, 1H), 5.30 (s, 2H), 3.93 (m, 1H), 1.59-2.02 (m, 8H), 1.36 (s, 3H).

Intermediate 47

(E)- and (Z)-6-bromo-4-((5-hydroxyadamantan-2-yl)amino)pyrrolo[1,2-b]pyridazine-3-carboxamide

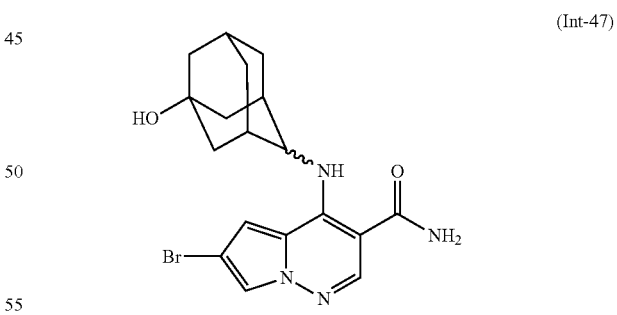

(Int-47)

A mixture of 6-bromo-4-chloropyrrolo[1,2-b]pyridazine-3-carboxamide (Preparation 5, 60 mg, 0.219 mmol), (E)- and (Z)-5-hydroxy-2-adamantamine (~3:1 mixture prepared as in Intermediates 2 and 3, 36.6 mg, 0.219 mmol) and DIPEA (0.078 mL, 0.437 mmol) in acetonitrile (0.5 mL) was heated at 120° C. for 1 h in microwave oven. After cooling, the reaction was diluted with ethyl acetate (10 mL) and washed with sat. aqueous $NH_4Cl$, brine and dried over $Na_2SO_4$. The title compound was obtained as a mixture of isomers (84 mg, 0.191 mmol, 87% yield) as a yellow solid and was used without further purification. LCMS: 406.95 (M+2).

Intermediate 48

4-((1R,3S)-3-amino-2,2,3-trimethylcyclopentylamino)-6-bromopyrrolo[1,2-b]-pyridazine-3-carboxamide

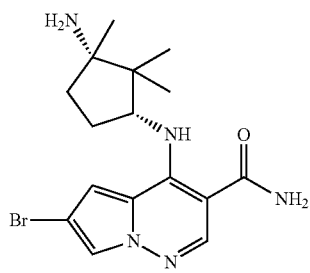
(Int-48)

A solution of 6-bromo-4-chloropyrrolo[1,2-b]pyridazine-3-carboxamide (Preparation 5, 638 mg, 2.325 mmol) and (1S,3R)-1,2,2-trimethylcyclopentane-1,3-diamine (prepared as described in Intermediate 10, 430 mg, 3.02 mmol) in DMF (3.5 mL) was added DIPEA (1.218 mL, 6.98 mmol). The reaction vessel was purged with $N_2$, sealed and heated to at 95° C. for 90 min. The reaction was cooled and partitioned between ethyl acetate (35 mL) and water (20 mL). The layers were separated and the aqueous layer further extracted with ethyl acetate (2×). The combined organic extracts were dried ($Na_2SO_4$), filtered and concentrated. The crude extracts were combined with two previous reactions and concentrated onto $SiO_2$ and eluted onto a silica gel column with 100% ethyl acetate. After the non-polar impurities had eluted, the solvent was changed to 5% MeOH/$CH_2Cl_2$ then 10% then 15% MeOH/$CH_2Cl_2$ to afford the title compound (2.113 grams, 67% yield). HPLC (condition 0): retention time=2.61 min; LCMS: 382.08 (M+2); $^1$H NMR (methanol-$d_4$, 400 MHz) δ 8.14 (s, 1H), 7.63 (d, J=1.8 Hz, 1H), 6.93 (d, J=1.8 Hz, 1H), 4.41 (t, J=8.4 Hz, 1H), 2.34 (m, 1H), 1.85 (m, 2H), 1.70 (m, 1H), 1.22 (s, 3H), 1.08 (s, 3H), 0.96 (s, 3H).

Intermediate 49

6-bromo-4-((3,5-dihydroxyadamantan-1-yl)amino)pyrrolo[1,2-b]pyridazine-3-carboxamide

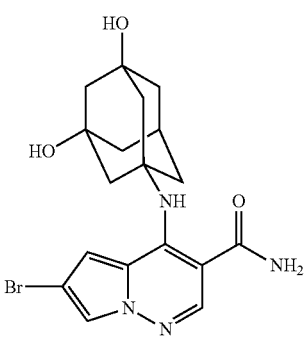
(Int-49)

6-bromo-4-chloropyrrolo[1,2-b]pyridazine-3-carboxamide (Preparation 5, 80 mg, 0.291 mmol), 3,5-dihydroxyadamantan-1-amine (53.4 mg, 0.291 mmol) and DIPEA (0.104 mL, 0.583 mmol) in DMF (1 mL) was heated in microwave oven at 130° C. for 1.5 h. The reaction mixture was cooled to rt, water added (4 volumes) and the resulting mixture was stirred rapidly overnight. The solids were filtered and rinsed with water to afford the title compound as a yellow solid (72 mg, 56% yield). HPLC (condition 0): retention time=2.16 min; LCMS: 423.00 (M+2); $^1$H NMR (CDCl$_3$, 400 MHz) δ 7.95 (s, 1H), 7.65 (d, J=1.7 Hz, 1H), 7.01 (d, J=1.8 Hz, 1H), 6.23 (s, 2H), 2.52 (m, 1H), 2.14 (app dd, J=7.1 Hz, 4H), 2.01 (m, 2H), 1.82 (m, 2H), 1.72 (s, 4H).

Intermediate 50

(R)-6-bromo-4-(2,2-dimethylcyclopentylamino)pyrrolo[1,2-b]pyridazine-3-carboxamide

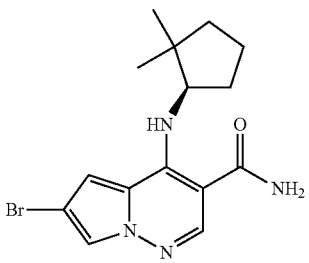
(Int-50)

A mixture of 6-bromo-4-chloropyrrolo[1,2-b]pyridazine-3-carboxamide (Preparation 5, 300 mg, 1.093 mmol) and (R)-2,2-dimethylcyclopentanamine (from Step 3 of Intermediate 5, 164 mg, 1.093 mmol) in DMF (4 mL) was added DIPEA (0.573 mL, 3.28 mmol). The mixture was heated at 120° C. for 60 min in a microwave reactor. Water (4 volumes) was added and the resulting suspension was stirred for 1 h. The solids were filtered, rinsed with water (2×), and then dried to afford the title compound (324 mg, 84% yield) as a pale yellow solid. HPLC (conditions 0): retention time=4.07 min; LCMS: 351.01 (M+), 353.00 (M+2); $^1$H NMR (methanol-$d_4$, 400 MHz) δ 8.14 (s, 1H), 7.62 (d, J=1.8 Hz, 1H), 7.02 (d, J=1.8 Hz, 1H), 4.15 (t, J=7.3 Hz, 1H), 2.32 (m, 1H), 1.61-1.86 (m, 5H), 1.13 (s, 3H), 1.10 (s, 3H).

Intermediate 51

6-bromo-4-((1R,3R)-3-hydroxy-2,2,3-trimethylcyclopentylamino)pyrrolo[1,2-b]-pyridazine-3-carboxamide

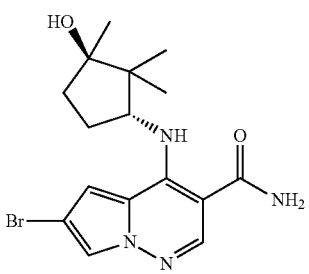
(Int-51)

A solution of 6-bromo-4-chloropyrrolo[1,2-b]pyridazine-3-carboxamide (Preparation 5, 38.3 mg, 0.140 mmol) and (1R,3R)-3-amino-1,2,2-trimethylcyclopentanol (from Step 2 of Intermediate 20, 20 mg, 0.140 mmol) in MeCN (1 mL) was added DIPEA (0.050 mL, 0.279 mmol). The reaction was sealed and heated to at 120° C. for 60 min. The reaction was cooled and concentrated then purified by flash chromatography on silica gel using 30-70% ethyl acetate/hexanes as the eluent to afford the title compound (47 mg, 86% yield). HPLC (Conditions L): retention time=7.21 min., (condition P): retention time=8.31 min.; LCMS: 382.97 (M+2); $^1$H NMR (CDCl$_3$, 400 MHz) δ 10.51 (br d, J=9.4 Hz, 1H), 7.84 (s, 1H), 7.57 (d, J=1.7 Hz, 1H), 6.97 (d, J=1.8 Hz, 1H), 5.45 (br s, 2H), 4.69 (q, J=9.5 Hz, 1H), 2.38 (m, 1H), 1.99 (m, 1H), 1.79 (m, 1H), 1.56 (m, 1H), 1.27 (s, 3H), 1.01 (s, 3H), 0.98 (s, 3H).

Examples 160-174

Examples 160-174 in the table below were prepared from 6-bromo-cis-4-(-4-hydroxy-4-methylcyclohexylamino)pyrrolo[1,2-b]pyridazine-3-carboxamide (Intermediate 46) and the appropriate commercially available boronic acid or ester using a similar method as described for the preparation of Example 31.

| Ex# | Name | Structure | HPLC Rt, min (Condition) | LCMS m/z (Condition) |
|---|---|---|---|---|
| 160 | 4-((4-hydroxy-4-methylcyclohexyl)amino)-6-phenylpyrrolo[1,2-b]pyridazine-3-carboxamide | 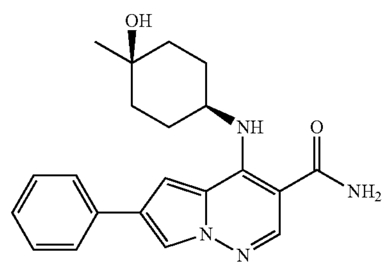 [SMILES: C[C@]1(O)CC[C@@H](Nc2c(C(N)=O)cnn3cc(-c4ccccc4)cc23)CC1] | 4.01 (B) | 365.12 |
| 161 | 6-(3-cyanophenyl)-4-((4-hydroxy-4-methylcyclohexyl)amino)pyrrolo[1,2-b]pyridazine-3-carboxamide | 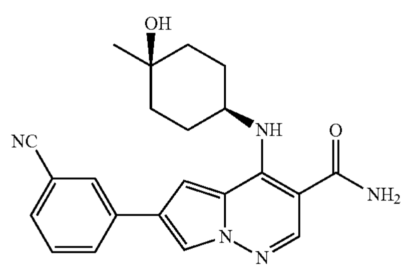 [SMILES: C[C@]1(O)CC[C@@H](Nc2c(C(N)=O)cnn3cc(-c4cccc(C#N)c4)cc23)CC1] | 3.80 (B) | 390.03 |
| 162 | 4-((4-hydroxy-4-methylcyclohexyl)amino)-6-(1-methyl-1H-pyrazol-5-yl)pyrrolo[1,2-b]pyridazine-3-carboxamide | 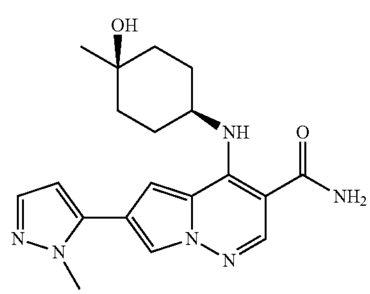 [SMILES: Cn1nccc1-c1cc2c(N[C@H]3CC[C@@](C)(O)CC3)c(C(N)=O)cnn2c1] | 3.37 (B) | 369.14 |
| 163 | 4-((4-hydroxy-4-methylcyclohexyl)amino)-6-(3-pyridinyl)pyrrolo[1,2-b]pyridazine-3-carboxamide | 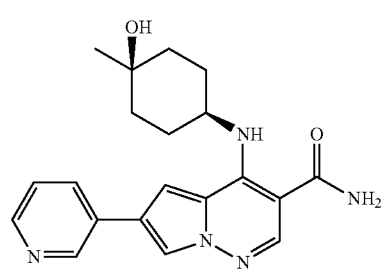 [SMILES: C[C@]1(O)CC[C@@H](Nc2c(C(N)=O)cnn3cc(-c4cccnc4)cc23)CC1] | 1.02 (C) | 366.2 |

-continued

| Ex# | Name | Structure | HPLC Rt, min (Condition) | LCMS m/z (Condition) |
|---|---|---|---|---|
| 164 | 4-((cis-4-hydroxy-4-methylcyclohexyl)amino)-6-(4-isopropoxyphenyl)pyrrolo[1,2-b]pyridazine-3-carboxamide | 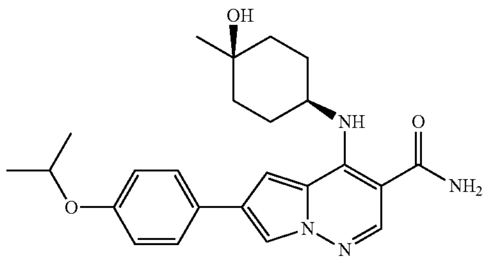 [SMILES: CC(C)Oc1ccc(-c2cc3c(N[C@H]4CC[C@@](C)(O)CC4)c(C(N)=O)cnn3c2)cc1] | 2.37 (C) | 423.08 |
| 165 | 4-((cis-4-hydroxy-4-methylcyclohexyl)amino)-6-(4-pyridinyl)pyrrolo[1,2-b]pyridazine-3-carboxamide | 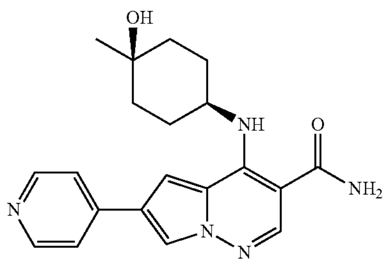 [SMILES: C[C@]1(O)CC[C@@H](Nc2c(C(N)=O)cnn3cc(-c4ccncc4)cc23)CC1] | 3.74 (L) | 366.12 |
| 166 | 6-(2-carbamoylphenyl)-4-((cis-4-hydroxy-4-methylcyclohexyl)amino)pyrrolo[1,2-b]pyridazine-3-carboxamide | 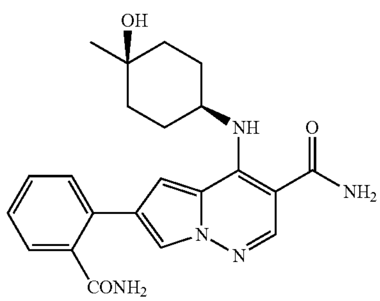 [SMILES: C[C@]1(O)CC[C@@H](Nc2c(C(N)=O)cnn3cc(-c4ccccc4C(N)=O)cc23)CC1] | 5.39 (L) | 408.11 |
| 167 | 6-(4-cyanophenyl)-4-((cis-4-hydroxy-4-methylcyclohexyl)amino)pyrrolo[1,2-b]pyridazine-3-carboxamide | 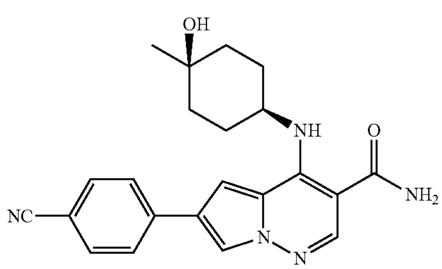 [SMILES: C[C@]1(O)CC[C@@H](Nc2c(C(N)=O)cnn3cc(-c4ccc(C#N)cc4)cc23)CC1] | 1.95 (C) | 390.70 |
| 168 | 4-((cis-4-hydroxy-4-methylcyclohexyl)amino)-6-(5-pyrimidinyl)pyrrolo[1,2-b]pyridazine-3-carboxamide | 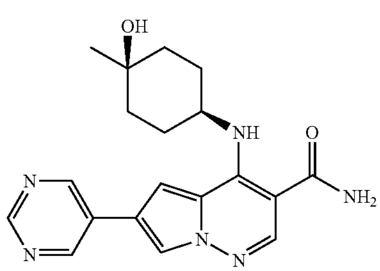 [SMILES: C[C@]1(O)CC[C@@H](Nc2c(C(N)=O)cnn3cc(-c4cncnc4)cc23)CC1] | 2.42 (Q) | 367.3 |

-continued

| Ex# | Name | Structure | HPLC Rt, min (Condition) | LCMS m/z (Condition) |
|---|---|---|---|---|
| 169 | 4-((cis-4-hydroxy-4-methylcyclohexyl)amino)-6-(1H-pyrazol-5-yl)pyrrolo[1,2-b]pyridazine-3-carboxamide | 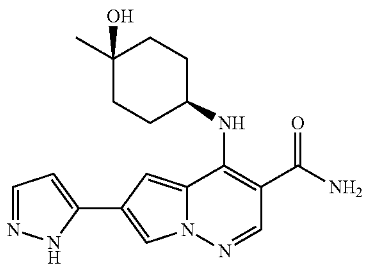 [SMILES: C[C@]1(O)CC[C@@H](Nc2c(C(N)=O)cnn3cc(-c4ccn[nH]4)cc23)CC1] | 4.73 (L) | 355.1 |
| 170 | 6-(5-fluoro-3-pyridinyl)-4-((cis-4-hydroxy-4-methylcyclohexyl)amino)pyrrolo[1,2-b]pyridazine-3-carboxamide | 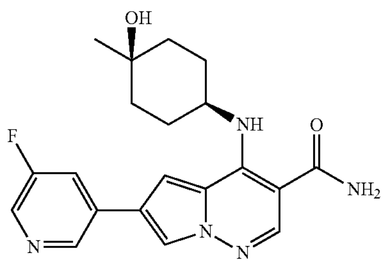 [SMILES: C[C@]1(O)CC[C@@H](Nc2c(C(N)=O)cnn3cc(-c4cncc(F)c4)cc23)CC1] | 1.60 (C) | 384.01 |
| 171 | 6-(3-aminophenyl)-4-((cis-4-hydroxy-4-methylcyclohexyl)amino)pyrrolo[1,2-b]pyridazine-3-carboxamide | 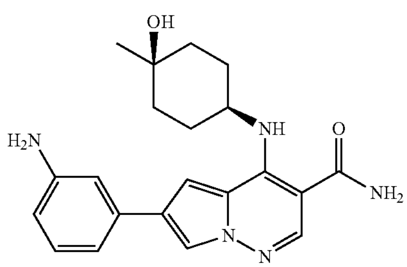 [SMILES: C[C@]1(O)CC[C@@H](Nc2c(C(N)=O)cnn3cc(-c4cccc(N)c4)cc23)CC1] | 1.16 (C) | 380.04 |
| 172 | 6-(3-acetamidophenyl)-4-((cis-4-hydroxy-4-methylcyclohexyl)amino)pyrrolo[1,2-b]pyridazine-3-carboxamide | 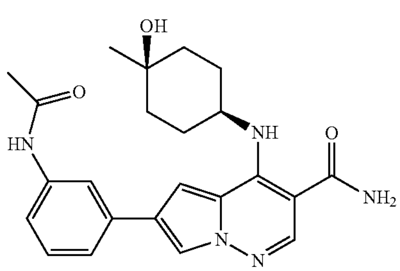 [SMILES: CC(=O)Nc1cccc(-c2cc3c(N[C@H]4CC[C@@](C)(O)CC4)c(C(N)=O)cnn3c2)c1] | 1.63 (C) | 422.1 |
| 173 | 6-(4-acetamidophenyl)-4-((cis-4-hydroxy-4-methylcyclohexyl)amino)pyrrolo[1,2-b]pyridazine-3-carboxamide | 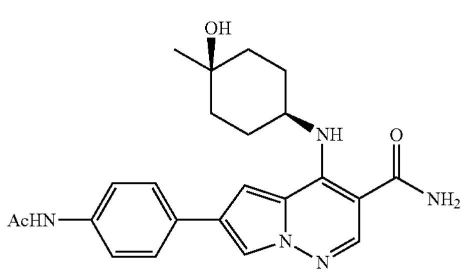 [SMILES: CC(=O)Nc1ccc(-c2cc3c(N[C@H]4CC[C@@](C)(O)CC4)c(C(N)=O)cnn3c2)cc1] | 1.51 (C) | 422.06 |

-continued

| Ex# | Name | Structure | HPLC Rt, min (Condition) | LCMS m/z (Condition) |
|---|---|---|---|---|
| 174 | 6-(4-carbamoylphenyl)-4-((cis-4-hydroxy-4-methylcyclohexyl)amino)pyrrolo[1,2-b]pyridazine-3-carboxamide | 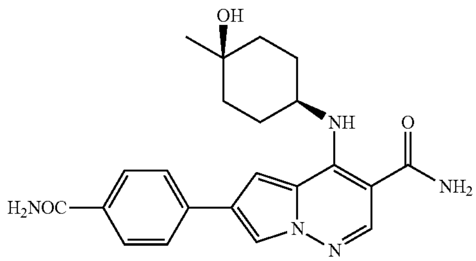 [SMILES: C[C@]1(O)CC[C@@H](Nc2c(C(N)=O)cnn3cc(-c4ccc(C(N)=O)cc4)cc23)CC1] | 5.19 (L) | 408.23 |

Examples 175 to 189

Examples 175 through 189 in the table below were prepared from (E)- and (Z)-6-bromo-4-((5-hydroxyadamantan-2-yl)amino)pyrrolo[1,2-b]pyridazine-3-carboxamide (Intermediate 47) and the appropriate commercially available boronic acid or ester using a similar method as described for the preparation of Example 28. In some cases, pure cis or trans isomers were obtained after HPLC purification and are denoted as Isomer 1 or Isomer 2. Cis and trans isomers were not assigned.

| Ex# | Name | Structure | HPLC Rt, min (Condition) | LCMS m/z (Condition) |
|---|---|---|---|---|
| 175 | 4-((5-hydroxyadamantan-2-yl)amino)-6-(3-methoxyphenyl)pyrrolo[1,2-b]pyridazine-3-carboxamide | Isomer 1 | 1.91 (I) | 433.1 |
| 176 | 4-((5-hydroxyadamantan-2-yl)amino)-6-(3-methoxyphenyl)pyrrolo[1,2-b]pyridazine-3-carboxamide | Isomer 2 | 2.23 (I) | 433.0 |

| Ex# | Name | Structure | HPLC Rt, min (Condition) | LCMS m/z (Condition) |
|---|---|---|---|---|
| 177 | 6-(2,6-dimethylphenyl)-4-((5-hydroxyadamantan-2-yl)amino)pyrrolo[1,2-b]pyridazine-3-carboxamide | Isomer 1 | 3.99 (B) | 431.19 |
| 178 | 4-((5-hydroxyadamantan-2-yl)amino)-6-(2-methoxyphenyl)pyrrolo[1,2-b]pyridazine-3-carboxamide | Isomer 1 | 2.37 (C) | 433.11 |
| 179 | 4-((5-hydroxyadamantan-2-yl)amino)-6-(2-methoxyphenyl)pyrrolo[1,2-b]pyridazine-3-carboxamide | Isomer 2 | 2.30 (C) | 433.24 |
| 180 | 4-((5-hydroxyadamantan-2-yl)amino)-6-phenylpyrrolo[1,2-b]pyridazine-3-carboxamide | Isomer 1 | 2.04 (C) | 403.15 |

-continued

| Ex# | Name | Structure | HPLC Rt, min (Condition) | LCMS m/z (Condition) |
|---|---|---|---|---|
| 181 | 4-((5-hydroxyadamantan-2-yl)amino)-6-phenylpyrrolo[1,2-b]pyridazine-3-carboxamide | 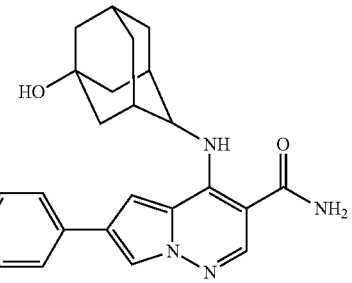<br>Isomer 2 | 2.31 (C) | 403.26 |
| 182 | 6-(3-cyanophenyl)-4-((5-hydroxyadamantan-2-yl)amino)pyrrolo[1,2-b]pyridazine-3-carboxamide | 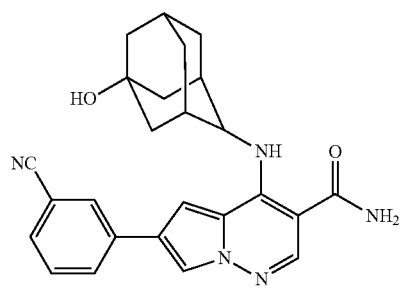<br>Isomer 1 | 1.92 (C) | 428.13 |
| 183 | 6-(3-cyanophenyl)-4-((5-hydroxyadamantan-2-yl)amino)pyrrolo[1,2-b]pyridazine-3-carboxamide | 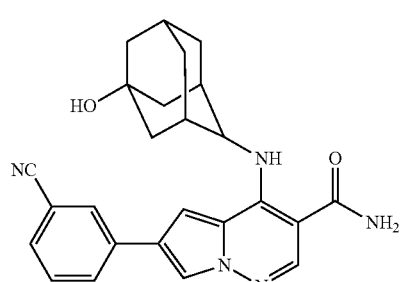<br>Isomer 2 | 1.92 (C) | 428.13 |
| 184 | 4-((5-hydroxyadamantan-2-yl)amino)-6-(1-methyl-1H-pyrazol-5-yl)pyrrolo[1,2-b]pyridazine-3-carboxamide | 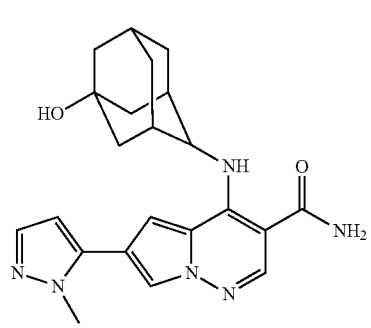<br>Isomer 1 | 1.42 (C) | 407.16 |

| Ex# | Name | Structure | HPLC Rt, min (Condition) | LCMS m/z (Condition) |
|---|---|---|---|---|
| 185 | 4-((5-hydroxyadamantan-2-yl)amino)-6-(1-methyl-1H-pyrazol-5-yl)pyrrolo[1,2-b]pyridazine-3-carboxamide | Isomer 2 | 1.60 (C) | 407.28 |
| 186 | 4-((5-hydroxyadamantan-2-yl)amino)-6-(4-methylphenyl)pyrrolo[1,2-b]pyridazine-3-carboxamide | Isomer 1 | 2.12 (C) | 417.13 |
| 187 | 4-((5-hydroxyadamantan-2-yl)amino)-6-(4-methylphenyl)pyrrolo[1,2-b]pyridazine-3-carboxamide | Isomer 2 | 2.46 (C) | 417.14 |
| 188 | methyl 4-(3-carbamoyl-4-((5-hydroxyadamantan-2-yl)amino)pyrrolo[1,2-b]pyridazin-6-yl)benzoate | Isomer 1 | 1.96 (C) | 461.13 |

| Ex# | Name | Structure | HPLC Rt, min (Condition) | LCMS m/z (Condition) |
|---|---|---|---|---|
| 189 | methyl 4-(3-carbamoyl-4-((5-hydroxyadamantan-2-yl)amino)pyrrolo[1,2-b]pyridazin-6-yl)benzoate | 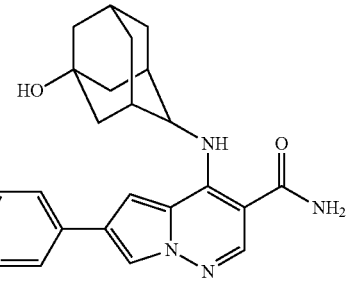 Isomer 2 | 1.96 (C) | 461.16 |

Examples 190-292

Examples 190 to 292 in the table below were prepared from 4-((1R,3S)-3-amino-2,2,3-trimethylcyclopentylamino)-6-bromopyrrolo[1,2-b]-pyridazine-3-carboxamide (Intermediate 48) and the appropriate commercially available boronic acid or boronic ester using a similar method as described for the preparation of Example 28

| Ex# | Name | Structure | HPLC Rt, min (Condition) | LCMS m/z (Condition) |
|---|---|---|---|---|
| 190 | 4-(((1R,3S)-3-amino-2,2,3-trimethylcyclopentyl)amino)-6-phenylpyrrolo[1,2-b]pyridazine-3-carboxamide | 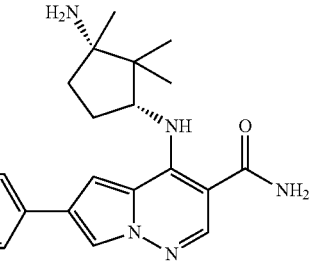 | 3.22 (B) | 378.1 |
| 191 | 4-(((1R,3S)-3-amino-2,2,3-trimethylcyclopentyl)amino)-6-(4-pyridinyl)pyrrolo[1,2-b]pyridazine-3-carboxamide | 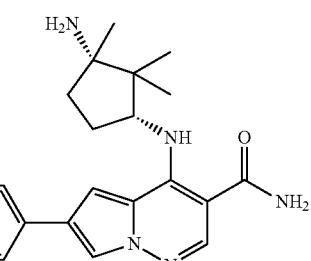 | 2.10 (B) | 379.13 |
| 192 | 4-(((1R,3S)-3-amino-2,2,3-trimethylcyclopentyl)amino)-6-(3-pyridinyl)pyrrolo[1,2-b]pyridazine-3-carboxamide | 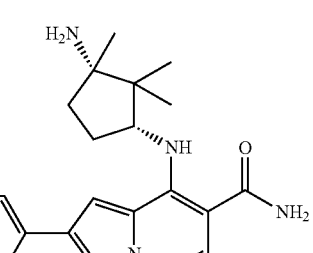 | 2.02 (B) | 379.2 |

-continued

| Ex# | Name | Structure | HPLC Rt, min (Condition) | LCMS m/z (Condition) |
|---|---|---|---|---|
| 193 | 4-(((1R,3S)-3-amino-2,2,3-trimethylcyclopentyl)amino)-6-(1-methyl-1H-pyrazol-5-yl)pyrrolo[1,2-b]pyridazine-3-carboxamide | 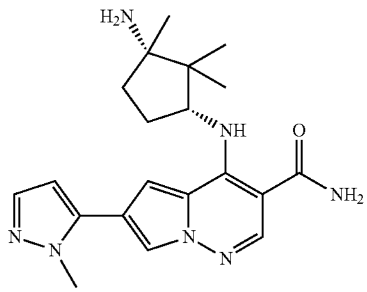 [SMILES: Cn1nccc1-c1cc2c(N[C@@H]3CC[C@](C)(N)C3(C)C)c(C(N)=O)cnn2c1] | 2.67 (B) | 382.2 |
| 194 | 4-(((1R,3S)-3-amino-2,2,3-trimethylcyclopentyl)amino)-6-(2-fluorophenyl)pyrrolo[1,2-b]pyridazine-3-carboxamide | 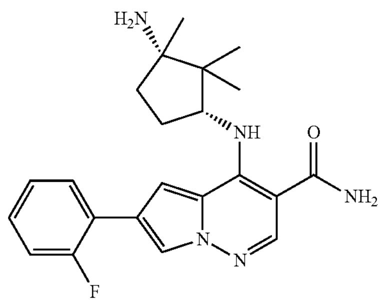 | 3.16 (B) | 396.14 |
| 195 | 4-(((1R,3S)-3-amino-2,2,3-trimethylcyclopentyl)amino)-6-(4-methyl-3-pyridinyl)pyrrolo[1,2-b]pyridazine-3-carboxamide | 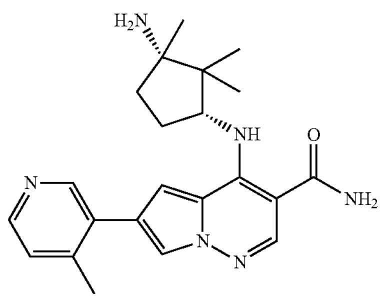 [SMILES: Cc1ccncc1-c1cc2c(N[C@@H]3CC[C@](C)(N)C3(C)C)c(C(N)=O)cnn2c1] | 2.07 (B) | 393.14 |
| 196 | 4-(((1R,3S)-3-amino-2,2,3-trimethylcyclopentyl)amino)-6-(4-cyanophenyl)pyrrolo[1,2-b]pyridazine-3-carboxamide | 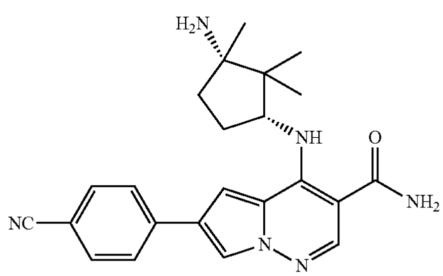 [SMILES: CC1(C)[C@H](Nc2c(C(N)=O)cnn3cc(-c4ccc(C#N)cc4)cc23)CC[C@]1(C)N] | 3.11 (B) | 403.1 |
| 197 | 4-(((1R,3S)-3-amino-2,2,3-trimethylcyclopentyl)amino)-6-(5-fluoro-3-pyridinyl)pyrrolo[1,2-b]pyridazine-3-carboxamide | 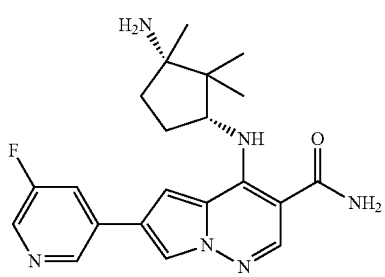 [SMILES: CC1(C)[C@H](Nc2c(C(N)=O)cnn3cc(-c4cncc(F)c4)cc23)CC[C@]1(C)N] | 1.22 (C) | 397.1 |

| Ex# | Name | Structure | HPLC Rt, min (Condition) | LCMS m/z (Condition) |
|---|---|---|---|---|
| 198 | 4-(((1R,3S)-3-amino-2,2,3-trimethylcyclopentyl)amino)-6-(2-fluoro-3-pyridinyl)pyrrolo[1,2-b]pyridazine-3-carboxamide | 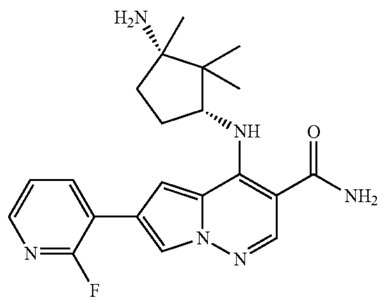 | 1.29 (C) | 397.09 |
| 199 | 4-(((1R,3S)-3-amino-2,2,3-trimethylcyclopentyl)amino)-6-(1H-pyrazol-5-yl)pyrrolo[1,2-b]pyridazine-3-carboxamide | 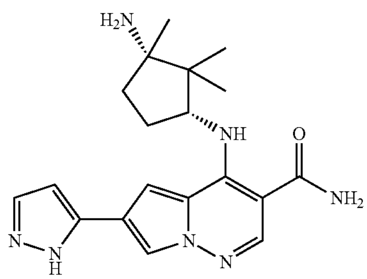 [SMILES: CC1(C)[C@H](Nc2c(C(N)=O)cnn3cc(-c4ccn[nH]4)cc23)CC[C@]1(C)N] | 2.58 (B) | 368.1 |
| 200 | 4-(((1R,3S)-3-amino-2,2,3-trimethylcyclopentyl)amino)-6-(2-cyanophenyl)pyrrolo[1,2-b]pyridazine-3-carboxamide | 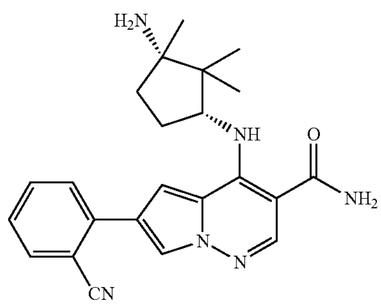 | 3.17 (B) | 403.1 |
| 201 | 4-(((1R,3S)-3-amino-2,2,3-trimethylcyclopentyl)amino)-6-(5-pyrimidinyl)pyrrolo[1,2-b]pyridazine-3-carboxamide | 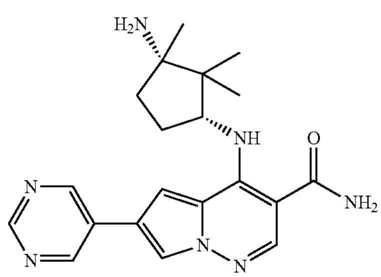 [SMILES: CC1(C)[C@H](Nc2c(C(N)=O)cnn3cc(-c4cncnc4)cc23)CC[C@]1(C)N] | 2.63 (B) | 380.2 |
| 202 | 4-(((1R,3S)-3-amino-2,2,3-trimethylcyclopentyl)amino)-6-(3-fluoro-4-pyridinyl)pyrrolo[1,2-b]pyridazine-3-carboxamide | 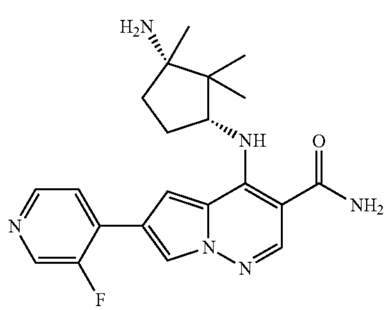 [SMILES: CC1(C)[C@H](Nc2c(C(N)=O)cnn3cc(-c4ccncc4F)cc23)CC[C@]1(C)N] | 2.57 (B) | 397.2 |

| Ex# | Name | Structure | HPLC Rt, min (Condition) | LCMS m/z (Condition) |
|---|---|---|---|---|
| 203 | 4-(((1R,3S)-3-amino-2,2,3-trimethylcyclopentyl)amino)-6-(4-methoxyphenyl)pyrrolo[1,2-b]pyridazine-3-carboxamide | 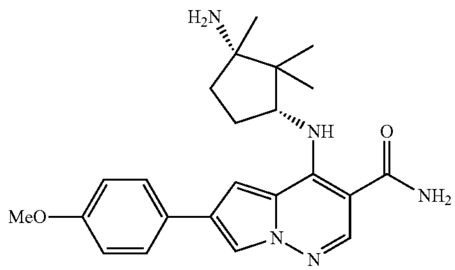 [SMILES: COc1ccc(-c2cc3c(N[C@@H]4CC[C@](C)(N)C4(C)C)c(C(N)=O)cnn3c2)cc1] | 3.26 (B) | 408.2 |
| 204 | 4-(((1R,3S)-3-amino-2,2,3-trimethylcyclopentyl)amino)-6-(4-fluorophenyl)pyrrolo[1,2-b]pyridazine-3-carboxamide | 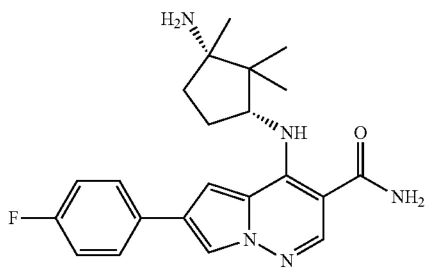 | 3.28 (B) | 396.2 |
| 205 | 4-(((1R,3S)-3-amino-2,2,3-trimethylcyclopentyl)amino)-6-(3-cyanophenyl)pyrrolo[1,2-b]pyridazine-3-carboxamide | 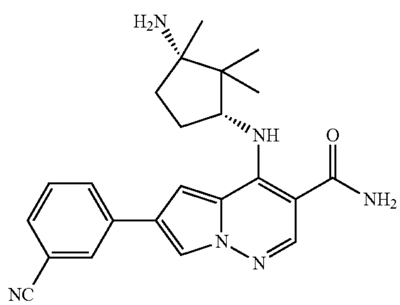 [SMILES: CC1(C)[C@H](Nc2c(C(N)=O)cnn3cc(-c4cccc(C#N)c4)cc23)CC[C@]1(C)N] | 3.17 (B) | 403.1 |
| 206 | 4-(((1R,3S)-3-amino-2,2,3-trimethylcyclopentyl)amino)-6-(2-fluoro-4-pyridinyl)pyrrolo[1,2-b]pyridazine-3-carboxamide | 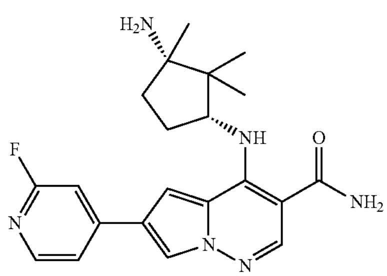 [SMILES: CC1(C)[C@H](Nc2c(C(N)=O)cnn3cc(-c4ccnc(F)c4)cc23)CC[C@]1(C)N] | 2.96 (B) | 397.1 |
| 207 | 4-(((1R,3S)-3-amino-2,2,3-trimethylcyclopentyl)amino)-6-(4-isopropoxyphenyl)pyrrolo[1,2-b]pyridazine-3-carboxamide | 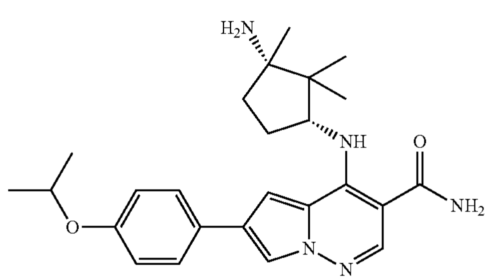 [SMILES: CC(C)Oc1ccc(-c2cc3c(N[C@@H]4CC[C@](C)(N)C4(C)C)c(C(N)=O)cnn3c2)cc1] | 3.50 (B) | 436.2 |

-continued

| Ex# | Name | Structure | HPLC Rt, min (Condition) | LCMS m/z (Condition) |
|---|---|---|---|---|
| 208 | 4-(((1R,3S)-3-amino-2,2,3-trimethylcyclopentyl)amino)-6-(3-fluorophenyl)pyrrolo[1,2-b]pyridazine-3-carboxamide | 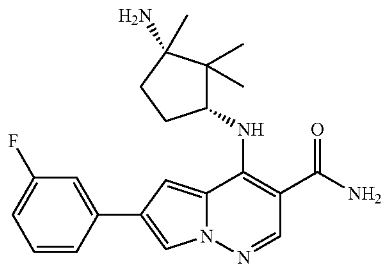 | 1.37 (C) | 396.3 |
| 209 | 4-(((1R,3S)-3-amino-2,2,3-trimethylcyclopentyl)amino)-6-(4-cyano-3-fluorophenyl)pyrrolo[1,2-b]pyridazine-3-carboxamide | 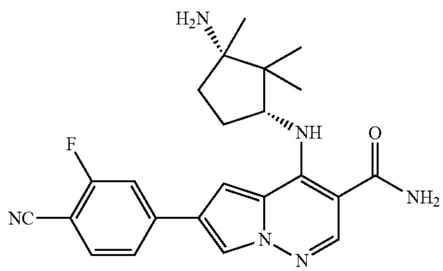 | 1.57 (C) | 421.06 |
| 210 | 4-(((1R,3S)-3-amino-2,2,3-trimethylcyclopentyl)amino)-6-(6-cyano-3-pyridinyl)pyrrolo[1,2-b]pyridazine-3-carboxamide | 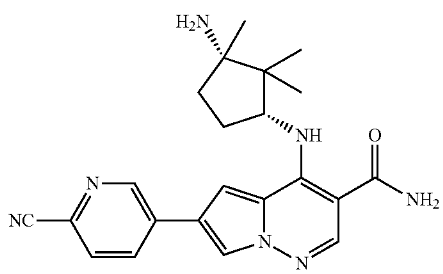 [SMILES: CC1(C)[C@H](Nc2c(C(N)=O)cnn3cc(-c4ccc(C#N)nc4)cc23)CC[C@]1(C)N] | 1.33 (C) | 404.08 |
| 211 | 4-(((1R,3S)-3-amino-2,2,3-trimethylcyclopentyl)amino)-6-(6-(trifluoromethyl)-3-pyridinyl)pyrrolo[1,2-b]pyridazine-3-carboxamide | 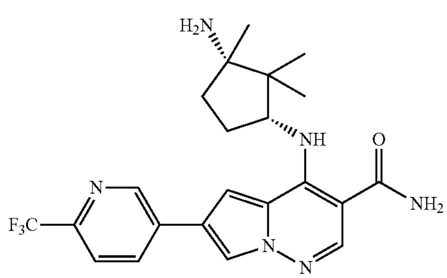 [SMILES: CC1(C)[C@H](Nc2c(C(N)=O)cnn3cc(-c4ccc(C(F)(F)F)nc4)cc23)CC[C@]1(C)N] | 3.17 (B) | 447.1 |
| 212 | 4-(((1R,3S)-3-amino-2,2,3-trimethylcyclopentyl)amino)-6-(2,4-dimethyl-1,3-thiazol-5-yl)pyrrolo[1,2-b]pyridazine-3-carboxamide | 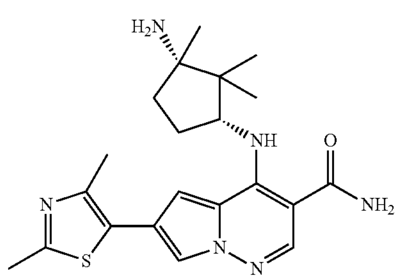 [SMILES: Cc1nc(C)c(-c2cc3c(N[C@@H]4CC[C@](C)(N)C4(C)C)c(C(N)=O)cnn3c2)s1] | 2.82 (B) | 413.1 |

-continued

| Ex# | Name | Structure | HPLC Rt, min (Condition) | LCMS m/z (Condition) |
|---|---|---|---|---|
| 213 | 4-(((1R,3S)-3-amino-2,2,3-trimethylcyclopentyl)amino)-6-(6-(1-pyrrolidinyl)-3-pyridinyl)pyrrolo[1,2-b]pyridazine-3-carboxamide | 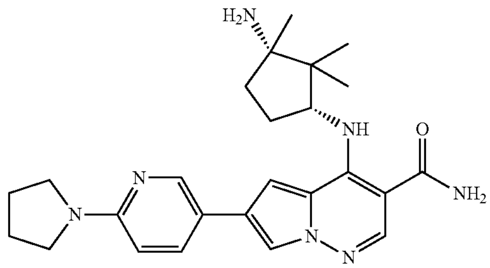 [SMILES: CC1(C)[C@H](Nc2c(C(N)=O)cnn3cc(-c4ccc(N5CCCC5)nc4)cc23)CC[C@]1(C)N] | 1.13 (C) | 448.2 |
| 214 | 4-(((1R,3S)-3-amino-2,2,3-trimethylcyclopentyl)amino)-6-(3-fluoro-4-methoxyphenyl)pyrrolo[1,2-b]pyridazine-3-carboxamide | 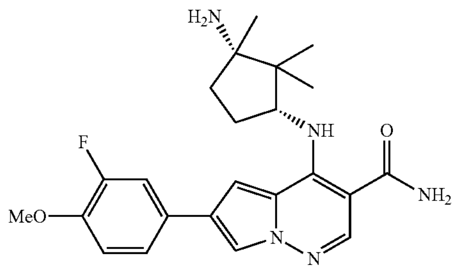 [SMILES: COc1ccc(-c2cc3c(N[C@@H]4CC[C@](C)(N)C4(C)C)c(C(N)=O)cnn3c2)cc1F] | 1.57 (C) | 426.08 |
| 215 | 4-(((1R,3S)-3-amino-2,2,3-trimethylcyclopentyl)amino)-6-(2-methoxy-4-pyridinyl)pyrrolo[1,2-b]pyridazine-3-carboxamide | 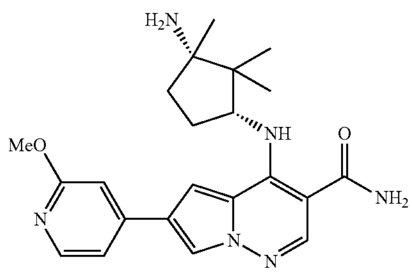 [SMILES: COc1cc(-c2cc3c(N[C@@H]4CC[C@](C)(N)C4(C)C)c(C(N)=O)cnn3c2)ccn1] | 1.14 (C) | 409.0 |
| 216 | 4-(((1R,3S)-3-amino-2,2,3-trimethylcyclopentyl)amino)-6-(6-isopropoxy-3-pyridinyl)pyrrolo[1,2-b]pyridazine-3-carboxamide | 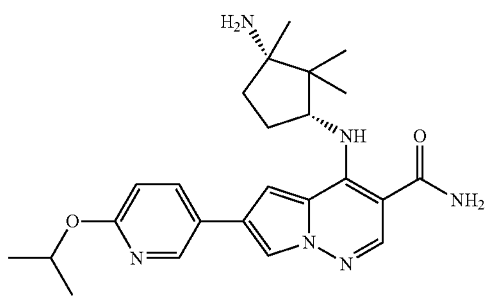 [SMILES: CC(C)Oc1ccc(-c2cc3c(N[C@@H]4CC[C@](C)(N)C4(C)C)c(C(N)=O)cnn3c2)cn1] | 1.56 (C) | 437.3 |
| 217 | 6-(6-acetamido-3-pyridinyl)-4-(((1R,3S)-3-amino-2,2,3-trimethylcyclopentyl)amino)pyrrolo[1,2-b]pyridazine-3-carboxamide | 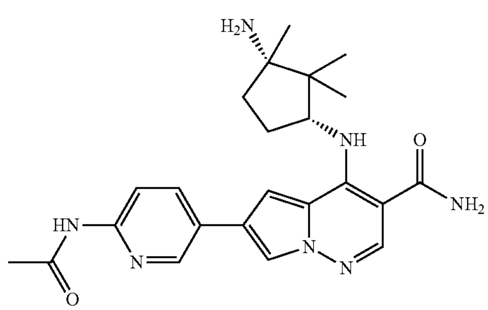 [SMILES: CC(=O)Nc1ccc(-c2cc3c(N[C@@H]4CC[C@](C)(N)C4(C)C)c(C(N)=O)cnn3c2)cn1] | 1.01 (C) | 436.0 |

| Ex# | Name | Structure | HPLC Rt, min (Condition) | LCMS m/z (Condition) |
|---|---|---|---|---|
| 218 | 4-(((1R,3S)-3-amino-2,2,3-trimethylcyclopentyl)amino)-6-(4-(1-hydroxy-1-methylethyl)phenyl)pyrrolo[1,2-b]pyridazine-3-carboxamide | 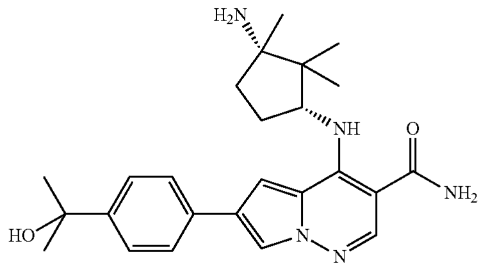 [SMILES: CC(C)(O)c1ccc(-c2cc3c(N[C@@H]4CC[C@](C)(N)C4(C)C)c(C(N)=O)cnn3c2)cc1] | 1.40 (C) | 436.17 |
| 219 | 4-(((1R,3S)-3-amino-2,2,3-trimethylcyclopentyl)amino)-6-(1,3-benzothiazol-5-yl)pyrrolo[1,2-b]pyridazine-3-carboxamide | 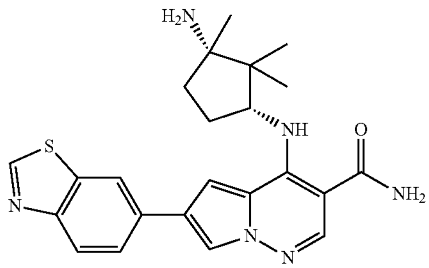 [SMILES: CC1(C)[C@H](Nc2c(C(N)=O)cnn3cc(-c4ccc5ncsc5c4)cc23)CC[C@]1(C)N] | 1.41 (C) | 435.09 |
| 220 | 4-(((1R,3S)-3-amino-2,2,3-trimethylcyclopentyl)amino)-6-(1H-indol-5-yl)pyrrolo[1,2-b]pyridazine-3-carboxamide | 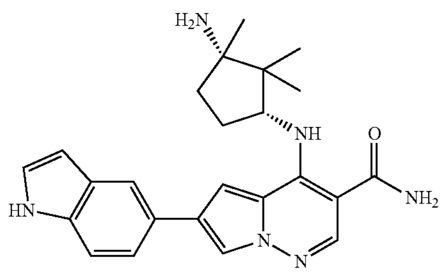 [SMILES: CC1(C)[C@H](Nc2c(C(N)=O)cnn3cc(-c4ccc5[nH]ccc5c4)cc23)CC[C@]1(C)N] | 1.50 (C) | 417.2 |
| 221 | 4-(((1R,3S)-3-amino-2,2,3-trimethylcyclopentyl)amino)-6-(4-(cyclopropylcarbamoyl)phenyl)pyrrolo[1,2-b]pyridazine-3-carboxamide | 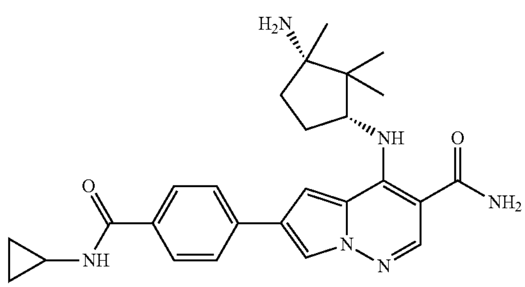 [SMILES: CC1(C)[C@H](Nc2c(C(N)=O)cnn3cc(-c4ccc(C(=O)NC5CC5)cc4)cc23)CC[C@]1(C)N] | 2.69 (B) | 461.27 |
| 222 | 4-(((1R,3S)-3-amino-2,2,3-trimethylcyclopentyl)amino)-6-(1-methyl-1H-pyrazol-4-yl)pyrrolo[1,2-b]pyridazine-3-carboxamide | 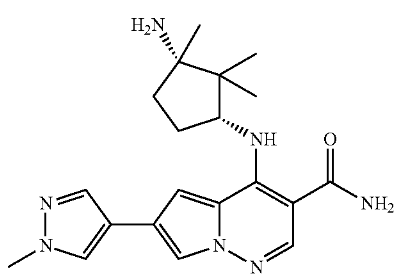 [SMILES: Cn1cc(-c2cc3c(N[C@@H]4CC[C@](C)(N)C4(C)C)c(C(N)=O)cnn3c2)cn1] | 2.69 (B) | 382.24 |

| Ex# | Name | Structure | HPLC Rt, min (Condition) | LCMS m/z (Condition) |
|---|---|---|---|---|
| 223 | 4-(((1R,3S)-3-amino-2,2,3-trimethylcyclopentyl)amino)-6-(6-fluoro-3-pyridinyl)pyrrolo[1,2-b]pyridazine-3-carboxamide | 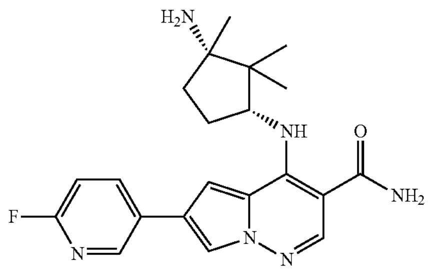 [SMILES: CC1(C)[C@H](Nc2c(C(N)=O)cnn3cc(-c4ccc(F)nc4)cc23)CC[C@]1(C)N] | 2.91 (B) | 397.1 |
| 224 | 4-(((1R,3S)-3-amino-2,2,3-trimethylcyclopentyl)amino)-6-(4-(ethylcarbamoyl)phenyl)pyrrolo[1,2-b]pyridazine-3-carboxamide | 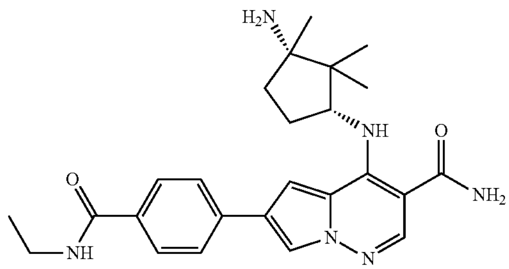 [SMILES: CCNC(=O)c1ccc(-c2cc3c(N[C@@H]4CC[C@](C)(N)C4(C)C)c(C(N)=O)cnn3c2)cc1] | 2.83 (O) | 449.29 |
| 225 | 4-(((1R,3S)-3-amino-2,2,3-trimethylcyclopentyl)amino)-6-(4-(isopropylcarbamoyl)phenyl)pyrrolo[1,2-b]pyridazine-3-carboxamide | 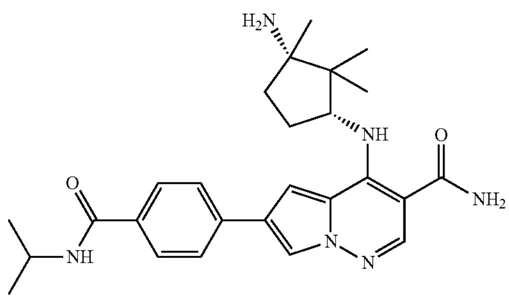 [SMILES: CC(C)NC(=O)c1ccc(-c2cc3c(N[C@@H]4CC[C@](C)(N)C4(C)C)c(C(N)=O)cnn3c2)cc1] | 2.94 (L) | 463.27 |
| 226 | 4-(((1R,3S)-3-amino-2,2,3-trimethylcyclopentyl)amino)-6-(1H-indazol-5-yl)pyrrolo[1,2-b]pyridazine-3-carboxamide | 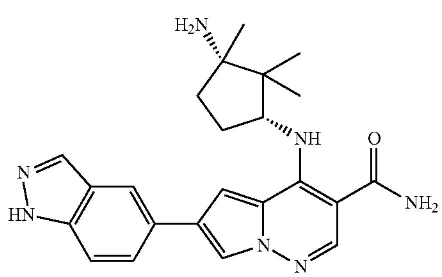 [SMILES: CC1(C)[C@H](Nc2c(C(N)=O)cnn3cc(-c4ccc5[nH]ncc5c4)cc23)CC[C@]1(C)N] | 1.23 (C) | 418.5 |
| 227 | 4-(((1R,3S)-3-amino-2,2,3-trimethylcyclopentyl)amino)-6-(4-(methylcarbamoyl)phenyl)pyrrolo[1,2-b]pyridazine-3-carboxamide | 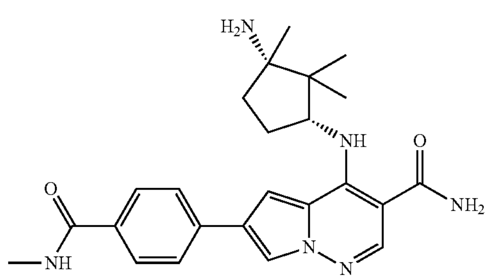 [SMILES: CNC(=O)c1ccc(-c2cc3c(N[C@@H]4CC[C@](C)(N)C4(C)C)c(C(N)=O)cnn3c2)cc1] | 1.26 (C) | 435.13 |

| Ex# | Name | Structure | HPLC Rt, min (Condition) | LCMS m/z (Condition) |
|---|---|---|---|---|
| 228 | 4-(((1R,3S)-3-amino-2,2,3-trimethylcyclopentyl)amino)-6-(4-(1H-tetrazol-5-yl)phenyl)pyrrolo[1,2-b]pyridazine-3-carboxamide | 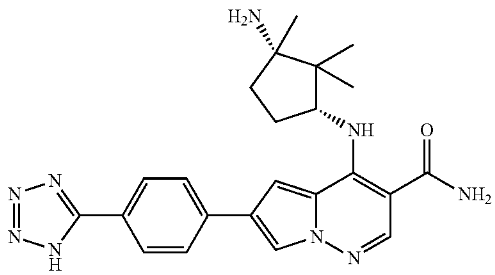 [SMILES: CC1(C)[C@H](Nc2c(C(N)=O)cnn3cc(-c4ccc(-c5nnn[nH]5)cc4)cc23)CC[C@]1(C)N] | 1.29 (C) | 446.13 |
| 229 | 4-(((1R,3S)-3-amino-2,2,3-trimethylcyclopentyl)amino)-6-(1-benzyl-1H-pyrazol-4-yl)pyrrolo[1,2-b]pyridazine-3-carboxamide | 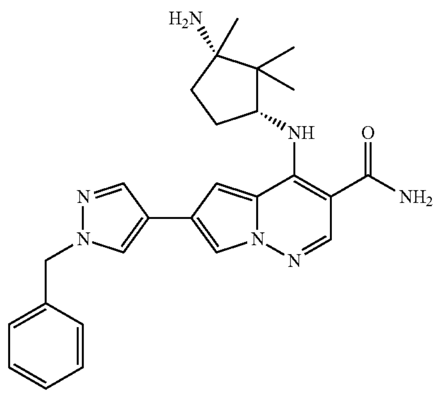 [SMILES: CC1(C)[C@H](Nc2c(C(N)=O)cnn3cc(-c4cnn(Cc5ccccc5)c4)cc23)CC[C@]1(C)N] | 1.52 (C) | 458.06 |
| 230 | 4-(((1R,3S)-3-amino-2,2,3-trimethylcyclopentyl)amino)-6-(4-(1H-pyrazol-1-yl)phenyl)pyrrolo[1,2-b]pyridazine-3-carboxamide | 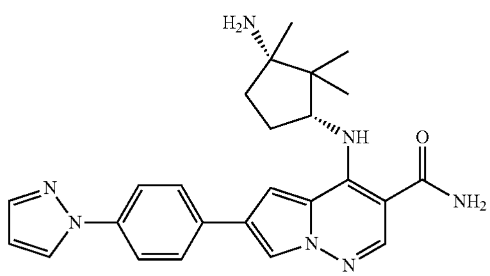 [SMILES: CC1(C)[C@H](Nc2c(C(N)=O)cnn3cc(-c4ccc(-n5cccn5)cc4)cc23)CC[C@]1(C)N] | 1.55 (C) | 444.06 |
| 231 | 4-(((1R,3S)-3-amino-2,2,3-trimethylcyclopentyl)amino)-6-(4-(2-methyl-1,3-thiazol-4-yl)phenyl)pyrrolo[1,2-b]pyridazine-3-carboxamide | 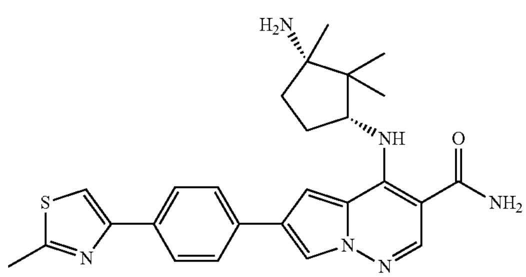 [SMILES: Cc1nc(-c2ccc(-c3cc4c(N[C@@H]5CC[C@](C)(N)C5(C)C)c(C(N)=O)cnn4c3)cc2)cs1] | 3.48 (B) | 475.1 |
| 232 | 4-(((1R,3S)-3-amino-2,2,3-trimethylcyclopentyl)amino)-6-(6-methoxy-3-pyridinyl)pyrrolo[1,2-b]pyridazine-3-carboxamide | 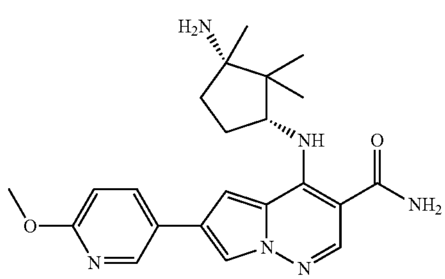 [SMILES: COc1ccc(-c2cc3c(N[C@@H]4CC[C@](C)(N)C4(C)C)c(C(N)=O)cnn3c2)cn1] | 3.04 (B) | 409.2 |

-continued

| Ex# | Name | Structure | HPLC Rt, min (Condition) | LCMS m/z (Condition) |
|---|---|---|---|---|
| 233 | 4-(((1R,3S)-3-amino-2,2,3-trimethylcyclopentyl)amino)-6-(5-fluoro-6-methoxy-3-pyridinyl)pyrrolo[1,2-b]pyridazine-3-carboxamide | 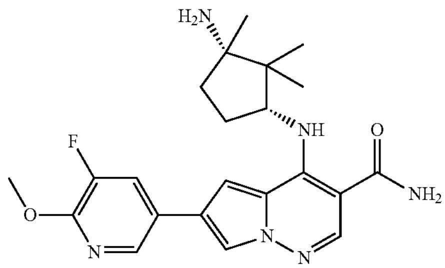 [SMILES: COc1ncc(-c2cc3c(N[C@@H]4CC[C@](C)(N)C4(C)C)c(C(N)=O)cnn3c2)cc1F] | 3.28 (B) | 427.22 |
| 234 | 6-(4-(aminomethyl)phenyl)-4-(((1R,3S)-3-amino-2,2,3-trimethylcyclopentyl)amino)pyrrolo[1,2-b]pyridazine-3-carboxamide | 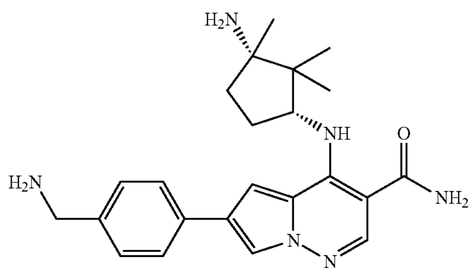 [SMILES: CC1(C)[C@H](Nc2c(C(N)=O)cnn3cc(-c4ccc(CN)cc4)cc23)CC[C@]1(C)N] | 3.65 (L) | 407.23 |
| 235 | 6-(5-amino-3-pyridinyl)-4-(((1R,3S)-3-amino-2,2,3-trimethylcyclopentyl)amino)pyrrolo[1,2-b]pyridazine-3-carboxamide | 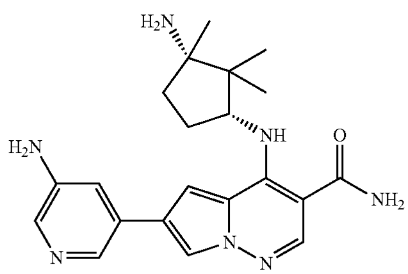 [SMILES: CC1(C)[C@H](Nc2c(C(N)=O)cnn3cc(-c4cncc(N)c4)cc23)CC[C@]1(C)N] | 0.89 (C) | 394.4 |
| 236 | 4-(((1R,3S)-3-amino-2,2,3-trimethylcyclopentyl)amino)-6-(4-(4-morpholinylcarbonyl)phenyl)pyrrolo[1,2-b]pyridazine-3-carboxamide | 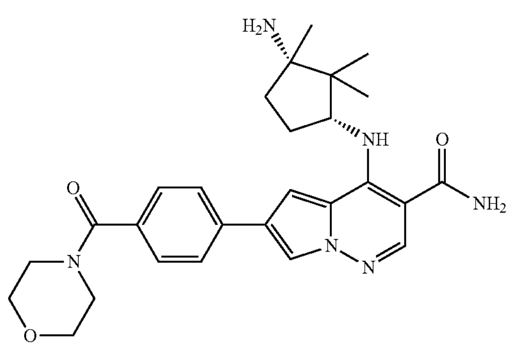 [SMILES: CC1(C)[C@H](Nc2c(C(N)=O)cnn3cc(-c4ccc(C(=O)N5CCOCC5)cc4)cc23)CC[C@]1(C)N] | 1.41 (C) | 491.2 |
| 237 | 4-(((1R,3S)-3-amino-2,2,3-trimethylcyclopentyl)amino)-6-(1H-indol-6-yl)pyrrolo[1,2-b]pyridazine-3-carboxamide | 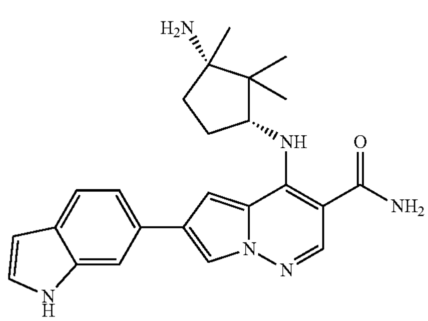 [SMILES: CC1(C)[C@H](Nc2c(C(N)=O)cnn3cc(-c4ccc5cc[nH]c5c4)cc23)CC[C@]1(C)N] | 1.63 (C) | 417.2 |

-continued

| Ex# | Name | Structure | HPLC Rt, min (Condition) | LCMS m/z (Condition) |
|---|---|---|---|---|
| 238 | 4-(((1R,3S)-3-amino-2,2,3-trimethylcyclopentyl)amino)-6-(3,5-dimethyl-4-isoxazolyl)pyrrolo[1,2-b]pyridazine-3-carboxamide | 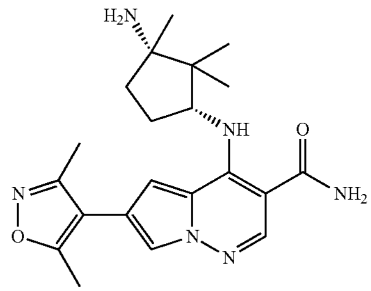 [SMILES: Cc1noc(C)c1-c1cc2c(N[C@@H]3CC[C@](C)(N)C3(C)C)c(C(N)=O)cnn2c1] | 1.30 (C) | 397.4 |
| 239 | 4-(((1R,3S)-3-amino-2,2,3-trimethylcyclopentyl)amino)-6-(4-((3-methoxypropanoyl)amino)phenyl)pyrrolo[1,2-b]pyridazine-3-carboxamide | 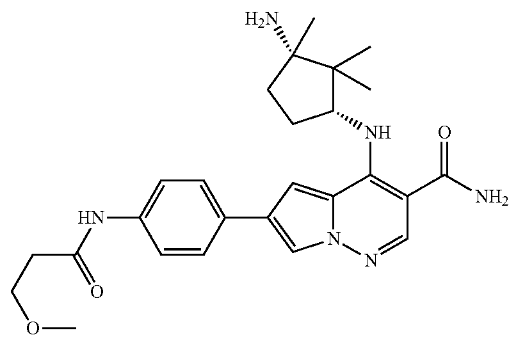 [SMILES: COCCC(=O)Nc1ccc(-c2cc3c(N[C@@H]4CC[C@](C)(N)C4(C)C)c(C(N)=O)cnn3c2)cc1] | 1.23 (C) | 479.5 |
| 240 | 4-(((1R,3S)-3-amino-2,2,3-trimethylcyclopentyl)amino)-6-(4-methyl-3,4-dihydro-2H-1,4-benzoxazin-7-yl)pyrrolo[1,2-b]pyridazine-3-carboxamide | 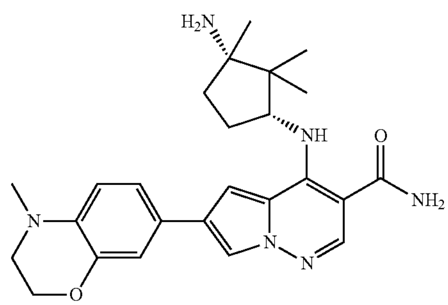 [SMILES: CN1CCOc2cc(-c3cc4c(N[C@@H]5CC[C@](C)(N)C5(C)C)c(C(N)=O)cnn4c3)ccc21] | 1.57 (C) | 449.4 |
| 241 | 4-(((1R,3S)-3-amino-2,2,3-trimethylcyclopentyl)amino)-6-(4-(difluoromethoxy)phenyl)pyrrolo[1,2-b]pyridazine-3-carboxamide | 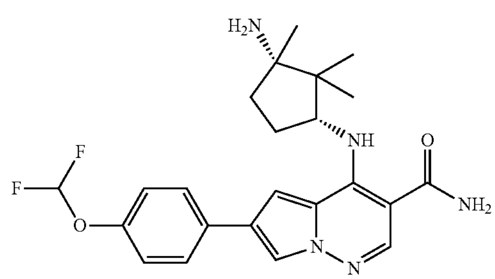 [SMILES: CC1(C)[C@H](Nc2c(C(N)=O)cnn3cc(-c4ccc(OC(F)F)cc4)cc23)CC[C@]1(C)N] | 1.97 (C) | 444.04 |
| 242 | 4-(((1R,3S)-3-amino-2,2,3-trimethylcyclopentyl)amino)-6-(2,6-difluoro-4-pyridinyl)pyrrolo[1,2-b]pyridazine-3-carboxamide | 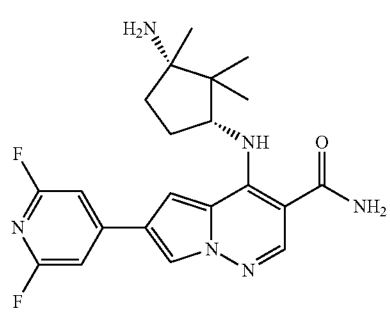 [SMILES: CC1(C)[C@H](Nc2c(C(N)=O)cnn3cc(-c4cc(F)nc(F)c4)cc23)CC[C@]1(C)N] | 3.13 (B) | 415.17 |

| Ex# | Name | Structure | HPLC Rt, min (Condition) | LCMS m/z (Condition) |
|---|---|---|---|---|
| 243 | 4-(((1R,3S)-3-amino-2,2,3-trimethylcyclopentyl)amino)-6-(4-(4-morpholinyl)phenyl)pyrrolo[1,2-b]pyridazine-3-carboxamide | 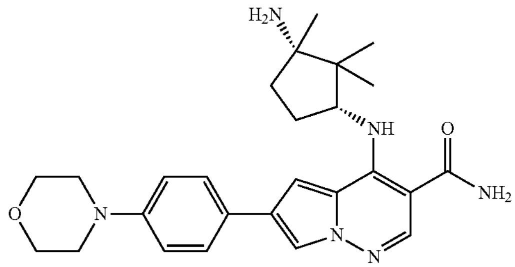 [SMILES: CC1(C)[C@H](Nc2c(C(N)=O)cnn3cc(-c4ccc(N5CCOCC5)cc4)cc23)CC[C@]1(C)N] | 1.34 (C) | 463.4 |
| 244 | methyl (4-(4-(((1R,3S)-3-amino-2,2,3-trimethylcyclopentyl)amino)-3-carbamoylpyrrolo[1,2-b]pyridazin-6-yl)phenyl)carbamate | 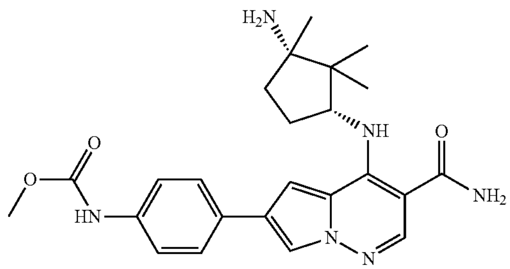 [SMILES: COC(=O)Nc1ccc(-c2cc3c(N[C@@H]4CC[C@](C)(N)C4(C)C)c(C(N)=O)cnn3c2)cc1] | 1.79 (C) | 451.11 |
| 245 | 6-(3-aminophenyl)-4-(((1R,3S)-3-amino-2,2,3-trimethylcyclopentyl)amino)pyrrolo[1,2-b]pyridazine-3-carboxamide | 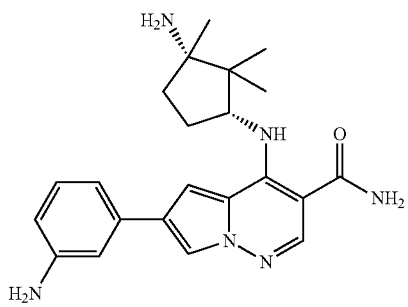 [SMILES: CC1(C)[C@H](Nc2c(C(N)=O)cnn3cc(-c4cccc(N)c4)cc23)CC[C@]1(C)N] | 1.28 (E) | 393.11 |
| 246 | 4-(((1R,3S)-3-amino-2,2,3-trimethylcyclopentyl)amino)-6-(4-chlorophenyl)pyrrolo[1,2-b]pyridazine-3-carboxamide | 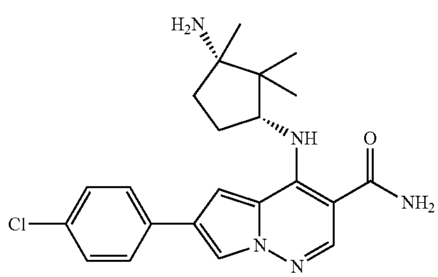 [SMILES: CC1(C)[C@H](Nc2c(C(N)=O)cnn3cc(-c4ccc(Cl)cc4)cc23)CC[C@]1(C)N] | 1.96 (E) | 412.02 |
| 247 | 4-(((1R,3S)-3-amino-2,2,3-trimethylcyclopentyl)amino)-6-(2-methylphenyl)pyrrolo[1,2-b]pyridazine-3-carboxamide | 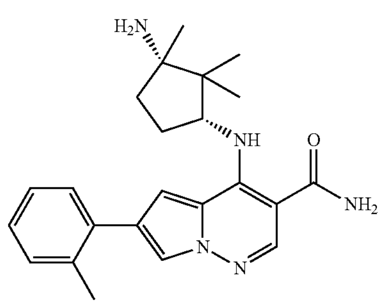 | 1.84 (E) | 392.09 |

-continued

| Ex# | Name | Structure | HPLC Rt, min (Condition) | LCMS m/z (Condition) |
|---|---|---|---|---|
| 248 | 4-(((1R,3S)-3-amino-2,2,3-trimethylcyclopentyl)amino)-6-(3-chlorophenyl)pyrrolo[1,2-b]pyridazine-3-carboxamide | 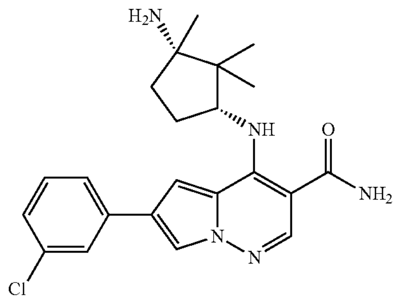 [SMILES: CC1(C)[C@H](Nc2c(C(N)=O)cnn3cc(-c4cccc(Cl)c4)cc23)CC[C@]1(C)N] | 1.96 (E) | 412.03 |
| 249 | 4-(((1R,3S)-3-amino-2,2,3-trimethylcyclopentyl)amino)-6-(3-methoxyphenyl)pyrrolo[1,2-b]pyridazine-3-carboxamide | 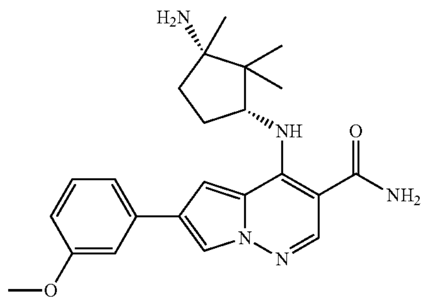 [SMILES: COc1cccc(-c2cc3c(N[C@@H]4CC[C@](C)(N)C4(C)C)c(C(N)=O)cnn3c2)c1] | 1.73 (E) | 408.09 |
| 250 | 4-(((1R,3S)-3-amino-2,2,3-trimethylcyclopentyl)amino)-6-(3,5-dimethylphenyl)pyrrolo[1,2-b]pyridazine-3-carboxamide | 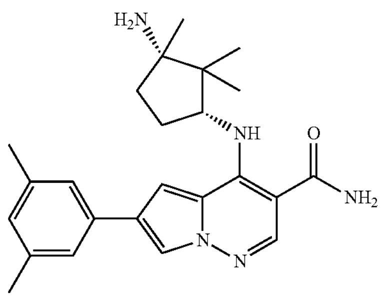 [SMILES: Cc1cc(C)cc(-c2cc3c(N[C@@H]4CC[C@](C)(N)C4(C)C)c(C(N)=O)cnn3c2)c1] | 2.05 (E) | 406.1 |
| 251 | 6-(3-acetamidophenyl)-4-(((1R,3S)-3-amino-2,2,3-trimethylcyclopentyl)amino)pyrrolo[1,2-b]pyridazine-3-carboxamide | 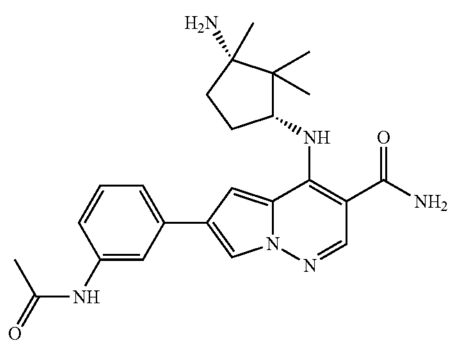 [SMILES: CC(=O)Nc1cccc(-c2cc3c(N[C@@H]4CC[C@](C)(N)C4(C)C)c(C(N)=O)cnn3c2)c1] | 1.29 (E) | 435.11 |
| 252 | 4-(((1R,3S)-3-amino-2,2,3-trimethylcyclopentyl)amino)-6-(2-methoxyphenyl)pyrrolo[1,2-b]pyridazine-3-carboxamide | 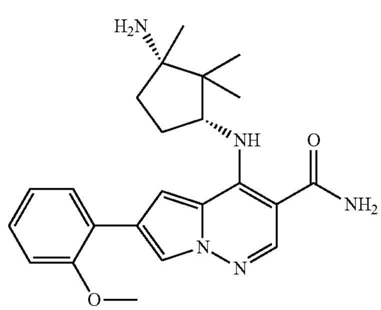 [SMILES: COc1ccccc1-c1cc2c(N[C@@H]3CC[C@](C)(N)C3(C)C)c(C(N)=O)cnn2c1] | 1.74 (E) | 408.09 |

| Ex# | Name | Structure | HPLC Rt, min (Condition) | LCMS m/z (Condition) |
|---|---|---|---|---|
| 253 | 4-(((1R,3S)-3-amino-2,2,3-trimethylcyclopentyl)amino)-6-(3-(dimethylamino)phenyl)pyrrolo[1,2-b]pyridazine-3-carboxamide | 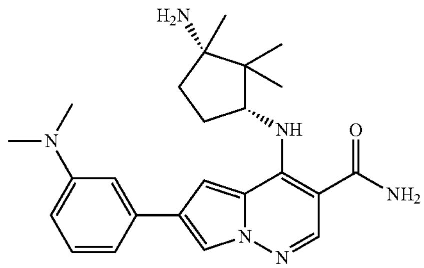 [SMILES: CN(C)c1cccc(-c2cc3c(N[C@@H]4CC[C@](C)(N)C4(C)C)c(C(N)=O)cnn3c2)c1] | 1.84 (E) | 421.11 |
| 254 | 6-(4-acetamidophenyl)-4-(((1R,3S)-3-amino-2,2,3-trimethylcyclopentyl)amino)pyrrolo[1,2-b]pyridazine-3-carboxamide | 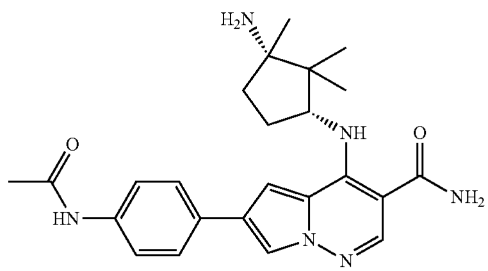 [SMILES: CC(=O)Nc1ccc(-c2cc3c(N[C@@H]4CC[C@](C)(N)C4(C)C)c(C(N)=O)cnn3c2)cc1] | 1.25 (E) | 435.07 |
| 255 | 4-(((1R,3S)-3-amino-2,2,3-trimethylcyclopentyl)amino)-6-(2-carbamoylphenyl)pyrrolo[1,2-b]pyridazine-3-carboxamide | 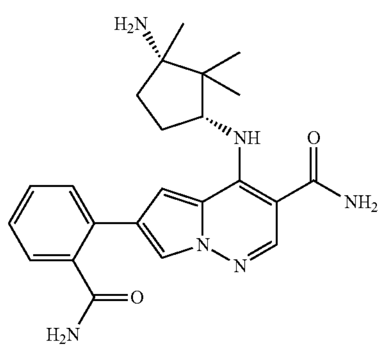 [SMILES: CC1(C)[C@H](Nc2c(C(N)=O)cnn3cc(-c4ccccc4C(N)=O)cc23)CC[C@]1(C)N] | 1.17 (E) | 421.07 |
| 256 | 4-(((1R,3S)-3-amino-2,2,3-trimethylcyclopentyl)amino)-6-(2-((methylsulfonyl)amino)phenyl)pyrrolo[1,2-b]pyridazine-3-carboxamide | 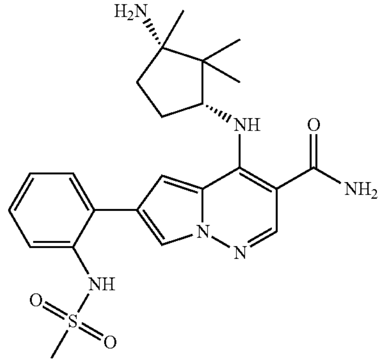 [SMILES: CC1(C)[C@H](Nc2c(C(N)=O)cnn3cc(-c4ccccc4NS(C)(=O)=O)cc23)CC[C@]1(C)N] | 1.39 (E) | 471.02 |

-continued

| Ex# | Name | Structure | HPLC Rt, min (Condition) | LCMS m/z (Condition) |
|---|---|---|---|---|
| 257 | 6-(2-acetamidophenyl)-4-(((1R,3S)-3-amino-2,2,3-trimethylcyclopentyl)amino)pyrrolo[1,2-b]pyridazine-3-carboxamide | 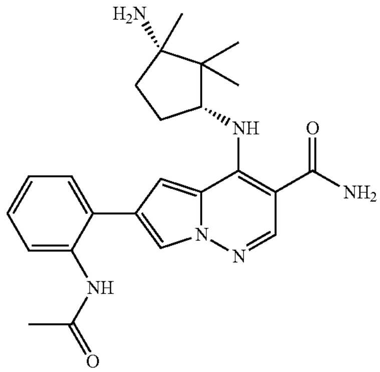 [SMILES: CC(=O)Nc1ccccc1-c1cc2c(N[C@@H]3CC[C@](C)(N)C3(C)C)c(C(N)=O)cnn2c1] | 1.25 (E) | 435.07 |
| 258 | 4-(((1R,3S)-3-amino-2,2,3-trimethylcyclopentyl)amino)-6-(4-carbamoylphenyl)pyrrolo[1,2-b]pyridazine-3-carboxamide | 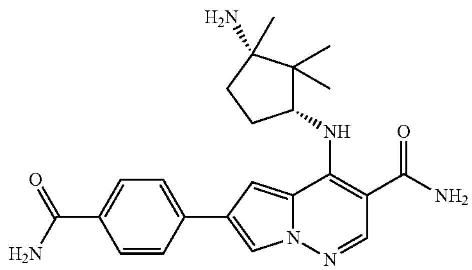 [SMILES: CC1(C)[C@H](Nc2c(C(N)=O)cnn3cc(-c4ccc(C(N)=O)cc4)cc23)CC[C@]1(C)N] | 1.10 (E) | 421.07 |
| 259 | 4-(((1R,3S)-3-amino-2,2,3-trimethylcyclopentyl)amino)-6-(3-carbamoylphenyl)pyrrolo[1,2-b]pyridazine-3-carboxamide | 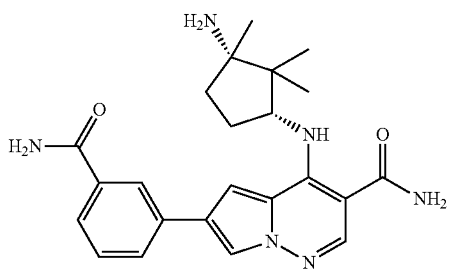 [SMILES: CC1(C)[C@H](Nc2c(C(N)=O)cnn3cc(-c4cccc(C(N)=O)c4)cc23)CC[C@]1(C)N] | 1.19 (E) | 421.07 |
| 260 | 4-(((1R,3S)-3-amino-2,2,3-trimethylcyclopentyl)amino)-6-(3-(dimethylcarbamoyl)phenyl)pyrrolo[1,2-b]pyridazine-3-carboxamide | 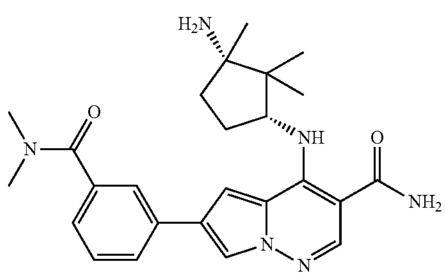 [SMILES: CN(C)C(=O)c1cccc(-c2cc3c(N[C@@H]4CC[C@](C)(N)C4(C)C)c(C(N)=O)cnn3c2)c1] | 1.34 (E) | 449.08 |
| 261 | 4-(((1R,3S)-3-amino-2,2,3-trimethylcyclopentyl)amino)-6-(1-methyl-1H-indol-5-yl)pyrrolo[1,2-b]pyridazine-3-carboxamide | 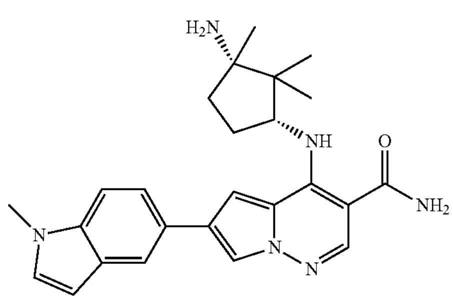 [SMILES: Cn1ccc2cc(-c3cc4c(N[C@@H]5CC[C@](C)(N)C5(C)C)c(C(N)=O)cnn4c3)ccc21] | 1.8 (E) | 431.13 |

-continued

| Ex# | Name | Structure | HPLC Rt, min (Condition) | LCMS m/z (Condition) |
|---|---|---|---|---|
| 262 | 4-(((1R,3S)-3-amino-2,2,3-trimethylcyclopentyl)amino)-6-(4-(((methylsulfonyl)amino)methyl)phenyl)pyrrolo[1,2-b]pyridazine-3-carboxamide | 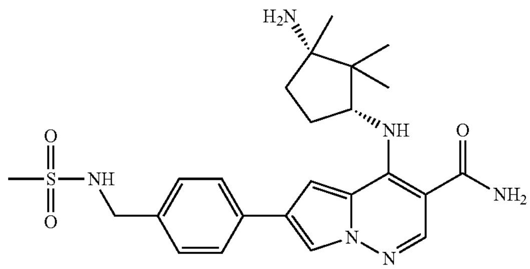 [SMILES: CC1(C)[C@H](Nc2c(C(N)=O)cnn3cc(-c4ccc(CNS(C)(=O)=O)cc4)cc23)CC[C@]1(C)N] | 1.37 (E) | 485.02 |
| 263 | 4-(((1R,3S)-3-amino-2,2,3-trimethylcyclopentyl)amino)-6-(3-(((methylsulfonyl)amino)methyl)phenyl)pyrrolo[1,2-b]pyridazine-3-carboxamide | 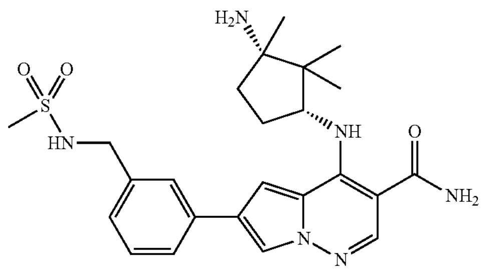 [SMILES: CC1(C)[C@H](Nc2c(C(N)=O)cnn3cc(-c4cccc(CNS(C)(=O)=O)c4)cc23)CC[C@]1(C)N] | 1.4 (E) | 485.02 |
| 264 | 6-(4-(acetamidomethyl)phenyl)-4-(((1R,3S)-3-amino-2,2,3-trimethylcyclopentyl)amino)pyrrolo[1,2-b]pyridazine-3-carboxamide | 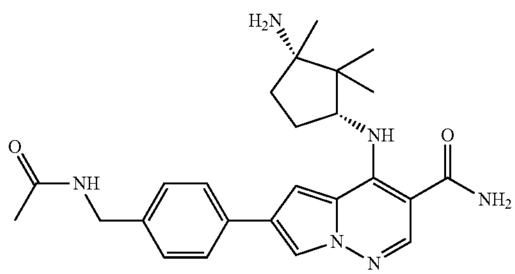 [SMILES: CC(=O)NCc1ccc(-c2cc3c(N[C@@H]4CC[C@](C)(N)C4(C)C)c(C(N)=O)cnn3c2)cc1] | 1.24 (E) | 449.09 |
| 265 | 6-(3-(acetamidomethyl)phenyl)-4-(((1R,3S)-3-amino-2,2,3-trimethylcyclopentyl)amino)pyrrolo[1,2-b]pyridazine-3-carboxamide | 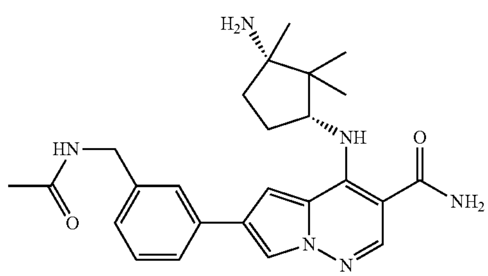 [SMILES: CC(=O)NCc1cccc(-c2cc3c(N[C@@H]4CC[C@](C)(N)C4(C)C)c(C(N)=O)cnn3c2)c1] | 1.3 (E) | 449.08 |
| 266 | 4-(((1R,3S)-3-amino-2,2,3-trimethylcyclopentyl)amino)-6-(4-(dimethylcarbamoyl)phenyl)pyrrolo[1,2-b]pyridazine-3-carboxamide | 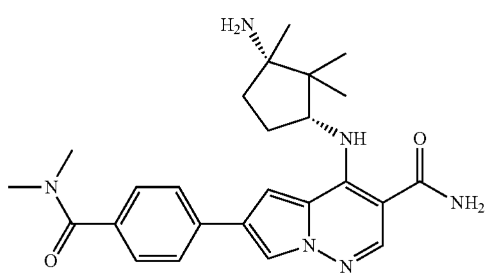 [SMILES: CN(C)C(=O)c1ccc(-c2cc3c(N[C@@H]4CC[C@](C)(N)C4(C)C)c(C(N)=O)cnn3c2)cc1] | 1.32 (E) | 449.09 |

-continued

| Ex# | Name | Structure | HPLC Rt, min (Condition) | LCMS m/z (Condition) |
|---|---|---|---|---|
| 267 | 4-(((1R,3S)-3-amino-2,2,3-trimethylcyclopentyl)amino)-6-(4-methylphenyl)pyrrolo[1,2-b]pyridazine-3-carboxamide | 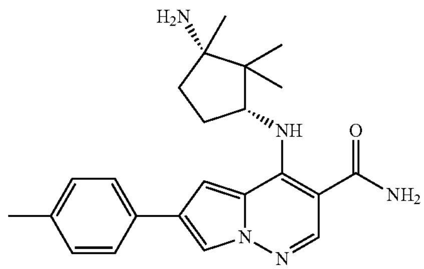 [SMILES: Cc1ccc(-c2cc3c(N[C@@H]4CC[C@](C)(N)C4(C)C)c(C(N)=O)cnn3c2)cc1] | 1.83 (E) | 392.1 |
| 268 | 4-(((1R,3S)-3-amino-2,2,3-trimethylcyclopentyl)amino)-6-(4-((methylsulfonyl)amino)phenyl)pyrrolo[1,2-b]pyridazine-3-carboxamide | 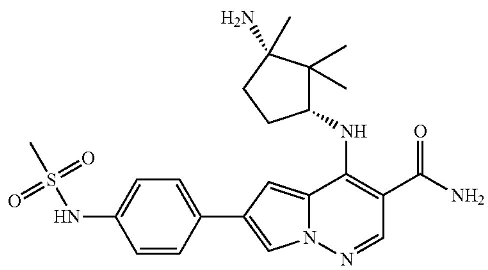 [SMILES: CC1(C)[C@H](Nc2c(C(N)=O)cnn3cc(-c4ccc(NS(C)(=O)=O)cc4)cc23)CC[C@]1(C)N] | 1.29 (E) | 471.03 |
| 269 | 4-(((1R,3S)-3-amino-2,2,3-trimethylcyclopentyl)amino)-6-(3-methylphenyl)pyrrolo[1,2-b]pyridazine-3-carboxamide | 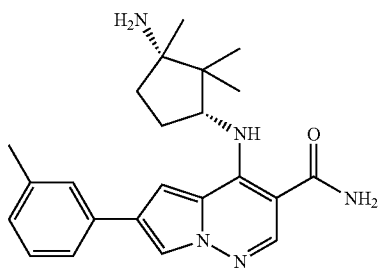 [SMILES: Cc1cccc(-c2cc3c(N[C@@H]4CC[C@](C)(N)C4(C)C)c(C(N)=O)cnn3c2)c1] | 1.87 (E) | 392.13 |
| 270 | 4-(((1R,3S)-3-amino-2,2,3-trimethylcyclopentyl)amino)-6-(6-quinolinyl)pyrrolo[1,2-b]pyridazine-3-carboxamide | 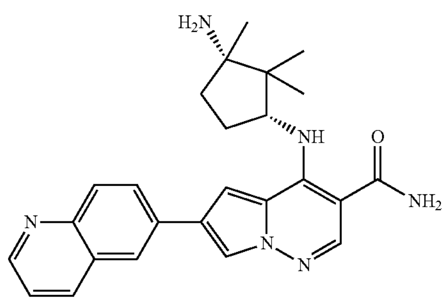 [SMILES: CC1(C)[C@H](Nc2c(C(N)=O)cnn3cc(-c4ccc5ncccc5c4)cc23)CC[C@]1(C)N] | 1.48 (E) | 429.09 |
| 271 | 4-(((1R,3S)-3-amino-2,2,3-trimethylcyclopentyl)amino)-6-(4-(hydroxymethyl)phenyl)pyrrolo[1,2-b]pyridazine-3-carboxamide | 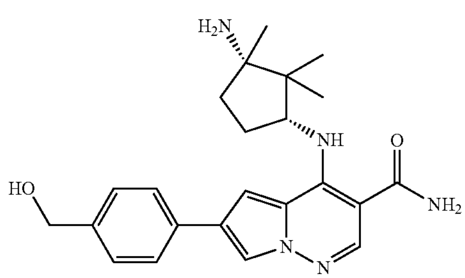 | 1.25 (E) | 408.11 |

-continued

| Ex# | Name | Structure | HPLC Rt, min (Condition) | LCMS m/z (Condition) |
|---|---|---|---|---|
| 272 | 4-(((1R,3S)-3-amino-2,2,3-trimethylcyclopentyl)amino)-6-(5-quinolinyl)pyrrolo[1,2-b]pyridazine-3-carboxamide | 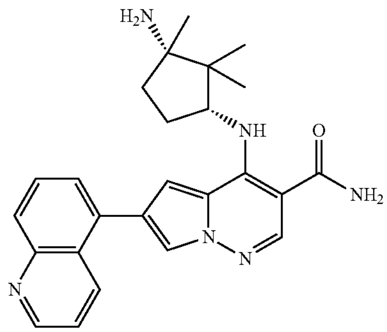 [SMILES: CC1(C)[C@H](Nc2c(C(N)=O)cnn3cc(-c4cccc5ncccc45)cc23)CC[C@]1(C)N] | 1.45 (E) | 429.08 |
| 273 | 4-(((1R,3S)-3-amino-2,2,3-trimethylcyclopentyl)amino)-6-(3-((methylsulfonyl)amino)phenyl)pyrrolo[1,2-b]pyridazine-3-carboxamide | 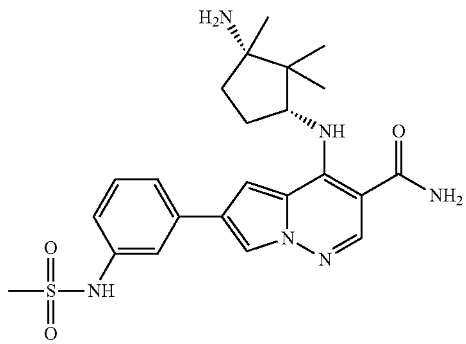 [SMILES: CC1(C)[C@H](Nc2c(C(N)=O)cnn3cc(-c4cccc(NS(C)(=O)=O)c4)cc23)CC[C@]1(C)N] | 1.45 (E) | 471.02 |
| 274 | 4-(((1R,3S)-3-amino-2,2,3-trimethylcyclopentyl)amino)-6-(2-chlorophenyl)pyrrolo[1,2-b]pyridazine-3-carboxamide | 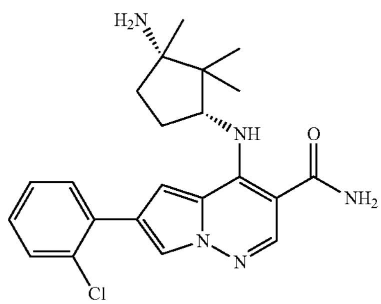 [SMILES: CC1(C)[C@H](Nc2c(C(N)=O)cnn3cc(-c4ccccc4Cl)cc23)CC[C@]1(C)N] | 1.86 (E) | 412.04 |
| 275 | 4-(((1R,3S)-3-amino-2,2,3-trimethylcyclopentyl)amino)-6-(6-ethoxy-3-pyridinyl)pyrrolo[1,2-b]pyridazine-3-carboxamide | 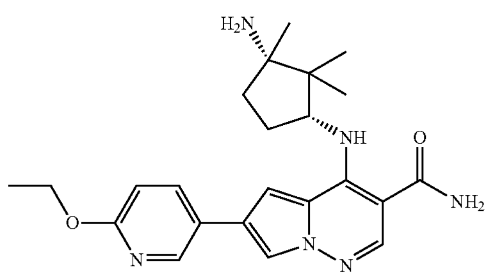 [SMILES: CCOc1ccc(-c2cc3c(N[C@@H]4CC[C@](C)(N)C4(C)C)c(C(N)=O)cnn3c2)cn1] | 1.79 (Q) | 423.2 |
| 276 | 5-(4-(((1R,3S)-3-amino-2,2,3-trimethylcyclopentyl)amino)-3-carbamoylpyrrolo[1,2-b]pyridazin-6-yl)nicotinic acid | 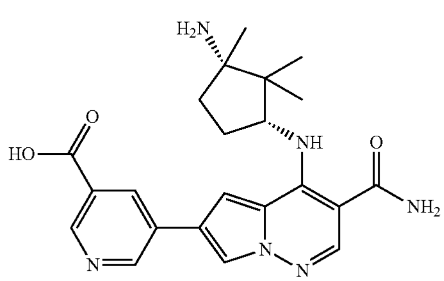 [SMILES: CC1(C)[C@H](Nc2c(C(N)=O)cnn3cc(-c4cncc(C(=O)O)c4)cc23)CC[C@]1(C)N] | 1.01 (Q) | 423.17 |

-continued

| Ex# | Name | Structure | HPLC Rt, min (Condition) | LCMS m/z (Condition) |
|---|---|---|---|---|
| 277 | 4-(((1R,3S)-3-amino-2,2,3-trimethylcyclopentyl)amino)-6-(2-methyl-3-pyridinyl)pyrrolo[1,2-b]pyridazine-3-carboxamide | 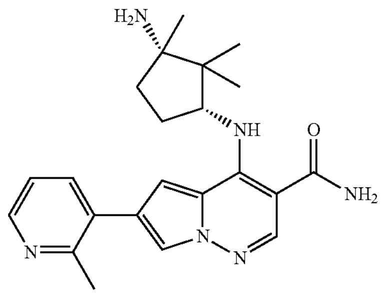 [SMILES: Cc1ncccc1-c1cc2c(N[C@@H]3CC[C@](C)(N)C3(C)C)c(C(N)=O)cnn2c1] | 1.42 (Q) | 393.22 |
| 278 | 4-(((1R,3S)-3-amino-2,2,3-trimethylcyclopentyl)amino)-6-(2-methoxy-5-pyrimidinyl)pyrrolo[1,2-b]pyridazine-3-carboxamide | 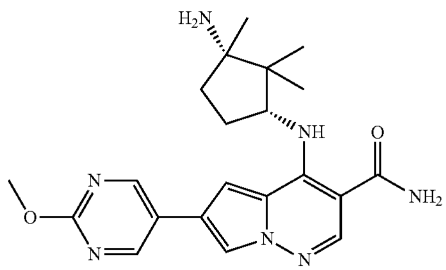 [SMILES: COc1ncc(-c2cc3c(N[C@@H]4CC[C@](C)(N)C4(C)C)c(C(N)=O)cnn3c2)cn1] | 1.43 (Q) | 410.08 |
| 279 | 4-(((1R,3S)-3-amino-2,2,3-trimethylcyclopentyl)amino)-6-(3-quinolinyl)pyrrolo[1,2-b]pyridazine-3-carboxamide | 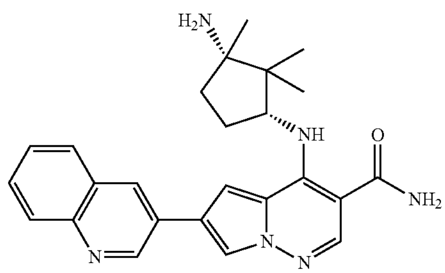 [SMILES: CC1(C)[C@H](Nc2c(C(N)=O)cnn3cc(-c4cnc5ccccc5c4)cc23)CC[C@]1(C)N] | 1.73 (Q) | 429.19 |
| 280 | 4-(((1R,3S)-3-amino-2,2,3-trimethylcyclopentyl)amino)-6-(2,6-difluoro-3-pyridinyl)pyrrolo[1,2-b]pyridazine-3-carboxamide | 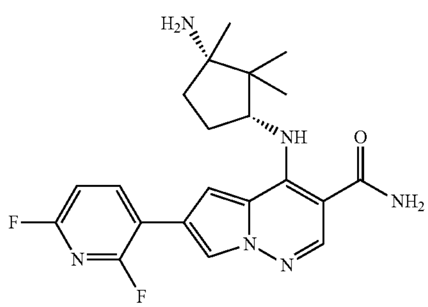 [SMILES: CC1(C)[C@H](Nc2c(C(N)=O)cnn3cc(-c4ccc(F)nc4F)cc23)CC[C@]1(C)N] | 1.61 (Q) | 415.05 |
| 281 | 4-(((1R,3S)-3-amino-2,2,3-trimethylcyclopentyl)amino)-6-(6-(benzyloxy)-3-pyridinyl)pyrrolo[1,2-b]pyridazine-3-carboxamide | 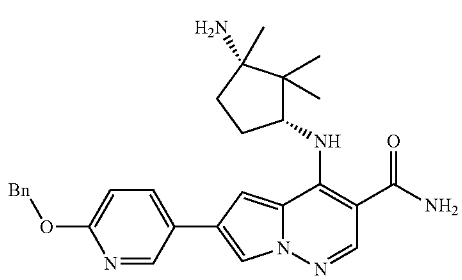 [SMILES: CC1(C)[C@H](Nc2c(C(N)=O)cnn3cc(-c4ccc(OCc5ccccc5)nc4)cc23)CC[C@]1(C)N] | 2.09 (Q) | 485.07 |

-continued

| Ex# | Name | Structure | HPLC Rt, min (Condition) | LCMS m/z (Condition) |
|---|---|---|---|---|
| 282 | 4-(((1R,3S)-3-amino-2,2,3-trimethylcyclopentyl)amino)-6-(6-methyl-3-pyridinyl)pyrrolo[1,2-b]pyridazine-3-carboxamide | 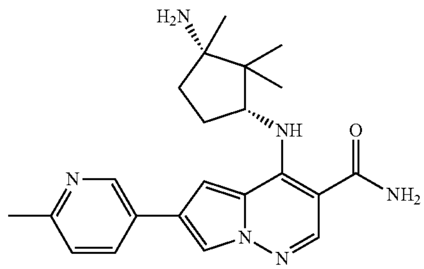 [SMILES: Cc1ccc(-c2cc3c(N[C@@H]4CC[C@](C)(N)C4(C)C)c(C(N)=O)cnn3c2)cn1] | 1.33 (Q) | 393.12 |
| 283 | 4-(((1R,3S)-3-amino-2,2,3-trimethylcyclopentyl)amino)-6-(6-fluoro-3-pyridinyl)pyrrolo[1,2-b]pyridazine-3-carboxamide | 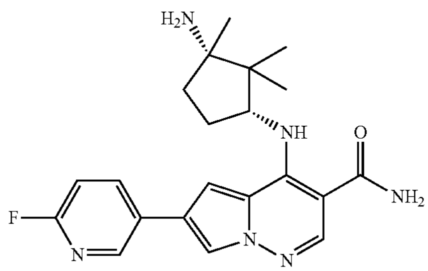 [SMILES: CC1(C)[C@H](Nc2c(C(N)=O)cnn3cc(-c4ccc(F)nc4)cc23)CC[C@]1(C)N] | 1.39 (Q) | 397.07 |
| 284 | 4-(((1R,3S)-3-amino-2,2,3-trimethylcyclopentyl)amino)-6-(1-methyl-3-(trifluoromethyl)-1H-pyrazol-5-yl)pyrrolo[1,2-b]pyridazine-3-carboxamide | 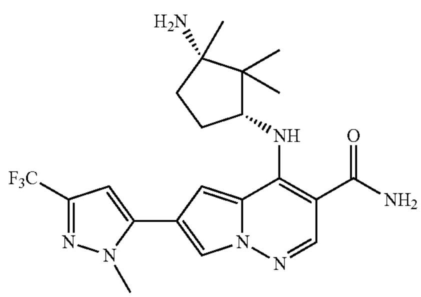 [SMILES: Cn1nc(C(F)(F)F)cc1-c1cc2c(N[C@@H]3CC[C@](C)(N)C3(C)C)c(C(N)=O)cnn2c1] | 1.64 (C) | 450.2 |
| 285 | 4-(((1R,3S)-3-amino-2,2,3-trimethylcyclopentyl)amino)-6-(4-(4-morpholinylmethyl)phenyl)pyrrolo[1,2-b]pyridazine-3-carboxamide | 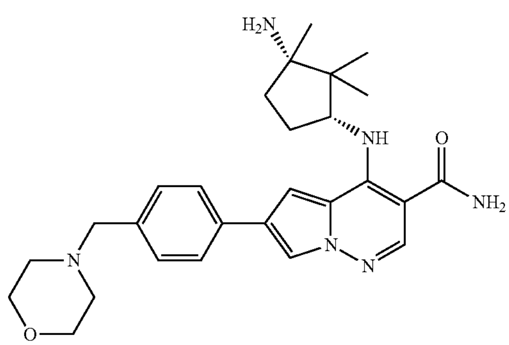 [SMILES: CC1(C)[C@H](Nc2c(C(N)=O)cnn3cc(-c4ccc(CN5CCOCC5)cc4)cc23)CC[C@]1(C)N] | 1.34 (C) | 477.25 |
| 286 | 4-(((1R,3S)-3-amino-2,2,3-trimethylcyclopentyl)amino)-6-(5-methoxy-3-pyridinyl)pyrrolo[1,2-b]pyridazine-3-carboxamide | 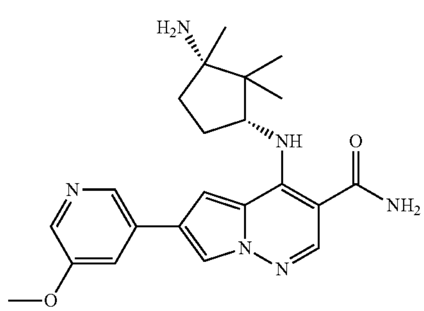 [SMILES: COc1cncc(-c2cc3c(N[C@@H]4CC[C@](C)(N)C4(C)C)c(C(N)=O)cnn3c2)c1] | 2.42 (B) | 409.24 |

-continued

| Ex# | Name | Structure | HPLC Rt, min (Condition) | LCMS m/z (Condition) |
|---|---|---|---|---|
| 287 | 4-(((1R,3S)-3-amino-2,2,3-trimethylcyclopentyl)amino)-6-(5-methyl-1-phenyl-1H-pyrazol-4-yl)pyrrolo[1,2-b]pyridazine-3-carboxamide | 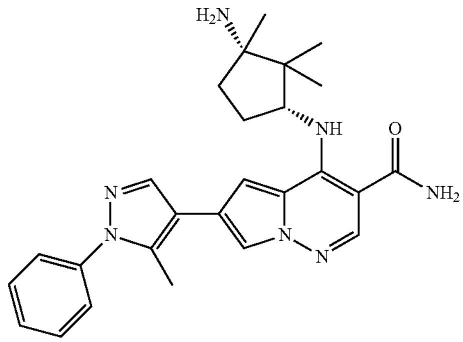 [SMILES: Cc1c(-c2cc3c(N[C@@H]4CC[C@](C)(N)C4(C)C)c(C(N)=O)cnn3c2)cnn1-c1ccccc1] | 1.80 (C) | 458.22 |
| 288 | 4-(((1R,3S)-3-amino-2,2,3-trimethylcyclopentyl)amino)-6-(5-fluoro-2-methoxy-4-pyridinyl)pyrrolo[1,2-b]pyridazine-3-carboxamide | 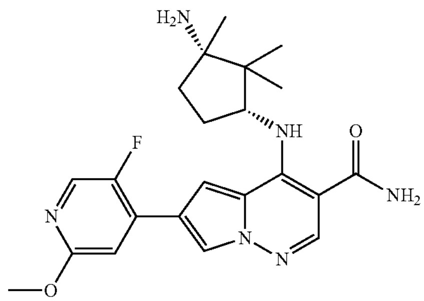 [SMILES: COc1cc(-c2cc3c(N[C@@H]4CC[C@](C)(N)C4(C)C)c(C(N)=O)cnn3c2)c(F)cn1] | 3.17 (O) | 427.22 |
| 289 | 4-(((1R,3S)-3-amino-2,2,3-trimethylcyclopentyl)amino)-6-(3-methyl-4-pyridinyl)pyrrolo[1,2-b]pyridazine-3-carboxamide | 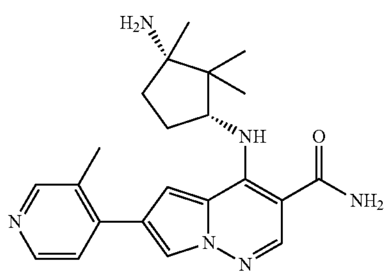 [SMILES: Cc1cnccc1-c1cc2c(N[C@@H]3CC[C@](C)(N)C3(C)C)c(C(N)=O)cnn2c1] | 2.06 (O) | 393.2 |
| 290 | 4-(((1R,3S)-3-amino-2,2,3-trimethylcyclopentyl)amino)-6-(4-(cyclopentylcarbamoyl)phenyl)pyrrolo[1,2-b]pyridazine-3-carboxamide | 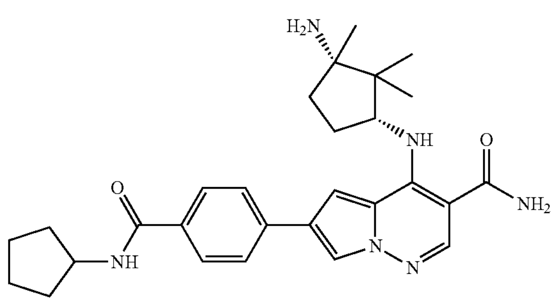 [SMILES: CC1(C)[C@H](Nc2c(C(N)=O)cnn3cc(-c4ccc(C(=O)NC5CCCC5)cc4)cc23)CC[C@]1(C)N] | 3.14 (O) | 489.35 |

| Ex# | Name | Structure | HPLC Rt, min (Condition) | LCMS m/z (Condition) |
|---|---|---|---|---|
| 291 | 4-(((1R,3S)-3-amino-2,2,3-trimethylcyclopentyl)amino)-6-(4-(butylcarbamoyl)phenyl)pyrrolo[1,2-b]pyridazine-3-carboxamide | 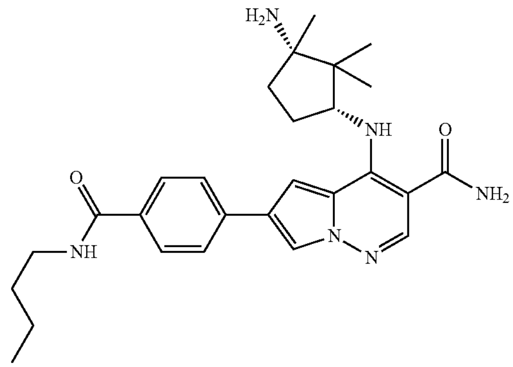 [SMILES: CCCCNC(=O)c1ccc(-c2cc3c(N[C@@H]4CC[C@](C)(N)C4(C)C)c(C(N)=O)cnn3c2)cc1] | 3.17 (O) | 477.33 |
| 292 | 4-(((1R,3S)-3-amino-2,2,3-trimethylcyclopentyl)amino)-6-(5-isoquinolinyl)pyrrolo[1,2-b]pyridazine-3-carboxamide | 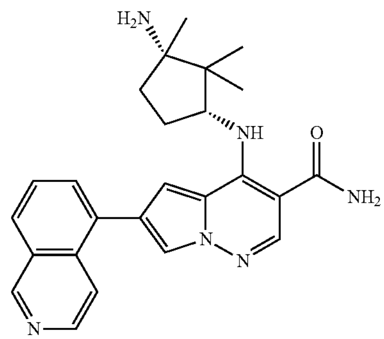 [SMILES: CC1(C)[C@H](Nc2c(C(N)=O)cnn3cc(-c4cccc5cnccc45)cc23)CC[C@]1(C)N] | 2.33 (B) | 429.13 |

Examples 293 and 294

Examples 293 and 294 in the table below were prepared from 6-bromo-4-((1R,3R)-3-hydroxy-2,2,3-trimethylcyclopentylamino)pyrrolo[1,2-b]-pyridazine-3-carboxamide (Intermediate 51) and the appropriate commercially available boronic acid using a similar procedure described for the preparation of Example 28.

| Ex # | Name | Structure | HPLC Rt, min (Condition) | LCMS m/z (Condition) |
|---|---|---|---|---|
| 293 | 4-(((1R,3R)-3-hydroxy-2,2,3-trimethylcyclopentyl)amino)-6-phenylpyrrolo[1,2-b]pyridazine-3-carboxamide | 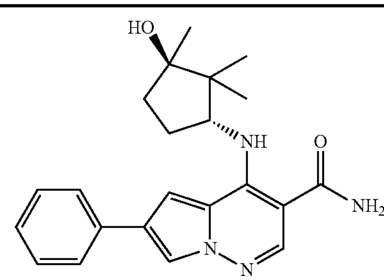 | 3.79 (B) | 379.14 |
| 294 | 4-(((1R,3R)-3-hydroxy-2,2,3-trimethylcyclopentyl)amino)-6-(2-methylphenyl)pyrrolo[1,2-b]pyridazine-3-carboxamide | 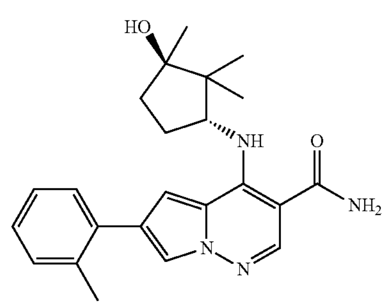 [SMILES: Cc1ccccc1-c1cc2c(N[C@@H]3CC[C@@](C)(O)C3(C)C)c(C(N)=O)cnn2c1] | 3.87 (B) | 393.18 |

Examples 295-299

Examples 295-299 in the table below were prepared from 6-bromo-4-((3,5-dihydroxyadamantan-1-yl)amino)pyrrolo[1,2-b]pyridazine-3-carboxamide (Intermediate 49) and the appropriate commercially available boronic acid or boronic ester using a similar procedure as described for the preparation of Example 28.

| Ex # | Name | Structure | HPLC Rt, min (Condition) | LCMS m/z (Condition) |
|---|---|---|---|---|
| 295 | 4-((3,5-dihydroxyadamantan-1-yl)amino)-6-phenylpyrrolo[1,2-b]pyridazine-3-carboxamide | 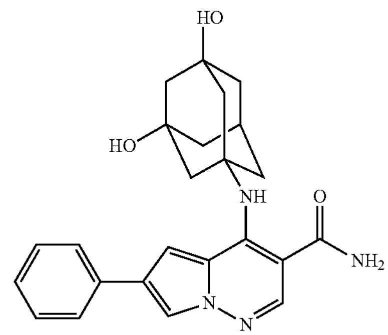 [SMILES: NC(=O)c1cnn2cc(-c3ccccc3)cc2c1NC12CC3CC(O)(CC(O)(C3)C1)C2] | 1.73 (C) | 419.1 |
| 296 | 4-((3,5-dihydroxyadamantan-1-yl)amino)-6-(6-fluoro-3-pyridinyl)pyrrolo[1,2-b]pyridazine-3-carboxamide | 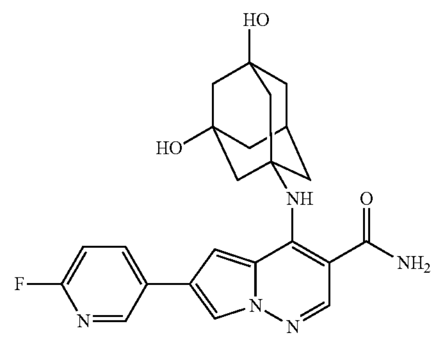 [SMILES: NC(=O)c1cnn2cc(-c3ccc(F)nc3)cc2c1NC12CC3CC(O)(CC(O)(C3)C1)C2] | 3.18 (B) | 438.12 |
| 297 | 4-((3,5-dihydroxyadamantan-1-yl)amino)-6-(4-pyridinyl)pyrrolo[1,2-b]pyridazine-3-carboxamide | 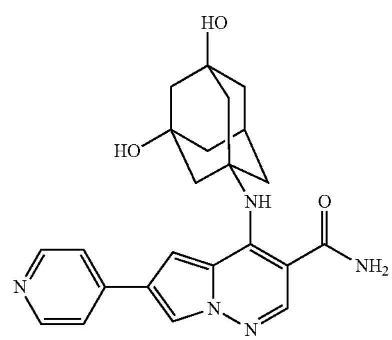 [SMILES: NC(=O)c1cnn2cc(-c3ccncc3)cc2c1NC12CC3CC(O)(CC(O)(C3)C1)C2] | 2.36 (B) | 420.18 |
| 298 | 4-((3,5-dihydroxyadamantan-1-yl)amino)-6-(4-fluorophenyl)pyrrolo[1,2-b]pyridazine-3-carboxamide | 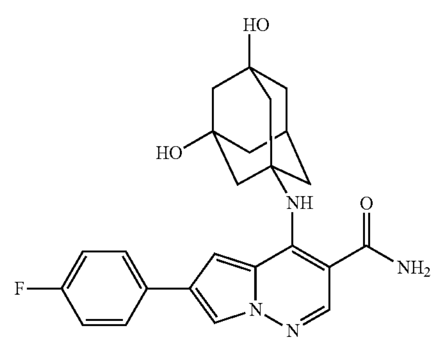 [SMILES: NC(=O)c1cnn2cc(-c3ccc(F)cc3)cc2c1NC12CC3CC(O)(CC(O)(C3)C1)C2] | 3.57 (B) | 437.11 |

-continued

| Ex # | Name | Structure | HPLC Rt, min (Condition) | LCMS m/z (Condition) |
|---|---|---|---|---|
| 299 | 6-(1,3-benzothiazol-5-yl)-4-((3,5-dihydroxyadamantan-1-yl)amino)pyrrolo[1,2-b]pyridazine-3-carboxamide | 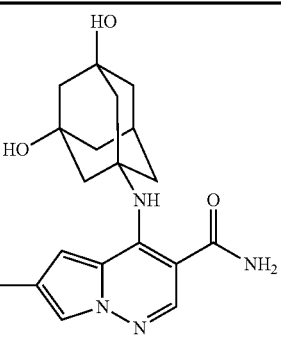 | 3.50 (B) | 476.11 |

Examples 300 to 309

Examples 300 to 309 in the table below were prepared from (R)-6-bromo-4-(2,2-dimethylcyclopentylamino)pyrrolo[1,2-b]pyridazine-3-carboxamide (Intermediate 50) and the appropriate commercially available boronic acid or ester using a similar procedure as described for the preparation of Example 28.

| Ex # | Name | Structure | HPLC Rt, min (Condition) | LCMS m/z (Condition) |
|---|---|---|---|---|
| 300 | 4-(((1R)-2,2-dimethylcyclopentyl)amino)-6-(3-pyridinyl)pyrrolo[1,2-b]pyridazine-3-carboxamide | 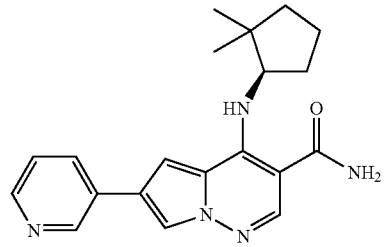 [SMILES: CC1(C)CCC[C@H]1Nc1c(C(N)=O)cnn2cc(-c3cccnc3)cc12] | 2.89 (O) | 350.13 |
| 301 | 4-(((1R)-2,2-dimethylcyclopentyl)amino)-6-(4-pyridinyl)pyrrolo[1,2-b]pyridazine-3-carboxamide | 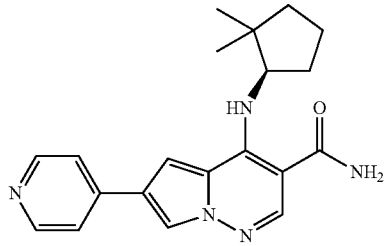 [SMILES: CC1(C)CCC[C@H]1Nc1c(C(N)=O)cnn2cc(-c3ccncc3)cc12] | 2.54 (O) | 350.13 |
| 302 | 6-(4-cyanophenyl)-4-(((1R)-2,2-dimethylcyclopentyl)amino)pyrrolo[1,2-b]pyridazine-3-carboxamide | 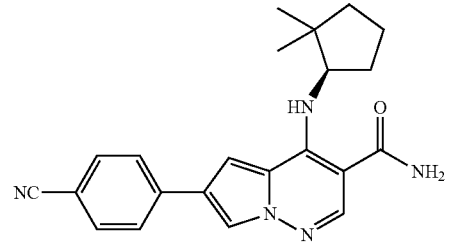 [SMILES: CC1(C)CCC[C@H]1Nc1c(C(N)=O)cnn2cc(-c3ccc(C#N)cc3)cc12] | 9.58 (L) | 374.11 |

-continued

| Ex # | Name | Structure | HPLC Rt, min (Condition) | LCMS m/z (Condition) |
|---|---|---|---|---|
| 303 | 6-(3-cyanophenyl)-4-(((1R)-2,2-dimethylcyclopentyl)amino)pyrrolo[1,2-b]pyridazine-3-carboxamide | 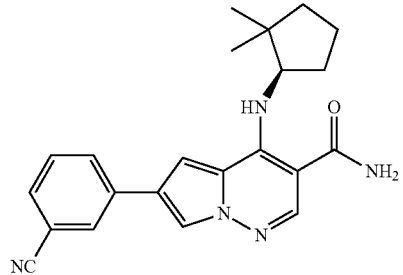 [SMILES: CC1(C)CCC[C@H]1Nc1c(C(N)=O)cnn2cc(-c3cccc(C#N)c3)cc12] | 9.60 (L) | 374.13 |
| 304 | 4-(((1R)-2,2-dimethylcyclopentyl)amino)-6-phenylpyrrolo[1,2-b]pyridazine-3-carboxamide | 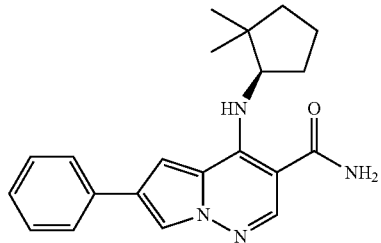 | 9.99 (L) | 349.19 |
| 305 | 4-(((1R)-2,2-dimethylcyclopentyl)amino)-6-(2-fluorophenyl)pyrrolo[1,2-b]pyridazine-3-carboxamide | 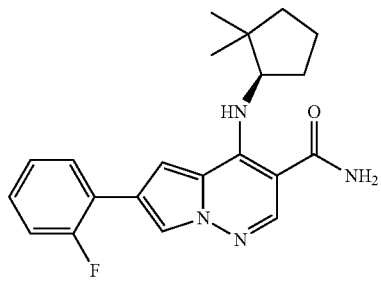 [SMILES: CC1(C)CCC[C@H]1Nc1c(C(N)=O)cnn2cc(-c3ccccc3F)cc12] | 10.11 (L) | 367.13 |
| 306 | 4-(((1R)-2,2-dimethylcyclopentyl)amino)-6-(1-methyl-1H-pyrazol-5-yl)pyrrolo[1,2-b]pyridazine-3-carboxamide | 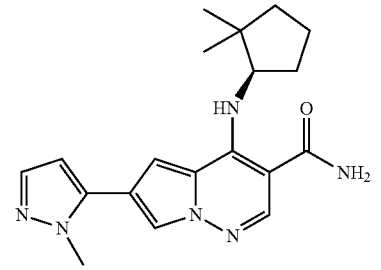 [SMILES: Cn1nccc1-c1cc2c(N[C@@H]3CCCC3(C)C)c(C(N)=O)cnn2c1] | 2.03 (C) | 353.12 |
| 307 | 6-(3-acetamidophenyl)-4-(((1R)-2,2-dimethylcyclopentyl)amino)pyrrolo[1,2-b]pyridazine-3-carboxamide | 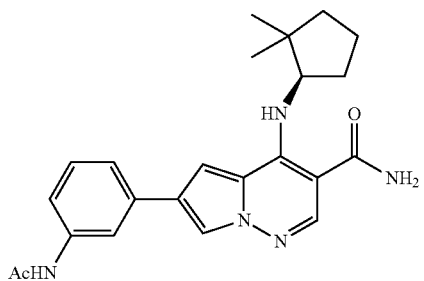 [SMILES: CC(=O)Nc1cccc(-c2cc3c(N[C@@H]4CCCC4(C)C)c(C(N)=O)cnn3c2)c1] | 2.13 (C) | 406.08 |

| Ex # | Name | Structure | HPLC Rt, min (Condition) | LCMS m/z (Condition) |
|---|---|---|---|---|
| 308 | 6-(4-acetamidophenyl)-4-(((1R)-2,2-dimethylcyclopentyl)amino)pyrrolo[1,2-b]pyridazine-3-carboxamide | 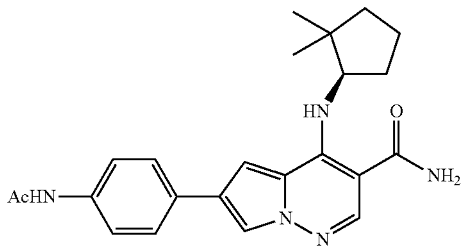 [SMILES: CC(=O)Nc1ccc(-c2cc3c(N[C@@H]4CCCC4(C)C)c(C(N)=O)cnn3c2)cc1] | 2.06 (C) | 406.09 |
| 309 | 6-(4-carbamoylphenyl)-4-(((1R)-2,2-dimethylcyclopentyl)amino)pyrrolo[1,2-b]pyridazine-3-carboxamide | 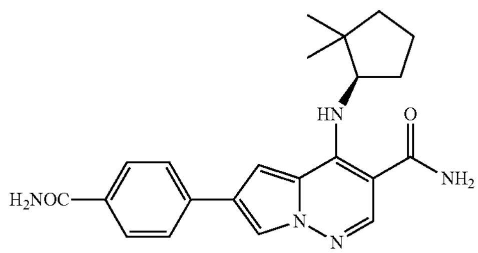 [SMILES: CC1(C)CCC[C@H]1Nc1c(C(N)=O)cnn2cc(-c3ccc(C(N)=O)cc3)cc12] | 1.86 (C) | 392.07 |

Intermediate 52

6-cyano-4-(((1R,3R)-3-hydroxy-2,2,3-trimethylcyclopentyl)amino)pyrrolo[1,2-b]-pyridazine-3-carboxamide

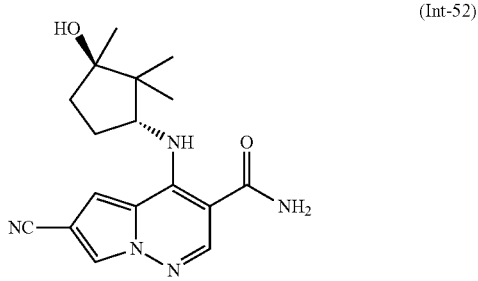 [SMILES: CC1(C)[C@H](Nc2c(C(N)=O)cnn3cc(C#N)cc23)CC[C@@]1(C)O]

(Int-52)

A mixture of 6-bromo-4-((1R,3R)-3-hydroxy-2,2,3-trimethylcyclopentylamino)pyrrolo[1,2-b]-pyridazine-3-carboxamide (Intermediate 51, 18 mg, 0.047 mmol), Zn(CN)$_2$ (3 mg, 0.025 mmol), Pd(COCF$_3$)$_2$ 1.6 mg, 0.005 mmol), 1,1'-binaphthyl-2-yldi-tert-butylphosphine (1.9 mg, 0.005 mmol), and zinc (0.62 mg, 0.09 mmol) in DMA (0.2 mL) was purged with N$_2$ then heated at 90° C. for 8 h. The product was isolated via reverse-phase preparative HPLC to afford the title compound (1.1 mg) as a white solid. LCMS: 328.07 (M+H)$^+$; HPLC (condition B): retention time=3.15 min. $^1$H NMR (MeOD, 400 MHz) δ 8.24 (s, 1H), 8.07 (d, J=1.8 Hz, 1H), 7.48 (d, J=1.8 Hz, 1H), 4.66 (t, J=9.0 Hz, 1H), 2.35 (m, 1H), 2.01 (m, 1H), 1.78 (m, 1H), 1.59 (m, 1H), 1.24 (s, 3H), 1.00 (s, 3H), 0.95 (s, 3H).

Examples 310 and 311

4-(4-(((1R,3S)-3-amino-2,2,3-trimethylcyclopentyl)amino)-3-carbamoylpyrrolo[1,2-b]-pyridazin-6-yl)-1H-pyrrole-2-carboxylic acid (Example 310) and methyl 4-(4-(((1R,3S)-3-amino-2,2,3-trimethylcyclopentyl)amino)-3-carbamoylpyrrolo[1,2-b]-pyridazin-6-yl)-1H-pyrrole-2-carboxylate (Example 311)

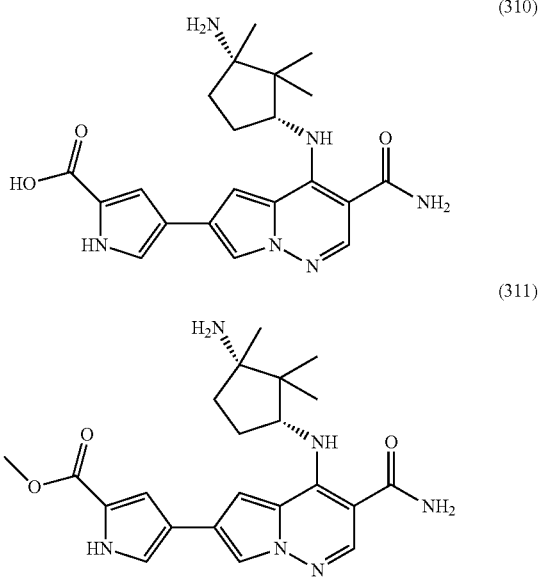

A mixture of 4-((1R,3S)-3-amino-2,2,3-trimethylcyclopentylamino)-6-bromopyrrolo[1,2-b]-pyridazine-3-carboxamide (Intermediate 48, 15 mg, 0.039 mmol), 1-tert-butyl 2-methyl 4-(4,4,5,5-tetramethyl-1,3,2-dioxaborolan-2-yl)-1H-pyrrole-1,2-dicarboxylate (14 mg, 0.039 mmol), 2M K₃PO₄ (0.059 mL, 0.118 mmol) and PdCl₂(dppf)CH₂Cl₂ (1.4 mg, 1.9 μmol) in DMF (0.5 mL) was purged with N₂ and heated at 140° C. for 0.5 h. After cooling to rt, the reaction mixture was directly subjected to purification by reverse-phase preparative HPLC to afford 2 major products determined to be the TFA salt of methyl 4-(4-(((1R,3S)-3-amino-2,2,3-trimethylcyclopentyl)amino)-3-carbamoylpyrrolo[1,2-b]pyridazin-6-yl)-1H-pyrrole-2-carboxylate (Example 311, 1.5 mg, 7% yield). LCMS: 425.15 (M+H)⁺; HPLC (Condition B): retention time=3.01 min. ¹H NMR (MeOD, 400 MHz) δ 8.16 (s, 1H), 7.81 (d, J=1.5 Hz, 1H), 7.33 (d, J=1.5 Hz, 1H), 7.17 (m, 1H), 7.05 (d, J=1.5 Hz, 1H), 4.70 (t, J=9.3 Hz, 1H), 3.88 (m, 1H), 2.49 (m, 1H), 2.09 (m, 2H), 1.86 (m, 1H), 1.52 (s, 3H), 1.20 (s, 3H), 1.09 (s, 3H) and 4-(4-(((1R,3S)-3-amino-2,2,3-trimethylcyclopentyl)amino)-3-carbamoylpyrrolo[1,2-b]pyridazin-6-yl)-1H-pyrrole-2-carboxylic acid, TFA salt (Example 310, 1.8 mg, 8% yield). LCMS: 411.11 (M+H)⁺; HPLC (conditions B)=retention time=2.77 min. ¹H NMR (MeOD, 400 MHz) δ 8.15 (s, 1H), 7.81 (d, J=1.5 Hz, 1H), 7.32 (m, 1H), 7.16 (m, 1H), 7.05 (d, J=1.5 Hz, 1H), 4.70 (t, J=9.0 Hz, 1H), 2.49 (m, 1H), 2.11 (m, 2H), 1.87 (m, 1H), 1.52 (s, 3H), 1.20 (s, 3H), 1.09 (s, 3H).

Example 312

4-(((1R,3S)-3-amino-2,2,3-trimethylcyclopentyl)amino)-6-(3-oxo-4-morpholinyl)pyrrolo[1,2-b]pyridazine-3-carboxamide

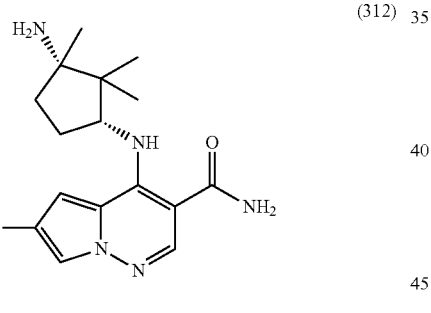

(312)

A mixture of 4-((1R,3S)-3-amino-2,2,3-trimethylcyclopentylamino)-6-bromopyrrolo[1,2-b]-pyridazine-3-carboxamide (Intermediate 48, 20 mg, 0.053 mmol), morpholine-3-one (6.4 mg, 0.063 mmol), K₂CO₃ (14.5 mg, 0.11 mmol) in dioxane (1 mL) was added CuI (1 mg, 0.005 mmol) and N1,N2-dimethylethane-1,2-diamine (0.93 mg, 0.011 mmol) and the reaction mixture was sealed and heated at 110° C. for 18 h. After cooling to rt, the reaction mixture was subjected to purification via reverse-phase preparative HPLC to afford the TFA salt of the title compound (1.5 mg, 5% yield) as a yellow solid. LCMS: 401.16 (M+H)⁺; HPLC (conditions B): retention time=2.46 min. ¹H NMR (MeOD, 400 MHz) δ 8.21 (s, 1H), 7.96 (d, J=1.8 Hz, 1H), 7.38 (d, J=1.8 Hz, 1H), 4.64 (t, J=8.8 Hz, 1H), 4.33 (s, 2H), 4.10 (m, 2H), 3.91 (m, 2H), 2.44 (m, 1H), 2.16 (m, 1H), 2.03 (m, 1H), 1.83 (m, 1H), 1.49 (s, 3H), 1.18 (s, 3H), 1.09 (s, 3H).

Example 313

4-(((1R)-2,2-dimethylcyclopentyl)amino)-6-(2-oxo-1-pyrrolidinyl)pyrrolo[1,2-b]-pyridazine-3-carboxamide

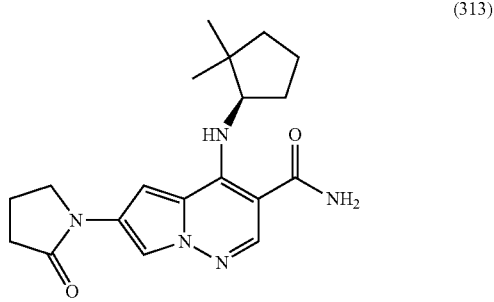 [SMILES: CC1(C)CCC[C@H]1Nc1c(C(N)=O)cnn2cc(N3CCCC3=O)cc12]

(313)

4-(((1R)-2,2-dimethylcyclopentyl)amino)-6-(2-oxo-1-pyrrolidinyl) pyrrolo[1,2-b]pyridazine-3-carboxamide was prepared from Intermediate 50 and pyrrolidin-2-one using a similar procedure as described for the preparation of Example 312 LCMS: 356.18 (M+H)⁺; HPLC (condition L): retention time=7.44 min.

Example 314

(+/−)-4-(((1S,2S)-2-hydroxy-2-methylcyclohexyl)amino)-6-phenylpyrrolo[1,2-b]-pyridazine-3-carboxamide

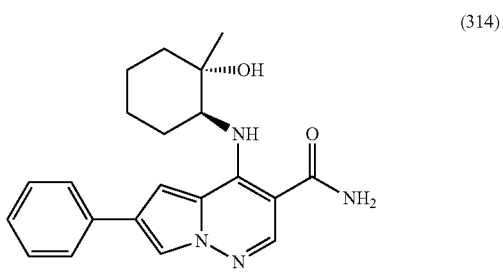 [SMILES: C[C@]1(O)CCCC[C@@H]1Nc1c(C(N)=O)cnn2cc(-c3ccccc3)cc12]

(314)

Step 1: (±)-benzyl (1S,2S)-2-hydroxy-2-methylcyclohexylcarbamate

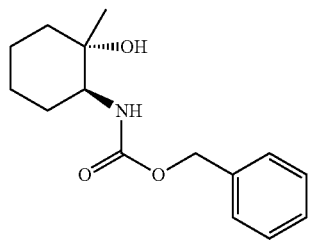 [SMILES: C[C@]1(O)CCCC[C@@H]1NC(=O)OCc1ccccc1]

Benzyl 2-oxocyclohexylcarbamate (173 mg, 0.7 mmol) in THF (3 mL) was cooled to −78° C. and added MeMgBr in ether (0.7 mL, 2.1 mmol) dropwise via syringe. The ice bath was removed and the reaction was allowed to stir at rt for 3 h. The reaction was quenched with sat. aqueous NH₄Cl (1 mL) and partitioned between ethyl acetate and water. The layers were separated and the organic layer washed with brine, dried (Na₂SO₄), filtered and concentrated. The product was subjected to flash chromatography on silica gel (10% to 70% ethyl acetate/hexanes) to afford the title compound (81 mg, 88% yield) as a single diastereomer. This material was used as is in the next transformation.

Step 2: (±)-(1S,2S)-2-amino-1-methylcyclohexanol hydrobromide

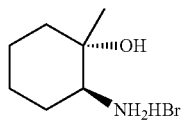

To (±)-Benzyl (1S,2S)-2-hydroxy-2-methylcyclohexylcarbamate (81.4 mg, 0.309 mmol) was added HBr in AcOH, 33% (1 mL, 6.1 mmol) and the resulting mixture was stirred at rt under N₂ for 2 h. The solvents were removed and the crude residue concentrated with EtOH (2×) and dried on high vacuum overnight to afford an orange low-melting solid which was used directly in the next step.

Step 3: (±)-6-bromo-4-((1S,2S)-2-hydroxy-2-methylcyclohexylamino)pyrrolo[1,2-b]pyridazine-3-carboxamide

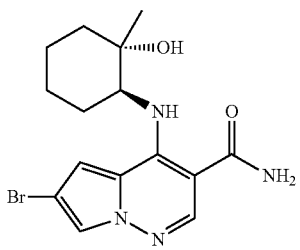 [SMILES: C[C@]1(O)CCCC[C@@H]1Nc1c(C(N)=O)cnn2cc(Br)cc12]

A mixture of Preparation 5 (41.8 mg, 0.152 mmol) and (±)-(1S,2S)-2-amino-1-methylcyclohexanol hydrobromide (32 mg, 0.152 mmol) in DMF (0.4 mL) was added DIPEA (0.08 mL, 0.46 mmol) and the mixture was heated to 90° C. for 18 h. The reaction was cooled to rt and added water (3 mL) then stirred rapidly for 3 h and filtered. The solids were purified on silica gel (100% heptane to 50% ethyl acetate/heptane to 100% ethyl acetate) to afford the title compound (31.6 mg, 57% yield). LCMS 369.05 (M+2)⁺.

Step 4: (±)-4-(((1S,2S)-2-hydroxy-2-methylcyclohexyl)amino)-6-phenylpyrrolo[1,2-b]pyridazine-3-carboxamide (Example 314)

A mixture of 6-bromo-4-((1S,2S)-2-hydroxy-2-methylcyclohexylamino)pyrrolo[1,2-b]pyridazine-3-carboxamide (31 mg, 0.084 mmol), phenylboronic acid (21 mg, 0.17 mmol), Pd(OAc)₂ (1.0 mg, 0.004 mmol), and dicyclohexyl(2',4',6'-triisopropylbiphenyl-2-yl)phosphine (X-Phos, 4 mg, 0.0084 mmol) in DMF (0.5 mL) were added 2M K₃PO₄ (0.13 mL, 0.25 mmol) and the solution degassed via N₂ sparging. The mixture was sealed and heated at 130° C. for 30 min. The reaction was cooled and the product was isolated via preparative HPLC to afford the title compound (17.5 mg, 52% yield) as a pale yellow solid. LCMS: 365.15 (M+H)⁺; HPLC (condition L): retention time=8.34 min; ¹H NMR (methanol-d₄, 400 MHz) δ 8.16 (s, 1H), 7.94 (d, J=1.7 Hz, 1H), 7.70 (m, 2H), 7.41 (t, J=7.5 Hz, 2H), 7.27 (m, 2H), 4.35 (m, 1H), 2.21 (m, 2H), 1.50-1.88 (m, 6H), 1.35 (s, 3H).

Example 315

6-(4-(acetamidomethyl)phenyl)-4-(((1R,3 S)-3-acetamido-2,2,3-trimethylcyclopentyl)amino)pyrrolo[1,2-b]pyridazine-3-carboxamide

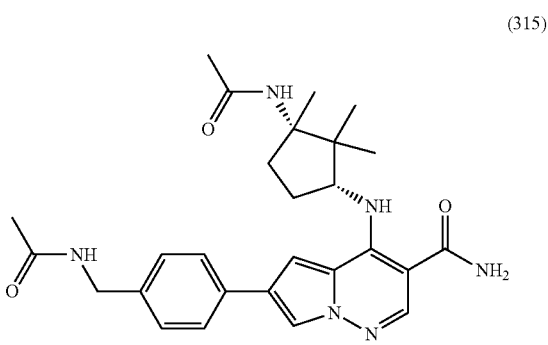 [SMILES: CC(=O)NCc1ccc(-c2cc3c(N[C@@H]4CC[C@](C)(NC(C)=O)C4(C)C)c(C(N)=O)cnn3c2)cc1]

(315)

A mixture of 4-((1R,3S)-3-amino-2,2,3-trimethylcyclopentylamino)-6-(4-(aminomethyl)phenyl)pyrrolo[1,2-b]pyridazine-3-carboxamide (Example 234, 8 mg, 0.020 mmol), acetic acid (1.8 mg, 0.03 mmol), BOP (1.3 mg, 0.022 mmol) and DIPEA (6.35 mg, 0.05 mmol) in DMF (0.5 mL) was stirred at rt for 2 h. The reaction was purified by preparative HPLC to afford the title compound (4 mg, 38% yield). LCMS: 491.32 (M+H); HPLC (condition B): retention time=3.51 min; ¹H NMR (CDCl₃, 400 MHz) δ 7.95 (s, 1H), 7.78 (s, 1H), 7.51 (m, 2H), 7.29 (m, 2H), 7.00 (m, 1H), 4.46 (M, 1H), 4.37 (s, 2H), 2.34 (m, 2H), 1.97 (m, 6H), 1.72 (m, 1H), 3.28 (s, 3H), 1.06 (s, 6H).

Example 316

6-(4-amino-5-pyrimidinyl)-4-((cis-4-hydroxy-4-methylcyclohexyl)amino)pyrrolo[1,2-b]pyridazine-3-carboxamide

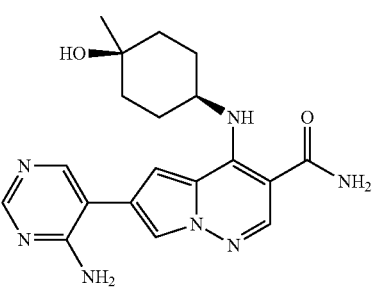

(316)

To a mixture of 6-bromo-cis-4-(-4-hydroxy-4-methylcyclohexylamino) pyrrolo[1,2-b]pyridazine-3-carboxamide (Intermediate 46, 40 mg, 0.11 mmol), bis(pinacolato)diboron (83 mg, 0.33 mmol) and KOAc (32 mg, 0.33 mmol) in DMSO (0.63 mL) was added Pd(Ph₃P)₂Cl₂ and the mixture was degassed via N₂ sparge for 5 min. The reaction vessel was sealed and the contents heated at 80-85° C. for 18 h. The mixture was cooled and divided into 2 portions. To one of these portions was added 5-bromopyrimidin-4-amine (8.70 mg, 0.05 mmol), 2M K$_3$PO$_4$ (0.125 mL, 0.25 mmol) and Pd(Ph$_3$P)$_4$ (5.8 mg, 5.0 μmol). The vial was purged with N$_2$, sealed and heated at 90° C. for 2 h. The mixture was cooled, diluted with MeOH, and purified via reverse-phase preparative HPLC to afford the title compound which was presumed to be the bis TFA salt (2.8 mg, 9.2% yield) as a white solid. LCMS: 382.21 (M+H)$^+$; HPLC (condition 0): retention time=2.08 min; $^1$H NMR (methanol-d$_4$, 400 MHz) δ 8.64 (d, J=1.5 Hz, 1H), 8.27 (d, J=1.5 Hz, 1H), 8.22 (s, 1H), 7.93 (d, J=2.0 Hz, 1H), 7.12 (d, J=1.8 Hz, 1H), 4.17 (m, 1H), 2.02 (m, 2H), 1.85 (m, 4H), 1.64 (m, 2H), 1.26 (s, 3H).

Example 317

4-(Cis-2-fluoro-2-methylcyclopentyl)amino)-6-(2-oxo-1,3-oxazolidin-3-yl)pyrrolo[1,2-b]pyridazine-3-carboxamide

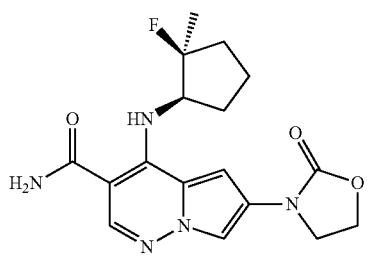
(317)

A reaction vial charged with 6-bromo-4-((cis)-2-fluoro-2-methylcyclopentylamino)yrrolo[1,2-b]pyridazine-3-carboxamide (Intermediate 36, 20 mg, 0.056 mmol), oxazolidin-2-one (14.71 mg, 0.169 mmol), copper (I) iodide (2.145 mg, 0.011 mmol), and potassium carbonate (15.56 mg, 0.113 mmol) was flushed with a gentle stream of nitrogen. Dioxane (375 μL) and N1,N2-dimethylethane-1,2-diamine (24.86 μL, 0.230 mmol) were added. The suspension was purged with nitrogen. The reaction was heated to 105° C. for 16 hrs. The reaction was cooled to room temperature and diluted with methanol (10 mL). The solution was filtered and concentrated under reduced pressure. The residue was diluted with methanol (2 mL) and purified via reverse-phase HPLC to afford the title compound as its TFA salt (11.8 mg, 0.025 mmol, 44.1% yield) as a white solid. $^1$H NMR (400 MHz, MeOD) δ ppm 8.37-8.45 (1 H, m), 7.95-8.01 (1 H, m), 7.28-7.34 (1 H, m), 4.45-4.67 (2 H, m), 4.33-4.44 (3 H, m), 2.61-2.74 (1 H, m), 2.36-2.54 (1 H, m), 2.02-2.35 (4 H, m), 1.74-1.87 (3 H, m). HPLC (method R): ret. Time 1.733 min. LC/MS [m/z, (M+H)] 362.03.

Examples 318 to 327

In a similar manner to Example 317, Examples 318 to 327 in the table below were prepared from 6-bromo-4-(cis-2-fluoro-2-methylcyclopentylamino) pyrrolo-[1,2-b]pyridazine-3-carboxamide (Intermediate 36) and the appropriate commercially available lactams, amides, or carbamates. All Examples/Intermediates are racemic. All Examples were analyzed using HPLC conditions H unless otherwise noted.

| Ex # | Structure | HPLC Rt minute (conditions) | LCMS [m/z (M + H)] |
|---|---|---|---|
| 318 | 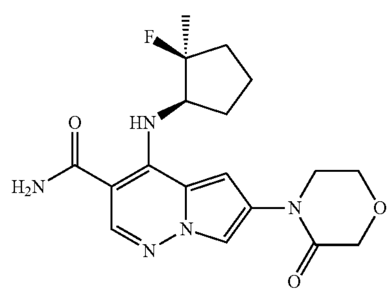 [SMILES: C[C@]1(F)CCC[C@H]1Nc1c(C(N)=O)cnn2cc(N3CCOCC3=O)cc12] | 1.685 (R) | 376.05 |
| 319 | 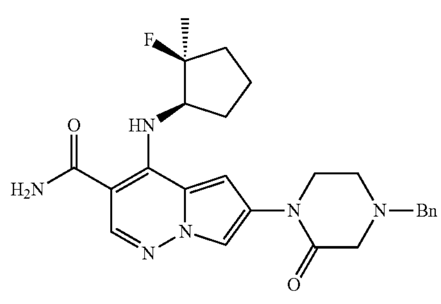 [SMILES: C[C@]1(F)CCC[C@H]1Nc1c(C(N)=O)cnn2cc(N3CCN(Cc4ccccc4)CC3=O)cc12] | 2.815 (R) | 465.0 |

-continued

| Ex # | Structure | HPLC Rt minute (conditions) | LCMS [m/z (M + H)] |
|---|---|---|---|
| 320 | 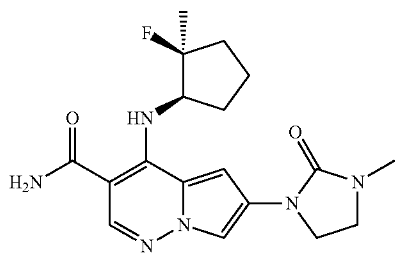 [SMILES: CN1CCN(c2cc3c(N[C@@H]4CCC[C@]4(C)F)c(C(N)=O)cnn3c2)C1=O] | 2.04 | 375.12 |
| 321 | 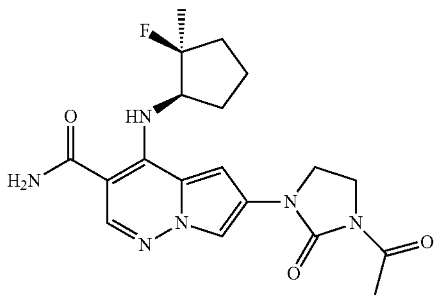 [SMILES: CC(=O)N1CCN(c2cc3c(N[C@@H]4CCC[C@]4(C)F)c(C(N)=O)cnn3c2)C1=O] | 2.07 | 403.06 |
| 322 | 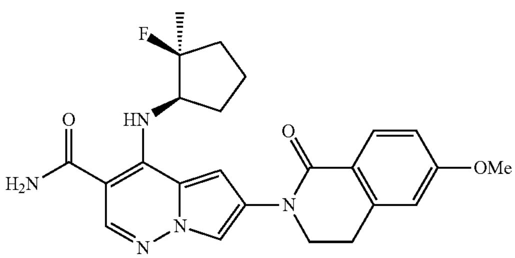 [SMILES: COc1ccc2c(c1)CCN(c1cc3c(N[C@@H]4CCC[C@]4(C)F)c(C(N)=O)cnn3c1)C2=O] | 2.52 | 452.08 |
| 323 | 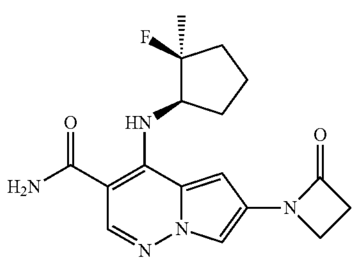 [SMILES: C[C@]1(F)CCC[C@H]1Nc1c(C(N)=O)cnn2cc(N3CCC3=O)cc12] | 2.00 | 346.10 |
| 324 | 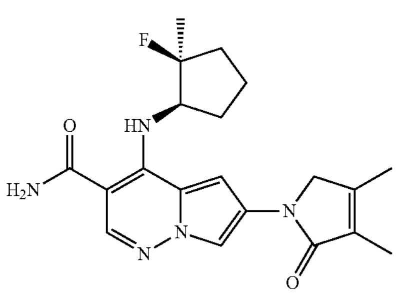 [SMILES: CC1=C(C)C(=O)N(c2cc3c(N[C@@H]4CCC[C@]4(C)F)c(C(N)=O)cnn3c2)C1] | 2.31 | 386.08 |

-continued
| Ex # | Structure | HPLC Rt minute (conditions) | LCMS [m/z (M + H)] |
|---|---|---|---|
| 325 | 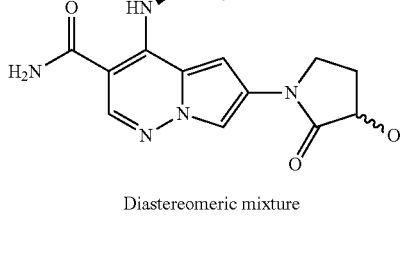 Diastereomeric mixture | 1.80 | 376.09 |
| 326 | 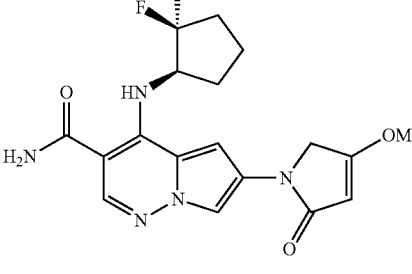 | 2.08 | 388.08 |
| 327 | 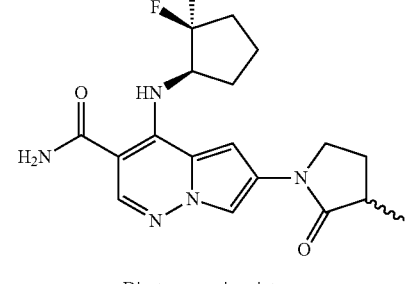 Diastereomeric mixture | 2.21 | 374.08 |

Examples 328 to 333

In a similar manner to Example 317, Examples 328 to 332 were prepared from 4-(((1R,3S)-3-amino-2,2,3-trimethylcyclopentyl)amino)-6-bromo-pyrrolo[1,2-b]pyridazine-3-carboxamide (Intermediate 48) and the appropriate commercially available lactam, amide, carbamate, or pyrazole. Similarly, Example 333 was prepared from 6-bromo-4-((1R,3R)-3-hydroxy-2,2,3-trimethylcyclopentylamino)-pyrrolo[L2-b]-pyridazine-3-carboxamide (Intermediate 51). All Examples were analyzed using HPLC conditions R unless otherwise noted.

| Ex. | Structure | HPLC Rt minute (conditions) | LC MS [m/z (M + H)] |
|---|---|---|---|
| 328 | 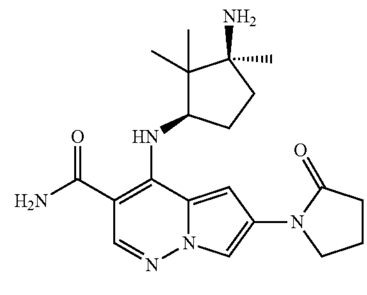 [SMILES: CC1(C)[C@H](Nc2c(C(N)=O)cnn3cc(N4CCCC4=O)cc23)CC[C@]1(C)N] | 2.158 | 385.3 |
| 329 | 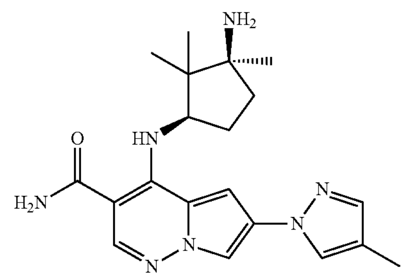 [SMILES: Cc1cnn(-c2cc3c(N[C@@H]4CC[C@](C)(N)C4(C)C)c(C(N)=O)cnn3c2)c1] | 2.908 | 382.0 |
| 330 | 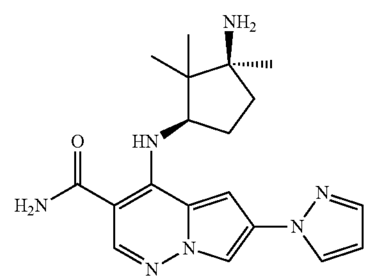 [SMILES: CC1(C)[C@H](Nc2c(C(N)=O)cnn3cc(-n4cccn4)cc23)CC[C@]1(C)N] | 1.220 | 368.3 |
| 331 | 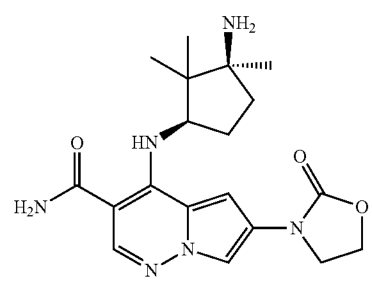 [SMILES: CC1(C)[C@H](Nc2c(C(N)=O)cnn3cc(N4CCOC4=O)cc23)CC[C@]1(C)N] | 1.067 | 387.2 |
| 332 | 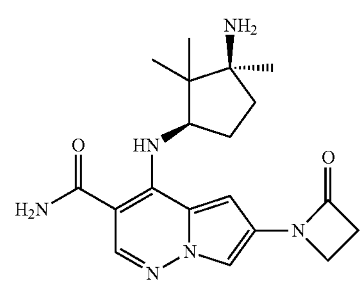 [SMILES: CC1(C)[C@H](Nc2c(C(N)=O)cnn3cc(N4CCC4=O)cc23)CC[C@]1(C)N] | 1.877 | 371.3 |

| Ex. | Structure | HPLC Rt minute (conditions) | LC MS [m/z (M + H)] |
|-----|-----------|-----------------------------|----------------------|
| 333 | 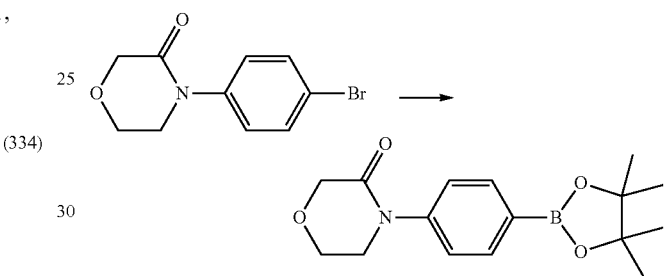 | 2.567 | 402.3 |

Example 334

4-(((1R,3S)-3-amino-2,2,3-trimethylcyclopentyl)amino)-6-(4-(3-oxo-4-morpholinyl)phenyl)pyrrolo[1,2-b]pyridazine-3-carboxamide (334)

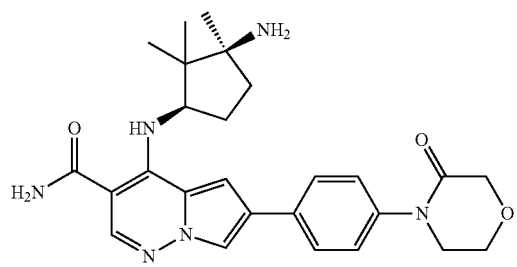

Step 1: 4-(4-bromophenyl)morpholin-3-one

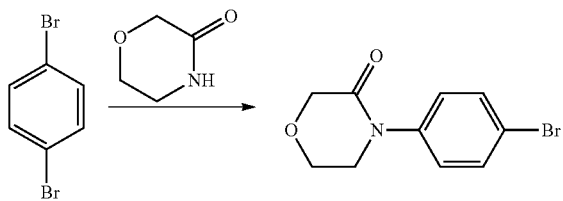

A solution of 1,4-dibromobenzene (283 mg, 1.200 mmol), morpholin-3-one (101.104 mg, 1.000 mmol), dibasic potassium phosphate (348 mg, 2.000 mmol), copper (I) iodide (38.1 mg, 0.200 mmol) and N,N'-dimethylethylenediamine (0.043 ml, 0.400 mmol) in dioxane (3 ml) was purged with nitrogen for 2 min, sealed in a reaction vial and heated in a heating block at 105° C. for 15 h. The crude product mixture was filtered, and charged to a 12 g silica gel cartridge which was eluted with 0-50% EtOAc in hexanes to give the title compound (173 mg, 0.676 mmol, 67.6% yield) as a white solid. $^1$H NMR (400 MHz, CHLOROFORM-d) δ ppm 10.56 (1H, none), 7.55 (2 H, d, J=8.80 Hz), 7.24 (2 H, d, J=8.58 Hz), 4.04 (2 H, dd, J=5.83, 4.29 Hz), 3.73-3.79 (2 H, m). HPLC (condition F): ret. Time 2.213 min; LC/MS [m/z, (M+H)] 258.0.

Step 2: 4-(4-(4,4,5,5-tetramethyl-1,3,2-dioxaborolan-2-yl)phenyl)morpholin-3-one A solution of 4-(4-bromophenyl)morpholin-3-one (150 mg, 0.586 mmol), 4,4,4',4',5,5,5',5'-octamethyl-2,2'-bi(1,3,2-dioxaborolane) (297 mg, 1.171 mmol) and potassium acetate (172 mg, 1.757 mmol) in dioxane (2 ml) was purged with $N_2$ for 5 min, followed by addition of $PdCl_2$(dppf) $CH_2Cl_2$ adduct (1:1) (47.8 mg, 0.059 mmol). After purging with $N_2$ for additional 2 min, the reaction mixture was sealed in a small vial and heated in a heating block at 100° C. for 12 hrs. The reaction mixture was diluted with ethyl acetate, washed with water and concentrated to give a brown residue. The crude product was charged to a 12 g silica gel cartridge which was eluted with 10-50% EtOAc in hexane to collect the title compound (113 mg, 0.373 mmol, 63.6% yield) as a white solid. $^1$H NMR (400 MHz, MeOD) δ ppm 7.81 (2 H, d, J=8.36 Hz), 7.36-7.42 (2 H, m), 4.29 (2 H, s), 4.04 (2 H, dd, J=5.83, 4.29 Hz), 3.80 (2 H, dd, J=5.83, 4.29 Hz), 1.35 (12 H, s). HPLC (condition F): ret. Time 3.886 min.; LC/MS [m/z, (M+H)] 304.0.

Step 3: 4-(((1R,3S)-3-amino-2,2,3-trimethylcyclopentyl)amino)-6-(4-(3-oxo-4-morpholinyl)phenyl)pyrrolo[1,2-b]pyridazine-3-carboxamide (Example 337)

A solution of 4-(4-(4,4,5,5-tetramethyl-1,3,2-dioxaborolan-2-yl)phenyl)morpholin-3-one (31.9 mg, 0.105 mmol), 4-((1R,3S)-3-amino-2,2,3-trimethylcyclopentylamino)-6-bromopyrrolo[1,2-b]pyridazine-3-carboxamide (Intermediate 48, 20 mg, 0.053 mmol), 1,1'-bis(di-t-butyl/diphenylphosphino) ferrocene (2.495 mg, 5.26 μmol), palladium (II) acetate (1.181 mg, 5.26 μmol) and dibasic potassium phosphate (0.079 mL, 0.158 mmol) in DMF (0.5 mL) was purged with $N_2$ for 5 min. The reaction mixture was sealed and heated at 93° C. for 120 min. The reaction mixture was cooled and diluted with methanol and filtered. The filtrate was purified by prep HPLC [Column: YMC 20×100; Mobil phase: B in A: 20%-100% (A: 10% MeOH in H$_2$O with 0.1% TFA, B: 90% MeOH in H$_2$O with 0.1% TFA; gradient time: 15 min., hold time: 5 min] to afford the title compound, assumed to be TFA salt (7.2 mg, 0.012 mmol, 23.18% yield) as a white solid. $^1$H NMR (400 MHz, MeOD) δ ppm 8.19 (1 H, s), 8.02 (1 H, d, J=1.54 Hz), 7.73-7.87 (2 H, m), 7.42 (2 H, d, J=8.58 Hz), 7.25 (1 H, d, J=1.54 Hz), 4.72 (1 H, t, J=9.02 Hz), 4.31 (2 H, s), 4.00-4.13 (2 H, m), 3.76-3.86 (2 H, m), 2.42-2.65 (1 H, m), 2.11-2.24 (1 H, m), 2.00-2.10 (1 H, m), 1.77-1.92 (1 H, m), 1.50 (3 H, s), 1.18 (3H, s), 1.08 (3H, s). HPLC (condition F): ret. Time 3.143 min.; LC/MS [m/z, (M+H)] 477.1.

Example 335

4-(((1R,3 S)-3-amino-2,2,3-trimethylcyclopentyl) amino)-6-(3-(3-oxo-4-morpholinyl)phenyl)pyrrolo[1, 2-b]pyridazine-3-carboxamide

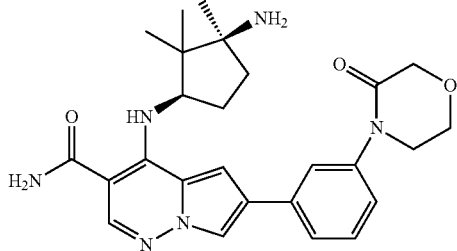

(335)

Example 335 was prepared in a similar manner as described in Example 334 by substituting 1,4-dibromobenzene with 1,3-dibromobenzene to afford the title compound assumed to be as its TFA salt as a white solid. $^1$H NMR (400 MHz, MeOD) δ ppm 8.19 (1H, s), 8.02 (2H, d, J=1.76 Hz), 7.73 (1H, t, J=1.76 Hz), 7.66-7.70 (1 H, m), 7.49 (2 H, t, J=7.81 Hz), 7.22-7.29 (2 H, m), 4.71 (1 H, t, J=9.02 Hz), 4.32 (2 H, s), 4.08 (2 H, dd, J=5.83, 4.29 Hz), 3.82-3.87 (2 H, m), 2.45-2.56 (1H, m), 2.10-2.21 (1 H, m), 2.00-2.09 (1 H, m), 1.77-1.90 (1 H, m), 1.50 (3 H, s), 1.18 (3 H, s), 1.07 (3 H, s). HPLC (condition F): ret. Time 2.476 min.; LC/MS [m/z, (M+H)] 477.3.

Example 336

6-(6-methoxy-3-pyridinyl)-4-(((1R,3S)-2,2,3-trimethyl-3-((methylsulfonyl)amino)cyclopentyl)amino) pyrrolo[1,2-b]pyridazine-3-carboxamide

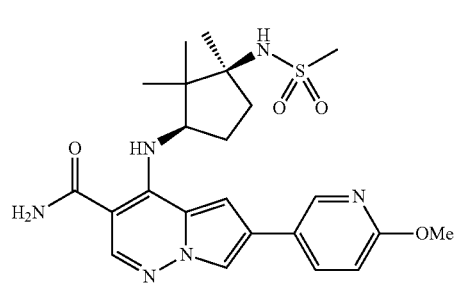

(336)

4-(N,N-dimethylamino)pyridine (15.7 mg, 0.129 mmol) was added to a solution of 4-((1R,3S)-3-amino-2,2,3-trimethylcyclopentylamino)-6-(6-methoxypyridin-3-yl)pyrrolo[1, 2-b]pyridazine-3-carboxamide (97.5 mg, 0.138 mmol, from Example 232), N,N-diisopropylethylamine (0.080 mL, 0.458 mmol) and methanesulfonyl chloride (0.030 mL, 0.385 mmol) in dichloromethane (1 mL). After 1 h at room temperature, the mixture was purified by silica gel chromatography, eluting with 0-10% methanol in dichloromethane. The fractions containing the desired product were concentrated. The material was further purified with reverse phase HPLC (Waters Xbridge 19×100 mm), eluting with 20-80% solvent B (10% methanol-90% water-0.1% TFA) in solvent A (90% methanol-10% water-0.1% TFA), to give 6-(6-methoxy-3-pyridinyl)-4-(((1R,3S)-2,2,3-trimethyl-3-((methylsulfonyl) amino)-cyclopentyl)amino)pyrrolo[1,2-b]pyridazine-3-carboxamide as white solid (25.1 mg, 37% yield). $^1$H NMR (400 MHz, methanol-d$_4$) δ ppm 8.47 (1 H, d, J=1.98 Hz), 8.15 (1 H, s), 8.07 (1 H, dd, J=8.58, 2.42 Hz), 7.95 (1 H, d, J=1.76 Hz), 7.15 (1 H, d, J=1.54 Hz), 6.94 (1 H, d, J=8.58 Hz), 4.58 (1 H, t, J=8.25 Hz), 3.98 (3 H, s), 3.06 (3 H, s), 2.42-2.53 (2 H, m), 1.93-2.05 (1 H, m), 1.73-1.84 (1 H, m), 1.53 (3 H, s), 1.16 (3 H, s), 1.04 (3 H, s); MS (ES+) m/z: 487.3 (M+H); LC retention time: 3.843 min (analytical HPLC Method F).

Example 337

4-((1R,3S)-3-carbamoyl-2,2,3-trimethylcyclopentylamino)-6-phenylpyrrolo[1,2-b]pyridazine-3-carboxamide

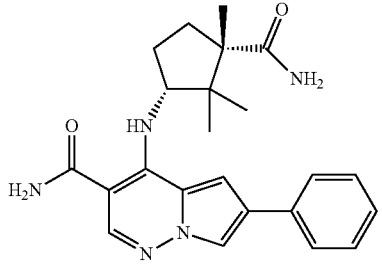

(337)

Step 1: (1S,3R)-dimethyl 1,2,2-trimethylcyclopentane-1,3-dicarboxylate

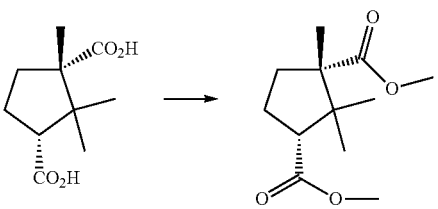 [SMILES: CC1(C)[C@H](C(=O)O)CC[C@]1(C)C(=O)O ; COC(=O)[C@@H]1CC[C@](C)(C(=O)OC)C1(C)C]

Potassium carbonate (8.28 g, 59.9 mmol) and iodomethane (2.186 ml, 35.0 mmol) were added to a solution of (1S,3R)-1,2,2-trimethylcyclopentane-1,3-dicarboxylic acid (2 g, 9.99 mmol) in DMSO (19.98 ml). The suspension was stirred at room temperature for 16 hrs. The reaction was partitioned between water (50 ml) and ethyl acetate (3×). The ethyl acetate extracts were combined, washed with (sat.) sodium chloride, dried with sodium sulfate, filtered, and concentrated under reduced pressure, yielding the title compound (2.213 g, 9.69 mmol, 97% yield) as a colorless oil. LC/MS found [M+Na]+=251.1 ¹H NMR (400 MHz, CHLOROFORM-d) δ ppm 3.68 (6 H, d, J=4.6 Hz), 2.77-2.84 (1 H, m), 2.54-2.62 (1 H, m), 2.15-2.25 (1 H, m), 1.78-1.86 (1 H, m), 1.48-1.56 (1 H, m), 1.25 (3 H, s), 1.21 (3 H, s), 0.76 (3 H, s).

Step 2: (1R,3S)-3-(methoxycarbonyl)-2,2,3-trimethylcyclopentanecarboxylic acid

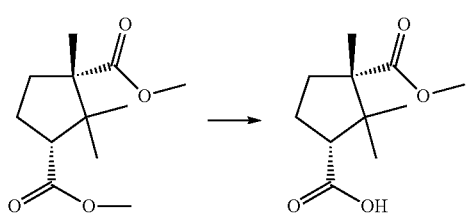 [SMILES: COC(=O)[C@@H]1CC[C@](C)(C(=O)OC)C1(C)C ; COC(=O)[C@@]1(C)CC[C@@H](C(=O)O)C1(C)C]

Lithium hydroxide hydrate (407 mg, 9.69 mmol) was added to a solution of (1S,3R)-dimethyl 1,2,2-trimethylcyclopentane-1,3-dicarboxylate (2.213 g, 9.69 mmol) in THF (27.7 ml), water (5.54 ml) and methanol (5.54 ml). The reaction was stirred at 55° C. for 14 hrs. The reaction was cooled to room temperature and concentrated under reduced pressure to yield an oil. The oil was diluted with ethyl acetate and washed with water. The aqueous layer was acidified with 1.0 N HCl, and was extracted with ethyl acetate (3×). The organic extracts were combined, dried with sodium sulfate, filtered and concentrated under reduced pressure, yielding the title compound (1.84 g, 8.59 mmol, 89% yield) as a colorless oil. LC/MS found [M+H]+=215.2. ¹H NMR (400 MHz, CHLOROFORM-d) δ ppm 3.69 (3H, s), 2.84 (1 H, s), 2.52-2.65 (1 H, m), 2.13-2.24 (1 H, m), 1.81-1.90 (1 H, m), 1.53 (1 H, s), 1.27-1.32 (3 H, m), 1.22 (3 H, s), 0.84 (3 H, s).

Step 3: (1S,3R)-methyl 3-(benzyloxycarbonylamino)-1,2,2-trimethylcyclopentanecarboxylate

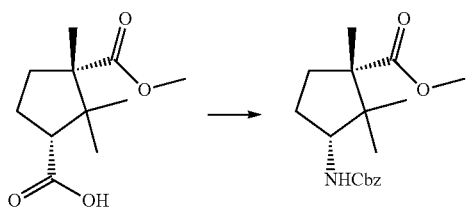 [SMILES: COC(=O)[C@@]1(C)CC[C@@H](C(=O)O)C1(C)C ; COC(=O)[C@@]1(C)CC[C@@H](NC(=O)OCc2ccccc2)C1(C)C]

Triethylamine (1.795 ml, 12.88 mmol) was added dropwise to a solution of (1R,3S)-3-(methoxycarbonyl)-2,2,3-trimethylcyclopentanecarboxylic acid (1.84 g, 8.59 mmol) in toluene (22.08 ml) and THF (2.454 ml), followed by addition of diphenylphosphoryl azide (2.221 ml, 10.31 mmol). The reaction was stirred at room temperature for 1.5 hours. Benzyl alcohol (1.339 ml, 12.88 mmol) was added. The reaction was heated at 110° C. for 6 hrs. The reaction was cooled to room temperature and diluted with ethyl acetate. The solution was washed successively with (sat.) sodium bicarbonate, water, and (sat.) sodium chloride. The organic extract was dried with sodium sulfate, filtered, and concentrated under reduced pressure to give an orange oil. The crude product was chromatographed on the silica gel column eluted with 0-50% ethyl acetate in hexane to afford the title compound (1.74 g, 5.45 mmol, 63.4% yield) as a colorless oil. LC/MS found [M+H]+=320.1. ¹H NMR (400 MHz, CHLOROFORM-d) δ 7.39-7.27 (m, 5H), 5.15-5.01 (m, 2H), 4.14-4.02 (m, 1H), 3.70-3.62 (m, 3H), 2.53-2.40 (m, 1H), 2.20-2.08 (m, 1H), 1.51-1.40 (m, 2H), 1.22-1.19 (m, 3H), 1.05 (s, 3H), 0.73 (s, 3H).

Step 4: (1S,3R)-methyl 3-amino-1,2,2-trimethylcyclopentanecarboxylate

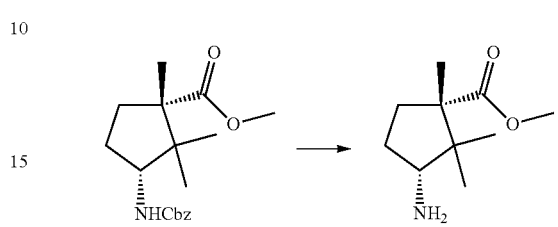

To a flask, charged with 10% palladium on carbon (90 mg, 0.845 mmol), under a steady nitrogen flow was added ethanol (5 ml), followed by addition of a solution of (1S,3R)-methyl 3-(benzyloxycarbonylamino)-1,2,2-trimethylcyclopentanecarboxylate (900 mg, 2.82 mmol) in ethanol (11.300 ml). The flask was evacuated and flushed with hydrogen and then filled with one atmosphere of hydrogen. The reaction was stirred at room temperature for 14 hrs. The flask was evacuated and backfilled with nitrogen. The suspension was filtered through a pad of Celite. The Celite cake was washed with ethanol (3×, 20 ml). The ethanol wash was concentrated under reduced pressure to yield the title compound (478 mg, 2.58 mmol, 92% yield) as a colorless oil. LC/MS found [M+H]+=186.3. ¹H NMR (400 MHz, CHLOROFORM-d) δ 3.68 (s, 3H), 3.10 (t, J=9.1 Hz, 1H), 2.57-2.47 (m, 1H), 2.11-2.02 (m, 1H), 1.46-1.35 (m, 2H), 1.19-1.17 (m, 3H), 1.07-1.03 (m, 3H), 0.72 (s, 3H).

Step 5: (1S,3R)-methyl 3-(6-bromo-3-carbamoylpyrrolo[1,2-b]pyridazin-4-ylamino)-1,2,2-trimethylcyclopentanecarboxylate

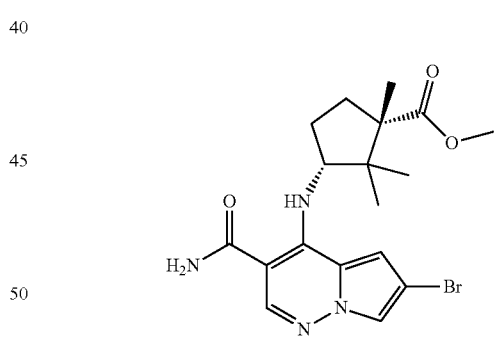

Hunig's base (1.27 mL, 7.29 mmol) was added to a solution of 6-bromo-4-chloropyrrolo[1,2-b]pyridazine-3-carboxamide (Preparation 5, 625 mg, 2.277 mmol) and (1S,3R)-methyl 3-amino-1,2,2-trimethylcyclopentanecarboxylate (464 mg, 2.505 mmol) in NMP (5692 n1). The reaction was heated at 90° C. for 14 hrs. The reaction was cooled to room temperature and diluted with ethyl acetate (20 ml). The ethyl acetate solution was washed with water (3×10 ml), dried with sodium sulfate, filtered, and concentrated under reduced pressure to give a light yellow oil. The crude product was chromatographed on the silica gel column eluted with 0-50% ethyl acetate in hexane to afford the title compound (583 mg, 1.308 mmol, 57.5% yield) as a white solid. LC/MS found [M+H]+=425.1. ¹H NMR (400 MHz, MeOD) δ ppm 8.13 (1 H, s), 7.60-7.66 (1 H, m), 6.88-6.95 (1 H, m), 4.43-4.52 (1 H, m), 3.71 (3 H, s), 2.62-2.71 (1 H, m), 2.31-2.39 (1 H, m), 1.65-1.76 (1 H, m), 1.55-1.64 (1 H, m), 1.32 (3 H, s), 1.09 (3 H, s), 0.98 (3 H, s).

Step 6: (1S,3R)-methyl 3-(3-carbamoyl-6-phenylpyrrolo[1,2-b]pyridazin-4-ylamino)-1,2,2-trimethylcyclopentanecarboxylate

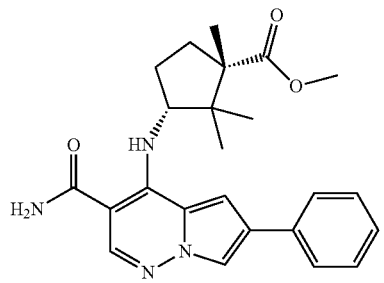 [SMILES: COC(=O)[C@@]1(C)CC[C@@H](Nc2c(C(N)=O)cnn3cc(-c4ccccc4)cc23)C1(C)C]

A solution of (1S,3R)-methyl 3-(6-bromo-3-carbamoylpyrrolo[1,2-b]pyridazin-4-ylamino)-1,2,2-trimethylcyclopentanecarboxylate (307 mg, 0.725 mmol) in DMF (4.8 ml) was added into a reaction vial charged with phenylboronic acid (177 mg, 1.450 mmol), 1,1'-bis(di-tert-butylphosphino)ferrocene (34.8 mg, 0.073 mmol) and palladium (II) acetate (16.28 mg, 0.073 mmol), followed by addition of a 2.0 M aqueous potassium phosphate, dibasic solution (1.1 ml, 2.176 mmol). The suspension was purged with nitrogen for 5 minutes. The vial was sealed and heated at 90° C. for 2 hrs. The reaction was cooled to room temperature and diluted with ethyl acetate (20 ml). The ethyl acetate solution was washed with water (3×10 ml), dried with sodium sulfate, filtered, and concentrated under reduced pressure to give a light yellow oil. The crude product was chromatographed on the silica gel column eluted with 0-50% ethyl acetate in hexane, yielding the title compound (182 mg, 0.433 mmol, 59.7% yield) as a white solid. LC/MS found [M+H]$^+$=420.9.

Step 7: (1S,3R)-3-(3-carbamoyl-6-phenylpyrrolo[1,2-b]pyridazin-4-ylamino)-1,2,2-trimethylcyclopentanecarboxylic acid

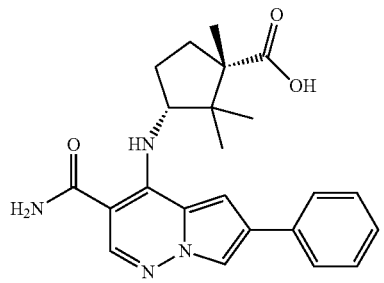 [SMILES: CC1(C)[C@H](Nc2c(C(N)=O)cnn3cc(-c4ccccc4)cc23)CC[C@]1(C)C(=O)O]

A 4.5 M aqueous potassium hydroxide (192 μl, 0.866 mmol) solution was added dropwise to a solution of (1S,3R)-methyl 3-(3-carbamoyl-6-phenylpyrrolo[1,2-b]pyridazin-4-ylamino)-1,2,2-trimethyl-cyclopentanecarboxylate (182 mg, 0.433 mmol) in ethanol (2885 μl). The reaction was heated at 75° C. for 24 hrs. The reaction was cooled to room temperature and concentrated under reduced pressure, yielding an oil. The oil was diluted with ethyl acetate and washed with water. The aqueous layer was acidified with 1.0 N HCl and was extracted with ethyl acetate (3×). The organic extracts were combined, dried with sodium sulfate, filtered and concentrated under reduced pressure, yielding (1S,3R)-3-(3-carbamoyl-6-phenylpyrrolo[1,2-b]pyridazin-4-ylamino)-1,2,2-trimethylcyclopentanecarboxylic acid (152.8 mg, 0.376 mmol, 87% yield) as a yellow solid. LC/MS found [M+H]$^+$=407.0.

Step 8: 4-((1R,3S)-3-carbamoyl-2,2,3-trimethylcyclopentylamino)-6-phenylpyrrolo[1,2-b]pyridazine-3-carboxamide (Example 337)

To a stirred solution of (1S,3R)-3-(3-carbamoyl-6-phenylpyrrolo[1,2-b]pyridazin-4-ylamino)-1,2,2-trimethylcyclopentanecarboxylic acid (30 mg, 0.074 mmol) in DMF (492 μl) were added Hunig's base (97 μl, 0.554 mmol) and HATU (42.1 mg, 0.111 mmol). After 15 minutes, ammonium chloride (19.74 mg, 0.369 mmol) was added. The reaction was heated at 75° C. for 24 hrs. The reaction mixture was cooled to room temperature and diluted with ethyl acetate. The solution was washed successively with water, (sat.) ammonium chloride and (sat.) sodium chloride. The ethyl acetate extract was dried with sodium sulfate, filtered, and concentrated under reduced pressure, yielding a yellow oil. The crude product was chromatographed using reverse-phase HPLC (Column: LUNA 5u C18 21×100). The collected fractions were combined and concentrated under reduced pressure. The product was taken up in ethyl acetate and neutralized with (sat.) sodium carbonate. The ethyl acetate extract was dried with sodium sulfate, filtered, and concentrated under reduced pressure to afford the title compound (12.7 mg, 0.030 mmol, 40.3% yield) as a white solid. LC/MS found [M+H]$^+$=406.2. $^1$H NMR (400 MHz, MeOD) δ ppm 8.13-8.17 (1 H, m), 7.92-7.96 (1 H, m), 7.64-7.70 (2 H, m), 7.35-7.44 (2 H, m), 7.23-7.30 (1 H, m), 7.15-7.20 (1 H, m), 4.68-4.77 (1 H, m), 2.54-2.67 (1 H, m), 2.41-2.54 (1 H, m), 1.70-1.80 (1 H, m), 1.60-1.69 (1 H, m), 1.35-1.42 (3 H, m), 1.13-1.19 (3 H, m), 1.06-1.13 (3H, m). HPLC Retention Time=3.058 (HPLC conditions: column. Phenominex Synergy, 4.6×50 mm, Mobile phase A: 90:10 water/methanol with 0.2% H$_3$PO$_4$; Mobile Phase B: 90:10 methanol/water with 0.2% H$_3$PO$_4$; Wavelength: 220 nm; Gradient: 0-100% B over 4 minutes, then a 1-minute hold at 100% B; Flow: 4 mL/min.)

Example 338

4-((1R,3S)-3-carbamoyl-2,2,3-trimethylcyclopentylamino)-6-(6-methoxypyridin-3-yl)pyrrolo[1,2-b]pyridazine-3-carboxamide (338)

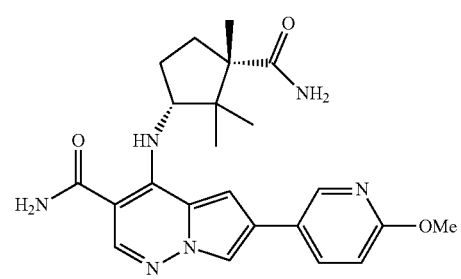

Step 1: (1S,3R)-3-(6-bromo-3-carbamoylpyrrolo[1,2-b]pyridazin-4-ylamino)-1,2,2-trimethylcyclopentanecarboxylic acid

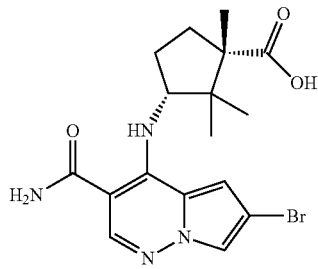 [SMILES: CC1(C)[C@H](Nc2c(C(N)=O)cnn3cc(Br)cc23)CC[C@]1(C)C(=O)O]

A 4.5 M aqueous solution of potassium hydroxide (210 μl, 0.945 mmol) was added dropwise to a solution of (1S,3R)-methyl 3-(6-bromo-3-carbamoylpyrrolo[1,2-b]pyridazin-4-ylamino)-1,2,2-trimethylcyclopentanecarboxylate (200 mg, 0.472 mmol) in ethanol (3.2 ml). The reaction was heated at 75° C. for 24 hrs. The reaction was cooled to room temperature and concentrated under reduced pressure to yield an oil. The oil was diluted with ethyl acetate and washed with water. The aqueous layer was acidified with 1.0 N HCl and was extracted with ethyl acetate (3×). The organic extracts were combined, dried with sodium sulfate, filtered and concentrated under reduced pressure, yielding the title compound (182 mg, 0.422 mmol, 89% yield) as a pale yellow solid. LC/MS found [M+H]$^+$=410.7.

Step 2: 6-bromo-4-((1R,3S)-3-carbamoyl-2,2,3-trimethylcyclopentylamino)-pyrrolo[1,2-b]pyridazine-3-carboxamide

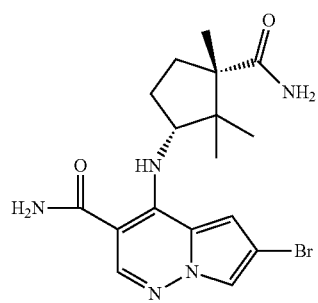 [SMILES: CC1(C)[C@H](Nc2c(C(N)=O)cnn3cc(Br)cc23)CC[C@]1(C)C(N)=O]

To a stirred solution of (1S,3R)-3-(6-bromo-3-carbamoylpyrrolo[1,2-b]pyridazin-4-ylamino)-1,2,2-trimethylcyclopentanecarboxylic acid (182 mg, 0.445 mmol) in DMF (3.0 ml), were added Hunig's base (582 μl, 3.34 mmol) and HATU (254 mg, 0.667 mmol). After 15 minutes, ammonium chloride (119 mg, 2.223 mmol) was added. The reaction was heated at 75° C. for 24 hrs. The reaction mixture was cooled to room temperature and diluted with ethyl acetate. The solution was washed successively with water, (sat.) ammonium chloride and (sat.) sodium chloride. The ethyl acetate extract was dried with sodium sulfate, filtered, and concentrated under reduced pressure to yield the title compound (104 mg, 0.255 mmol, 57.3% yield) as a white solid. LC/MS found [M+H]$^+$=409.9.

Step 3: 4-((1R,3S)-3-carbamoyl-2,2,3-trimethylcyclopentylamino)-6-(6-methoxypyridin-3-yl)pyrrolo[1,2-b]pyridazine-3-carboxamide (Example 341)

A solution of 6-bromo-4-((1R,3S)-3-carbamoyl-2,2,3-trimethylcyclopentylamino)pyrrolo[1,2-b]pyridazine-3-carboxamide (50 mg, 0.122 mmol) in DMF (816 μl) was added into a reaction vial charged with 6-methoxypyridin-3-ylboronic acid (37.5 mg, 0.245 mmol), 1,1'-bis(di-tert-butylphosphino)ferrocene (5.88 mg, 0.012 mmol) and palladium (II) acetate (2.75 mg, 0.012 mmol), followed by addition of a 2.0 M aqueous potassium phosphate, dibasic solution (184 μl, 0.367 mmol). The suspension was purged with nitrogen for 5 minutes. The vial was sealed and heated at 90° C. for 2 hrs. The reaction was cooled to room temperature and diluted with ethyl acetate (10 ml). The ethyl acetate solution was washed with water (3×5 ml), dried with sodium sulfate, filtered, and concentrated under reduced pressure, yielding a light yellow oil. The crude product was chromatographed using reverse-phase HPLC (Column: LUNA 5u C18 21×100). The collected fractions were combined and concentrated under reduced pressure. The product was taken up in ethyl acetate and neutralized with (sat.) sodium carbonate. The ethyl acetate extract was dried with sodium sulfate, filtered, and concentrated under reduced pressure to afford the title compound (11.3 mg, 0.025 mmol, 20.08% yield) as a white solid. LC/MS found [M+H]$^+$=437.3. $^1$H NMR (400 MHz, MeOD) δ ppm 8.42-8.48 (1 H, m), 8.11-8.18 (1 H, m), 7.96-8.04 (1 H, m), 7.89-7.96 (1 H, m), 7.10-7.19 (1 H, m), 6.84-6.91 (1 H, m), 4.66-4.74 (1 H, m), 3.94 (3 H, s), 2.53-2.65 (1 H, m), 2.41-2.53 (1 H, m), 1.69-1.81 (1 H, m), 1.57-1.69 (1 H, m), 1.34-1.42 (3 H, m), 1.11-1.18 (3 H, m), 1.02-1.11 (3 H, m). HPLC Retention Time=2.790 (HPLC conditions: column: Phenominex Synergy, 4.6×50 mm, Mobile phase A: 90:10 water/methanol with 0.2% H$_3$PO$_4$; Mobile Phase B: 90:10 methanol/water with 0.2% H$_3$PO$_4$; Wavelength: 220 nm; Gradient: 0-100% B over 4 minutes, then a 1-minute hold at 100% B; Flow: 4 mL/min.)

Example 339

4-(((1R,3S)-3-carbamoyl-2,2,3-trimethylcyclopentyl)amino)-6-(6-fluoropyridin-3-yl)pyrrolo[1,2-b]pyridazine-3-carboxamide (342)

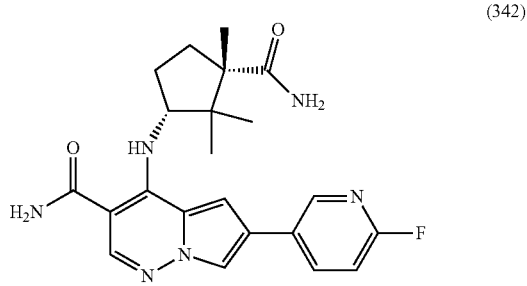 [SMILES: CC1(C)[C@H](Nc2c(C(N)=O)cnn3cc(-c4ccc(F)nc4)cc23)CC[C@]1(C)C(N)=O]

A solution of 6-bromo-4-(((1R,3S)-3-carbamoyl-2,2,3-trimethylcyclopentyl)amino)pyrrolo[1,2-b]pyridazine-3-carboxamide (20 mg, 0.049 mmol) in DMF (327 μl) was added into a reaction vial charged with (6-fluoropyridin-3-yl)boronic acid (13.80 mg, 0.098 mmol), 1,1'-bis(di-tert-butylphosphino)ferrocene (2.354 mg, 4.90 μmol) and palladium (II) acetate (1.100 mg, 4.90 μmol), followed by addition of a 2.0 M aqueous potassium phosphate, dibasic solution (73.5 µl, 0.147 mmol). The suspension was purged with nitrogen for 5 minutes. The vial was sealed and heated at 90° C. for 2 hrs. The reaction was cooled to room temperature and diluted with ethyl acetate (10 ml). The ethyl acetate solution was washed with water (3×5 ml), dried with sodium sulfate, filtered, and concentrated under reduced pressure, yielding a light yellow oil. The crude product was chromatographed using reverse-phase HPLC (Column: LUNA 5u C18 21×100) to afford the TFA salt of 4-(((1R,3S)-3-carbamoyl-2,2,3-trimethylcyclopentyl)amino)-6-(6-fluoropyridin-3-yl)pyrrolo[1,2-b]pyridazine-3-carboxamide (8.7 mg, 0.015 mmol, 31.3% yield) as a white solid. LC/MS found [M+H]$^+$=425.0.

A sample of 4-(((1R,3S)-3-carbamoyl-2,2,3-trimethylcyclopentyl)amino)-6-(6-fluoropyridin-3-yl)pyrrolo[1,2-b]pyridazine-3-carboxamide, TFA salt (5.5 mg, 10.21 µmol) was taken up in ethyl acetate (10 ml) and neutralized with (sat.) sodium carbonate (5 ml). The ethyl acetate extract was dried with sodium sulfate, filtered, and concentrated under reduced pressure to afford the free base of the title compound (3.3 mg, 7.39 µmol, 72.3% yield) as a white solid. LC/MS found [M+H]$^+$=425.3. $^1$H NMR (400 MHz, methanol-$d_4$) δ 8.53 (d, J=2.6 Hz, 1H), 8.25 (td, J=8.0, 2.6 Hz, 1H), 8.17 (s, 1H), 8.02 (d, J=1.5 Hz, 1H), 7.21 (d, J=1.5 Hz, 1H), 7.12 (dd, J=8.6, 2.6 Hz, 1H), 4.73-4.65 (m, 1H), 2.64-2.55 (m, 1H), 2.53-2.44 (m, 1H), 1.79-1.71 (m, 1H), 1.63 (td, J=8.9, 4.3 Hz, 1H), 1.38 (s, 3H), 1.14 (s, 3H), 1.09 (s, 3H). HPLC Retention Time=2.693. (HPLC conditions: column: Phenominex Synergy, 4.6×50 mm, Mobile phase A: 90:10 water/methanol with 0.2% $H_3PO_4$; Mobile Phase B: 90:10 methanol/water with 0.2% $H_3PO_4$; Wavelength: 220 nm; Gradient: 0-100% B over 4 minutes, then a 1-minute hold at 100% B; Flow: 4 mL/min)

Example 340

4-((1R,3S)-3-carbamoyl-2,2,3-trimethylcyclopentylamino)-6-(6-cyanopyridin-3-yl)pyrrolo[1,2-b]pyridazine-3-carboxamide

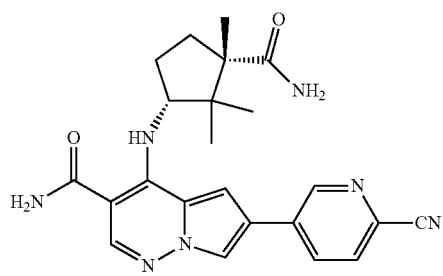
(340)

To a reaction vial charged with 5-(4,4,5,5-tetramethyl-1,3,2-dioxaborolan-2-yl)picolinonitrile (35.2 mg, 0.153 mmol), 1,1'-bis(di-tert-butylphosphino)ferrocene (2.94 mg, 6.12 mmol), and palladium acetate (1.375 mg, 6.12 mmol), was added a DMF (408 nl) solution of 6-bromo-4-(((1R,3S)-3-carbamoyl-2,2,3-trimethylcyclopentyl)amino)pyrrolo[1,2-b]pyridazine-3-carboxamide (25 mg, 0.061 mmol) followed by addition of a 2M aq solution of dibasic potassium phosphate (92 µl, 0.184 mmol). The suspension was purged with nitrogen for 5 minutes. The vial was sealed and heated at 90° C. for 2 hrs. The reaction was cooled to room temperature and diluted with ethyl acetate (10 ml). The ethyl acetate solution was washed with water (3×5 ml), dried with sodium sulfate, filtered, and concentrated under reduced pressure, yielding a light yellow oil. The crude product was chromatographed using reverse-phase HPLC (Column: LUNA 5u C18 21×100) to afford a white solid as the TFA salt of the title compound (4.3 mg, 7.49 mmol, 12.23% yield). LC/MS found [M+H]$^+$=425.0. Analy. HPLC Retention Time=2.663;. $^1$H NMR (400 MHz, methanol-$d_4$) δ 9.09 (d, J=1.5 Hz, 1H), 8.31 (dd, J=8.1, 2.4 Hz, 1H), 8.25-8.17 (m, 2H), 7.89 (d, J=8.8 Hz, 1H), 7.35 (d, J=2.0 Hz, 1H), 4.69 (t, J=8.8 Hz, 1H), 2.67-2.46 (m, 2H), 1.81-1.72 (m, 1H), 1.69-1.61 (m, 1H), 1.39 (s, 3H), 1.15 (s, 3H), 1.10 (s, 3H).

Example 341

4-(((1R,3 S)-3-amino-2,2,3-trimethylcyclopentyl)amino)-6-(1-(2-hydroxy-2-methylpropyl)-2-oxo-1,2-dihydropyridin-4-yl)pyrrolo[1,2-b]pyridazine-3-carboxamide

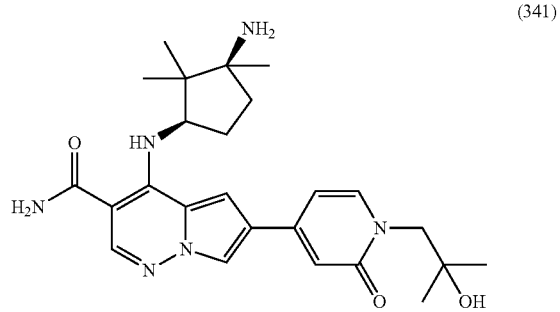 [SMILES: CC(C)(O)Cn1ccc(-c2cc3c(N[C@@H]4CC[C@](C)(N)C4(C)C)c(C(N)=O)cnn3c2)cc1=O]
(341)

Step 1: 4-bromo-1-(2-hydroxy-2-methylpropyl)pyridin-2(1H)-one

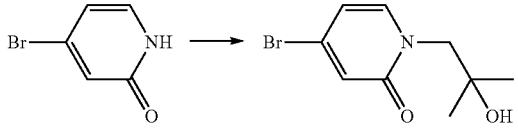

To a suspension of 4-bromopyridin-2(1H)-one (200 mg, 1.15 mmol), 2,2-dimethyloxirane (208 µL, 2.34 mmol) in DMF (2 mL) was added $K_2CO_3$ (320 mg, 2.32 mmol) and heated at 120° C. for 30 min in a microwave reactor. The reaction mixture was partitioned between ethyl acetate and water and the layers were separated. The organic extract was dried ($Na_2SO_4$), filtered and concentrated to afford a crystalline solid (240 mg, 85% yield) which was used without further purification. $^1$H NMR (400 MHz, $CCl_3D$) δ 7.25 (d, J=7.5 Hz, 1H), 6.88 (d, J=2.0 Hz, 1H), 6.38 (dd, J=7.3, 2.2 Hz, 1H), 4.01 (s, 2H), 3.43 (br s, 1H), 1.28 (m, 6H).

Step 2: 1-(2-hydroxy-2-methylpropyl)-4-(4,4,5,5-tetramethyl-1,3,2-dioxaborolan-2-yl)pyridin-2(1H)-one

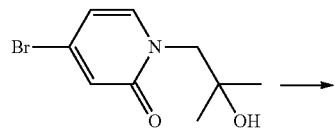

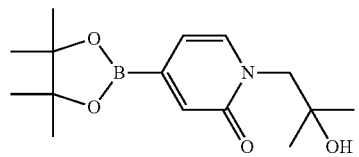

A mixture of 4-bromo-1-(2-hydroxy-2-methylpropyl)pyridin-2(1H)-one (128 mg, 0.52 mmol), bis(pinacolato)diboron (145 mg, 0.57 mmol), and KOAc (77 mg, 0.78 mmol) was added dioxane (2 mL) and the mixture was degassed via $N_2$ bubble. $PdCl_2(dppf)$ (38 mg, 0.05 mmol) was added and the reaction was heated at 85° C. After 1 h, TLC showed complete consumption of starting material and the reaction was cooled and filtered through a pad of celite and rinsed with ether. The filtrate was concentrated to give a dark oil which was dried under high vacuum for 1 h then used directly in the next step.

Step 3: 4-(((1R,3S)-3-amino-2,2,3-trimethylcyclopentyl)amino)-6-(1-(2-hydroxy-2-methylpropyl)-2-oxo-1,2-dihydropyridin-4-yl)pyrrolo[1,2-b]pyridazine-3-carboxamide A mixture of $Pd(OAc)_2$ (0.570 mg, 2.54 µmol), 1-(2-hydroxy-2-methylpropyl)-4-(4,4,5,5-tetramethyl-1,3,2-dioxaborolan-2-yl)pyridin-2(1H)-one (22.3 mg, 0.076 mmol), 4-(((1R,3S)-3-amino-2,2,3-trimethylcyclopentyl)amino)-6-bromopyrrolo[1,2-b]pyridazine-3-carboxamide (19.3 mg, 0.051 mmol, Intermediate 48), dicyclohexyl(2',4',6'-triisopropyl-[1,1'-biphenyl]-2-yl)phosphine (2.42 mg, 5.1 µmol), and 2 M $K_3PO_4$ (0.08 mL, 0.15 mmol) in dioxane (0.5 mL) was degassed then heated at 95° C. for 18 h. The reaction mixture was cooled to rt, diluted with MeOH and purified directly via preparative HPLC. $^1$H NMR ($CD_3OD$, 400 MHz) δ 8.24 (s, 1H), 8.16 (d, J=1.5 Hz, 1H), 7.71 (d, J=7.3 Hz, 1H), 7.33 (d, J=1.8 Hz, 1H), 6.93 (d, J=1.8 Hz, 1H), 6.83 (dd, J=7.0, 2.0 Hz, 1H), 4.71 (t, J=9.0 Hz, 1H), 4.10 (s, 2H), 2.52 (dtd, J=13.7, 9.0, 4.6 Hz, 1H), 2.23-2.00 (m, 2H), 1.92-1.73 (m, 1H), 1.61-1.47 (m, 3H), 1.28-1.16 (m, 9H), 1.16-0.98 (m, 3H). MS (ES+) m/z: 467.19 (M+H); LC retention time: 2.63 min (Analytical HPLC conditions: Chromalith Speedrod, C18, 4.6×50 mm, 10% MeOH/water to 90% MeOH/water with 0.2% $H_3PO_4$, 4 min gradient, 4 mL/min)

Example 342

4-(((1R,3 S)-3-carbamoyl-2,2,3-trimethylcyclopentyl)amino)-6-(pyridin-4-yl)pyrrolo[1,2-b]pyridazine-3-carboxamide

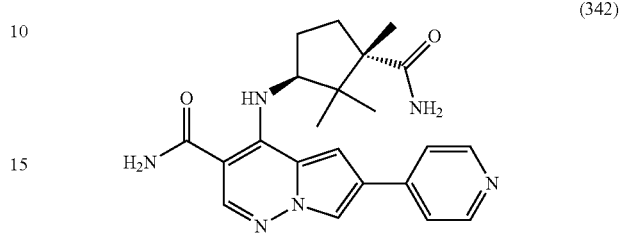

(342)

To a solution of 4-(4,4,5,5-tetramethyl-1,3,2-dioxaborolan-2-yl)pyridine (20.09 mg, 0.098 mmol), 1,1'-bis(di-tert-butylphosphino)ferrocene (2.354 mg, 4.90 µmol), palladium (II) acetate (1.100 mg, 4.90 µmol) and 6-bromo-4-(((1R,3S)-3-carbamoyl-2,2,3-trimethylcyclopentyl)amino)pyrrolo[1,2-b]pyridazine-3-carboxamide (20 mg, 0.049 mmol, from Step 2 of Example 340) in DMF (327 nl) in a reaction vial was added 2 M aqueous solution of potassium phosphate (184 µl, 0.367 mmol). The suspension was purged with nitrogen for 5 minutes. The vial was sealed and heated at 90° C. for 2 h. The reaction was cooled to room temperature and diluted with ethyl acetate (10 ml). The ethyl acetate solution was washed with water (3×5 ml), dried with sodium sulfate, filtered, and concentrated under reduced pressure to give an oil. The crude product was chromatographed using reverse-phase HPLC (Column: LUNA 5u C18 21×100). The collected fractions were combined and concentrated under reduced pressure to afford the title compound as TFA salt (5.1 mg, 9.31 mmol, 19.0% yield) as a white solid. $^1$H NMR (500 MHz, methanol-$d_4$) δ 8.68 (d, J=6.9 Hz, 2H), 8.46 (d, J=1.9 Hz, 1H), 8.33 (d, J=6.9 Hz, 2H), 8.24 (s, 1H), 7.52 (d, J=1.9 Hz, 1H), 4.67 (t, J=9.0 Hz, 1H), 2.64-2.56 (m, 1H), 2.55-2.48 (m, 1H), 1.81-1.71 (m, 1H), 1.66 (ddd, J=13.4, 8.9, 4.9 Hz, 1H), 1.40 (s, 3H), 1.14 (s, 3H), 1.10 (s, 3H). ESI-MS m/z 407.3 ([M+H]$^+$). HPLC retention time: 1.848 min (analytical HPLC Method F).

Examples 343 and 344

According to the procedure described for Example 342, Examples 344 to 345 were prepared by Suzuki coupling of 6-bromo-4-((1R,3S)-3-carbamoyl-2,2,3-trimethylcyclopentylamino)pyrrolo[1,2-b]pyridazine-3-carboxamide (from Step 2 of Example 340) with appropriate boronic acids or boronic acid esters, which were commercially available. Retention times for Examples 343 and 344 were determined using analyzed LCMS method I.

| Ex # | Structure | HPLC Rt (minute) | LCMS m/z (M + H)] |
|---|---|---|---|
| 343 | 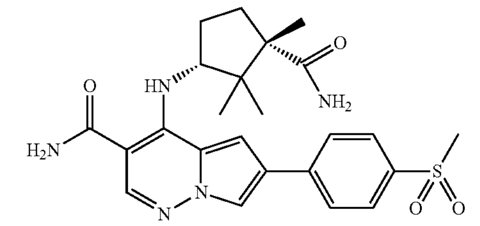 [SMILES: CC1(C)[C@H](Nc2c(C(N)=O)cnn3cc(-c4ccc(S(C)(=O)=O)cc4)cc23)CC[C@]1(C)C(N)=O] | 1.517 | 484.19 |
| 344 | 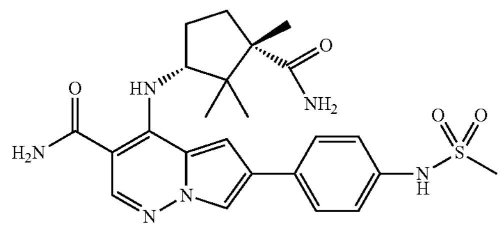 [SMILES: CC1(C)[C@H](Nc2c(C(N)=O)cnn3cc(-c4ccc(NS(C)(=O)=O)cc4)cc23)CC[C@]1(C)C(N)=O] | 1.380 | 499.0 |

4-(((1R,3S)-3-carbamoyl-2,2,3-trimethylcyclopentyl)amino)-6-(4-(methylsulfonyl)phenyl)pyrrolo[1,2-b]pyridazine-3-carboxamide (343);

4-(((1R,3S)-3-carbamoyl-2,2,3-trimethylcyclopentyl)amino)-6-(4-(methylsulfonamido)phenyl)pyrrolo[1,2-b]pyridazine-3-carboxamide (344);

Example 345

4-((1S,3S)-3-(((S)-2-hydroxypropanamido)methyl)-2,2,3-trimethylcyclopentylamino)-6-phenylpyrrolo[1,2-b]pyridazine-3-carboxamide (345)

Step 1: (1S,3R)-3-(methoxycarbonyl)-1,2,2-trimethylcyclopentanecarboxylic acid

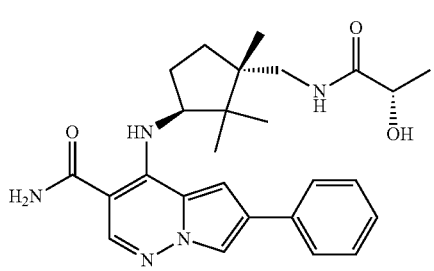

To a solution of (1S,3R)-1,2,2-trimethylcyclopentane-1,3-dicarboxylic acid (5.1 g, 25.5 mmol) in methanol (63.7 ml) at −78° C. was added thionyl chloride (2.045 ml, 28.0 mmol). After stirring at −78° C. for 30 minutes, the reaction was allowed to warm to room temperature. Stirring was continued for 14 hrs. The reaction mixture was concentrated under reduced pressure, yielding a yellow oil. The oil was taken into water. The solution was adjusted to pH 12 with 1.0 N NaOH and was washed with ethyl acetate. The basic aqueous layer was acidified with 1.0 N HCl, and was extracted with ethyl acetate (3×, 100 ml). The ethyl acetate extracts were combined, dried with sodium sulfate, filtered, and concentrated under reduced pressure to afford (1S,3R)-3-(methoxycarbonyl)-1,2,2-trimethylcyclopentanecarboxylic acid (5.35 g, 24.97 mmol, 98% yield) as a colorless oil. ESI-MS m/z 237.1 ([M+H]$^+$).

Step 2: (1R,3S)-methyl 3-carbamoyl-2,2,3-trimethylcyclopentanecarboxylate

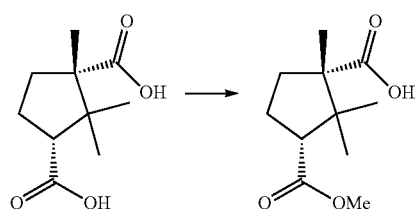

To a suspension of (1S,3R)-3-(methoxycarbonyl)-1,2,2-trimethylcyclopentanecarboxylic acid (5.35 g, 24.97 mmol) in ethyl ether (33.3 ml) was added phosphorus pentachloride (5.98 g, 28.7 mmol). The reaction mixture was stirred for 1 hr, forming an acid chloride. Acetonitrile (133 ml) was cooled to −40° C. and was saturated with ammonia gas. The acid chloride was added dropwise to the ammonia solution cooled at −40° C. Reaction was stirred at the same temperature for 1 hr. The reaction was concentrated under reduced pressure to give a white solid. The solid was treated with hot ethyl acetate. The resulting suspension was filtered and evaporated under reduced pressure, yielding (1R,3S)-methyl 3-carbamoyl-2,2,3-trimethylcyclopentanecarboxylate (4.49 g, 21.05 mmol, 84% yield) as a white solid. ESI-MS m/z 214.2 ([M+H]$^+$).

Step 3: (1R,3S)-methyl 3-cyano-2,2,3-trimethylcyclopentanecarboxylate

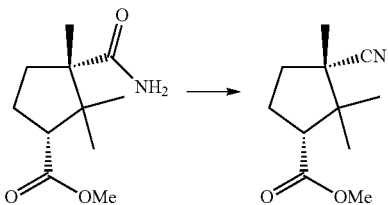

To a solution of (1R,3S)-methyl 3-carbamoyl-2,2,3-trimethylcyclopentane carboxylate (4.49 g, 21.05 mmol) in DMF (35 ml) at room temperature was added cyanuric chloride (2.329 g, 12.63 mmol). The reaction mixture was stirred for 14 hrs. The reaction solution was partitioned between water and ethyl acetate. The ethyl acetate extracts were combined, washed with brine, dried over sodium sulfate, filtered, and concentrated under reduced pressure, yielding (1R,3S)-methyl 3-cyano-2,2,3-trimethylcyclopentanecarboxylate (3.73 g, 19.10 mmol, 91% yield) as a white solid. ESI-MS m/z 218.2 ([M+H]$^+$).

Step 4: (1R,3S)-3-cyano-2,2,3-trimethylcyclopentanecarboxylic acid

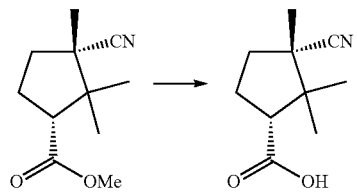

To a solution of (1R,3S)-methyl 3-cyano-2,2,3-trimethyl cyclopentanecarboxylate (3.73 g, 19.10 mmol) in THF (54.6 ml), water (10.92 ml) and methanol (10.92 ml) was added lithium hydroxide monohydrate (1.062 ml, 38.2 mmol). The reaction was stirred at 55° C. for 3 hrs, and then was concentrated under reduced pressure, yielding an oil. The oil was diluted with ethyl acetate and washed with water. The aqueous layer was acidified with 1.0 N HCl, and extracted with ethyl acetate (3×). The organic extracts were combined, dried with sodium sulfate, filtered and concentrated under reduced pressure, yielding (1R,3S)-3-cyano-2,2,3-trimethylcyclopentanecarboxylic acid (2.71 g, 14.95 mmol, 78% yield) as a white solid. ESI-MS: m/z 180.3 [M−H]$^−$.

Step 5: Benzyl (1R,3S)-3-cyano-2,2,3-trimethylcyclopentylcarbamate

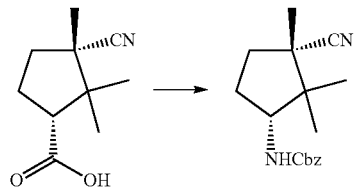 [SMILES: CC1(C)[C@H](C(=O)O)CC[C@]1(C)C#N ; CC1(C)[C@H](NC(=O)OCc2ccccc2)CC[C@]1(C)C#N]

To a solution of (1R,3S)-3-cyano-2,2,3-trimethylcyclopentanecarboxylic acid (2.71 g, 14.95 mmol) in toluene (38.5 ml) and THF (4.27 ml) was added triethylamine (3.13 ml, 22.43 mmol) dropwise, followed by addition of diphenylphosphoryl azide (3.87 ml, 17.94 mmol). The reaction was stirred at room temperature for 1.5 hrs. Benzyl alcohol (1.866 ml, 17.94 mmol) was added. The reaction was heated at 110° C. for 2 hrs. The reaction was cool to room temperature, and diluted with ethyl acetate. The solution was washed successively with saturated sodium bicarbonate, water, and brine. The organic extract was dried with sodium sulfate, filtered, and concentrated under reduced pressure, yielding an orange oil. The oil was dissolved in 50% ethyl acetate/hexanes (5 ml) and loaded directly on a pre-packed silica gel column. The crude product was purified via medium pressure chromatography (0-50% EtOAc-hexanes solvent system over 20 minutes) to afford benzyl (1R,3S)-3-cyano-2,2,3-trimethylcyclopentylcarbamate (2.78 g, 9.71 mmol, 64.9% yield) as a colorless oil. ESI-MS m/z 287.2 ([M+H]$^+$).

Step 6: Benzyl ((1R,3S)-3-(aminomethyl)-2,2,3-trimethyl cyclopentyl)carbamate

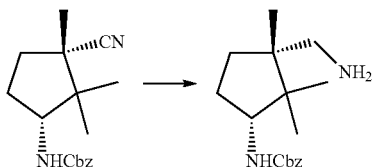 [SMILES: CC1(C)[C@H](NC(=O)OCc2ccccc2)CC[C@]1(C)C#N ; CC1(C)[C@H](NC(=O)OCc2ccccc2)CC[C@]1(C)CN]

To a solution of benzyl ((1R,3S)-3-cyano-2,2,3-trimethylcyclopentyl)carbamate (1.53 g, 5.34 mmol) in THF (10.69 ml) at 0° C. was added a 2 M THF solution of borane-methyl sulfide complex (9.35 ml, 18.70 mmol). The reaction was allowed to warm to room temperature and stirring was continued for 14 hrs. The reaction was cooled to 0° C. and quenched with methanol (8 ml). The reaction solution was partitioned between ethyl acetate and 1.0 N NaOH. The organic extract was washed with brine, dried with sodium sulfate, filtered, and concentrated under reduced pressure, yielding benzyl ((1R,3S)-3-(aminomethyl)-2,2,3-trimethyl cyclopentyl)carbamate (1.39 g, 4.79 mmol, 90% yield) as a colorless oil. ESI-MS m/z 291.3 ([M+H]$^+$).

Step 7: (1R,3S)-1-(benzyloxycarbonylamino)-3-(tert-butoxycarbonylaminomethyl)-2,2,3-trimethylcyclopentane

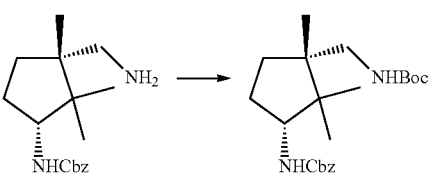 [SMILES: CC1(C)[C@H](NC(=O)OCc2ccccc2)CC[C@]1(C)CN ; CC(C)(C)OC(=O)NC[C@@]1(C)CC[C@@H](NC(=O)OCc2ccccc2)C1(C)C]

To a solution of benzyl ((1R,3S)-3-(aminomethyl)-2,2,3-trimethylcyclo pentyl)carbamate (1.39 g, 4.79 mmol) in THF (31.9 ml) were added triethylamine (2.67 ml, 19.15 mmol) and di-tert-butyl dicarbonate (2.223 ml, 9.57 mmol). The reaction was heated at 50° C. for 14 hrs. The reaction mixture was cooled to room temperature and diluted with ethyl acetate. The solution was washed successively with 0.1 M HCl, water, and saturated sodium chloride; dried with sodium sulfate, filtered, and concentrated under reduced pressure, yielding (1R,3S)-1-(benzyloxycarbonylamino)-3-(tert-butoxycarbonylaminomethyl)-2,2,3-trimethylcyclopentane (1.69 g, 4.33 mmol, 90% yield) as a colorless oil. ESI-MS m/z 391.1 ([M+H]$^+$).

Step 8: Tert-butyl ((1S,3R)-3-amino-1,2,2-trimethyl-cyclopentyl)methylcarbamate

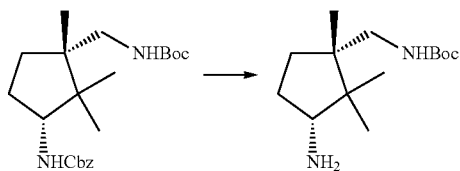 [SMILES: CC(C)(C)OC(=O)NC[C@@]1(C)CC[C@@H](NC(=O)OCc2ccccc2)C1(C)C ; CC(C)(C)OC(=O)NC[C@@]1(C)CC[C@@H](N)C1(C)C]

A pressure bottle was flushed with nitrogen. The bottle was charged with 10% palladium on carbon-Degussa Type (51.2 mg, 0.481 mmol). The catalyst was wet with methanol (1 ml) while under a gentle stream of nitrogen. A premixed methanol (14.6 ml) and 1.0 N hydrochloric acid (1.459 ml) solution of the title compound of Step 7 of Example 345 (940 mg, 2.407 mmol) was added. The suspension was flushed with nitrogen. The reaction evacuated and pressurized to 50 psi with hydrogen at room temperature, and continued stirring for 14 hrs. The reaction was evacuated and backfilled with nitrogen, and filtered over a pad of celite. The filtrate was concentrated under reduced pressure to afford tert-butyl (((1S,3R)-3-amino-1,2,2-trimethylcyclopentyl)methyl)-carbamate (417.4 mg, 1.628 mmol, 67.6% yield) as a colorless oil. ESI-MS m/z 257.3 ([M+H]$^+$).

Step 9: (((1S,3R)-3-((6-bromo-3-carbamoylpyrrolo[1,2-b]pyridazin-4-yl)amino)-1,2,2-trimethylcyclopentyl)methyl)carbamate

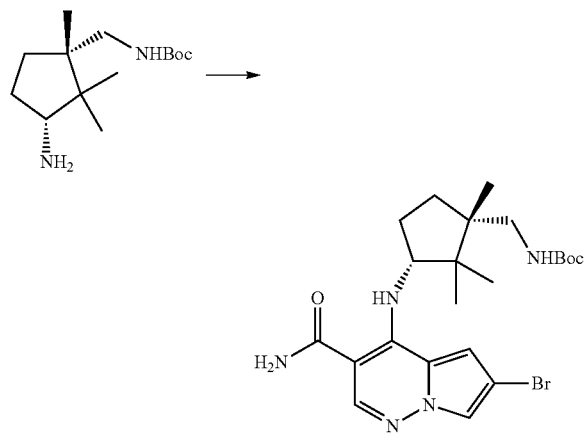

To a solution of tert-butyl (((1S,3R)-3-amino-1,2,2-trimethylcyclopentyl)methyl)carbamate (417 mg, 1.626 mmol) and 6-bromo-4-chloropyrrolo[1,2-b]pyridazine-3-carboxamide (446 mg, 1.626 mmol, from preparation 5) in DMF (4.07 ml) was added DIEA (625 µl, 3.58 mmol). The reaction mixture was heated at 90° C. for 2 hrs. The reaction mixture was cooled to room temperature and diluted with ethyl acetate (100 ml). The ethyl acetate solution was washed with water (3×100 ml), dried with sodium sulfate, filtered, and concentrated under reduced pressure, yielding a light yellow oil. The solid was dissolved in 50% EtOAc/hexanes (5 ml) and loaded directly on a pre-packed silica gel column. The crude product was purified via medium pressure chromatography (10-60% EtOAc-hexanes solvent system over 30 minutes) to afford tert-butyl (((1S,3R)-3-((6-bromo-3-carbamoylpyrrolo[1,2-b]pyridazin-4-yl)amino)-1,2,2-trimethylcyclopentyl)methyl) carbamate (580 mg, 1.173 mmol, 72.1% yield) as a yellow solid. ESI-MS m/z 496.1 ([M+H]$^+$).

Step 10: tert-butyl (((1S,3S)-3-((3-carbamoyl-6-phenylpyrrolo[1,2-b]pyridazin-4-yl)amino)-1,2,2-trimethylcyclopentyl)methyl)carbamate

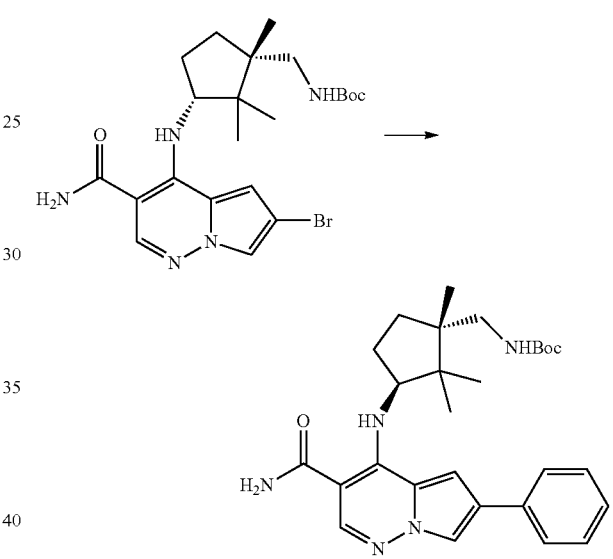

To a vial charged with a solution of phenylboronic acid (215 mg, 1.760 mmol), PdCl$_2$(dppf)-CH$_2$Cl$_2$ adduct (47.9 mg, 0.059 mmol) and tert-butyl (((1S,3R)-3-((6-bromo-3-carbamoylpyrrolo[1,2-b]pyridazin-4-yl)amino)-1,2,2-trimethylcyclopentyl)methyl)carbamate (290 mg, 0.587 mmol) in 1,4-dioxane (3.91 ml) was added a 2 M aqueous solution of potassium phosphate (880 µl, 1.760 mmol). The suspension was purged with nitrogen for 5 minutes. The vial was sealed and heated at 100° C. for 2 hrs. The reaction was diluted with methanol (10 ml), filtered, and concentrated, yielding a dark oil. The oil was taken up in ethyl acetate (50 ml). The solution was washed successively with water and brine. The ethyl acetate extract was dried with sodium sulfate, filtered, and concentrated under reduced pressure, yielding a dark oil. The oil was dissolved in 10% methanol-DCM (5 ml). The crude product mixture was loaded directly on a prepacked silica gel column. The crude product was purified via medium pressure chromatography (0-10% methanol-DCM solvent system over 25 minutes). The desired tert-butyl (((1S,3S)-3-((3-carbamoyl-6-phenylpyrrolo[1,2-b]pyridazin-4-yl)amino)-1,2, 2-trimethyl-cyclopentyl)methyl)carbamate (236 mg, 0.480 mmol, 82% yield) was obtained as a white solid. ESI-MS m/z 492.4 ([M+H]$^+$).

Step 11: 4-(((1S,3S)-3-(aminomethyl)-2,2,3-trimethylcyclopentyl)amino)-6-phenylpyrrolo[1,2-b]pyridazine-3-carboxamide

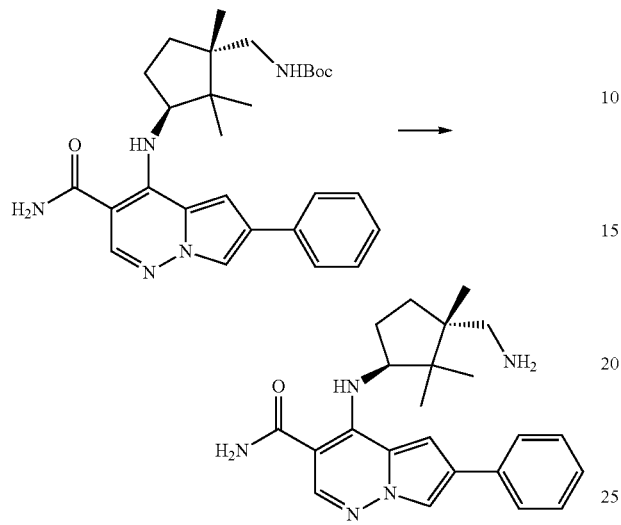

To a solution of tert-butyl (((1S,3S)-3-((3-carbamoyl-6-phenylpyrrolo[1,2-b]pyridazin-4-yl)amino)-1,2,2-trimethylcyclopentyl)methyl)carbamate (236 mg, 0.480 mmol) in dichloromethane (3910 µl) at 0° C. was added trifluoroacetic acid (452 µl, 5.87 mmol. The reaction mixture was allowed to warm to room temperature and stirring was continued for 1 hr. The reaction mixture was concentrated under reduced pressure, yielding a yellow oil. The oil was diluted with ethyl acetate (50 ml) and washed successively with saturated sodium bicarbonate, water, and saturated sodium chloride. The ethyl acetate extract was dried with sodium sulfate, filtered, and concentrated under reduce pressure, yielding 4-(((1S,3S)-3-(aminomethyl)-2,2,3-trimethylcyclopentyl)amino)-6-phenylpyrrolo[1,2-b]pyridazine-3-carboxamide (182 mg, 0.465 mmol, 97% yield) as a tan solid. ESI-MS m/z 392.3 ([M+H]+).

Step 12: Example 345

To a solution of 4-(((1S,3S)-3-(aminomethyl)-2,2,3-trimethylcyclopentyl)amino)-6-phenylpyrrolo[1,2-b]pyridazine-3-carboxamide (25 mg, 0.064 mmol) in dichloromethane (600 µl) were added DIPEA (55.8 µl, 0.319 mmol) and HATU (60.7 mg, 0.160 mmol). The reaction mixture was agitated at 400 rpm on an Innova platform shaker at room temperature for 14 hrs. The reaction mixture was blown down in the Zymark tabletop dryer at 45° C. for 2 hrs. The crude sample was taken up in 1.8 mL of DMF. The product was chromatographed using reverse-phase HPLC (Column: Waters XBridge C18, 19×250 mm, 5-µm). The collected fractions were combined and dried via centrifugal evaporation, yielding the title compound of Example 345 (8.6 mg, 0.0186 mmol, 29% yield). $^1$H NMR (500 MHz, 1:1 mixture of chloroform-d/methanol-d$_4$) δ 8.12 (s, 1H), 7.88 (d, J=2.0 Hz, 1H), 7.63 (s, 2H), 7.42 (t, J=7.9 Hz, 2H), 7.31-7.26 (m, 1H), 7.12 (d, J=2.0 Hz, 1H), 4.35 (br. s., 1H), 4.18 (q, J=6.9 Hz, 1H), 3.43-3.37 (m, 1H), 3.33-3.26 (m, 1H), 2.42 (dtd, J=14.1, 9.3, 5.0 Hz, 1H), 1.95-1.87 (m, 1H), 1.77-1.67 (m, 1H), 1.64-1.56 (m, 1H), 1.40 (d, J=6.9 Hz, 3H), 1.14 (d, J=3.5 Hz, 6H), 1.03 (s, 3H). ESI-MS m/z 464.3 ([M+H]+). HPLC Rf: 2.010 min (Analytical LCMS Method I).

Example 346

4-(((1R,3S)-3-amino-2,2,3-trimethylcyclopentyl)amino)-6-(5-(cyclobutylamino)-1,3,4-oxadiazol-2-yl)pyrrolo[1,2-b]pyridazine-3-carboxamide (346)

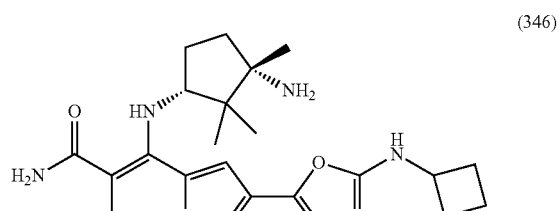

Step 1: ethyl 4-(((1R,3S)-3-amino-2,2,3-trimethylcyclopentyl)amino)-3-carbamoylpyrrolo[1,2-b]pyridazine-6-carboxylate

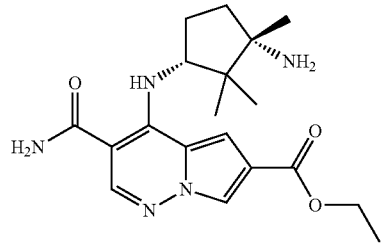 [SMILES: CCOC(=O)c1cc2c(N[C@@H]3CC[C@](C)(N)C3(C)C)c(C(N)=O)cnn2c1]

A solution of ethyl 3-carbamoyl-4-chloropyrrolo[1,2-b]pyridazine-6-carboxylate (6.0 g, 22.42 mmol) and DIPEA (15.66 mL, 90 mmol) in DMF (100 mL) was added (1S,3R)-1,2,2-trimethylcyclopentane-1,3-diamine, 2HCl (4.82 g, 22.42 mmol) which was heated to 85° C. for 16 hrs. The reaction mixture was concentrated to yield ethyl 4-((1R,3S)-3-amino-2,2,3-trimethylcyclopentylamino)-3-carbamoylpyrrolo[1,2-b]pyridazine-6-carboxylate. LC/MS (M+H)+= 374.2.

Step 2: Ethyl 4-(((1R,3 S)-3-((tert-butoxycarbonyl)amino)-2,2,3-trimethylcyclopentyl)amino)-3-carbamoylpyrrolo[1,2-b]pyridazine-6-carboxylate

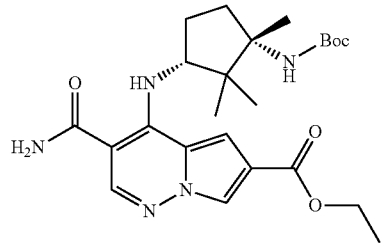 [SMILES: CCOC(=O)c1cc2c(N[C@@H]3CC[C@](C)(NC(=O)OC(C)(C)C)C3(C)C)c(C(N)=O)cnn2c1]

A solution of ethyl 4-((1R,3S)-3-amino-2,2,3-trimethylcyclopentylamino)-3-carbamoylpyrrolo[1,2-b]pyridazine-6-carboxylate (8.37 g, 22.42 mmol) and Et₃N (6.25 mL, 44.8 mmol) in THF (100 mL) was added BOC₂O (10.41 mL, 44.8 mmol), and then the reaction mixture was heated to 70° C. for 16 hrs. The reaction mixture was concentrated to afford ethyl 4-((1R,3S)-3-(tert-butoxycarbonylamino)-2,2,3-trimethylcyclopentylamino)-3-carbamoylpyrrolo[1,2-b]pyridazine-6-carboxylate. LC/MS (M+H)+=474.3.

Step 3: 4-(((1R,3S)-3-((tert-butoxycarbonyl)amino)-2,2,3-trimethylcyclopentyl)amino)-3-carbamoylpyrrolo[1,2-b]pyridazine-6-carboxylic acid

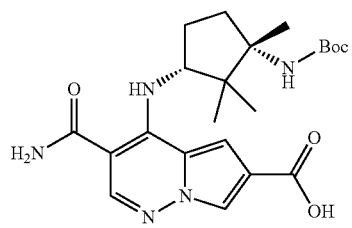 [SMILES: CC(C)(C)OC(=O)N[C@@]1(C)CC[C@@H](Nc2c(C(N)=O)cnn3cc(C(=O)O)cc23)C1(C)C]

A solution of ethyl 4-((1R,3S)-3-(tert-butoxycarbonylamino)-2,2,3-trimethylcyclopentylamino)-3-carbamoylpyrrolo[1,2-b]pyridazine-6-carboxylate (10.62 g, 22.42 mmol) and 1 N NaOH (120 mL) in THF (100 mL) and MeOH (100 mL) was heated to 60° C. for 16 hrs. and then the reaction mixture was added 120 ml of 1 N NaOH solution and heated to 70° C. for 8 hrs. The reaction mixture was added 120 ml of 1 N NaOH solution and heated to 70° C. for 8 hrs which was concentrated to remove THF and MeOH. The aqueous layer was acidified with conc. HCl solution until pH about 4 at 0-5° C. The solid was collected to give 4-(((1R,3S)-3-((tert-butoxycarbonyl)amino)-2,2,3-trimethylcyclopentyl)amino)-3-carbamoylpyrrolo[1,2-b]pyridazine-6-carboxylic acid (11.2 g, 76% yield). HPLC retention time=3.020 min., LC/MS (M+H)+=446.3.

Step 4: tert-butyl ((1S,3R)-3-((3-carbamoyl-6-(hydrazinecarbonyl)pyrrolo[1,2-b]pyridazin-4-yl)amino)-1,2,2-trimethylcyclopentyl)carbamate

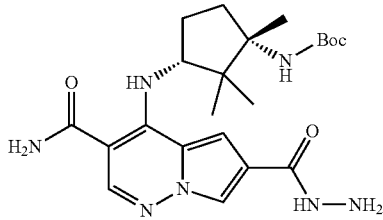 [SMILES: CC(C)(C)OC(=O)N[C@@]1(C)CC[C@@H](Nc2c(C(N)=O)cnn3cc(C(=O)NN)cc23)C1(C)C]

A solution of 4-(((1R,3S)-3-((tert-butoxycarbonyl)amino)-2,2,3-trimethylcyclopentyl)amino)-3-carbamoylpyrrolo[1,2-b]pyridazine-6-carboxylic acid (3.0 g, 6.73 mmol), BOP (3.57 g, 8.08 mmol) and hydrazine (1.057 mL, 33.7 mmol) in DMF (25 mL) was stirred for 30 minutes, and then the reaction mixture was added 350 mL of EtOAc which was washed with 10% LiCl solution (2×100 mL), 100 mL of brine and dried over Na2SO4. Filtration and concentration gave the desired tert-butyl ((1S,3R)-3-((3-carbamoyl-6-(hydrazinecarbonyl)pyrrolo[1,2-b]pyridazin-4-yl)amino)-1,2,2-trimethylcyclopentyl)carbamate (3.29 g, 99% yield). HPLC retention time=2.457 min., LC/MS (M+H)+=460.4.

Step 5: tert-butyl ((1S,3R)-3-((3-carbamoyl-6-(5-(methylthio)-1,3,4-oxadiazol-2-yl)pyrrolo[1,2-b]pyridazin-4-yl)amino)-1,2,2-trimethylcyclopentyl)carbamate

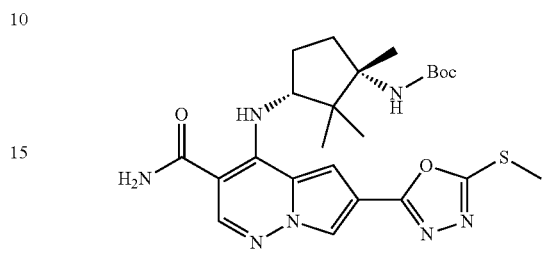

A solution of tert-butyl ((1S,3R)-3-((3-carbamoyl-6-(hydrazinecarbonyl)pyrrolo[1,2-b]pyridazin-4-yl)amino)-1,2,2-trimethylcyclopentyl)carbamate (3.29 g, 7.16 mmol) and 1,1'-thiocarbonyldiimidazole (1.659 g, 9.31 mmol) in THF (25 mL) was heated to 70° C. for 2 hrs. The reaction mixture was added Et₃N (2.59 mL, 18.61 mmol) and MeI (0.582 mL, 9.31 mmol) and stirred at RT for 16 hrs which was concentrated and added 150 mL of water which was stirred for 30 minutes. The solid was collected to give the desired tert-butyl ((1S,3R)-3-((3-carbamoyl-6-(5-(methylthio)-1,3,4-oxadiazol-2-yl)pyrrolo[1,2-b]pyridazin-4-yl)amino)-1,2,2-trimethylcyclopentyl)carbamate (2.35 g, 64% yield). LC/MS (M+H)+=516.3.

Step 6: tert-butyl ((1S,3R)-3-((3-carbamoyl-6-(5-(methylsulfinyl)-1,3,4-oxadiazol-2-yl)pyrrolo[1,2-b]pyridazin-4-yl)amino)-1,2,2-trimethylcyclopentyl)carbamate

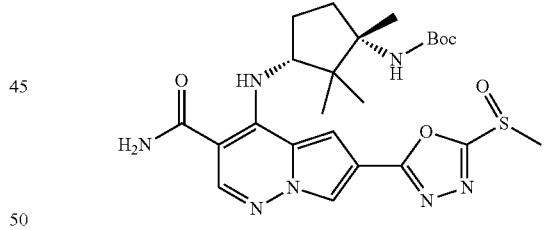

A solution of tert-butyl ((1S,3R)-3-((3-carbamoyl-6-(5-(methylthio)-1,3,4-oxadiazol-2-yl)pyrrolo[1,2-b]pyridazin-4-yl)amino)-1,2,2-trimethylcyclopentyl)carbamate (805 mg, 1.561 mmol) in acetone (16 mL) was added oxone (1.920 g, 3.12 mmol) in water (16.00 mL) and stirred for 2 hrs. The reaction mixture was diluted with 150 mL of EtOAc which was washed with 50 mL of 10% LiCl solution, 50 mL of brine and dried over Na₂SO₄. Filtration and concentration yielded a crude product which was purified on silica gel column with EtOAc to give tert-butyl ((1S,3R)-3-((3-carbamoyl-6-(5-(methylsulfinyl)-1,3,4-oxadiazol-2-yl)pyrrolo[1,2-b]pyridazin-4-yl)amino)-1,2,2-trimethylcyclopentyl)carbamate (186.6 mg, 23% yield). HPLC retention time=2.993 min. LC-MS: M+1 532.3. ¹H-NMR (400 MHz, methanol-d₄) δ 8.30 (d, J=1.8 Hz, 1H), 8.26 (s, 1H), 7.51 (d, J=1.8 Hz, 1H), 4.50 (d, J=9.0 Hz, 1H), 3.31 (s, 3H, under MeOH peak), 2.51-2.32 (m, 1H), 2.29-2.13 (m, 1H), 2.12-1.95 (m, 1H), 1.83-1.63 (m, 1H), 1.49 (s, 3H), 1.46 (s, 9H), 1.13 (s, 3H), 1.09 (s, 3H).

Step 7: Example 346

A mixture of tert-butyl ((1S,3R)-3-((3-carbamoyl-6-(5-(methylsulfinyl)-1,3,4-oxadiazol-2-yl)pyrrolo[1,2-b]pyridazin-4-yl)amino)-1,2,2-trimethylcyclopentyl)carbamate (15 mg, 0.028 mmol) and cyclobutylamine (60.2 mg, 0.846 mmol) was stirred at 23° C. for 1 hr. The reaction mixture was purified on prep HPLC to yield a product which was dissolved in CH$_2$Cl$_2$ (0.2 mL) and added 0.1 mL of TFA and stirred at RT for 30 minutes, and then it was concentrated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give Example 346 (8 mg, 65% yield). HPLC retention time=1.00 min (analytical LCMS Method J). LC-MS: M+1 439.1, $^1$H NMR (500 MHz, 1:1 mixture of chloroform-d/methanol-d$_4$) δ 8.17 (s, 1H), 7.97 (d, J=1.0 Hz, 1H), 7.32 (d, J=1.5 Hz, 1H), 4.50-4.44 (m, 1H), 4.19-4.11 (m, 1H), 2.50-2.38 (m, 3H), 2.10-2.00 (m, 2H), 1.95-1.89 (m, 2H), 1.84-1.72 (m, 3H), 1.31 (s, 3H), 1.12 (s, 3H), 1.02 (s, 3H).

Examples 347 to 351

According to the procedure described for Step 7 of Example 346, Examples 347 to 351 were prepared from tert-butyl ((1S,3R)-3-((3-carbamoyl-6-(5-(methylsulfinyl)-1,3,4-oxadiazol-2-yl)pyrrolo[1,2-b]pyridazin-4-yl)amino)-1,2,2-trimethylcyclopentyl)carbamate (from Step 6 of Example 346). Retention times for all the examples were measured using analytical LCMS Method I.

| Ex # | Structure | HPLC or LCMS Rt (minutes) | LCMS [m/z (M + H)] |
|---|---|---|---|
| 347 | 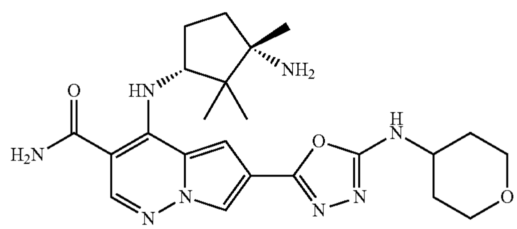 [SMILES: CC1(C)[C@H](Nc2c(C(N)=O)cnn3cc(-c4nnc(NC5CCOCC5)o4)cc23)CC[C@]1(C)N] | 0.77 | 469.1 |
| 348 | 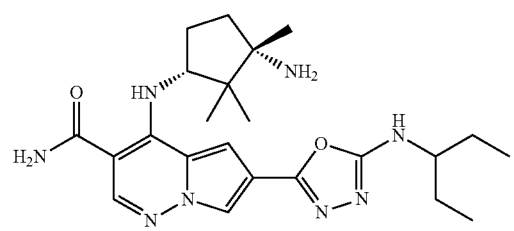 [SMILES: CCC(CC)Nc1nnc(-c2cc3c(N[C@@H]4CC[C@](C)(N)C4(C)C)c(C(N)=O)cnn3c2)o1] | 1.03 | 455.1 |
| 349 | 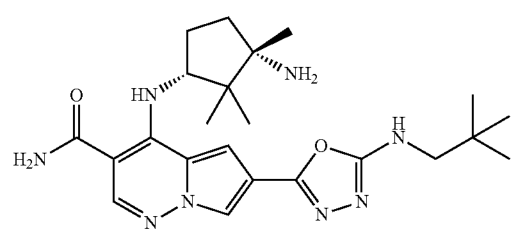 [SMILES: CC(C)(C)CNc1nnc(-c2cc3c(N[C@@H]4CC[C@](C)(N)C4(C)C)c(C(N)=O)cnn3c2)o1] | 1.06 | 455.1 |
| 350 | 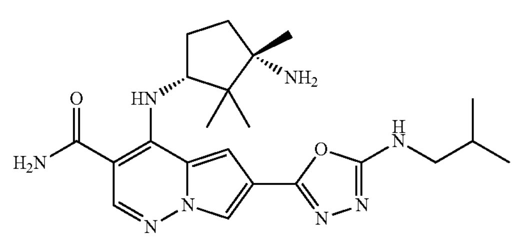 [SMILES: CC(C)CNc1nnc(-c2cc3c(N[C@@H]4CC[C@](C)(N)C4(C)C)c(C(N)=O)cnn3c2)o1] | 0.92 | 441.1 |

| Ex # | Structure | HPLC or LCMS Rt (minutes) | LCMS [m/z (M + H)] |
|---|---|---|---|
| 351 | 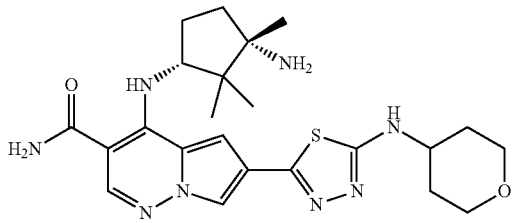 | 1.00 | 453.1 |

Example 352

4-(((1R,3S)-3-amino-2,2,3-trimethylcyclopentyl)amino)-6-(5-((tetrahydro-2H-pyran-4-yl)amino)-1,3,4-thiadiazol-2-yl)pyrrolo[1,2-b]pyridazine-3-carboxamide (352)

Step 1: Methyl hydrazinecarbodithioate

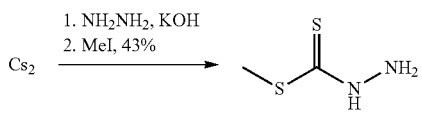

To a solution of KOH (0.759 g, 13.53 mmol) and hydrazine (0.437 mL, 13.92 mmol) in EtOH (3 mL) at 0° C. was added $CS_2$ (0.792 mL, 13.13 mmol) dropwise. After addition, the reaction mixture was stirred at 0° C. for 10 minutes which was added 6 mL of $Et_2O$ and stirred for 30 minutes at 0° C. The clear solution was decanted. The yellow residue was dissolved in 3 mL of water which was added methyl iodide (0.821 mL, 13.13 mmol) at 0° C. and stirred for 2 hrs. The white solid was collected to give methyl hydrazinecarbodithioate (703 mg, 43% yield). $^1$H NMR (400 MHz, chloroform-d) δ 2.70 (br. s., 3H), HPLC retention time: 0.418 min (analytical HPLC Method F).

Step 2: methyl 2-(4-(((1R,3 S)-3-((tert-butoxycarbonyl)amino)-2,2,3-trimethylcyclopentyl)amino)-3-carbamoylpyrrolo[1,2-b]pyridazine-6-carbonyl)hydrazinecarbodithioate

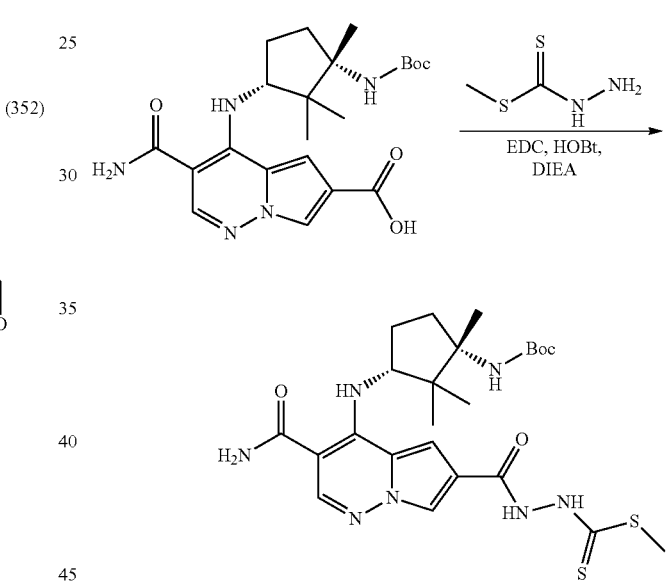

To a solution of 4-((1R,3S)-3-(tert-butoxycarbonylamino)-2,2,3-trimethylcyclopentylamino)-3-carbamoylpyrrolo[1,2-b]pyridazine-6-carboxylic acid (500 mg, 1.122 mmol, from Step 3 of Example 346). HOBT (206 mg, 1.347 mmol) and DIEA (0.490 mL, 2.81 mmol) in DMF (4 mL) were added EDCI (280 mg, 1.459 mmol) and methyl hydrazinecarbodithioate (144 mg, 1.178 mmol) at 23° C. The reaction mixture was stirred for 1.5 hrs followed by the addition of 25 mL of water. The solids were removed. The water phase was extracted with EtOAc (2×30 mL). The combined organic phase was washed with 10% LiCl solution (2×20 mL), 20 mL of brine and dried over $Na_2SO_4$. Filtration and concentration gave methyl 2-(4-(((1R,3S)-3-((tert-butoxycarbonyl)amino)-2,2,3-trimethylcyclopentyl)amino)-3-carbamoylpyrrolo[1,2-b]pyridazine-6-carbonyl)hydrazinecarbodithioate (466.5 mg, 76% yield). MS (ES+) m/z: 550.08 (M+H); HPLC retention time: 3.168 min (analytical HPLC Method F).

Step 3: 4-(((1R,3S)-3-amino-2,2,3-trimethylcyclopentyl)amino)-6-(5-(methylthio)-1,3,4-thiadiazol-2-yl)pyrrolo[1,2-b]pyridazine-3-carboxamide

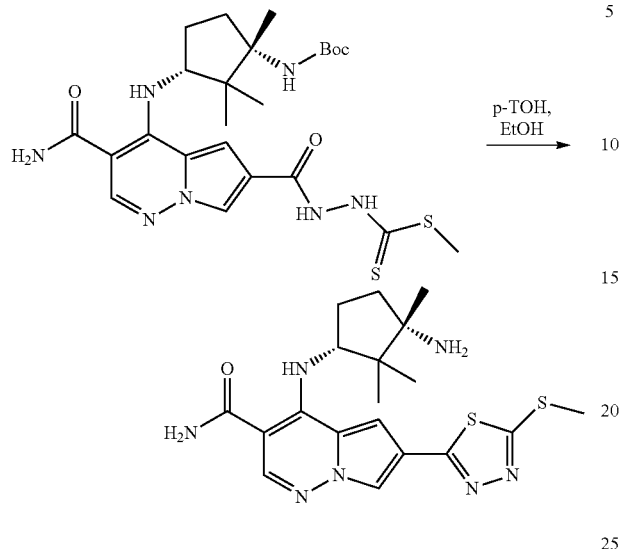

A solution of methyl 2-(4-((1R,3S)-3-(tert-butoxycarbonylamino)-2,2,3-trimethylcyclopentylamino)-3-carbamoylpyrrolo[1,2-b]pyridazine-6-carbonyl)hydrazinecarbodithioate (466.5 mg, 0.849 mmol) and p-toluenesulfonic acid monohydrate (404 mg, 2.122 mmol) in ethanol (4 mL) was heated to 120° C. for 50 minutes. The reaction mixture was concentrated to yield 4-(((1R,3S)-3-amino-2,2,3-trimethylcyclopentyl)amino)-6-(5-(methylthio)-1,3,4-thiadiazol-2-yl)pyrrolo[1,2-b]pyridazine-3-carboxamide (763 mg, 94% yield). MS (ES+) m/z: 432.08 (M+H); HPLC retention time: 2.493 min (analytical HPLC Method F).

Step 4: tert-butyl ((1S,3R)-3-((3-carbamoyl-6-(5-(methylthio)-1,3,4-thiadiazol-2-yl)pyrrolo[1,2-b]pyridazin-4-yl)amino)-1,2,2-trimethylcyclopentyl)carbamate

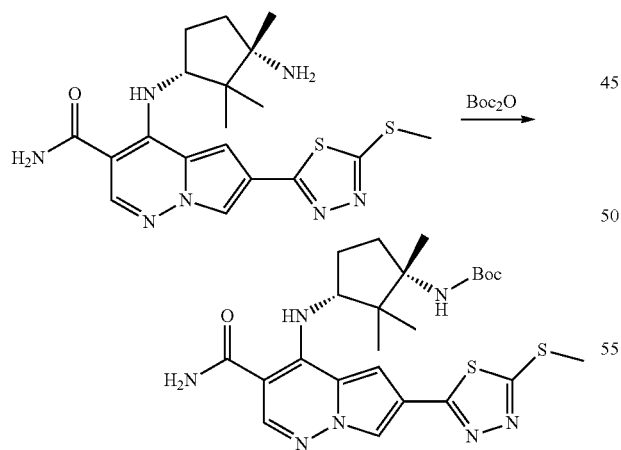

A solution of 4-(((1R,3S)-3-amino-2,2,3-trimethylcyclopentyl)amino)-6-(5-(methylthio)-1,3,4-thiadiazol-2-yl)pyrrolo[1,2-b]pyridazine-3-carboxamide, HCl (267 mg, 0.570 mmol), BOC$_2$O (0.265 mL, 1.141 mmol) and Et$_3$N (0.239 mL, 1.711 mmol) in THF (5 mL) was heated to 23° C. for 16 hrs. The reaction mixture was concentrated to yield a crude product which was diluted with 50 mL of EtOAc. The organic was washed with 10 mL of 10% LiCl solution, 10 mL of brine and dried over Na$_2$SO$_4$. Filtration and concentration yielded tert-butyl ((1S,3R)-3-((3-carbamoyl-6-(5-(methylthio)-1,3,4-thiadiazol-2-yl)pyrrolo[1,2-b]pyridazin-4-yl)amino)-1,2,2-trimethylcyclopentyl)carbamate (306.2 mg, 92% yield). MS (ES+) m/z: 532.17 (M+H); HPLC retention time: 3.583 min (analytical HPLC Method F).

Step 5: tert-butyl ((1S,3R)-3-((3-carbamoyl-6-(5-(methylsulfinyl)-1,3,4-thiadiazol-2-yl)pyrrolo[1,2-b]pyridazin-4-yl)amino)-1,2,2-trimethylcyclopentyl)carbamate

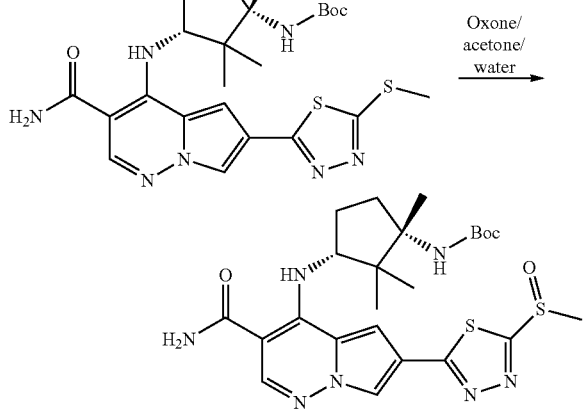

A solution of tert-butyl ((1S,3R)-3-((3-carbamoyl-6-(5-(methylthio)-1,3,4-thiadiazol-2-yl)pyrrolo[1,2-b]pyridazin-4-yl)amino)-1,2,2-trimethylcyclopentyl)carbamate (306.2 mg, 0.576 mmol) and oxone (531 mg, 0.864 mmol) in acetone (3 mL) and water (3 mL) was stirred at RT for 4 hrs. The reaction mixture was diluted with 30 mL of water which was stirred for 30 minutes. The solid was collected to give the desired tert-butyl ((1S,3R)-3-((3-carbamoyl-6-(5-(methylsulfinyl)-1,3,4-thiadiazol-2-yl)pyrrolo[1,2-b]pyridazin-4-yl)amino)-1,2,2-trimethylcyclopentyl)carbamate (264.5 mg, 77% yield). MS (ES+) m/z: 548.08 (M+H); HPLC retention time: 3.296 min (analytical HPLC Method F).

Step 6: 4-(((1R,3S)-3-amino-2,2,3-trimethylcyclopentyl)amino)-6-(5-((tetrahydro-2H-pyran-4-yl)amino)-1,3,4-thiadiazol-2-yl)pyrrolo[1,2-b]pyridazine-3-carboxamide

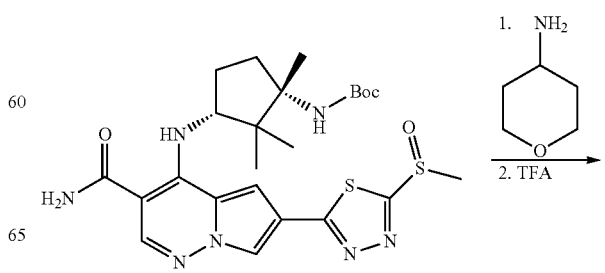

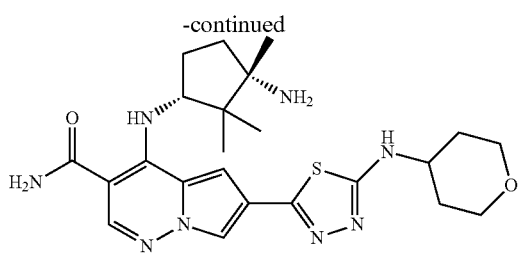

A mixture of tert-butyl ((1S,3R)-3-((3-carbamoyl-6-(5-(methylsulfinyl)-1,3,4-thiadiazol-2-yl)pyrrolo[1,2-b]pyridazin-4-yl)amino)-1,2,2-trimethylcyclopentyl)carbamate (30 mg, 0.055 mmol) and tetrahydro-2H-pyran-4-amine (166 mg, 1.643 mmol) was heated to 120° C. for 16 hrs. The reaction mixture was concentrated and redissolved in $CH_2Cl_2$ (0.2 mL) which was added 0.1 mL of TFA and stirred at RT for 16 hrs, and then concentrated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-45% B over 25 minutes, then a 15-minute hold at 45% B; Flow: 20 mL/min. Fractions containing the desired product were combined and dried via centrifugal evaporation to give Example 352 (3.8 mg, 14% yield). $^1$H NMR (500 MHz, 1:1 mixture of chloroform-d/methanol-$d_4$) δ 8.14 (s, 1H), 7.86 (d, J=1.5 Hz, 1H), 7.30 (d, J=1.5 Hz, 1H), 4.51 (s, 1H), 4.01 (dt, J=11.8, 3.3 Hz, 2H), 3.92-3.84 (m, 1H), 3.57 (td, J=11.4, 2.0 Hz, 2H), 2.46 (dtd, J=14.1, 9.1, 5.0 Hz, 1H), 2.12 (dd, J=12.4, 2.0 Hz, 2H), 1.98-1.88 (m, 2H), 1.84-1.72 (m, 1H), 1.68-1.58 (m, 2H), 1.34 (s, 3H), 1.15-1.11 (m, 3H), 1.03 (s, 3H); MS (ES+) m/z: 485.24 (M+H); HPLC retention time: 0.81 min (analytical LCMS Method I).

Example 353

4-(((1R,3S)-3-amino-2,2,3-trimethylcyclopentyl)amino)-6-(2-methyl-2H-tetrazol-5-yl)pyrrolo[1,2-b]pyridazine-3-carboxamide (353)

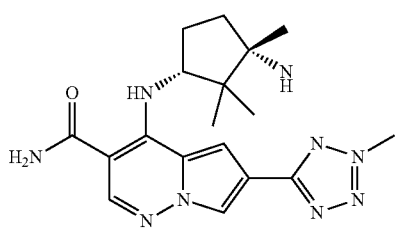

Step 1: 6-cyano-4-(ethylthio)pyrrolo[1,2-b]pyridazine-3-carboxamide

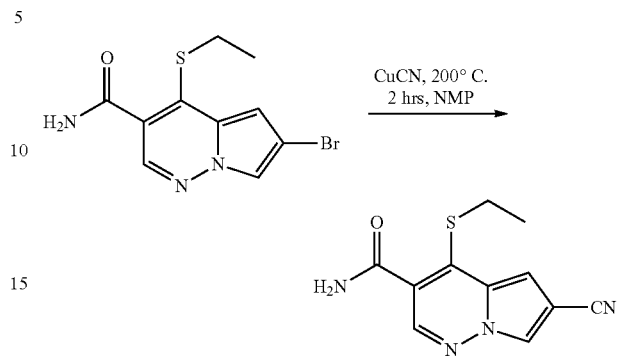

A solution of 6-bromo-4-(ethylthio)pyrrolo[1,2-b]pyridazine-3-carboxamide (200 mg, 0.666 mmol) and copper(I) cyanide (119 mg, 1.333 mmol) in NMP (3 mL) was heated to 180° C. for 1.5 hrs, and then 200° C. for 1.5 hrs under microwave oven (CEM). To the reaction mixture was added 50 mL of EtOAc. The mixture was washed with 30 mL of 10% LiCl solution, 30 mL of saturated $NH_4Cl$ solution, and 30 mL of brine and dried over $Na_2SO_4$. Filtration and concentration yielded 6-cyano-4-(ethylthio)pyrrolo[1,2-b]pyridazine-3-carboxamide (140 mg, 77% yield). MS (ES+) m/z: 247.08 (M+H); HPLC retention time: 1.902 min (analytical HPLC Method F).

Step 2: 4-(Ethylthio)-6-(1H-tetrazol-5-yl)pyrrolo[1,2-b]pyridazine-3-carboxamide

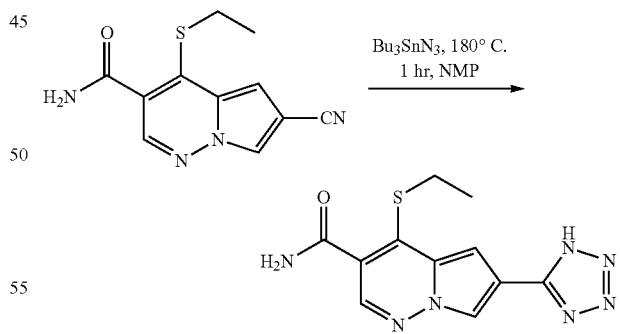

A solution of 6-cyano-4-(ethylthio)pyrrolo[1,2-b]pyridazine-3-carboxamide (140 mg, 0.568 mmol) and azidotributyltin (0.187 mL, 0.682 mmol) in NMP (2.0 mL) was heated to 180° C. for 60 minutes under microwave oven (CEM). The reaction mixture was taken to the next step without purification. MS (ES+) m/z: 290.08 (M+H).

Step 3: 4-(ethylthio)-6-(2-methyl-2H-tetrazol-5-yl) pyrrolo[1,2-b]pyridazine-3-carboxamide

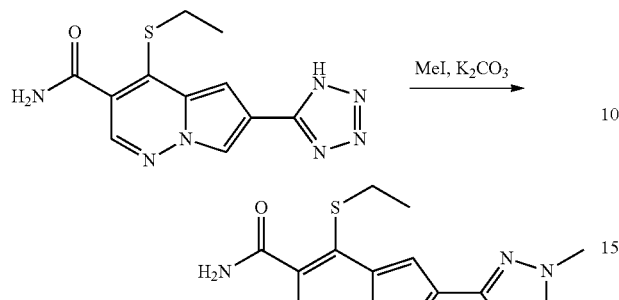

To a solution of 4-(ethylthio)-6-(1H-tetrazol-5-yl)pyrrolo[1,2-b]pyridazine-3-carboxamide (164 mg, 0.567 mmol) in NMP (2.0 mL) were added $K_2CO_3$ (196 mg, 1.417 mmol) and MeI (0.043 mL, 0.680 mmol). The solution was stirred at 23° C. for 1 hr. To the reaction mixture was added 30 mL of EtOAc which was washed with 10% LiCl solution (2×10 mL), 10 mL of brine and dried over $Na_2SO_4$. Filtration and concentration yielded a crude product which was purified on silica gel column with EtOAc to afford the desired product (64 mg, 35% yield). MS (ES+) m/z: 304.08 (M+H); HPLC retention time: 2.180 min (analytical HPLC Method F).

Step 4: 4-(ethylsulfinyl)-6-(2-methyl-2H-tetrazol-5-yl)pyrrolo[1,2-b]pyridazine-3-carboxamide

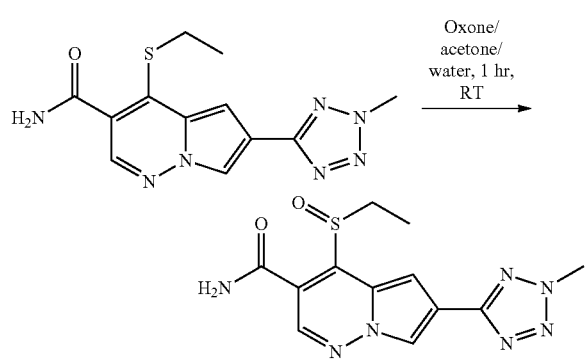

To a solution of 4-(ethylthio)-6-(2-methyl-2H-tetrazol-5-yl)pyrrolo[1,2-b]pyridazine-3-carboxamide (64 mg, 0.211 mmol) in acetone (1.0 mL) was added oxone (285 mg, 0.464 mmol) in water (1.0 mL). The reaction mixture was stirred at 23° C. for 1 hr. The reaction mixture was added 5 ml of water and stirred for 10 minutes. The solid was collected as the desired product (57.4 mg, 85% yield). $^1$H NMR (400 MHz, methanol-$d_4$) δ 8.59 (d, J=1.8 Hz, 1H), 8.52 (s, 1H), 8.27 (d, J=1.5 Hz, 1H), 4.46 (s, 3H), 3.55-3.42 (m, 2H), 1.53 (s, 3H). MS (ES+) m/z: 320.10 (M+H); HPLC retention time: 2.007 min (analytical HPLC Method F).

Step 5: 4-(((1R,3S)-3-amino-2,2,3-trimethylcyclopentyl)amino)-6-(2-methyl-2H-tetrazol-5-yl)pyrrolo[1,2-b]pyridazine-3-carboxamide

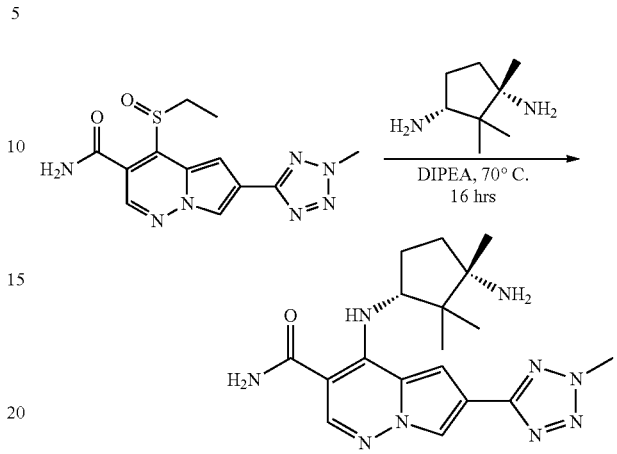

A solution of 4-(ethylsulfinyl)-6-(2-methyl-2H-tetrazol-5-yl)pyrrolo[1,2-b]pyridazine-3-carboxamide (25 mg, 0.078 mmol), (1S,3R)-1,2,2-trimethylcyclopentane-1,3-diamine, 2HCl (25.3 mg, 0.117 mmol) and DIPEA (0.062 mL, 0.352 mmol) in NMP (0.5 mL) was stirred at 75° C. for 16 hrs. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 0-40% B over 25 minutes, then a 15-minute hold at 40% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 0-40% B over 25 minutes, then a 15-minute hold at 40% B; Flow: 20 mL/min. Fractions containing the desired product were combined and dried via centrifugal evaporation to give Example 353 (7.1 mg, 22% yield). $^1$H NMR (500 MHz, 1:1 mixture of chloroform-d/methanol-$d_4$) δ 8.20 (s, 1H), 8.15 (d, J=1.5 Hz, 1H), 7.45-7.41 (m, 1H), 4.57 (t, J=8.7 Hz, 1H), 4.45-4.41 (m, 3H), 2.55-2.44 (m, 1H), 2.08-1.92 (m, 2H), 1.87-1.75 (m, 1H), 1.43-1.37 (m, 3H), 1.18-1.14 (m, 3H), 1.08-1.03 (m, 3H), MS (ES+) m/z: 384.22 (M+H); HPLC retention time: 0.85 min (analytical LCMS Method J).

What is claimed is:
1. A compound of Formula (II):

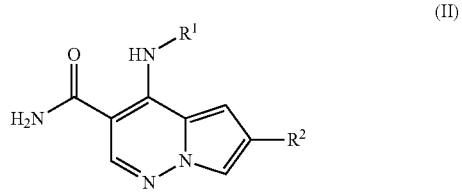

or stereoisomers or salts thereof; wherein:
R¹ is $C_{3-6}$ cycloalkyl or adamantanyl, each substituted with 1, 2, 3, or 4 substituents independently selected from F, Cl, —OH, —CN, $C_{1-4}$ alkyl, =O, —O($C_{1-6}$ alkyl), —NH₂, —NH($C_{1-4}$ alkyl), —NH(benzyl), —N($C_{1-4}$ alkyl)₂, —NHC(O)($C_{1-4}$ alkyl), —NHC(O)O($C_{1-4}$ alkyl), —NHS(O)₂($C_{1-4}$ alkyl), —NHC(O)NH($C_{1-4}$ alkyl), —NHC(O)NH($C_{1-4}$ alkyl), —NHC(O)NH(phenyl), —C(O)NH₂, and/or —CH₂NHC(O)CH(OH)($C_{1-4}$ alkyl);

R² is -L-R$^x$ or R$^y$;

L is —NHC(O)—, —NHS(O)₂—, —NHC(O)NH—, —NHC(O)O—, or —C(O)NH—;

R$^x$ is $C_{1-6}$ alkyl; benzyl; or phenyl substituted with zero or 1 substituent selected from F, Cl, and —O(Cl$_{1-4}$ alkyl); and R$^y$ is:
a) phenyl substituted with zero, 1, or 2 substituents independently selected from F, Cl, $C_{1-6}$ alkyl, —NH₂, —N($C_{1-4}$ alkyl)₂, —O($C_{1-4}$ alkyl), $C_{1-6}$ hydroxyalkyl, $C_{1-4}$ aminoalkyl, —CN, —C(O)($C_{1-4}$ alkyl), —CH₂NHC(O)($C_{1-4}$ alkyl), —C(O)OH, —C(O)O($C_{1-4}$ alkyl), —C(O)NH₂, —C(O)NH($C_{1-4}$ alkyl), —C(O)N($C_{1-4}$ alkyl)₂, —C(O)NH($C_{3-6}$ cycloalkyl), —C(O)NH ($C_{3-6}$ cycloalkyl), —S(O)₂($C_{1-4}$ alkyl), —NHC(O)($C_{1-4}$ alkyl), —NHC(O)O($C_{1-4}$ alkyl), —NHC(O)CH₂CH₂O ($C_{1-4}$ alkyl), —NHS(O)₂($C_{1-4}$ alkyl), —O($C_{1-4}$ alkyl), —O($C_{1-4}$ fluoroalkyl), —S(O)₂NH₂, —C(O)(morpholinyl), —CH₂(morpholinyl), phenyl, pyrazolyl, tetrazolyl, and/or morpholinyl;
b) azetidinonyl, pyrrolidinyl, pyrrolidinonyl, 1H-pyrrol-2 (5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1, or 2 substituents independently selected from —OH, $C_{1-4}$ alkyl, —O($C_{1-4}$ alkyl), —C(O)($C_{1-4}$ alkyl), phenyl, and/or benzyl; or
c) pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, $C_{1-4}$ alkyl, $C_{1-3}$ fluoroalkyl, —NH₂, —CN, $C_{1-4}$ hydroxyalkyl, —O($C_{1-4}$ alkyl), —O(phenyl), —O(benzyl), —C(O)OH, —C(O)O($C_{1-4}$ alkyl), —C(O)NH₂, —C(O)NH($C_{1-4}$ alkyl), —NHC(O)($C_{1-4}$ alkyl), phenyl, benzyl, fluorophenyl, chlorophenyl, —NH($C_{3-6}$ cycloalkyl), —NH(tetrahydropyranyl), —NH($C_{1-6}$ alkyl), —NH(CH₂—$C_{3-6}$ cycloalkyl), —NH (CH(CH₃)—$C_{3-6}$ cycloalkyl), and/or —NH(tetrahydropyranyl).

2. The compound according to claim 1, wherein:
R¹ is $C_{5-6}$ cycloalkyl or adamantanyl, each substituted with 1, 2, 3, or 4 substituents independently selected from F, —OH, —CN, —CH₃, =O, —OCH₃, —OCH(CH₃)₂, —NH₂, —NH($C_{1-2}$ alkyl), —NH(benzyl), —N(CH₃)₂, —NHC(O)($C_{1-2}$ alkyl), —NHC(O)O(t-butyl), —NHS (O)₂CH₃, —NHC(O)NH(CH₃), —NHC(O)NH(t-butyl), —NHC(O)NH(phenyl), —C(O)NH₂, and/or —CH₂NHC(O)CH(OH)CH₃;

R$^x$ is $C_{1-4}$ alkyl; benzyl; or phenyl substituted with zero or 1 substituent selected from F, Cl, and —O($C_{1-2}$ alkyl); and R$^y$ is:
a) phenyl substituted with zero, 1, or 2 substituents independently selected from F, Cl, $C_{1-4}$ alkyl, —NH₂, —N($C_{1-3}$ alkyl)₂, —O($C_{1-3}$ alkyl), $C_{1-4}$ hydroxyalkyl, $C_{1-3}$ aminoalkyl, —CN, —C(O)($C_{1-3}$ alkyl), —CH₂NHC(O)($C_{1-3}$ alkyl), —C(O)OH, —C(O)O($C_{1-3}$ alkyl), —C(O)NH₂, —C(O)NH($C_{1-4}$ alkyl), —C(O)N ($C_{1-3}$ alkyl)₂, —C(O)NH($C_{3-5}$ cycloalkyl), —C(O)NH ($C_{3-6}$ cycloalkyl), —S(O)₂($C_{1-3}$ alkyl), —NHC(O)($C_{1-4}$ alkyl), —NHC(O)O($C_{1-4}$ alkyl), —NHC(O)CH₂CH₂O ($C_{1-3}$ alkyl), —NHS(O)₂($C_{1-3}$ alkyl), —O($C_{1-4}$ alkyl), —O($C_{1-3}$ fluoroalkyl), —S(O)₂NH₂, —C(O)(morpholinyl), —CH₂(morpholinyl), phenyl, pyrazolyl, tetrazolyl, and/or morpholinyl;
b) azetidinonyl, pyrrolidinyl, pyrrolidinonyl, 1H-pyrrol-2 (5H)-onyl, 1H-pyrrol-2(5H)-onyl, oxazolidinonyl, piperazinyl, piperazinonyl, morpholinyl, morpholinonyl, 1H-pyrrol-2(5H)-onyl, or imidazolidinonyl, each substituted with zero, 1, or 2 substituents independently selected from —OH, —CH₃, —OCH₃, —C(O)CH₃, and/or benzyl; or
c) pyrrolyl, pyrazolyl, thiazolyl, isoxazolyl, oxadiazolyl, thiadiazolyl, tetrazolyl, pyridinyl, pyridinonyl, pyrimidinyl, pyrazinyl, dihydropyridinyl, indolyl, dihydroisoquinolinonyl, imidazo[1,2-a]pyridinyl, 3,4-dihydro-2H-benzo[b][1,4]oxazinyl, indazolyl, benzothiazolyl, isoquinolinyl, quinolinyl, or quinoxalinyl, each substituted with zero, 1, or 2 substituents independently selected from F, Cl, $C_{1-3}$ alkyl, —CF₃, —NH₂, —CN, $C_{1-4}$ hydroxyalkyl, —O($C_{1-3}$ alkyl), —O(benzyl), —C(O)OH, —C(O)O($C_{1-4}$ alkyl), —C(O)NH₂, —C(O)NH($C_{1-4}$ alkyl), —NHC(O)($C_{1-4}$ alkyl), phenyl, benzyl, chlorophenyl, —NH(cyclobutyl), —NH(tetrahydropyranyl), —NH($C_{4-5}$ alkyl), —NH(CH₂-cyclopropyl), —NH(CH(CH₃)-cyclopropyl), and/or —NH(tetrahydropyranyl);

or stereoisomers or salts thereof.

3. The compound according to claim 2, wherein:
R¹ is:
a) cyclopentyl substituted with 1, 2, 3, or 4 substituents independently selected from: F, —OH, —CN, —CH₃, =O, —OCH₃, —OCH(CH₃)₂, —NH₂, —NH($C_{1-2}$ alkyl), —NH(benzyl), —N(CH₃)₂, —NHC(O)($C_{1-2}$ alkyl), —NHC(O)O(t-butyl), —NHS(O)₂CH₃, —NHC (O)NH(CH₃), —NHC(O)NH(t-butyl), —NHC(O)NH (phenyl), —C(O)NH₂, and/or —CH₂NHC(O)CH(OH) CH₃,
b) cyclohexyl substituted with 2 substituents independently selected from methyl and —OH; or
c) adamantanyl substituted with 1 or 2 —OH;

R$^x$ is $C_{1-4}$ alkyl; benzyl; or phenyl substituted with zero or 1 substituent selected from Cl and —OCH₃; and R$^y$ is:
a) phenyl substituted with zero, 1, or 2 substituents independently selected from F, Cl, $C_{1-3}$ alkyl, —NH₂, —N(CH₃)₂, —OCH₃, —CH₂OH, —CH(CH₃)₂OH, —CH₂NH₂, —CN, —C(O)CH₃, —CH₂NHC(O)CH₃, —C(O)OH, —C(O)OCH₃, —C(O)NH₂, —C(O)N (CH₃)₂, —C(O)NH($C_{1-4}$ alkyl), —C(O)NH(cyclopropyl), —C(O)NH(cyclopentyl), —S(O)₂CH₃, —NHC (O)CH₃, —NHC(O)OCH₃, —NHC(O)CH₂CH₂OCH₃, —NHS(O)₂CH₃, —O(ethyl), —OCHF₂, —S(O)₂NH₂, —C(O)(morpholinyl), —CH₂(morpholinyl), phenyl, pyrazolyl, tetrazolyl, and/or morpholinyl;
b) azetidinonyl; pyrrolidinyl; pyrrolidinonyl; pyrrolidinonyl substituted with —OH; 3,4-dimethyl-1H-pyrrol-2(5H)-onyl; 4-methoxy-1H-pyrrol-2(5H)-onyl; oxazolidinonyl; piperazinyl; piperazinonyl substituted with benzyl; morpholinyl; morpholinonyl; 3-methyl-1H-pyrrol-2(5H)-onyl; or imidazolidinonyl substituted with zero or 1 substituent selected from —CH₃ and —C(O)CH₃;

c) pyrrolyl substituted with —C(O)OH or —C(O)OCH₃; pyrazolyl substituted with zero or 1 substituent selected from methyl, —CF₃, phenyl, benzyl, and chlorophenyl; thiazolyl substituted with 1 or 2 methyl groups; isoxazolyl substituted with two methyl groups; oxadiazolyl substituted with methyl, —NH(cyclobutyl), —NH(tetrahydropyranyl), —NH(C₄₋₅ alkyl), or —NH(CH(CH₃)-cyclopropyl); thiadiazolyl substituted with zero or 1 substituent selected from —CH₃ and —NH(tetrahydropyranyl); or tetrazolyl substituted with methyl;

d) pyridinyl substituted with zero, 1, or 2 substituents independently selected from F, Cl, —CH₃, —NH₂, —CF₃, —CN, —OCH₃, —OCH(CH₃)₂, —C(O)NH₂, —C(O)NH(CH₃), —NHC(O)CH₃, and/or —O(benzyl); or pyridinonyl substituted with hydroxybutyl; or e) pyrimidinyl substituted with zero or 1 substituent selected from —NH₂, pyrazinyl, dihydropyridinyl substituted with —C(O)O(t-butyl), dihydroisoquinolinonyl substituted with —OCH₃, 4-methyl-3,4-dihydro-2H-benzo[b][1,4]oxazinyl, 1-methyl-1H-indolyl, imidazo[1,2-a]pyridinyl, indolyl, indazolyl, benzothiazolyl, isoquinolinyl, quinolinyl, and quinoxalinyl;

or stereoisomers or salts thereof.

4. The compound according to claim 3, or stereoisomers or salts thereof, wherein:

R¹ is:

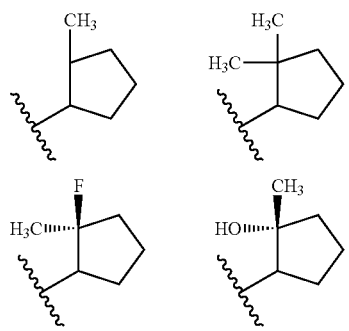
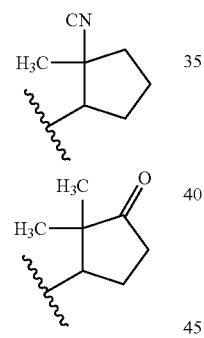
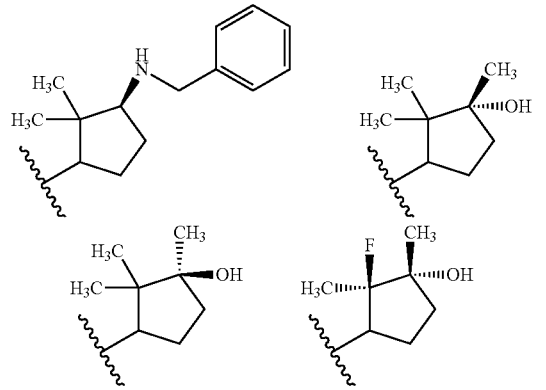
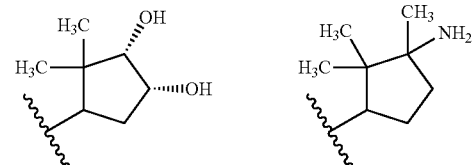
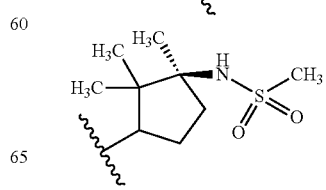
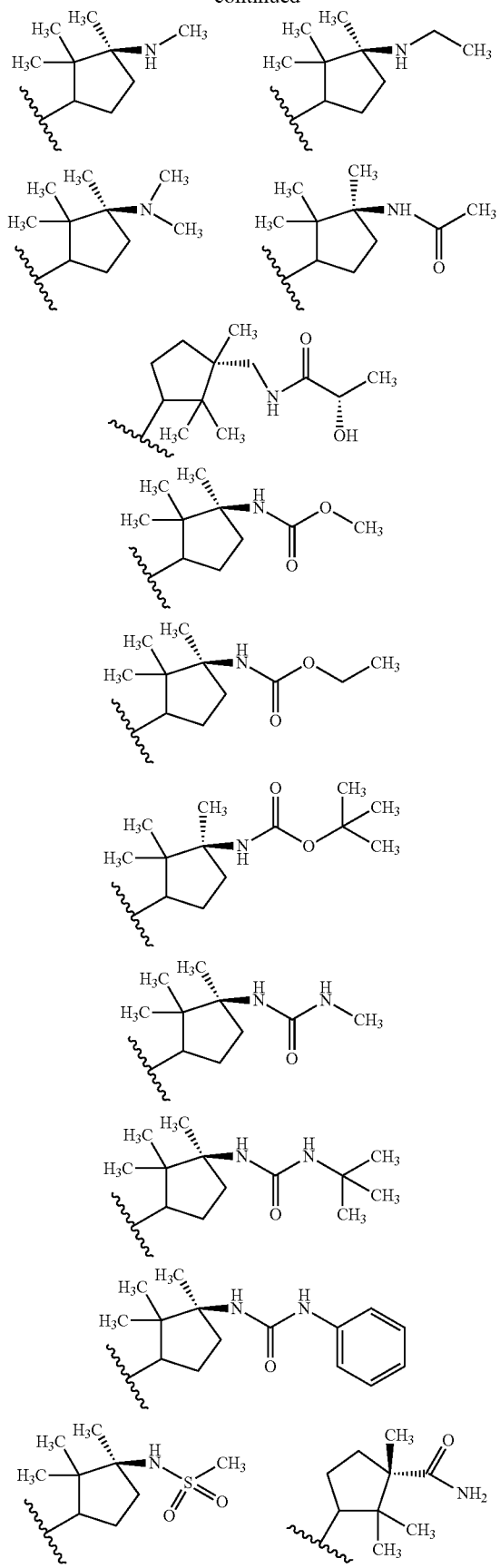

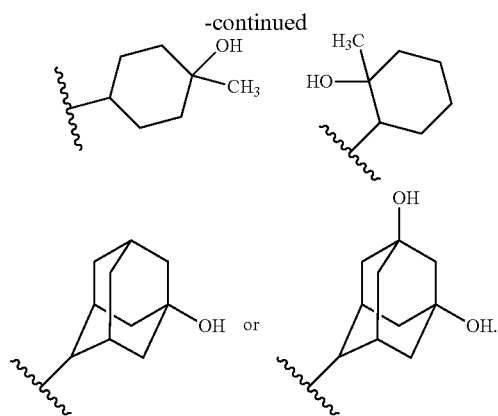

5. The compound according to claim 4 or stereoisomers or salts thereof, wherein:

$R^1$ is:

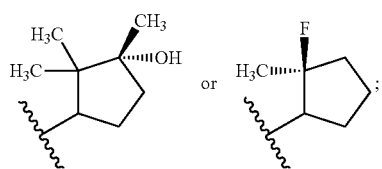

$R^2$ is -L-$R^x$;

L is —NHC(O)—, —NHS(O)$_2$—, —NHC(O)NH—, —NHC(O)O—, or —C(O)NH—; and $R^x$ is $C_{1-4}$ alkyl, benzyl, or phenyl substituted with zero or 1 substituent selected from Cl and —OCH$_3$.

6. The compound according to claim 4, or stereoisomers or salts thereof, wherein:

$R^2$ is $R^y$; and $R^y$ is phenyl substituted with zero, 1, or 2 substituents independently selected from F, Cl, $C_{1-3}$ alkyl, —NH$_2$, —N(CH$_3$)$_2$, —OCH$_3$, —CH$_2$OH, —CH(CH$_3$)$_2$OH, —CH$_2$NH$_2$, —CN, —C(O)CH$_3$, —CH$_2$NHC(O)CH$_3$, —C(O)OH, —C(O)OCH$_3$, —C(O)NH$_2$, —C(O)N(CH$_3$)$_2$, —C(O)NH(C$_{1-4}$ alkyl), —C(O)NH(cyclopropyl), —C(O)NH(cyclopentyl), —S(O)$_2$CH$_3$, —NHC(O)CH$_3$, —NHC(O)OCH$_3$, —NHC(O)CH$_2$CH$_2$OCH$_3$, —NHS(O)$_2$CH$_3$, —O(ethyl), —OCHF$_2$, —S(O)$_2$NH$_2$, —C(O)(morpholinyl), —CH$_2$(morpholinyl), phenyl, pyrazolyl, tetrazolyl, and/or morpholinyl.

7. The compound according to claim 4, or stereoisomers or salts thereof, wherein:

$R^1$ is:

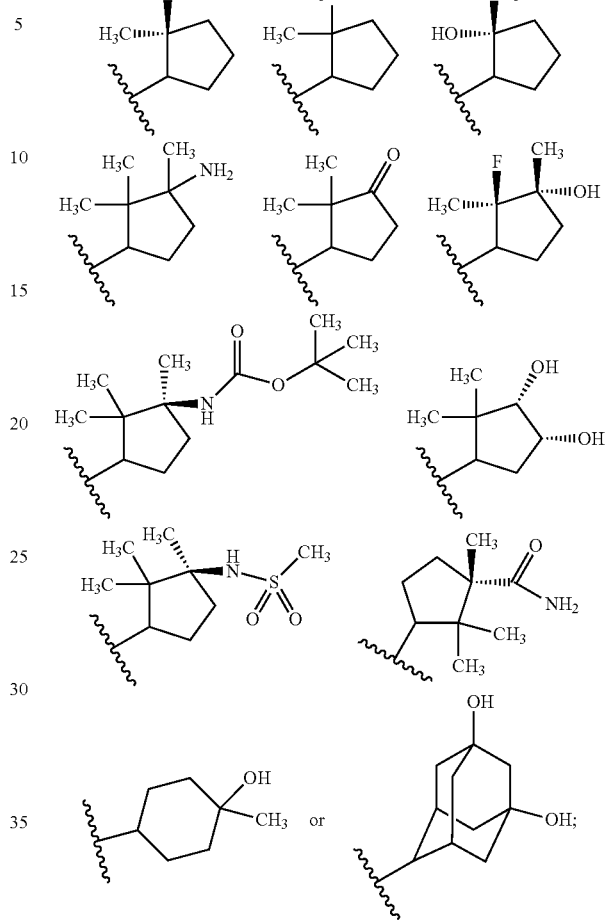

$R^2$ is $R^y$; and $R^y$ is pyridinyl substituted with zero, 1, or 2 substituents independently selected from F, Cl, —CH$_3$, —NH$_2$, —CF$_3$, —CN, —OCH$_3$, —OCH(CH$_3$)$_2$, —C(O)NH$_2$, —C(O)NH(CH$_3$), —NHC(O)CH$_3$, and/or —O(benzyl); or pyridinonyl substituted with hydroxybutyl.

8. A pharmaceutical composition comprising a pharmaceutically acceptable carrier and at least one of the compounds according to claim 1, or a stereoisomer or pharmaceutically acceptable salt thereof.

9. A method of treating an inflammatory and/or autoimmune disease comprising administering an affective amount of a compound of claim 1 to a patient in need thereof, wherein said inflammatory and/or autoimmune disease is selected from Crohn's, ulcerative colitis, rheumatoid arthritis, psoriasis, and solid organ transplant rejection.

* * * * *

UNITED STATES PATENT AND TRADEMARK OFFICE
CERTIFICATE OF CORRECTION

PATENT NO. : 8,921,368 B2  
APPLICATION NO. : 14/005570  
DATED : December 30, 2014  
INVENTOR(S) : Stephen Wrobleski et al.

Page 1 of 1

It is certified that error appears in the above-identified patent and that said Letters Patent is hereby corrected as shown below:

On the Title Page, item (75) Inventors:
Col. 1, line 2, delete "Landsdale" and insert -- Lansdale --, therefor In the Claims:
Claim 5, col. 315, line 21, delete "claim 4" and insert -- claim 4, --, therefor.

Signed and Sealed this
First Day of March, 2016

Michelle K. Lee
*Director of the United States Patent and Trademark Office*